US011696501B2

United States Patent
Jin et al.

(10) Patent No.: US 11,696,501 B2
(45) Date of Patent: Jul. 4, 2023

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Hyo Min Jin, Cheonan-si (KR); Yun Suk Lee, Cheonan-si (KR); Hyung Dong Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 0 days.

(21) Appl. No.: 18/057,570

(22) Filed: Nov. 21, 2022

(65) Prior Publication Data

US 2023/0125420 A1    Apr. 27, 2023

Related U.S. Application Data

(63) Continuation-in-part of application No. 17/212,886, filed on Mar. 25, 2021, which is a continuation of (Continued)

(30) Foreign Application Priority Data

Oct. 26, 2020 (KR) .................. 10-2020-0139441

(51) Int. Cl.
*C07D 251/24* (2006.01)
*C09K 11/06* (2006.01)
(Continued)

(52) U.S. Cl.
CPC ........ *H01L 51/0073* (2013.01); *C07D 251/24* (2013.01); *C09K 11/06* (2013.01);
(Continued)

(58) Field of Classification Search
CPC . C07D 251/24; H01L 51/0059; H01L 51/006; H01L 51/0061; H01L 51/0067;
(Continued)

(56) References Cited

U.S. PATENT DOCUMENTS

2014/0367654 A1* 12/2014 Kim .................... H01L 51/0052
257/40
2015/0303379 A1   10/2015 Lee et al.
(Continued)

FOREIGN PATENT DOCUMENTS

WO        2019124902 A1    6/2019
WO     WO-2020171531 A1 *  8/2020 ........... C07D 405/14

OTHER PUBLICATIONS

SciFinder Search, 4 pages, Apr. 7, 2021.
STN Search, 351 pages, Apr. 7, 2021.

*Primary Examiner* — Vu A Nguyen
(74) *Attorney, Agent, or Firm* — Vorys, Sater, Seymour and Pease LLP; Mih Suhn Koh

(57) ABSTRACT

The present invention provides a novel compound capable of improving the luminous efficiency, stability and lifespan of a device, an organic electronic element using the same, and an electronic device thereof, wherein the compound is represented by Formula (1):

(Continued)

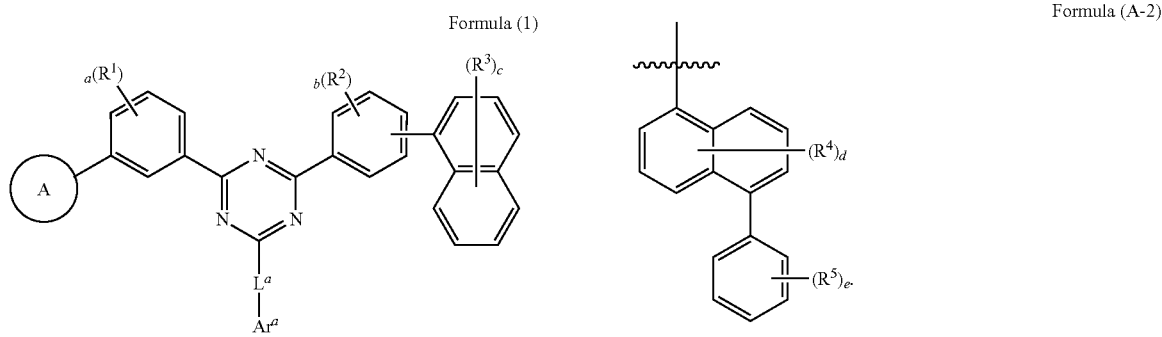

Formula (1)

wherein:

A is a substituent represented by Formula (A-1)-(A-2);

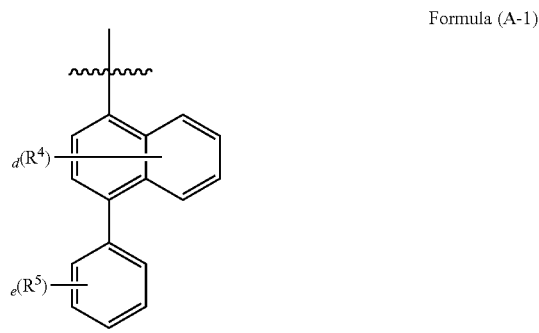

Formula (A-1)

Formula (A-2)

12 Claims, 2 Drawing Sheets

Related U.S. Application Data application No. 17/096,790, filed on Nov. 12, 2020, now Pat. No. 11,063,226.

(51) Int. Cl.
  *H01L 51/00* (2006.01)
  *H01L 51/50* (2006.01)

(52) U.S. Cl.
  CPC ...... *H01L 51/0058* (2013.01); *H01L 51/0059* (2013.01); *H01L 51/0065* (2013.01); *H01L 51/0067* (2013.01); *H01L 51/0072* (2013.01); *H01L 51/0074* (2013.01); *C07B 2200/05* (2013.01); *C09K 2211/1018* (2013.01); *H01L 51/5016* (2013.01); *H01L 51/5056* (2013.01); *H01L 51/5072* (2013.01); *H01L 51/5096* (2013.01); *H01L 2251/5384* (2013.01)

(58) Field of Classification Search
  CPC ............. H01L 51/0069; H01L 51/0071; H01L 51/0072
  See application file for complete search history.

(56) References Cited

U.S. PATENT DOCUMENTS

| | | |
|---|---|---|
| 2016/0133674 A1 | 5/2016 | Lee et al. |
| 2018/0072695 A1 | 3/2018 | Byun et al. |
| 2018/0123048 A1 | 5/2018 | So et al. |
| 2018/0151806 A2 | 5/2018 | Park et al. |
| 2018/0261774 A1 | 9/2018 | Park et al. |

\* cited by examiner

COMPOUND FOR ORGANIC ELECTRONIC ELEMENT, ORGANIC ELECTRONIC ELEMENT USING THE SAME, AND AN ELECTRONIC DEVICE THEREOF

BACKGROUND

Technical Field

The present invention relates to a compound for an organic electronic element, an organic electronic element using the same, and an electronic device thereof.

Background Art

In general, organic light emitting phenomenon refers to a phenomenon that converts electric energy into light energy by using an organic material. An organic electronic element using an organic light emitting phenomenon usually has a structure including an anode, a cathode, and an organic material layer interposed therebetween. Here, in order to increase the efficiency and stability of the organic electronic element, the organic material layer is often composed of a multi-layered structure composed of different materials, and for example, may include a hole injection layer, a hole transport layer, an emitting layer, an electron transport layer, an electron injection layer and the like.

A material used as an organic material layer in an organic electronic element may be classified into a light emitting material and a charge transport material, such as a hole injection material, a hole transport material, an electron transport material, an electron injection material and the like depending on its function. And the light emitting material can be classified into a high molecular weight type and a low molecular weight type according to the molecular weight, and according to the light emission mechanism, it can be classified into a fluorescent material derived from a singlet excited state of an electron and a phosphorescent material derived from a triplet excited state of an electron. Also, the light emitting material may be divided into blue, green, and red light emitting materials and yellow and orange light emitting materials necessary for realizing a better natural color according to the emission color.

However, when only one material is used as a light emitting material, due to intermolecular interaction, the maximum emission wavelength shifts to a longer wavelength, and there are problems in that the color purity is lowered or the device efficiency is reduced due to the emission attenuation effect, therefore in order to increase color purity and increase luminous efficiency through energy transfer, a host/dopant system may be used as a light emitting material. The principle is that when a small amount of a dopant having a smaller energy band gap than that of the host forming the emitting layer is mixed in the emitting layer, excitons generated in the emitting layer are transported to the dopant to emit light with high efficiency. At this time, since the wavelength of the host moves to the wavelength band of the dopant, light having a desired wavelength can be obtained according to the type of dopant used.

Currently, the portable display market is a large-area display, and the size thereof is increasing, and thus, more power consumption than the power consumption required for the existing portable display is required. Therefore, power consumption has become a very important factor for a portable display having a limited power supply such as a battery, and the problem of efficiency and lifespan must also be solved.

Efficiency, lifespan, and driving voltage are related to each other, and when the efficiency is increased, the driving voltage is relatively decreased, and as the driving voltage is decreased, crystallization of organic materials due to Joule heating generated during driving decreases, and consequently, the lifespan tends to increase. However, the efficiency cannot be maximized simply by improving the organic material layer. This is because, when the energy level and T1 value between each organic material layer, and the intrinsic properties (mobility, interfacial properties, etc.) of materials are optimally combined, long lifespan and high efficiency can be achieved at the same time.

Therefore, while delaying the penetration and diffusion of metal oxide from the anode electrode (ITO) into the organic layer, which is one of the causes of shortening the lifespan of the organic electronic element, it should have stable characteristics against Joule heating generated during device driving, and OLED devices are mainly formed by a deposition method, and it is necessary to develop a material that can withstand a long time during deposition, that is, a material with strong heat resistance.

In other words, in order to fully exhibit the excellent characteristics of an organic electronic element, it should be preceded that the material constituting the organic material layer in the device, such as a hole injection material, a hole transport material, a light emitting material, an electron transport material, an electron injection material, etc., is supported by a stable and efficient material. But the development of a stable and efficient organic material layer material for an organic electronic device has not yet been sufficiently made. Therefore, the development of new materials is continuously required, and in particular, the development of a host material for the emitting layer is urgently required.

BRIEF SUMMARY OF THE INVENTION

Summary

In order to solve the problems of the above-mentioned background art, the present invention has revealed a compound having a novel structure, and when this compound is applied to an organic electronic element, it has been found that the luminous efficiency, stability and lifespan of the device can be significantly improved.

Accordingly, an object of the present invention is to provide a novel compound, an organic electronic element using the same, and an electronic device thereof.

Technical Solution

The present invention provides a compound represented by Formula (1).

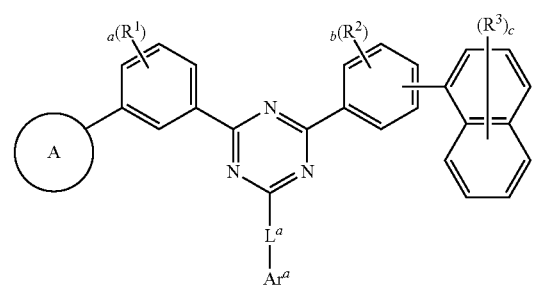

Formula (1)

In another aspect, the present invention provides an organic electronic element comprising the compound represented by Formula (1) and an electronic device thereof.

Effects of the Invention

By using the compound according to the present invention, high luminous efficiency, low driving voltage and high heat resistance of the device can be achieved, and color purity and lifespan of the device can be greatly improved.

Figure 1:
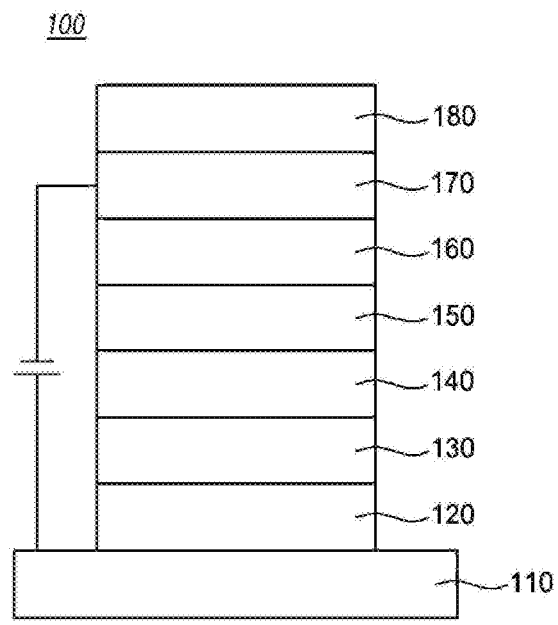
FIG. 1 to FIG. 3 are exemplary views of an organic electroluminescent device according to the present invention. In the drawings.

| | |
|---|---|
| 100, 200, 300: organic electronic element | 110: the first electrode |
| 120: hole injection layer | 130: hole transport layer |
| 140: emitting layer | 150: electron transport layer |
| 160: electron injection layer | 170: second electrode |
| 180: light efficiency enhancing Layer | 210: buffer layer |
| 220: emitting auxiliary layer | 320: first hole injection layer |
| 330: first hole transport layer | 340: first emitting layer |
| 350: first electron transport layer | 360: first charge generation layer |
| 361: second charge generation layer | 420: second hole injection layer |
| 430: second hole transport layer | 440: second emitting layer |
| 450: second electron transport layer | CGL: charge generation layer |
| ST1: first stack | ST2: second stack. |

DETAILED DESCRIPTION OF THE INVENTION

Hereinafter, some embodiments of the present invention will be described in detail. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used to define an essence, order or sequence of a corresponding component but used merely to distinguish the corresponding component from other component(s). It should be noted that if a component is described as being "connected", "coupled", or "connected" to another component, the component may be directly connected or connected to the other component, but another component may be "connected coupled" or "connected" between each component.

As used in the specification and the accompanying claims, unless otherwise stated, the following is the meaning of the term as follows.

Unless otherwise stated, the term "halo" or "halogen", as used herein, includes fluorine, bromine, chlorine, or iodine.

Unless otherwise stated, the term "alkyl" or "alkyl group", as used herein, has a single bond of 1 to 60 carbon atoms, and means saturated aliphatic functional radicals including a linear alkyl group, a branched chain alkyl group, a cycloalkyl group (alicyclic), a cycloalkyl group substituted with a alkyl or an alkyl group substituted with a cycloalkyl.

Unless otherwise stated, the term "alkenyl" or "alkynyl", as used herein, has double or triple bonds of 2 to 60 carbon atoms, but is not limited thereto, and includes a linear or a branched chain group.

Unless otherwise stated, the term "cycloalkyl", as used herein, means alkyl forming a ring having 3 to 60 carbon atoms, but is not limited thereto.

Unless otherwise stated, the term "alkoxyl group", "alkoxy group" or "alkyloxy group", as used herein, means an oxygen radical attached to an alkyl group, but is not limited thereto, and has 1 to 60 carbon atoms.

Unless otherwise stated, the term "aryloxyl group" or "aryloxy group", as used herein, means an oxygen radical attached to an aryl group, but is not limited thereto, and has 6 to 60 carbon atoms.

The terms "aryl group" and "arylene group" used in the present invention have 6 to 60 carbon atoms, respectively, unless otherwise specified, but are not limited thereto. In the present invention, an aryl group or an arylene group means a single ring or multiple ring aromatic, and includes an aromatic ring formed by an adjacent substituent joining or participating in a reaction.

For example, the aryl group may be a phenyl group, a biphenyl group, a fluorene group, or a spirofluorene group.

The prefix "aryl" or "ar" means a radical substituted with an aryl group. For example, an arylalkyl may be an alkyl substituted with an aryl, and an arylalkenyl may be an alkenyl substituted with aryl, and a radical substituted with an aryl has a number of carbon atoms as defined herein.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substituted with an arylcarbonyl, wherein the arylcarbonyl may be a carbonyl substituted with an aryl.

Unless otherwise stated, the term "heterocyclic group", as used herein, contains one or more heteroatoms, but is not limited thereto, has 2 to 60 carbon atoms, includes any one of a single ring or multiple ring, and may include heteroaliphadic ring and heteroaromatic ring. Also, the heterocyclic group may also be formed in conjunction with an adjacent group.

Unless otherwise stated, the term "heteroatom", as used herein, represents at least one of N, O, S, P, or Si.

Also, the term "heterocyclic group" may include a ring including SO2 instead of carbon consisting of cycle. For example, "heterocyclic group" includes the following compound.

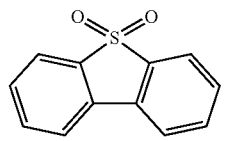 [SMILES: O=S1(=O)c2ccccc2-c2ccccc21]

Unless otherwise stated, the term "fluorenyl group" or "fluorenylene group", as used herein, means a monovalent or divalent functional group, in which R, R' and R" are all hydrogen in the following structures, and the term "substituted fluorenyl group" or "substituted fluorenylene group" means that at least one of the substituents R, R', R" is a substituent other than hydrogen, and include those in which R and R' are bonded to each other to form a spiro compound together with the carbon to which they are bonded.

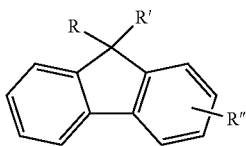

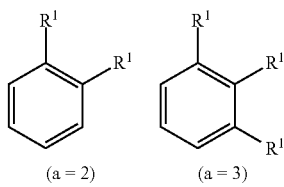

(a = 2)    (a = 3)

The term "spiro compound", as used herein, has a 'spiro union', and a spiro union means a connection in which two rings share only one atom. At this time, atoms shared in the two rings are called 'spiro atoms', and these compounds are called 'monospiro-', 'di-spiro-' and 'tri-spiro-', respectively, depending on the number of spiro atoms in a compound.

Unless otherwise stated, the term "aliphatic", as used herein, means an aliphatic hydrocarbon having 1 to 60 carbon atoms, and the term "aliphatic ring", as used herein, means an aliphatic hydrocarbon ring having 3 to 60 carbon atoms.

Unless otherwise stated, the term "ring", as used herein, means an aliphatic ring having 3 to 60 carbon atoms, or an aromatic ring having 6 to 60 carbon atoms, or a hetero ring having 2 to 60 carbon atoms, or a fused ring formed by the combination of them, and includes a saturated or unsaturated ring.

Other hetero compounds or hetero radicals other than the above-mentioned hetero compounds include, but are not limited thereto, one or more heteroatoms.

Also, unless expressly stated, as used herein, "substituted" in the term "substituted or unsubstituted" means substituted with one or more substituents selected from the group consisting of deuterium, halogen, an amino group, a nitrile group, a nitro group, a $C_1$-$C_{20}$ alkyl group, a $C_1$-$C_{20}$ alkoxyl group, a $C_1$-$C_{20}$ alkylamine group, a $C_1$-$C_{20}$ alkylthiopen group, a $C_6$-$C_{20}$ arylthiopen group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group, but is not limited to these substituents.

Also, unless there is an explicit explanation, the formula used in the present invention is the same as the definition of the substituent by the exponent definition of the following formula.

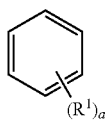

Here, when a is an integer of 0, the substituent $R^1$ is absent, when a is an integer of 1, the sole substituent $R^1$ is linked to any one of the carbon constituting the benzene ring, when a is an integer of 2 or 3, each is combined as follows, where $R^1$ may be the same or different from each other, when a is an integer of 4 to 6, it is bonded to the carbon of the benzene ring in a similar manner, while the indication of the hydrogen bonded to the carbon forming the benzene ring is omitted.

Hereinafter, a laminated structure of an organic electronic device including the compound of the present invention will be described with reference to FIGS. 1 to 3.

In adding reference numerals to elements of each figure, it should be noted that the same elements have the same numerals as possible even if they are indicated on different figures.

In addition, in describing the present invention, when it is determined that a detailed description of a related known configuration or function may obscure the subject matter of the present invention, a detailed description thereof will be omitted.

Figure 2:
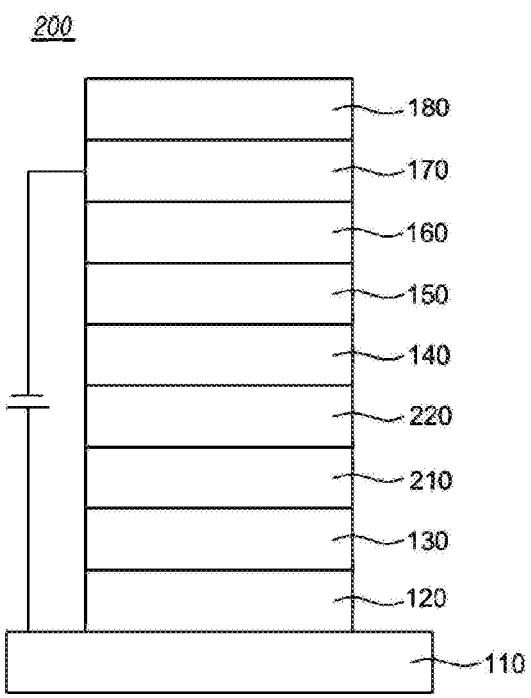
Figure 3:
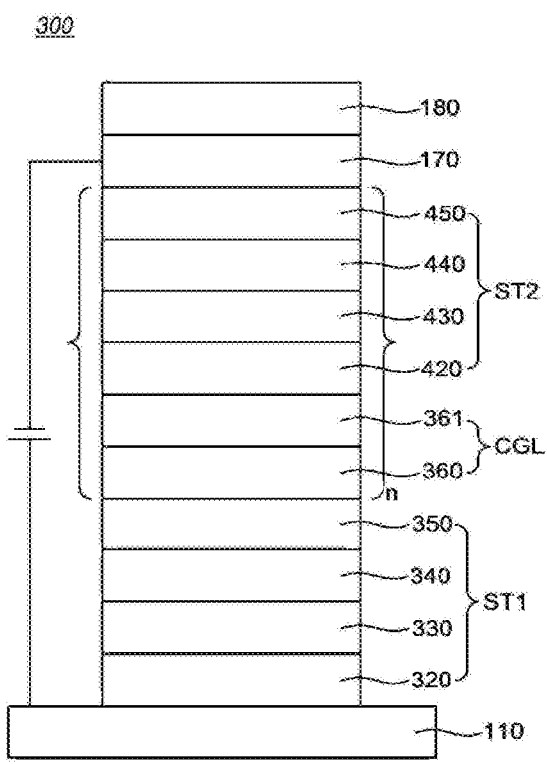

FIG. 1 to FIG. 3 illustrate an example of an organic electronic element according to an embodiment of the present invention.

Referring to FIG. 1, an organic electronic element (100) according to an embodiment of the present invention includes a first electrode (110), a second electrode (170) formed on a substrate (not shown) and an organic material layer formed between the first electrode (110) and the second electrode (170).

The first electrode (110) may be an anode, the second electrode (170) may be a cathode, and in the case of an inverted type, the first electrode may be a cathode and the second electrode may be an anode.

The organic material layer may include a hole injection layer (120), a hole transport layer (130), an emitting layer (140), an electron transport layer (150), and an electron injection layer (160). Specifically, a hole injection layer (120), a hole transport layer (130), an emitting layer (140), an electron transport layer (150), and an electron injection layer (160) may be sequentially formed on the first electrode (110).

The present invention may further include a light efficiency enhancing layer formed on one of not in contact with the organic material layer among one side of the first electrode (110) or of the second electrode (170), and when the light efficiency enhancing layer (180) is formed, the light efficiency of the organic electronic element may be improved.

For example, the light efficiency enhancing layer (180) may be formed on the second electrode (170), and in the case of a top emission organic light emitting device, the light efficiency enhancing layer (180) is formed, thereby reducing optical energy loss due to surface plasmon polaritons (SPPs) in the second electrode (170), and in the case of a bottom emission organic light emitting device, the light efficiency enhancing layer (180) may function as a buffer for the second electrode (170).

A buffer layer (210) or an emitting auxiliary layer (220) may be further formed between the hole transport layer (130) and the emitting layer (140), which will be described with reference to FIG. 2.

Referring to FIG. 2, an organic electric device (200) according to another embodiment of the present invention includes a hole injection layer (120), a hole transport layer (130), a buffer layer (210), an emitting auxiliary layer (220), an emitting layer (140), an electron transport layer (150), an electron injection layer (160), a second electrode (170), sequentially formed on the first electrode (110), and a light efficiency enhancing layer (180) formed on the second electrode.

Although not shown in FIG. 2, an electron transport auxiliary layer may be further formed between the emitting layer (140) and the electron transport layer (150).

Also, according to another embodiment of the present invention, the organic material layer may have a plurality of stacks including a hole transport layer, an emitting layer, and an electron transport layer. This will be described with reference to FIG. 3.

Referring to FIG. 3, in the organic electronic element (300) according to another embodiment of the present invention, 2 or more sets of stacks (ST1 and ST2) made of a multi-layered organic material layer may be formed between the first electrode (110) and the second electrode (170), and a charge generation layer (CGL) may be formed between the stacks of organic material layers.

Specifically, the organic electronic element according to an embodiment of the present invention includes a first electrode (110), a first stack (ST1), a charge generation layer (CGL), a second stack (ST2), and a second electrode. (170) and a light efficiency enhancing layer (180) may be included.

The first stack (ST1) is an organic material layer formed on the first electrode (110) and may include a first hole injection layer (320), a first hole transport layer (330), a first emitting layer (340), and a first electron transport layer (350), and the second stack (ST2) may include a second hole injection layer (420), a second hole transport layer (430), a second emitting layer (440), and a second electron transport layer (450). As described above, the first stack and the second stack may be organic material layers having the same laminated structure, but may be organic material layers having different laminated structures.

A charge generation layer (CGL) may be formed between the first stack (ST1) and the second stack (ST2). The charge generation layer (CGL) may include a first charge generation layer (360) and a second charge generation layer (361). The charge generation layer (CGL) is formed between the first emitting layer (340) and the second emitting layer (440) to increase the current efficiency generated in each emitting layer and smoothly distribute charge.

When a plurality of emitting layers are formed by the multilayer stack structure method as shown in FIG. 3, an organic electronic element that emits white light by a mixing effect of light emitted from each emitting layer can be manufactured, as well as an organic electronic element that emits light of various colors.

The compounds represented by Formulas 1 and 2 of the present invention may be used as a material for a hole injection layer (120, 320, 420), a hole transport layer (130, 330, 430), a buffer layer (210), an emitting auxiliary layer (220), and an electron transport layer (150, 350, 450), the electron injection layer (160), the emitting layer (140, 340, 440), or the light efficiency enhancing layer (180), but preferably, the compounds represented by Formulas 1 and 2 of the present invention may be used as a host of the emitting layers (140, 340, 440).

Otherwise, even if the same or similar core is used, the band gap, the electrical characteristics, the interface characteristics, and the like may vary depending on which substituent is bonded at which position, therefore the choice of core and the combination of sub-substituents associated therewith is also very important, and in particular, when the optimal combination of energy levels and T1 values and unique properties of materials (mobility, interfacial characteristics, etc.) of each organic material layer is achieved, a long lifespan and high efficiency can be achieved at the same time.

The organic electronic element according to an embodiment of the present invention may be manufactured using various deposition methods. It can be manufactured using a vapor deposition method such as PVD or CVD. For example, an anode (110) is formed by depositing a metal or a conductive metal oxide or an alloy thereof on a substrate, and after forming an organic material layer including the hole injection layer (120), the hole transport layer (130), the emitting layer (140), the electron transport layer (150) and the electron injection layer (160) thereon, the organic electroluminescent device according to an embodiment of the present invention can be manufactured by depositing a material that can be used as a cathode (170) thereon. Also, an emitting auxiliary layer (220) may be further formed between the hole transport layer (130) and the emitting layer (140), and an electron transport auxiliary layer (not shown) may be further formed between the emitting layer (140) and the electron transport layer (150), and as described above, may be formed in a stack structure.

Also, the organic material layer may be manufactured with a smaller number of layers by using various polymer materials and not by a deposition method, but by a solution process, a solvent process, such as a spin coating process, a nozzle printing process, an inkjet printing process, a slot coating process, a dip coating process or a roll-to-roll process, doctor blading process, screen printing process, or a thermal transfer method. Since the organic material layer according to the present invention can be formed by various methods, the scope of the present invention is not limited by the forming method.

In addition, the organic electric device according to an embodiment of the present invention may be selected from the group consisting of an organic electroluminescent device, an organic solar cell, an organic photoreceptor, an organic transistor, a monochromatic lighting device, and a quantum dot display device.

Another embodiment of the present invention may include an electronic device comprising a display device including the organic electronic element; and a control unit for driving the display device. At this time, the electronic device may be a current or future wired/wireless communication terminal, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electronic element according to an aspect of the present invention will be described.

The present invention provides a compound represented by Formula (1).

Formula (1)

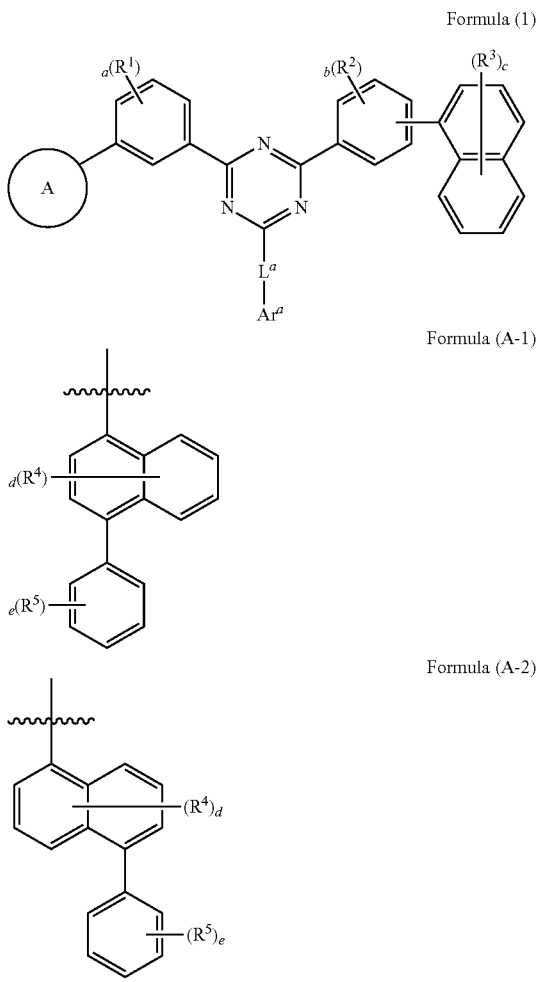

Formula (A-1)

Formula (A-2)

wherein:
A is a substituent represented by Formula (A-1); or a substituent represented by Formula (A-2);
$R^1$, $R^2$, $R^3$, $R^4$ and $R^5$ are the same or different from each other, and each independently represent hydrogen; or deuterium;
a and b are each independently an integer from 0 to 4, c is an integer from 0 to 7, d is an integer from 0 to 6, e is an integer from 0 to 5,
$L^a$ is a direct bond; or a $C_6$~$C_{60}$ arylene group;
wherein in case $L^a$ is an arylene group, it is preferably a $C_6$-$C_{30}$ arylene group, more preferably a $C_6$-$C_{24}$ arylene group, for example, it may be phenylene, biphenyl, naphthalene, terphenyl, and the like.
$Ar^a$ is a $C_6$~$C_{60}$ aryl group, it is preferably a $C_6$-$C_{30}$ aryl group, more preferably a $C_6$-$C_{24}$ aryl group, for example, it may be phenylene, biphenyl, naphthalene, terphenyl, and the like.
wherein the aryl group or arylene group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Also, Formula (1) is represented by Formula (1-1) or Formula (1-2)


wherein:
$R^1$, $R^2$, $R^3$, $R^4$, $R^5$, a, b, c, d, e, $L^a$ and $Ar^a$ are the same as defined above.

Also, Formula (1) is represented by any one of Formulas (2-1) to (2-6).

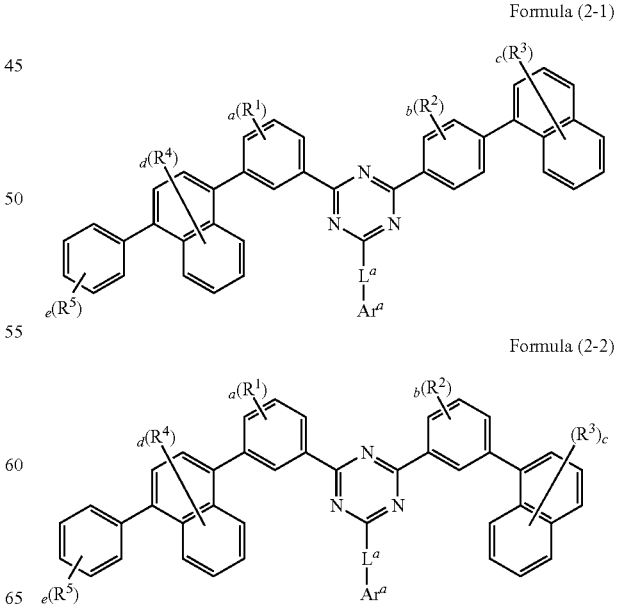

-continued

Formula (2-3)
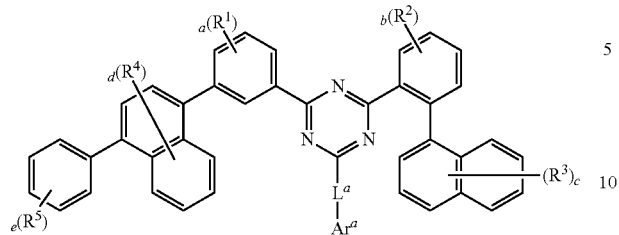

Formula (2-4)
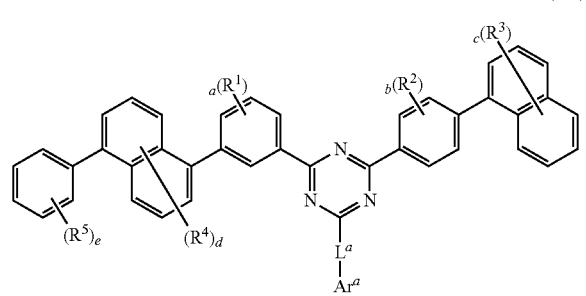

Formula (2-5)
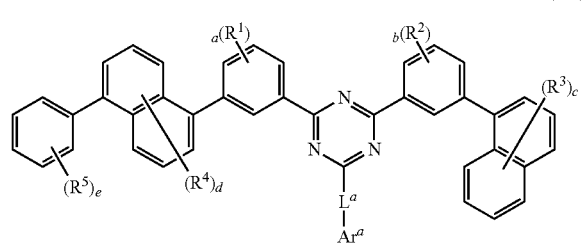

Formula (2-6)
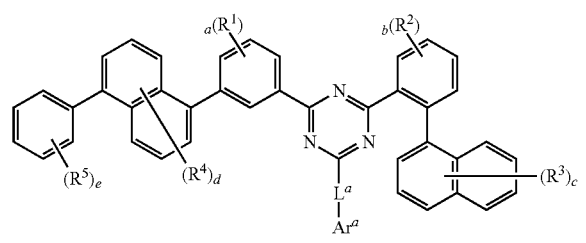

wherein:
$R^1$, $R^2$, $R^3$, $R^4$, $R^5$, a, b, c, d, e, $L^a$ and $Ar^a$ are the same as defined above.

Also, $Ar^a$ is represented by any one of Formulas (A-1) to (A-3).

Formula (A-1)
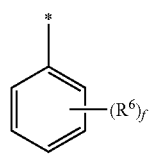

Formula (A-2)
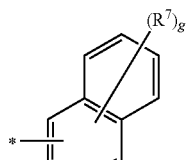

Formula (A-3)
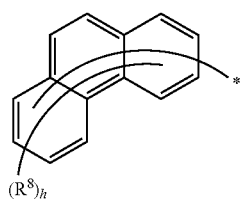

wherein:
* indicates the bonding position,
$R^6$, $R^7$ and $R^8$ are each the same or different, and each independently hydrogen; deuterium; or a $C_6$~$C_{36}$ aryl group; when $R^6$, $R^7$ and $R^8$ are an aryl group, it is preferably a $C_6$-$C_{30}$ aryl group, more preferably a $C_6$-$C_{24}$ aryl group, for example, it may be phenylene, biphenyl, naphthalene, terphenyl, and the like.
f is an integer from 0 to 5, g is an integer from 0 to 7, and h is an integer from 0 to 9.

Also, $L^a$ is represented by any one of Formulas (L-1) to (L-3)

Formula (L-1)
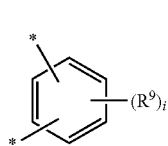

Formula (L-2)
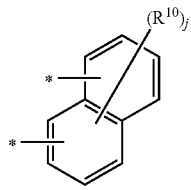

Formula (L-3)
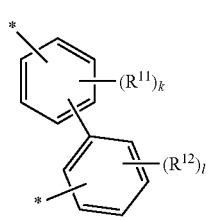

wherein:
* indicates the bonding position,
$R^9$, $R^{10}$, $R^{11}$ and $R^{12}$ are each the same or different, and each independently hydrogen; deuterium; or a $C_6$~$C_{36}$ aryl group, when $R^9$, $R^{10}$, $R^{11}$ and $R^{12}$ are an aryl group, it is preferably a $C_6$-$C_{30}$ aryl group, more preferably a $C_6$-$C_{24}$ aryl group, for example, it may be phenylene, biphenyl, naphthalene, terphenyl, and the like.
i, k and l are each independently an integer from 0 to 4, and j is an integer from 0 to 6.

$L^a$ is represented by any one of the following formulas (L-1) to (L-14):
Formula (L-1)
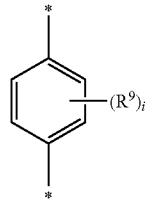
Formula (L-2)
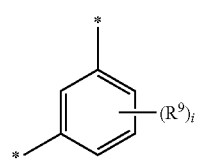
Formula (L-3)
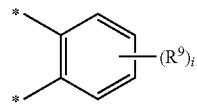
Formula (L-4)
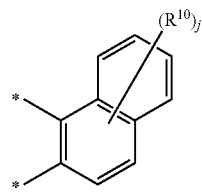
Formula (L-5)
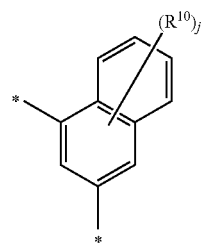
Formula (L-6)
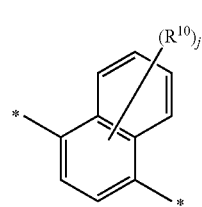
Formula (L-7)
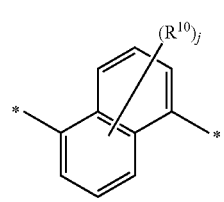
Formula (L-8)
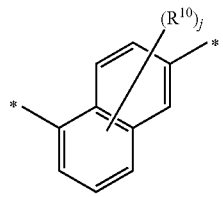
Formula (L-9)
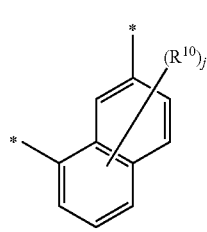
Formula (L-10)
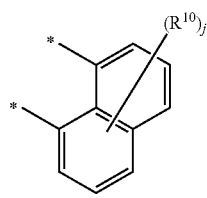
Formula (L-11)
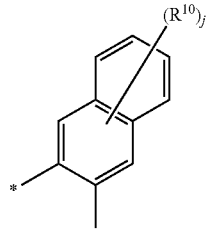
Formula (L-12)
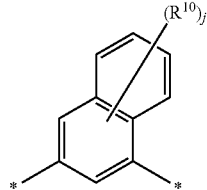
Formula (L-13)
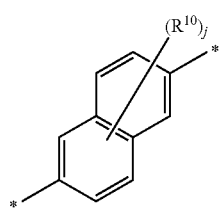
Formula (L-14)
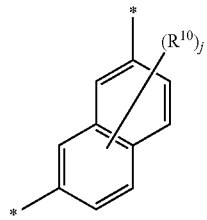

wherein:
* indicates the bonding position,
R⁹ and R¹⁰ are the same as defined above,
i is an integer from 0 to 4, and j is an integer from 0 to 6.
Also, the compound represented by Formula 1 is represented by any one of the following P-1 to P-98:
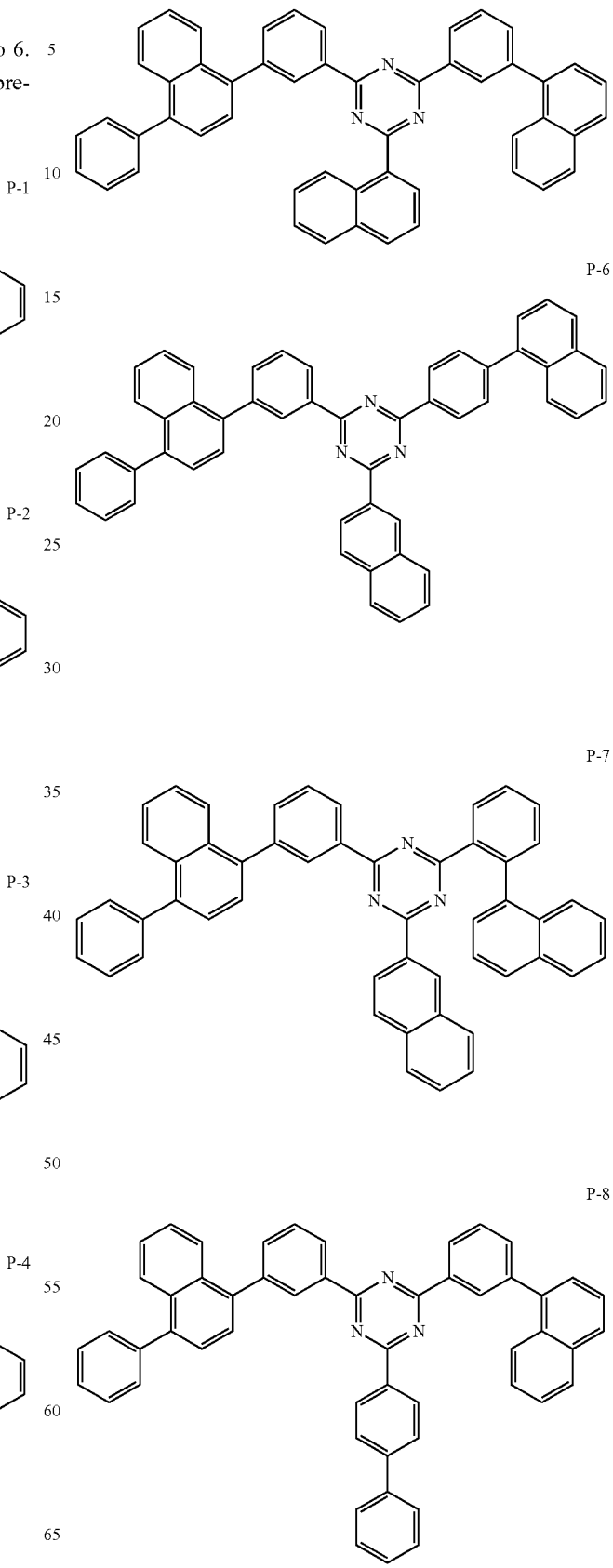

P-9
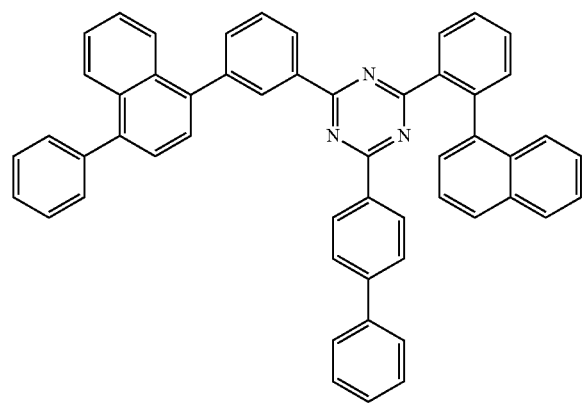
P-10
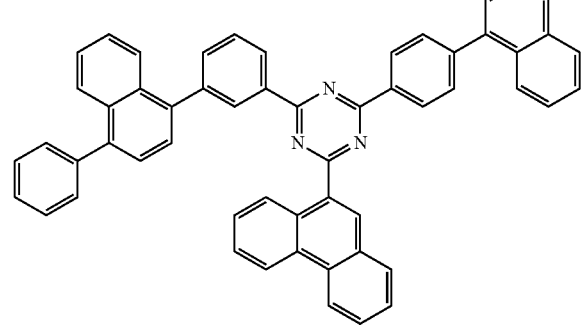
P-11
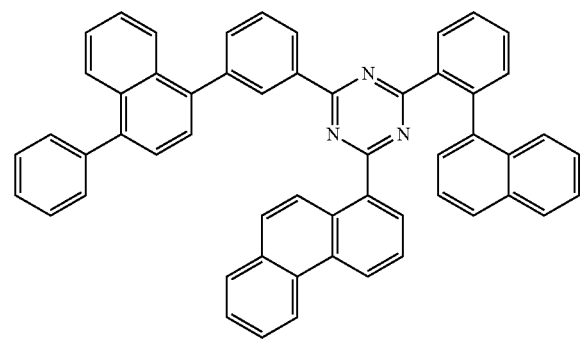
P-12
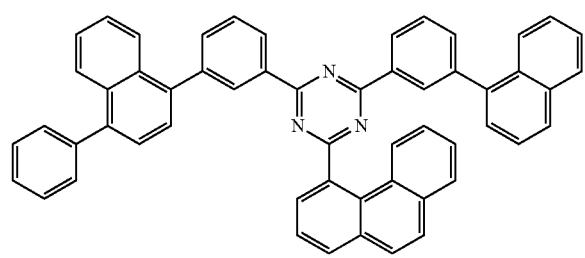
P-13
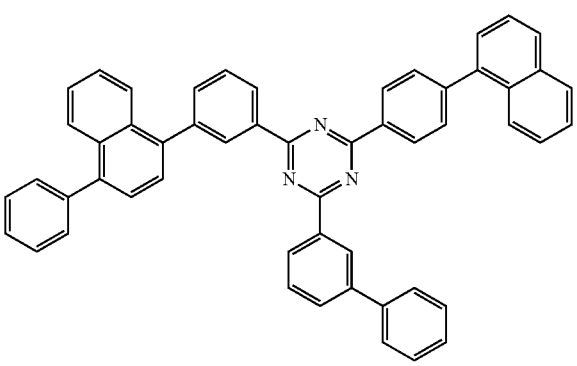
P-14
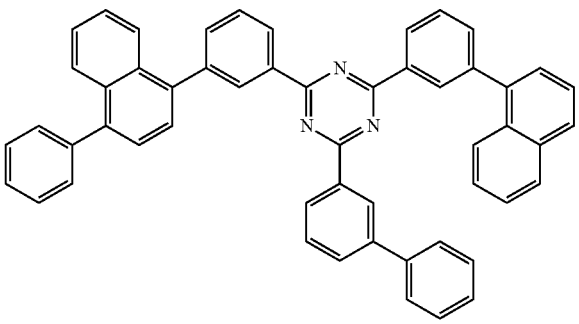
P-15
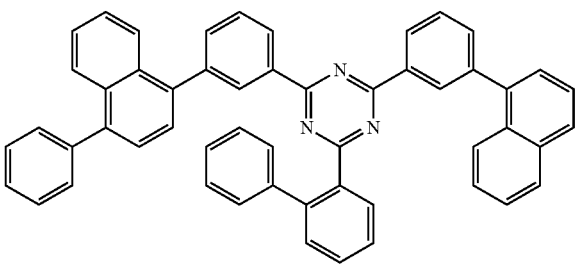
P-16
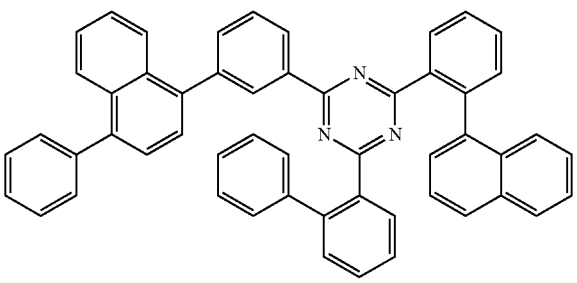

P-17
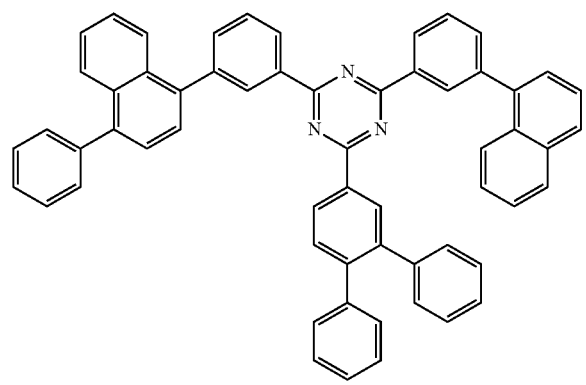
P-18
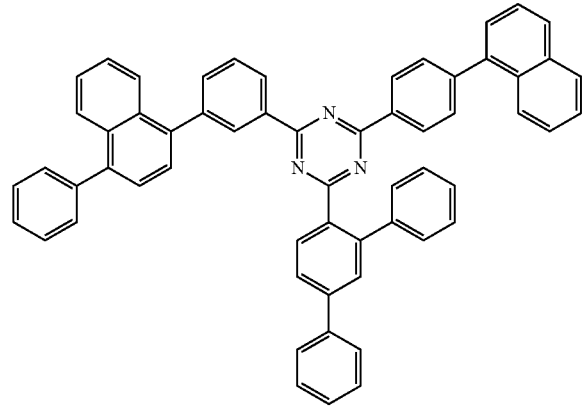
P-19
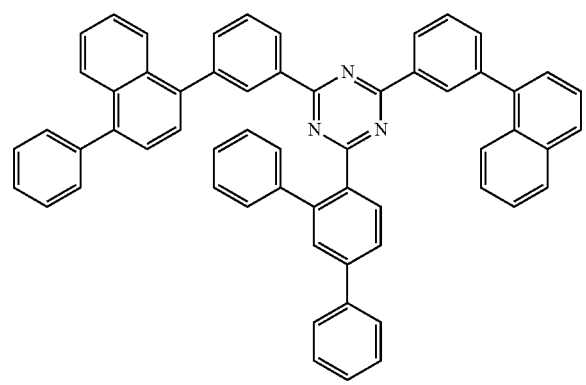
P-20
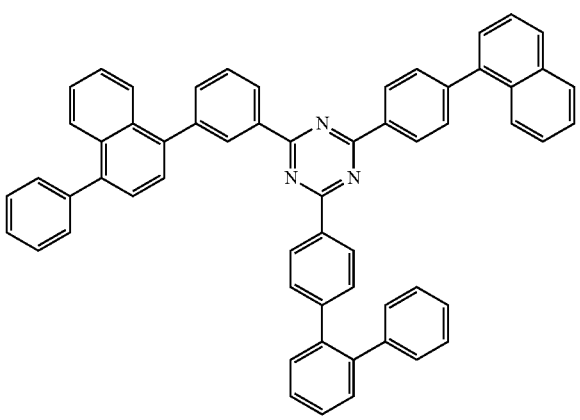
P-21
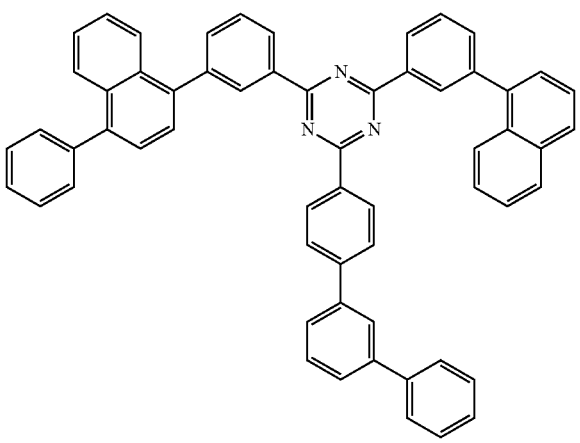
P-22
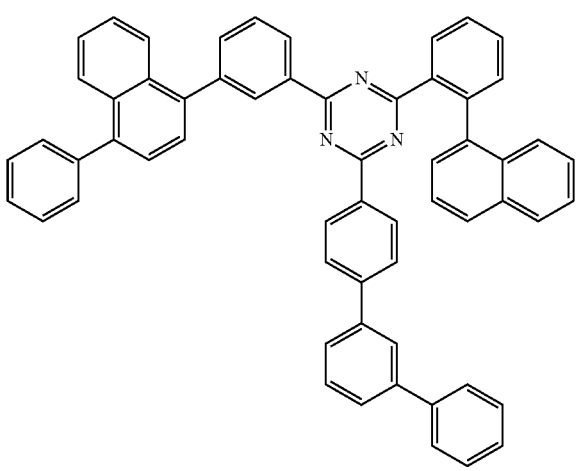

P-23
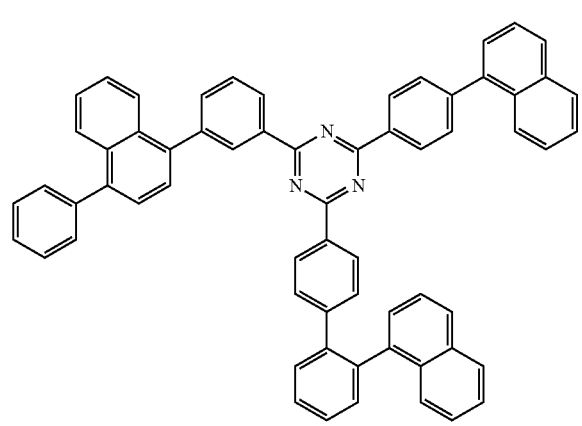
P-24
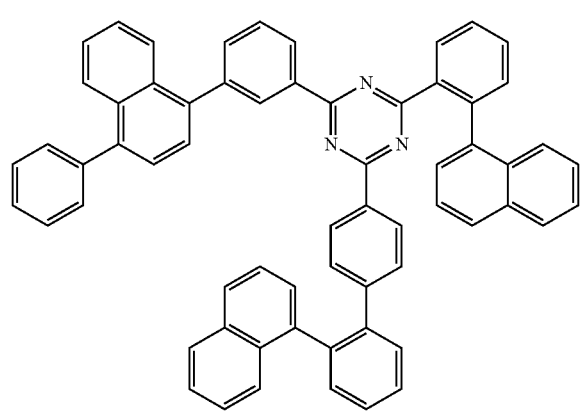
P-25
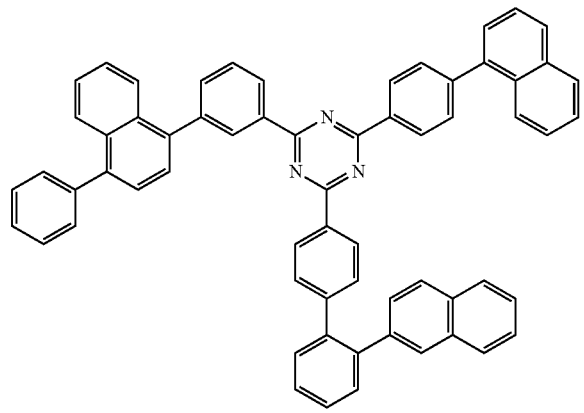
P-26
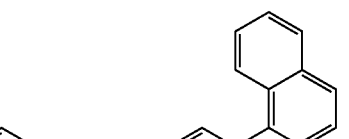
P-27
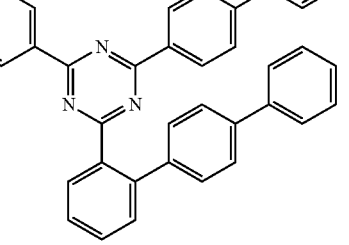
P-28
P-29
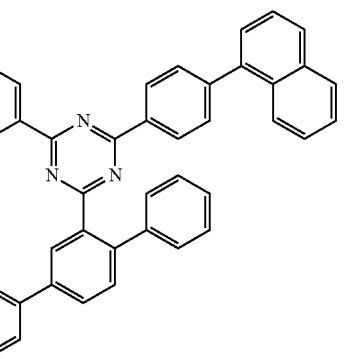

P-30
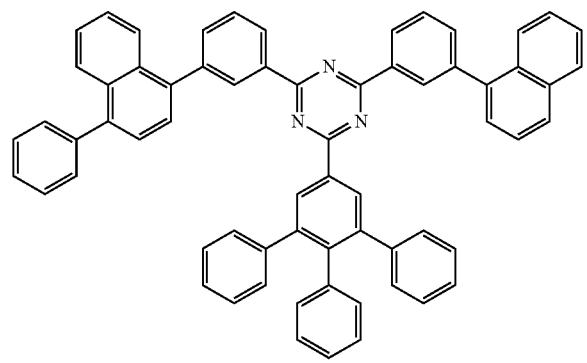
P-31
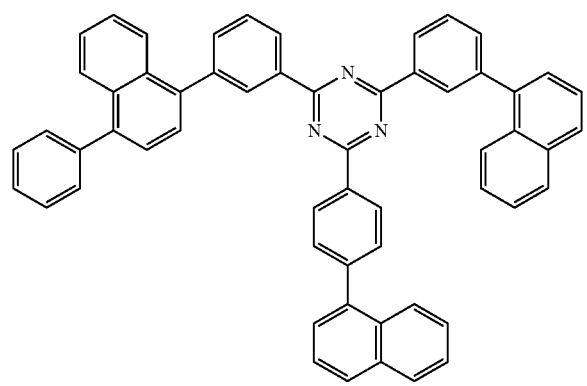
P-32
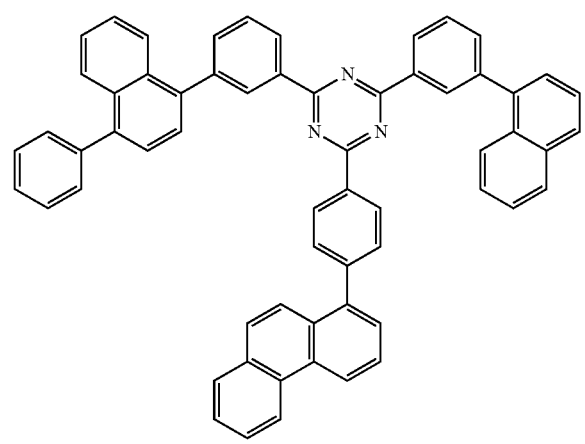
P-33
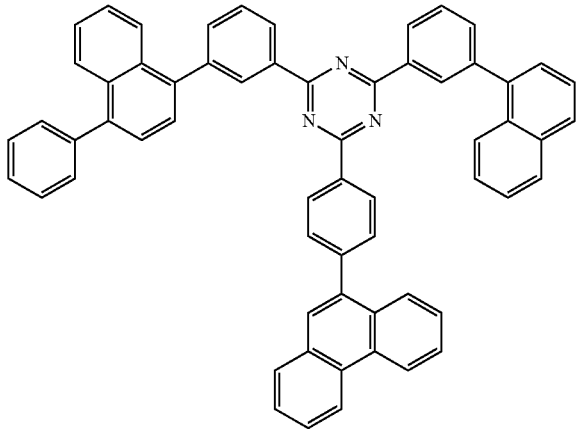
P-34
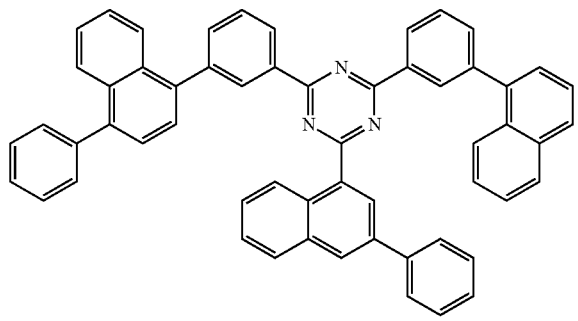
P-35
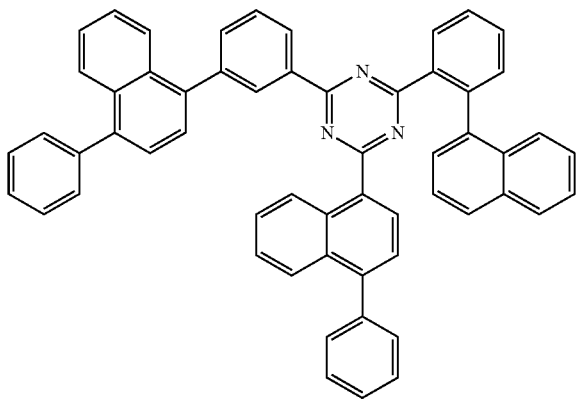
P-36
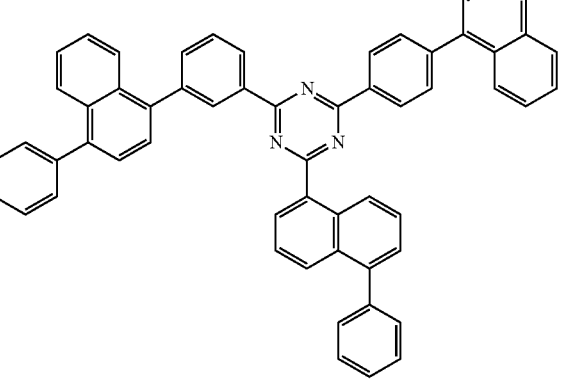

P-37
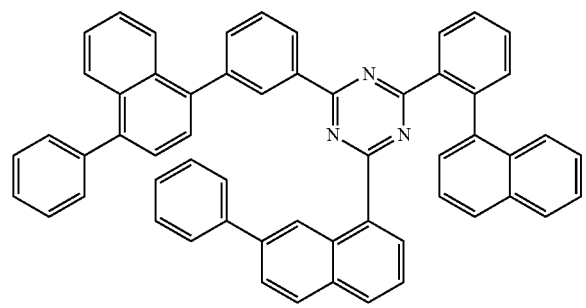
P-38
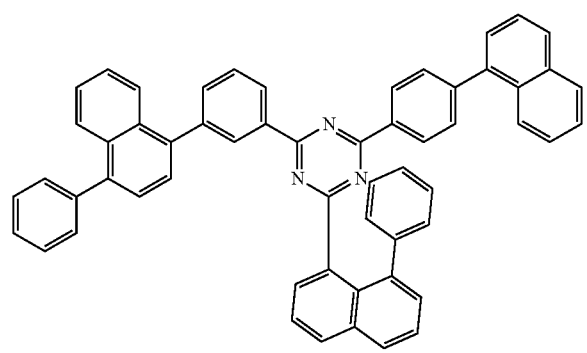
P-39
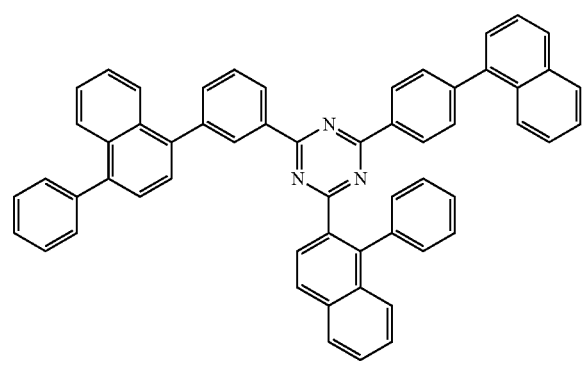
P-40
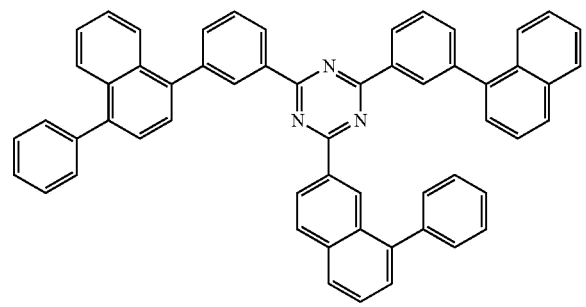
P-41
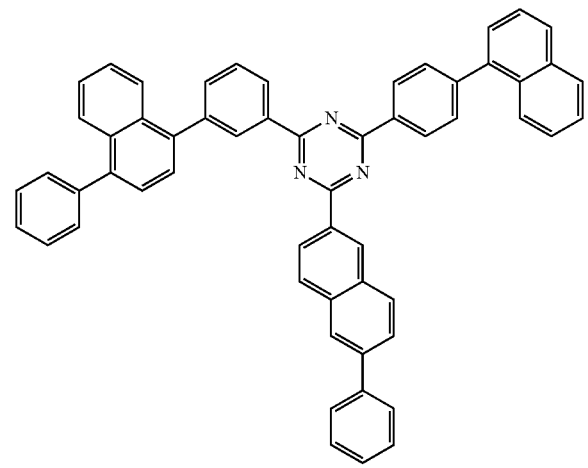
P-42
P-43
P-44
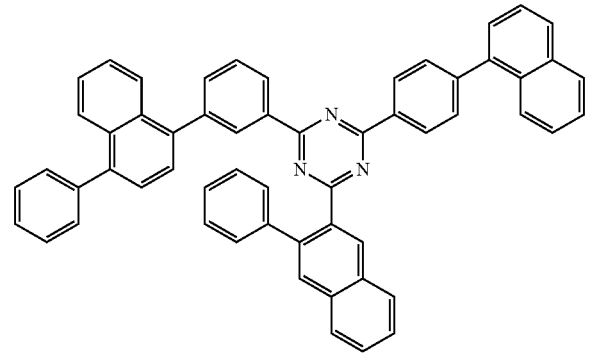

P-45
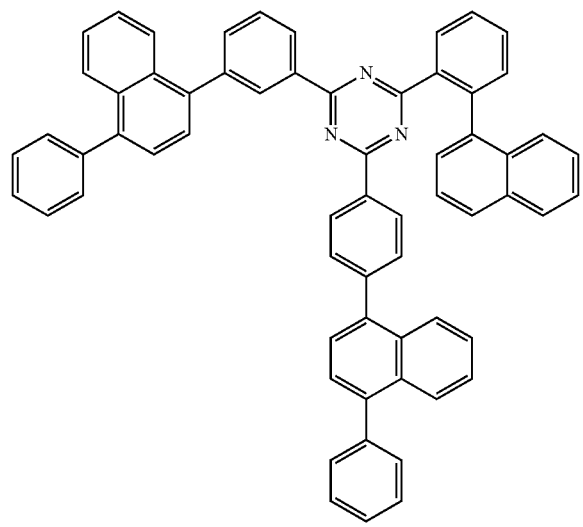
P-46
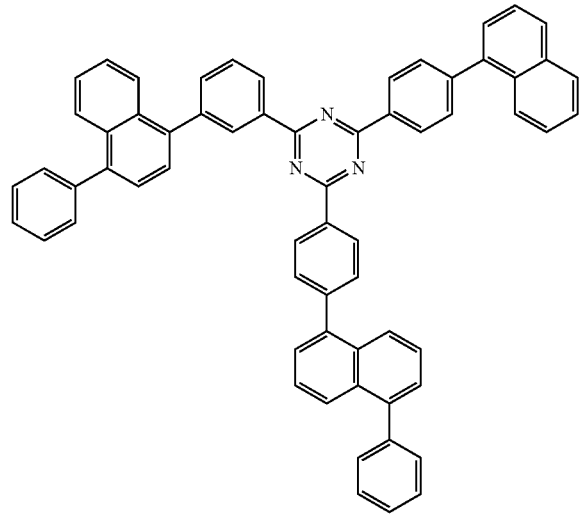
P-47
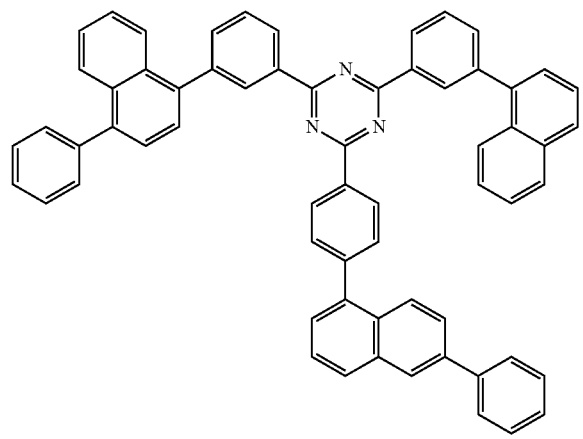
P-48
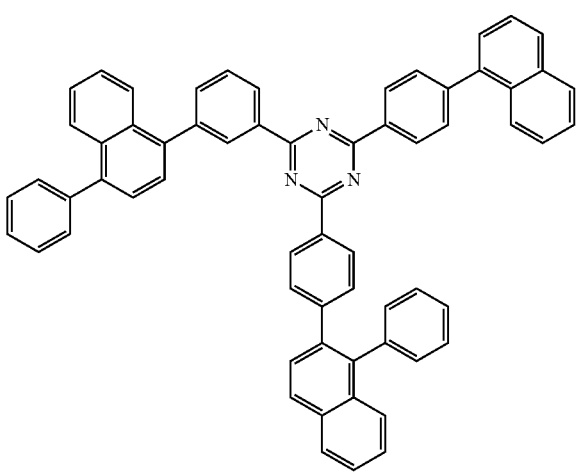
P-49
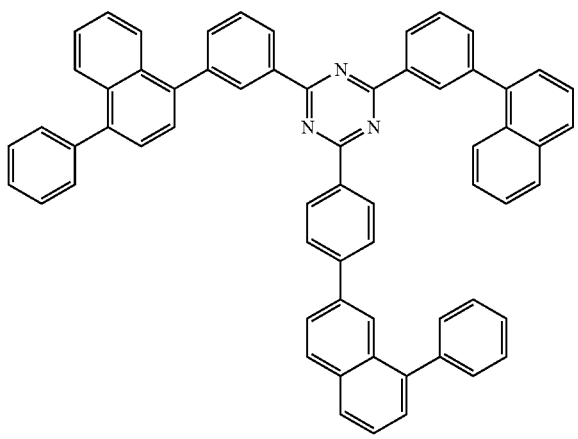
P-50
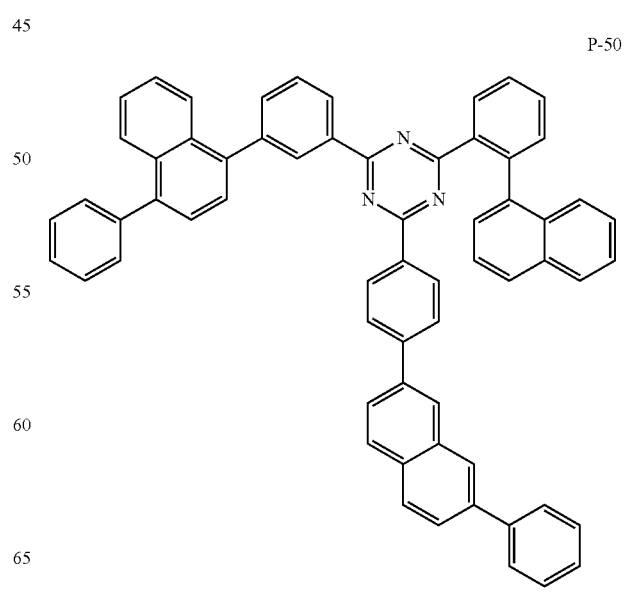

P-51
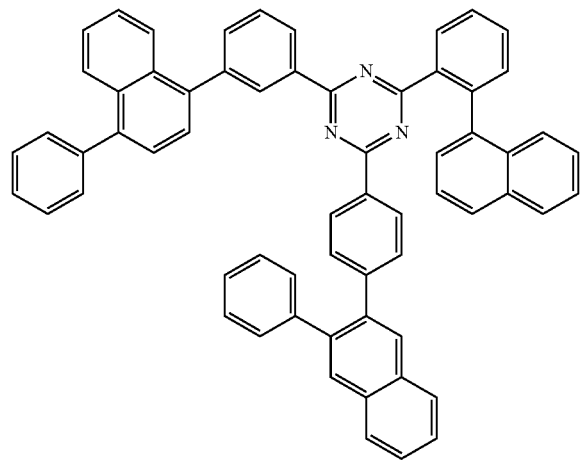
P-52
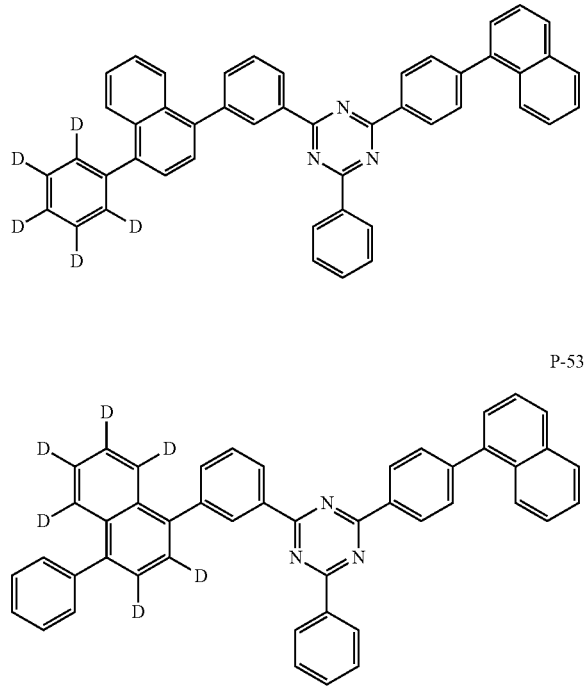
P-53
P-54
P-55
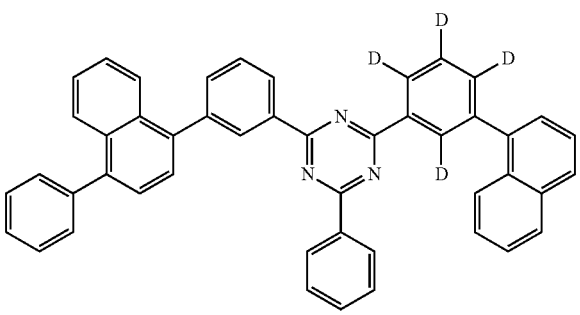
P-56
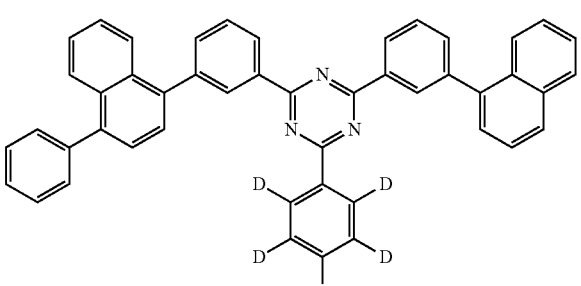
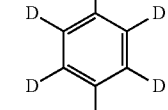
P-57
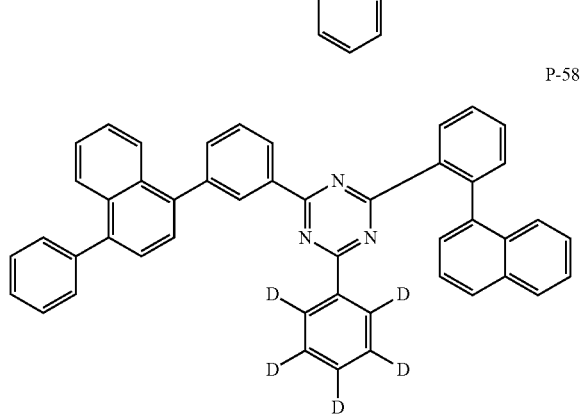
P-58
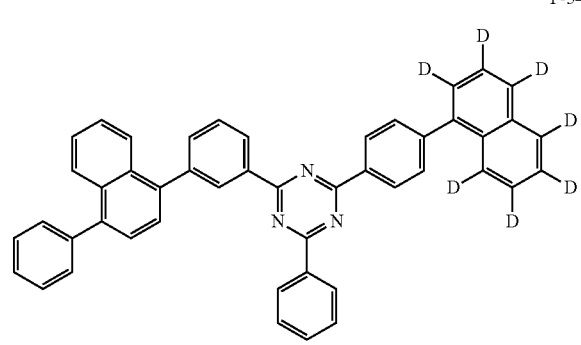
P-59
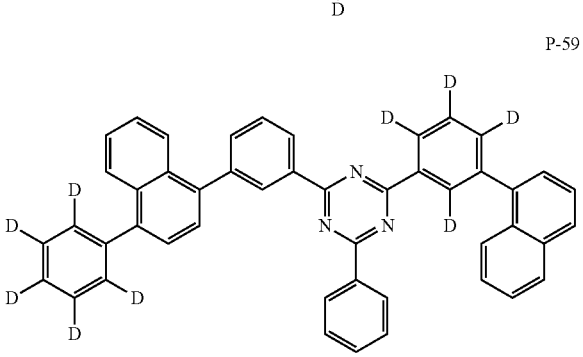

P-60
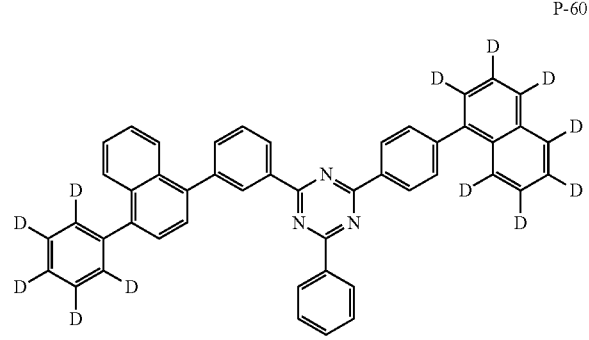
P-61
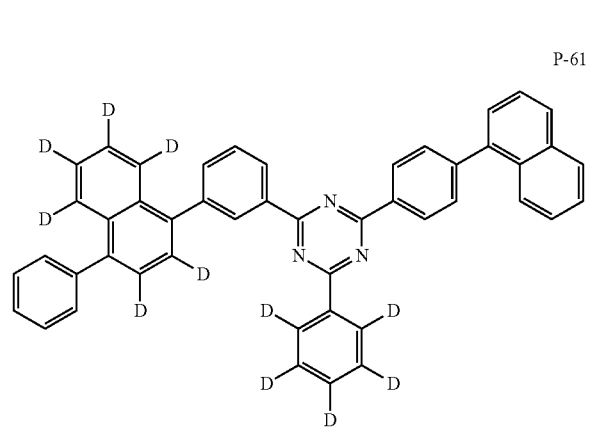
P-62
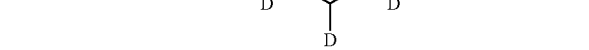
P-63
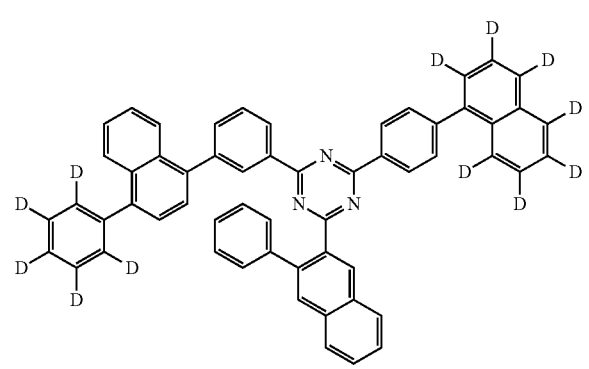
P-64
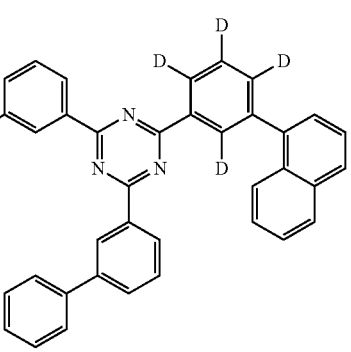
P-65
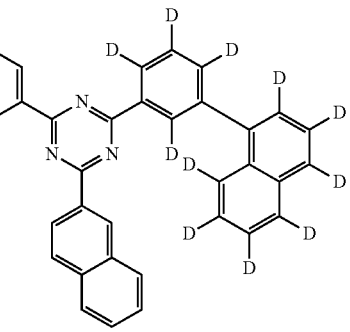
P-66
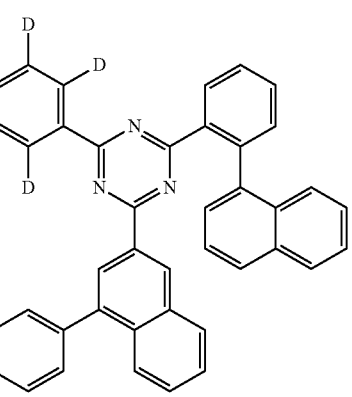
P-67
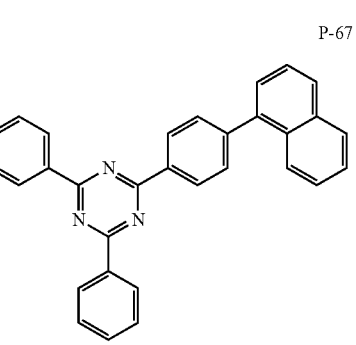

P-68
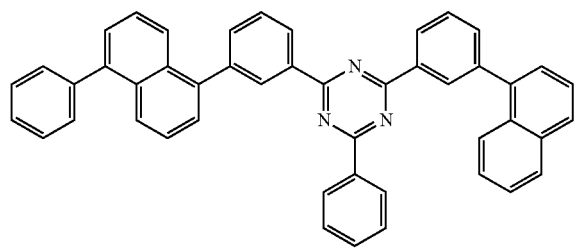
P-69
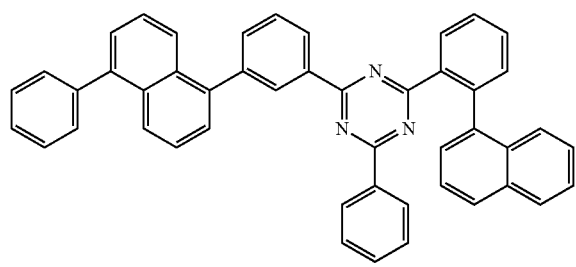
P-70
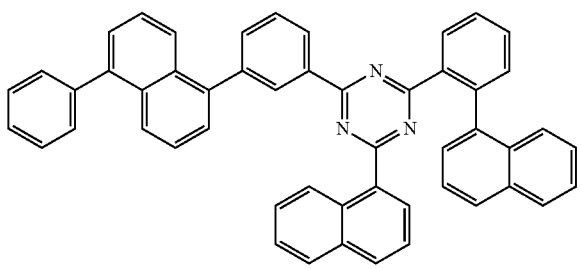
P-71
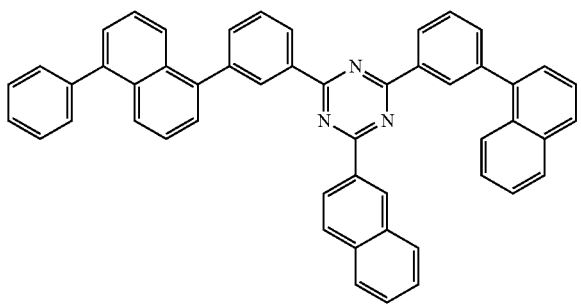
P-72
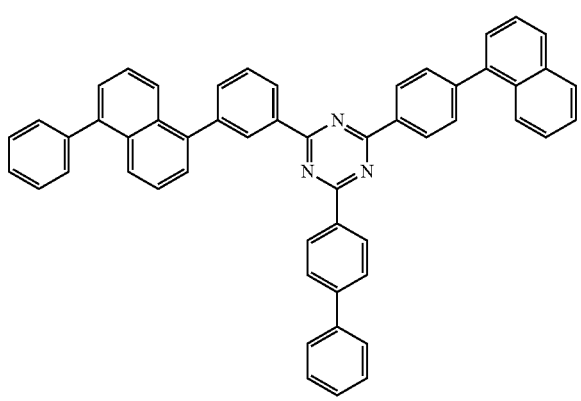
P-73
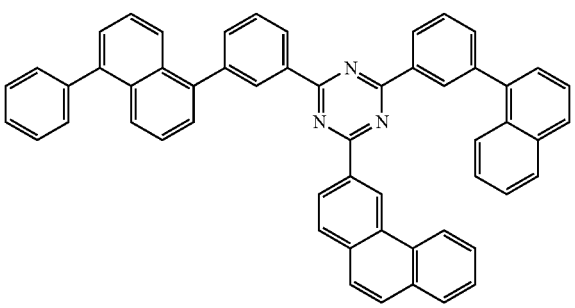
P-74
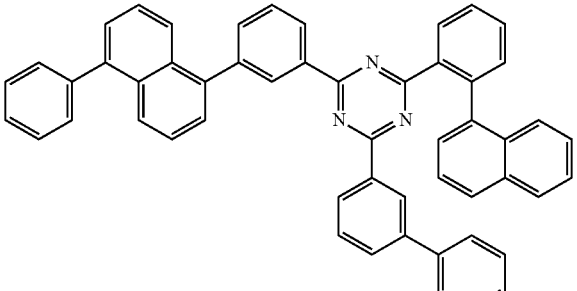
P-75
P-76
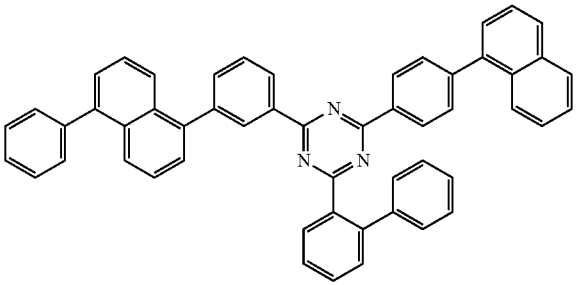

P-77
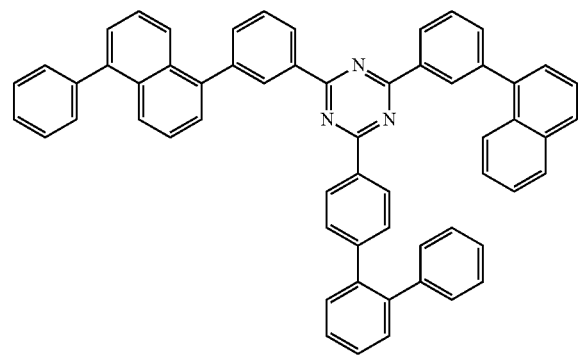
P-78
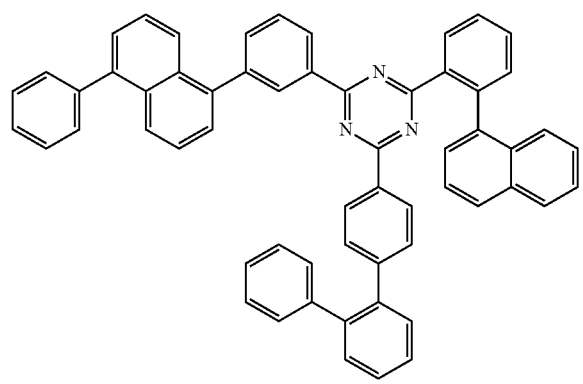
P-79
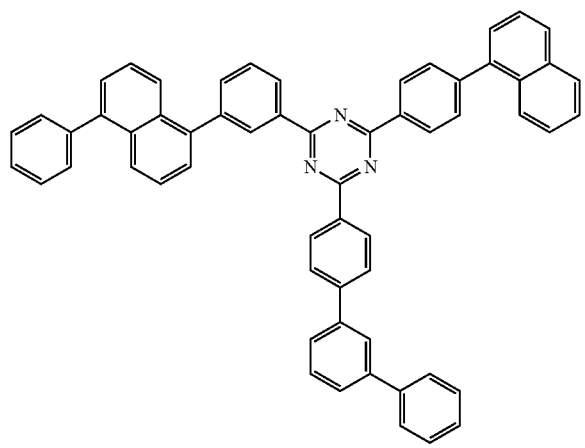
P-80
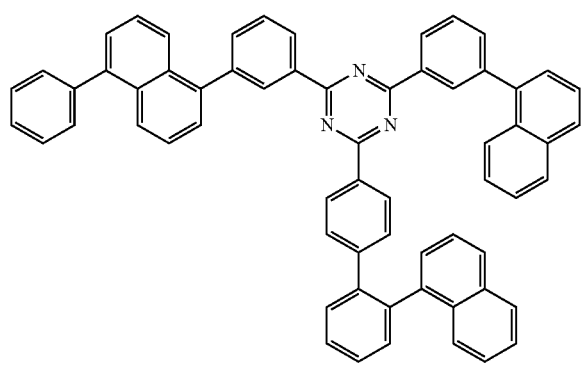
P-81
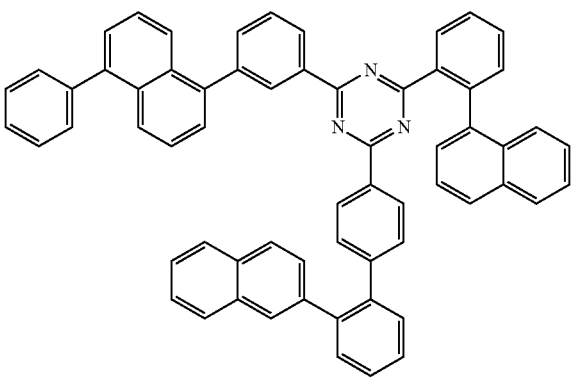
P-82
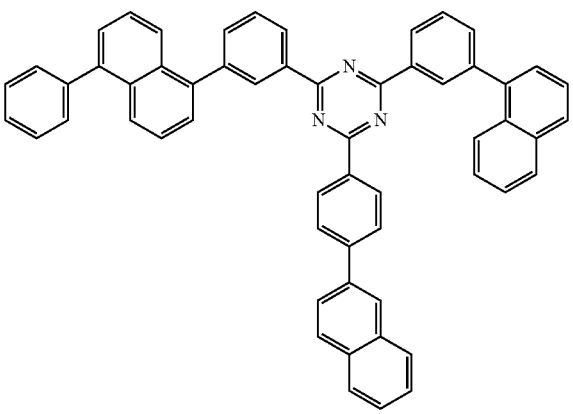
P-83
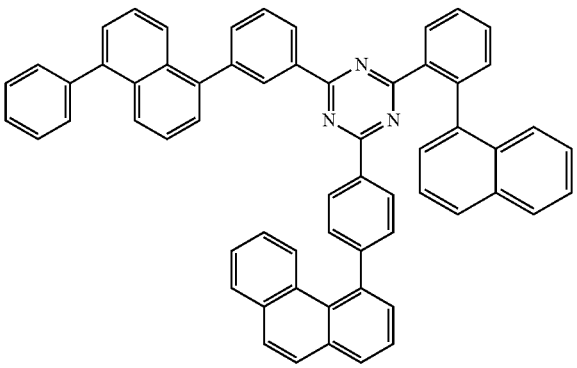
P-84
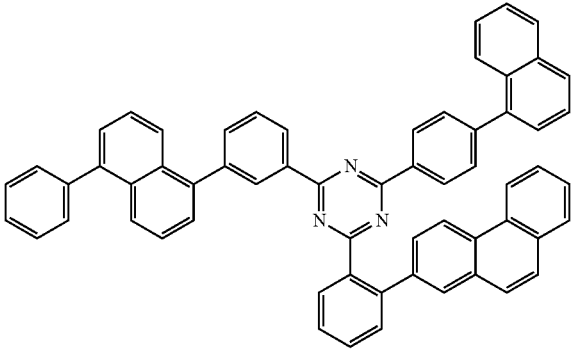

P-85
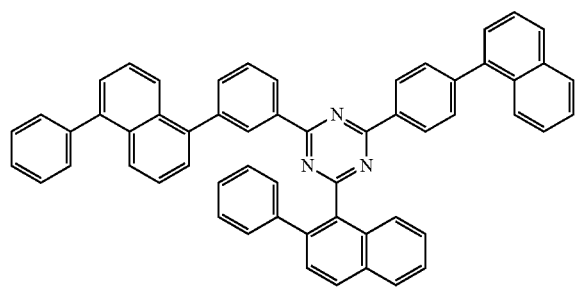
P-86
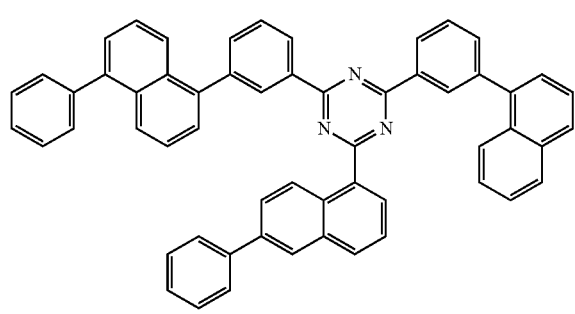
P-87
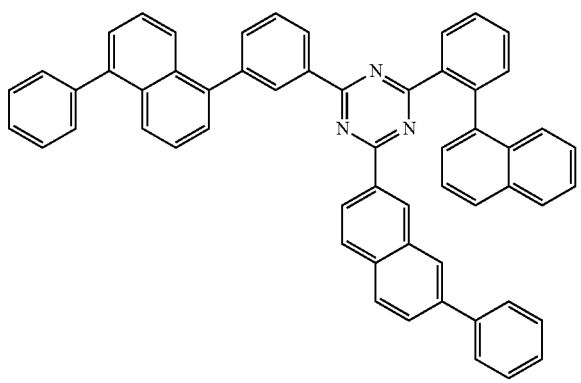
P-88
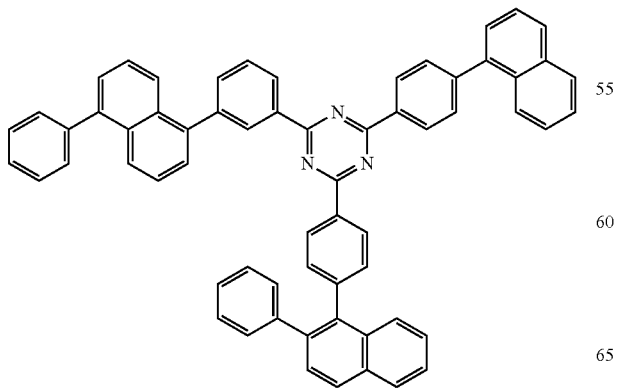
P-89
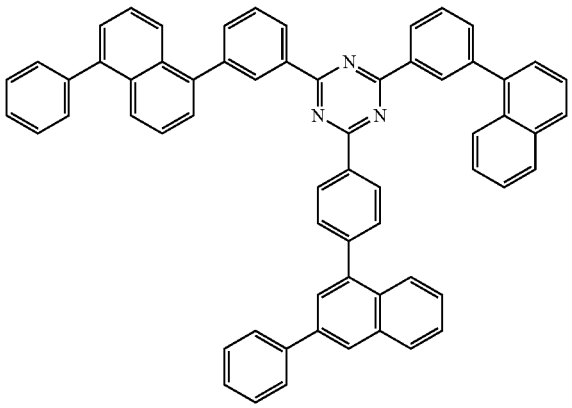
P-90
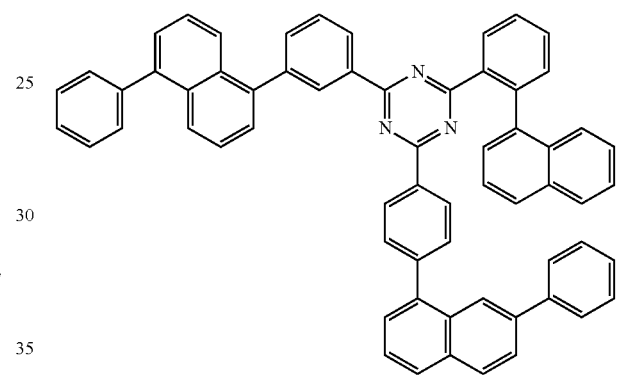
P-91
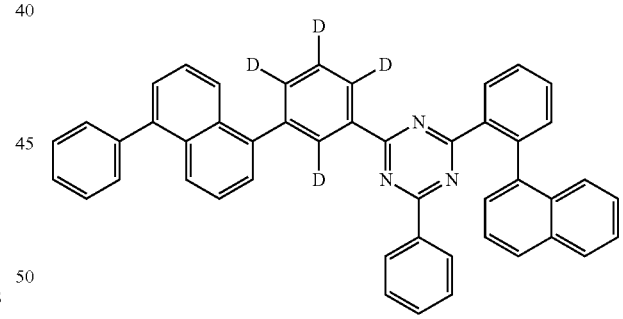
P-92
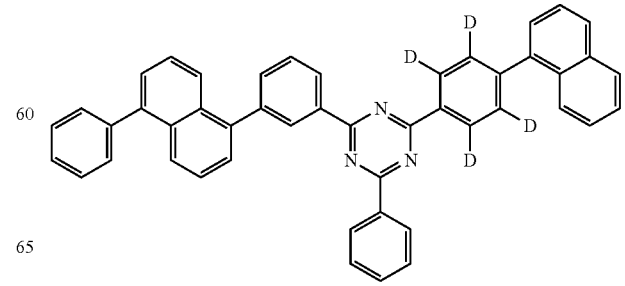

-continued

P-93
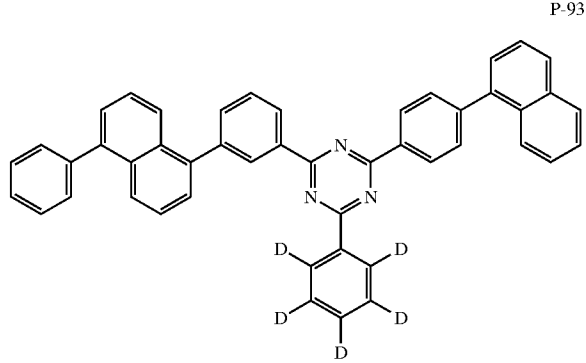

P-94
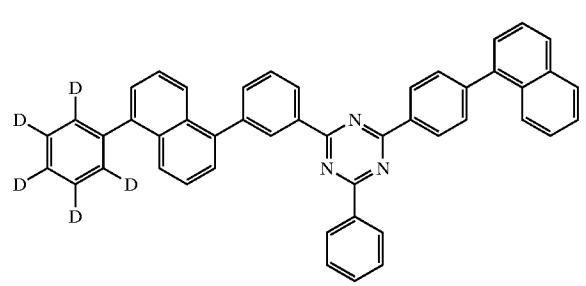

P-95
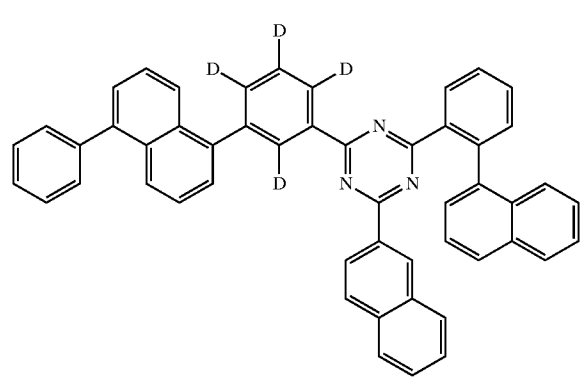

P-96
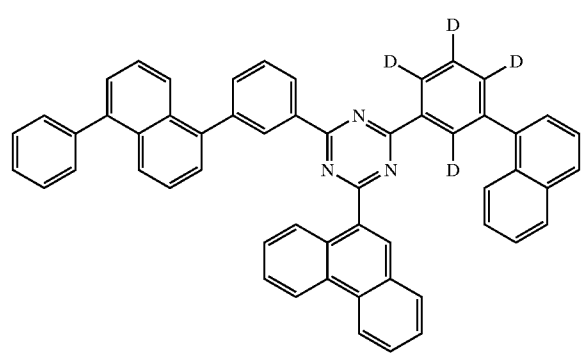

-continued

P-97
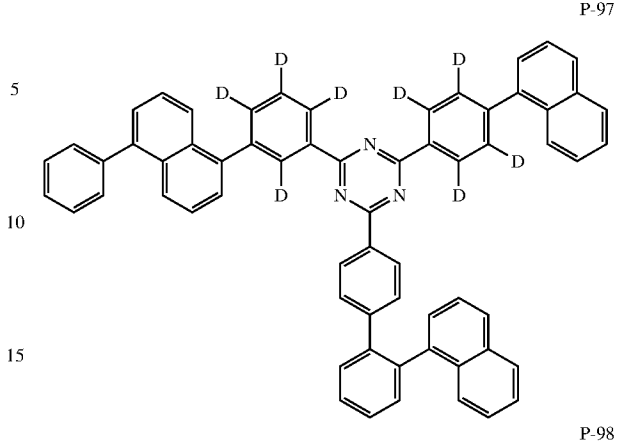

P-98

The RE value of the compound represented by Formula (1) is preferably 0.21 to 0.298, more preferably 0.22 to 0.293.

Reorganization Energy refers to energy lost due to changes in molecular structure arrangement when electric charges (electrons, holes) move. It depends on the Molecular geometry, and the smaller the difference between the PES (Potential Energy Surface) in the neutral state and the PES in the charge state, the smaller the value becomes. RE value can be obtained by the following formula.

$$RE_{hole}:\lambda^+=(E_{NOCE}-E_{COCE})+(E_{CONE}-E_{NONE})$$

$$RE_{elec}:\lambda^-=(E_{NOAE}-E_{AOAE})+(E_{AONE}-E_{NONE})$$

Each factor is described as NONE: Neutral geometry of neutral molecules (=NO opt.), NOAE: Anion geometry of neutral molecules, NOCE: Cation geometry of neutral molecules, AONE: Neutral geometry of anion molecule, AOAE: Anion, anion geometry of molecules (=AO opt.), CONE: Neutral geometry of cation molecules, COCE: Cation geometry of cation molecules (=CO opt.)

Reorganization Energy value and mobility are in inverse proportion to each other, and under the condition that they have the same r and T values, RE value of each material directly affects the mobility. The relation between RE value and mobility is expressed as follows.

$$\mu = k \frac{r^2}{2k_B T/e}$$

$$k = \left(\frac{4\pi^2}{h}\right)\frac{r^2}{\sqrt{4\pi\lambda k_B T}}\exp\left[-\frac{\lambda}{4k_B T}\right]$$

Each factor is described as λ: Reorganization energy/μ: mobility/r: dimer displacement/t: intermolecular charge transfer matrix element. From the above equation, it can be seen that the lower RE value, the faster the mobility.

Reorganization energy value requires a simulation tool that ca Calculate the potential energy according to the molecular structure, we used Gaussian09 (hereinafter G09) and Jaguar module of Schrodinger Materials Science (hereinafter JG). Both G09 and JG are tools to analyze the properties of molecules through quantum mechanical (QM) calculations, and have the function of optimizing the molecular structure or calculating the energy for a given molecular structure (single-point energy).

The process of performing QM calculations in molecular structures requires large computational resources, and our company uses 2 cluster servers for these calculations. Each cluster server consists of 4 node workstations and 1 master workstation, each node performed molecular QM calculations by Parallel computing through symmetric multi-processing (SMP) using a CPU with more than 36 cores.

Using G09, the optimized molecular structure and its potential energy (NONE/COCE) in the neutral/charged state required for rearrangement energy were calculated. The charge state potential energy (NOCE) of the structure optimized for the neutral state and the neutral state potential energy (CONE) of the structure optimized for the charge state were calculated by changing only the charges to the 2 optimized structures. After that, the rearrangement energy was calculated according to the following relation.

$$RE_{charge}:\lambda = (E_{NOCE} - E_{COCE}) + (E_{CONE} - E_{NONE})$$

Because Schrödinger provides a function to automatically perform such a calculation process, the potential energy according to each state was sequentially calculated through the JG module by providing the molecular structure (NO) of the basic state, and the RE value was calculated.

According to an embodiment of the present invention, more electrons are attracted to an element having a greater electronegativity among two atoms in one covalent bond.

Here, the relatively high electronegative atom has a δ− charge, the low electronegativity atoms have a δ+ charge. As described above, the difference in polarity of two atoms is called a dipole. At this time, Dipole moment can be calculated as a vector quantity multiplied by the intensity of the two poles and the distance between the two atomic nuclei. In other words, Dipole moment can be calculated by the following equation.

$$\mu = \delta * d$$

Each factor is the distance between: μ dipole moment/δ: magnitude of the partial charges $\delta^+$ and $\delta^-$/d: $\delta^+$ and $\delta^-$.

Our company used G09 to optimize the molecular structure with B3LYP/6-31G(d). Based on the result, Mulliken Charge value of each atom was obtained, and Dipole moment was calculated by multiplying the vector in the axial direction. Dipole moment is the vector sum of each bond dipole moment. Dipole moment value means the magnitude of the vector dipole moment, and it can be expressed as the value of the vector length as follows.

$$|\mu| = \sqrt{x^2 + y^2 + z^2}$$

Also, the present invention relates to an organic electronic element comprising a first electrode, a second electrode, and an organic material layer formed between the first electrode and the second electrode, wherein the organic material layer includes an emitting layer, wherein the emitting layer is a phosphorescent emitting layer, and the present invention provides an organic electronic element comprising a first host compound represented by Formula (1) of claim 1 and a second host compound represented by Formula 2 or Formula 3.

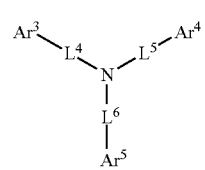
<Formula 2>

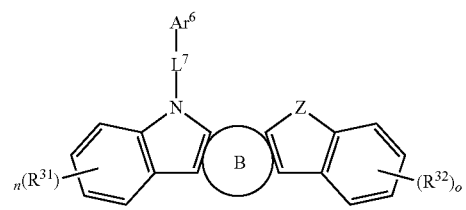
<Formula 3>

Wherein:

$L^4$, $L^5$, $L^6$ and $L^7$ are each independently selected from the group consisting of a single bond; a $C_6$-$C_{60}$ arylene group; fluorenylene group; a fused ring group of a $C_3$-$C_{60}$ aliphatic ring and a $C_6$-$C_{60}$ aromatic ring; a $C_2$-$C_{60}$ heterocyclic group;

wherein in case $L^4$, $L^5$, $L^6$ and $L^7$ are an arylene group, it is preferably a $C_6$-$C_{30}$ arylene group, more preferably a $C_6$-$C_{24}$ arylene group, for example, it may be phenylene, biphenyl, naphthalene, terphenyl, and the like.

when $L^4$, $L^5$, $L^6$ and $L^7$ are a heterocyclic group, it is preferably a $C_2$-$C_{30}$ heterocyclic group, and more preferably a $C_2$-$C_{24}$ heterocyclic group, for example, it may be Pyrazine, thiophene, pyridine, pyrimidoindole, 5-phenyl-5H-pyrimido[5,4-b]indole, quinazoline, benzoquinazoline, carbazole, dibenzoquinazole, dibenzofuran, Benzothienopyrimidine, benzofuropyrimidine, phenothiazine, phenylphenothiazine.

When $L^4$, $L^5$, $L^6$ and $L^7$ are a fused ring group, it is preferably a fused ring group of a $C_3$-$C_{30}$ aliphatic ring and a $C_6$-$C_{30}$ aromatic ring, and more preferably a fused ring group of a $C_3$-$C_{24}$ aliphatic ring and a $C_6$-$C_{24}$ aromatic ring, $Ar^3$, $Ar^4$ and $Ar^5$ are each independently selected from the group consisting of a $C_6$-$C_{60}$ aryl group; fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring;

$Ar^6$ are each independently selected from the group consisting of a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; and -L'-N($R^b$)($R^c$);

When $Ar^3$, $Ar^4$, $Ar^5$ and $Ar^6$ are an aryl group, it is preferably a $C_6$-$C_{30}$ aryl group, more preferably a $C_6$-$C_{24}$ aryl group, for example, it may be phenylene, biphenyl, naphthalene, terphenyl, and the like.

When $Ar^3$, $Ar^4$, $Ar^5$ and $Ar^6$ are a heterocyclic group, it is preferably a $C_2$-$C_{30}$ heterocyclic group, and more preferably a $C_2$-$C_{24}$ heterocyclic group, for example, it may be Pyrazine, thiophene, pyridine, pyrimidoindole, 5-phenyl-5H-pyrimido[5,4-b]indole, quinazoline, benzoquinazoline, carbazole, dibenzoquinazole, dibenzofuran, Benzothienopyrimidine, benzofuropyrimidine, phenothiazine, phenylphenothiazine.

When $Ar^3$, $Ar^4$, $Ar^5$ and $Ar^6$ are a fused ring group, it is preferably a fused ring group of a $C_3$-$C_{30}$ aliphatic ring and a $C_6$-$C_{30}$ aromatic ring, and more preferably a fused ring group of a $C_3$-$C_{24}$ aliphatic ring and a $C_6$-$C_{24}$ aromatic ring, Wherein L' is selected from the group consisting of a single bond; a $C_6$-$C_{60}$ arylene group; a $C_2$-$C_{60}$ heterocyclic group including at least one heteroatom of O, N, S, Si or P;

Wherein $R^b$ and $R^C$ are each independently selected from the group consisting of a $C_6$-$C_{60}$ aryl group; fluorenyl group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P; $C_1$-$C_{60}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group;

Z is O, S, CR'R" or NRa,

B is a $C_6$-$C_{20}$ aryl group,

R' and R" are each independently selected from a group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or may be bonded to each other to form a ring, $R^{31}$ and $R^{32}$ are each independently the same as or different from each other, and each independently selected from the group consisting of hydrogen; deuterium; halogen; cyano group; nitro group; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_6$ alkyl group; a $C_2$-$C_{60}$ alkenyl group; a $C_2$-$C_{60}$ alkynyl group; a $C_1$-$C_{60}$ alkoxy group; and a $C_6$-$C_{60}$ aryloxy group; or a plurality of adjacent $R^{31}$ or a plurality of $R^{32}$ may be bonded to each other to form a ring, n and o are each independently an integer from 0 to 4, When R', R", $R^{31}$ and $R^{32}$ are an aryl group, it is preferably a $C_6$-$C_{30}$ aryl group, more preferably a $C_6$-$C_{24}$ aryl group, for example, it may be phenylene, biphenyl, naphthalene, terphenyl, and the like.

When R', R", $R^{31}$ and $R^{32}$ are a heterocyclic group, it is preferably a $C_2$-$C_{30}$ heterocyclic group, and more preferably a $C_2$-$C_{24}$ heterocyclic group, for example, it may be Pyrazine, thiophene, pyridine, pyrimidoindole, 5-phenyl-5H-pyrimido[5,4-b]indole, quinazoline, benzoquinazoline, carbazole, dibenzoquinazole, dibenzofuran, Benzothienopyrimidine, benzofuropyrimidine, phenothiazine, phenylphenothiazine.

when R', R", $R^{31}$ and $R^{32}$ are a fused ring group, it is preferably a fused ring group of a $C_3$-$C_{30}$ aliphatic ring and a $C_6$-$C_{30}$ aromatic ring, and more preferably a fused ring group of a $C_3$-$C_{24}$ aliphatic ring and a $C_6$-$C_{24}$ aromatic ring, when R', R", $R^{31}$ and $R^{32}$ are an alkyl group, it is preferably a $C_1$-$C_{30}$ alkyl group, and more preferably a $C_1$-$C_{24}$ alkyl group.

when R', R", $R^{31}$ and $R^{32}$ are an alkoxyl group, it is preferably a $C_1$-$C_{24}$ alkoxyl group.

when R', R", $R^{31}$ and $R^{32}$ are an aryloxy group, it is preferably a $C_1$-$C_{24}$ aryloxy group.

Ra is a $C_6$-$C_{60}$ aryl group; or a $C_2$-$C_{60}$ heterocyclic group including at least one heteroatom of O, N, S, Si and P;

When Ra is an aryl group, it is preferably a $C_6$-$C_{30}$ aryl group, more preferably a $C_6$-$C_{24}$ aryl group, for example, it may be phenylene, biphenyl, naphthalene, terphenyl, and the like.

When Ra is a heterocyclic group, it is preferably a $C_2$-$C_{30}$ heterocyclic group, and more preferably a $C_2$-$C_{24}$ heterocyclic group, for example, it may be Pyrazine, thiophene, pyridine, pyrimidoindole, 5-phenyl-5H-pyrimido[5,4-b]indole, quinazoline, benzoquinazoline, carbazole, dibenzoqui-nazole, dibenzofuran, Benzothienopyrimidine, benzofuropyrimidine, phenothiazine, phenylphenothiazine.

wherein the aryl group, arylene group, heterocyclic group, fluorenyl group, fluorenylene group, fused ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; and also the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by the combination thereof.

Formula 2 is represented by any one of Formulas 2-1 to 2-3.

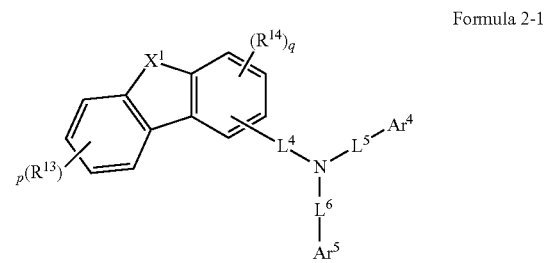

Formula 2-1

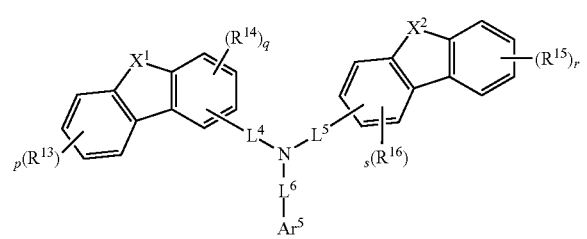

Formula 2-2

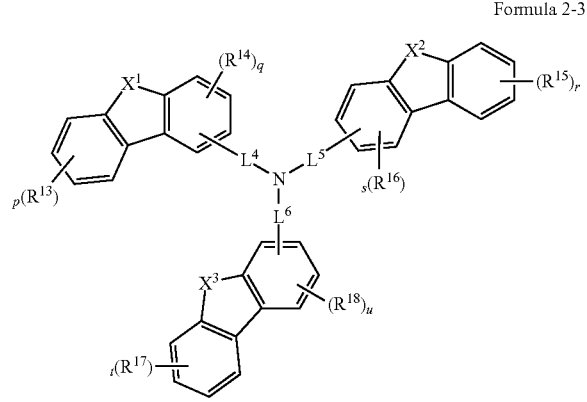

Formula 2-3

Wherein:

$Ar^4$, $Ar^5$, $L^4$, $L^5$ and $L^6$ are the same as defined in Formula 2, $X^1$, $X^2$ and $X^3$ are the same as defined for Z, $R^{13}$, $R^{14}$, $R^{15}$, $R^{16}$, $R^{17}$ and $R^{16}$ are the same as the definition of $R^{31}$, or a plurality of adjacent $R^{13}$s or a plurality of $R^{14}$s or a plurality of $R^{15}$s or a plurality of $R^{16}$s or a plurality of $R^{17}$s or a plurality of $R^1$s may be bonded to each other to form a ring, p, r and t are an integer of 0 to 4, q, s and u are each independently an integer from 0 to 3.

Formula 3 is represented by any one of Formulas 3-1 to 3-6.

Formula 3-1

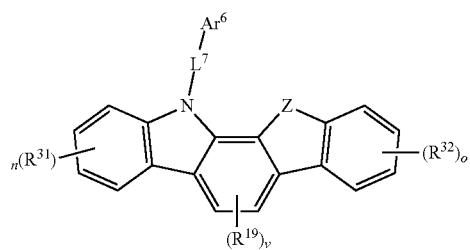

Formula 3-2

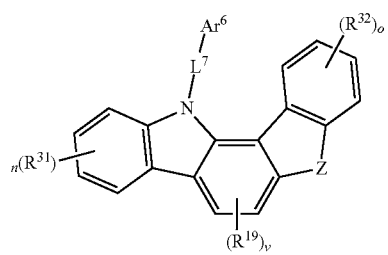

Formula 3-3

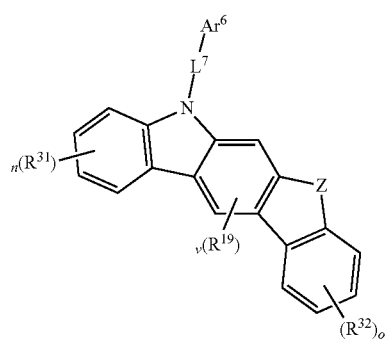

Formula 3-4

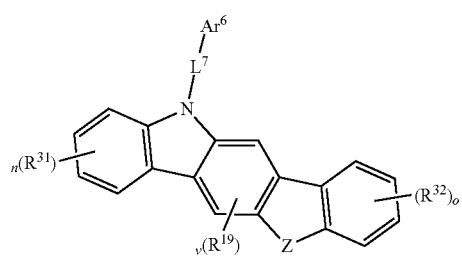

-continued

Formula 3-5

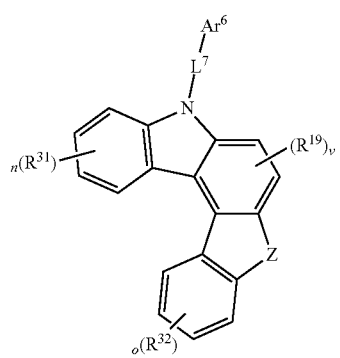

Formula 3-6

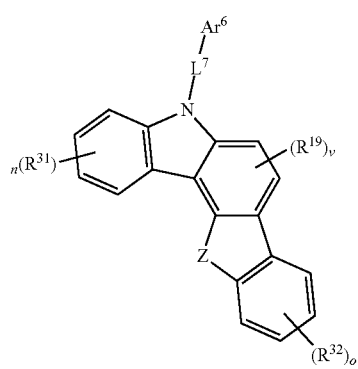

Wherein:

Z, $R^{31}$, $R^{32}$, $Ar^6$, $L^7$, n, o are the same as defined in Formula 3, $R^{19}$ is the same as the definition of $R^{31}$, v is an integer from 0 to 2.

Formula 3 is represented by any one of Formulas 3-7 to 3-9.

Formula 3-7

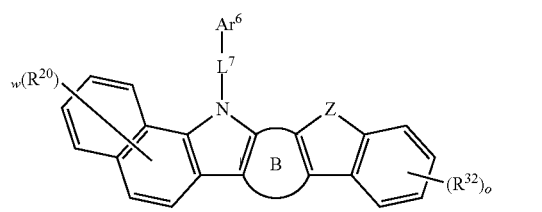

Formula 3-8

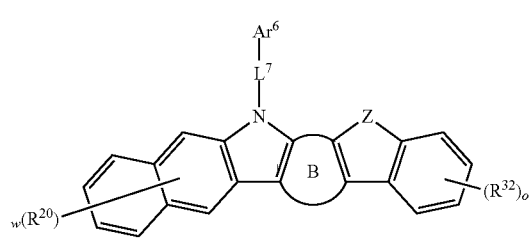

-continued

Formula 3-9

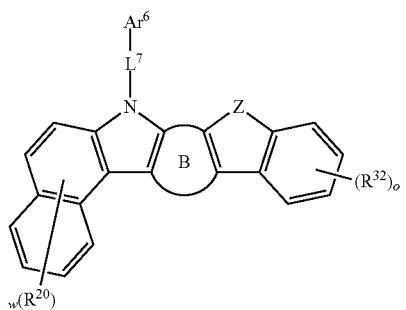

Wherein:

Z, B, $R^{32}$, o, $Ar^6$ and $L^7$ are the same as defined in Formula 3, $R^{20}$ is the same as the definition of $R^{31}$ above, w is an integer from 0 to 6 Formula 3 is represented by any one of Formulas 3-10 to 3-12.

Formula 3-10

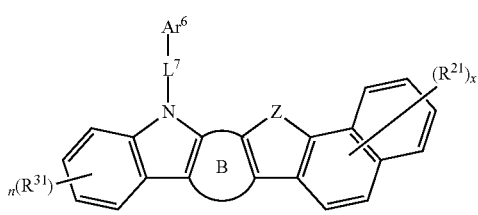

Formula 3-11

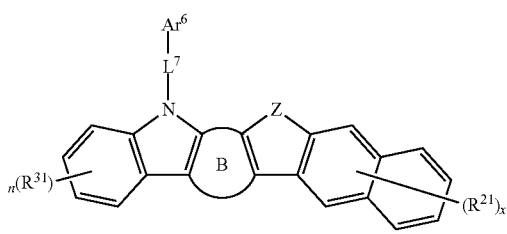

Formula 3-12

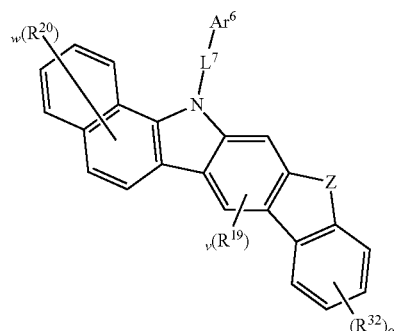

Wherein:

Z, B, $Ar^6$, $L^7$, $R^{31}$ and n are the same as defined in Formula 3, $R^{21}$ is the same as definition of $R^{31}$, x is an integer from 0 to 6.

Formula 3 is represented by Formulas 3-13 to 3-18

Formula 3-13

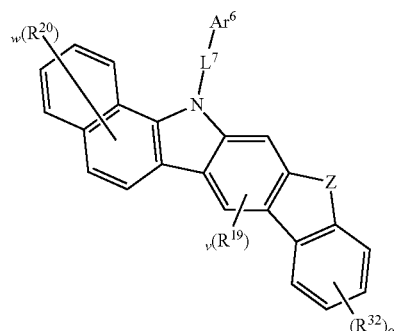

Formula 3-14

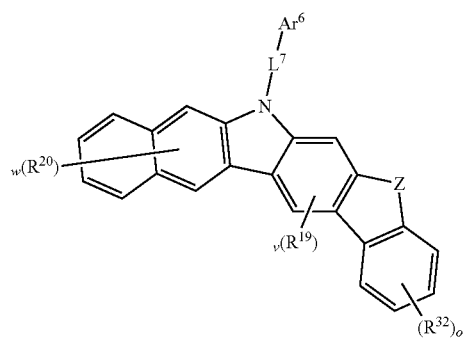

Formula 3-15

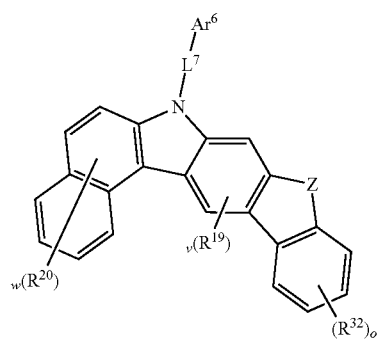

Formula 3-16

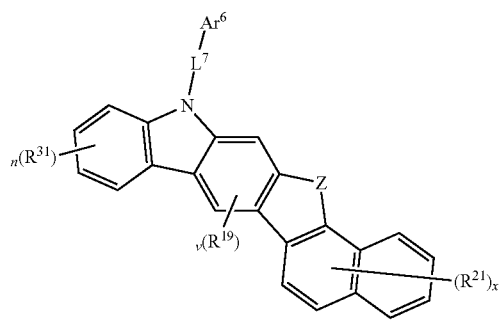

Formula 3-17

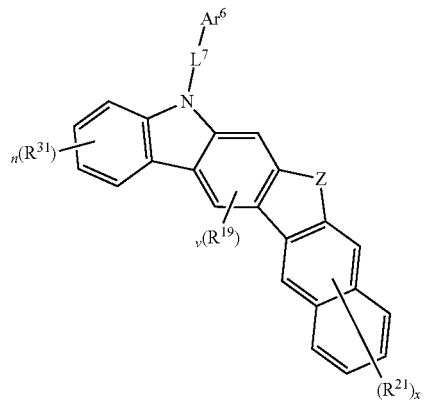

Formula 3-18

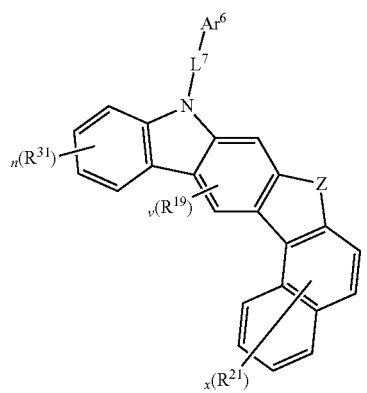

Wherein:

Y, L$^7$, Ar$^6$, R$^{31}$, R$^{32}$, n and o are the same as defined in Formula 3, R$^{19}$, R$^{20}$ and R$^{21}$ are the same as the definition of R$^{31}$, v is an integer from 0 to 2, w and x are each independently an integer from 0 to 6.

Formula 3 is represented by Formula 3-19

<Formula 3-19>

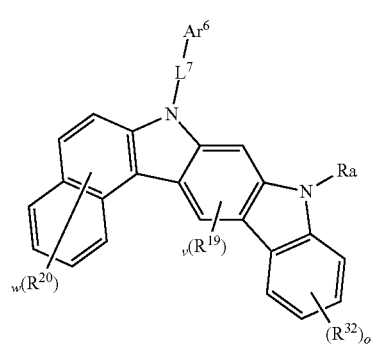

wherein:

L$^7$, Ar$^6$, Ra, R$^{32}$ and o are the same as defined in Formula 3,

R$^{19}$ and R$^{20}$ are the same as the definition of R$^{31}$, v is an integer from 0 to 2, w is an integer from 0 to 6.

Also, the compound represented by Formula 2 is any one of the following compounds N-1 to N-96.

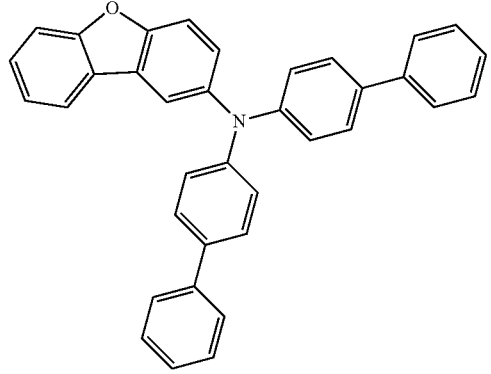

N-1

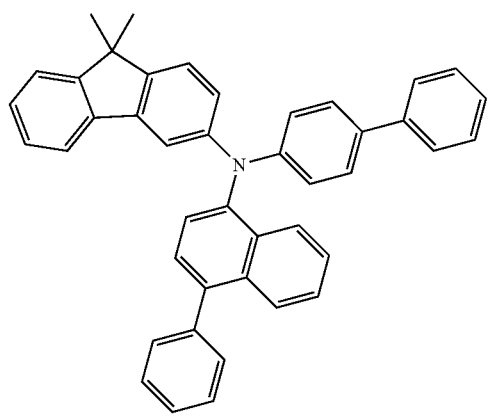

N-2

N-3

N-4
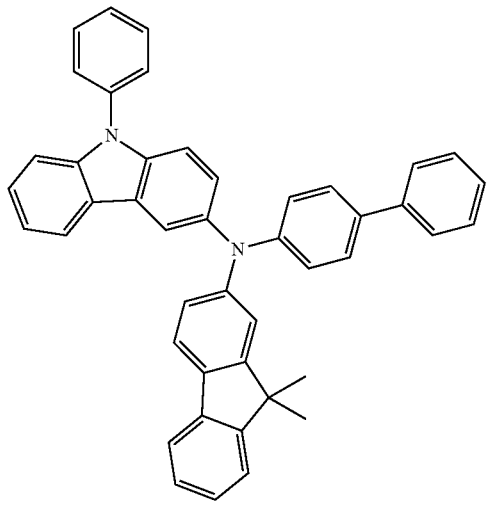
N-7
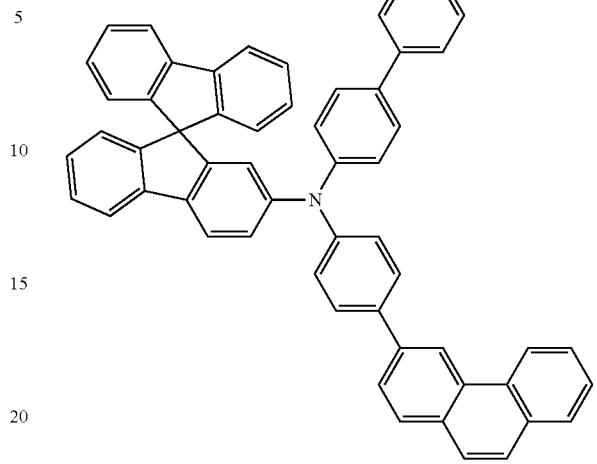
N-5
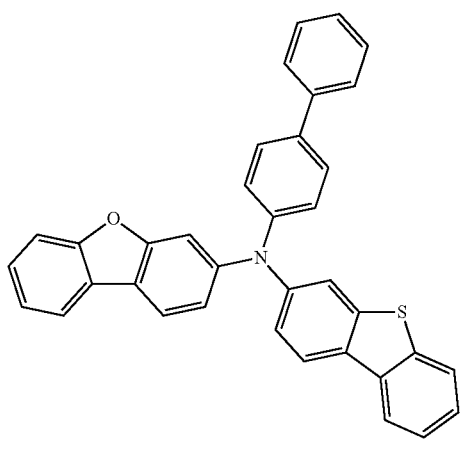
N-8
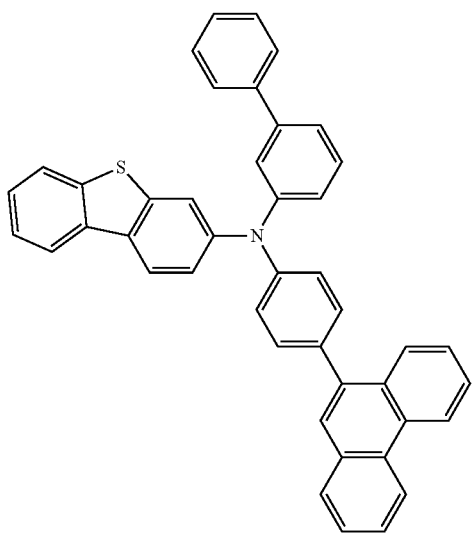
N-6
N-9
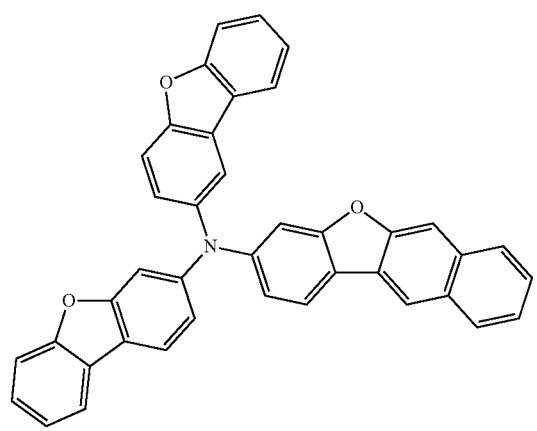

N-10
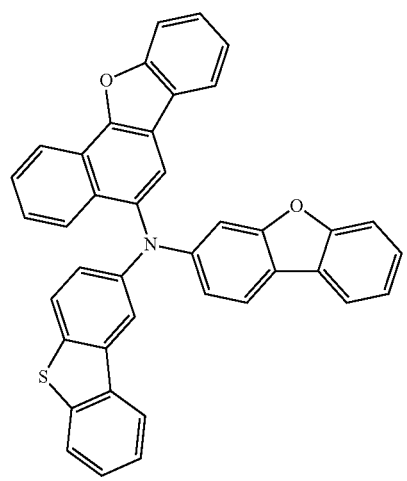
N-11
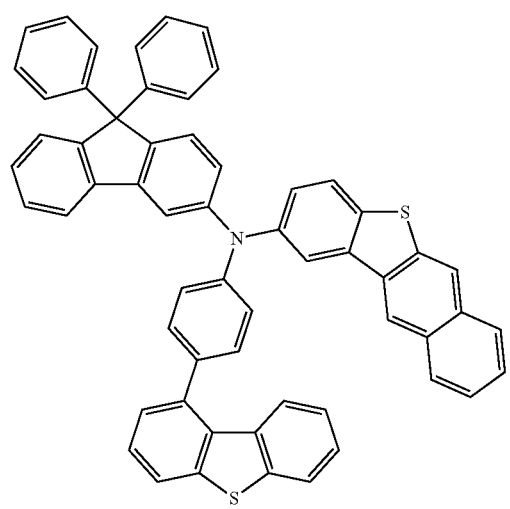
N-12
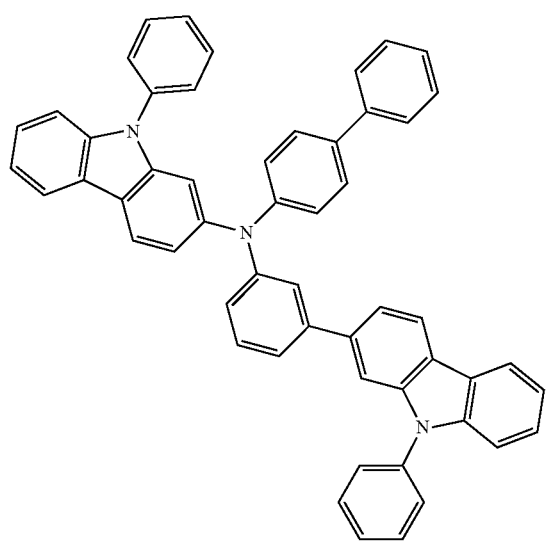
N-13
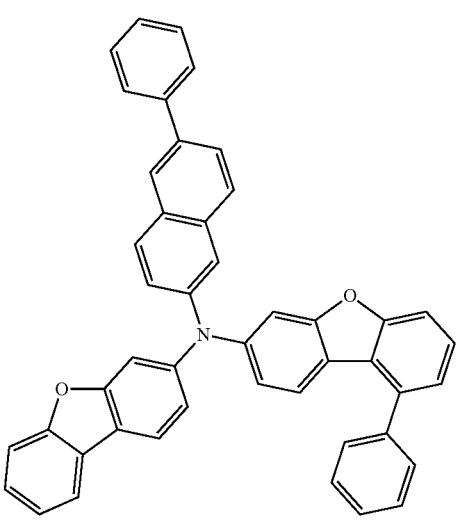
N-14
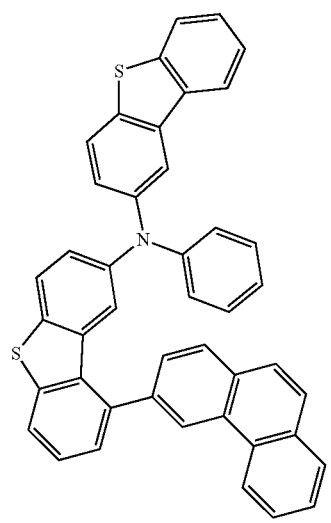
N-15
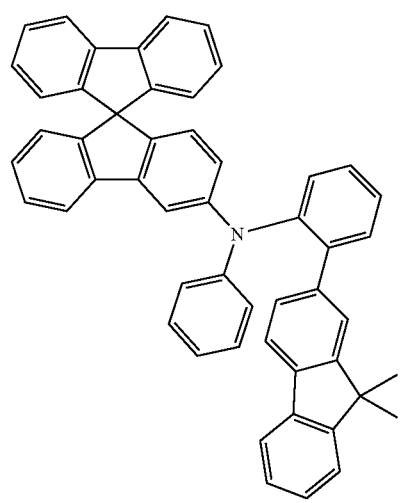

-continued
N-16
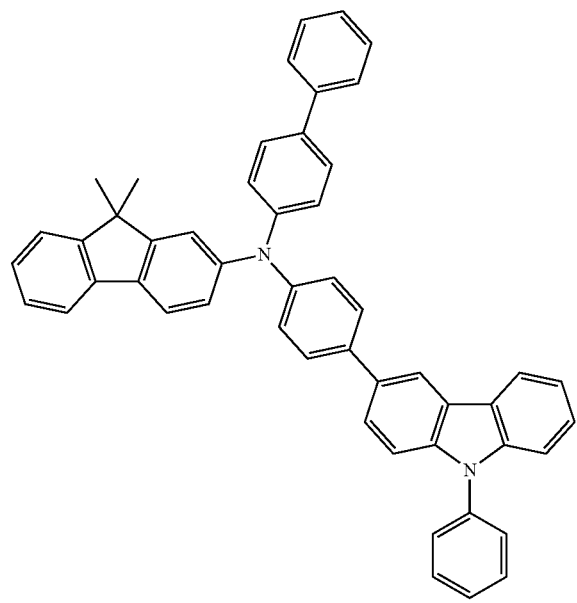
N-17
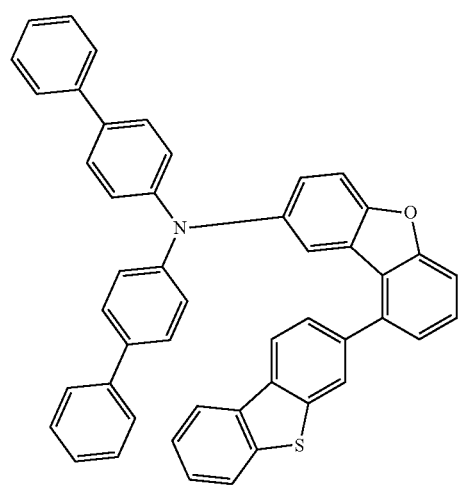
N-18
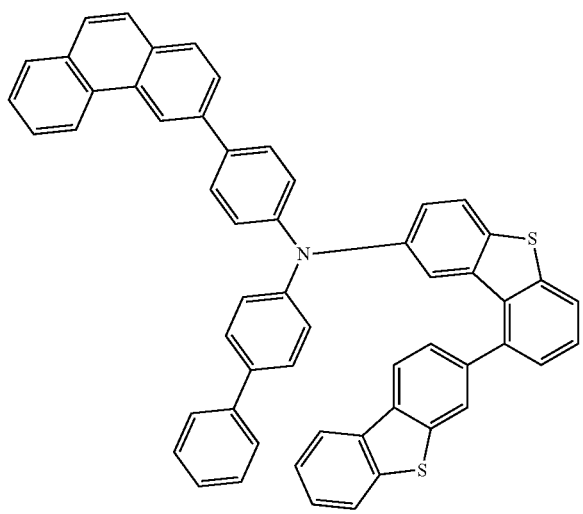
N-19
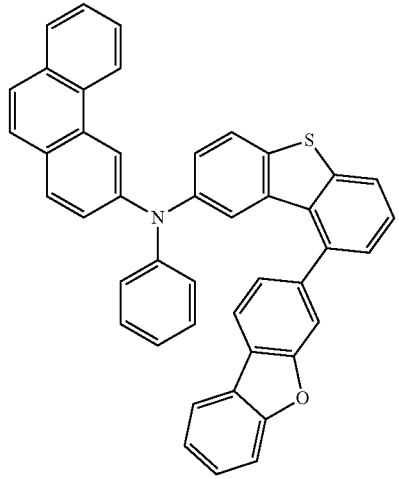
N-20
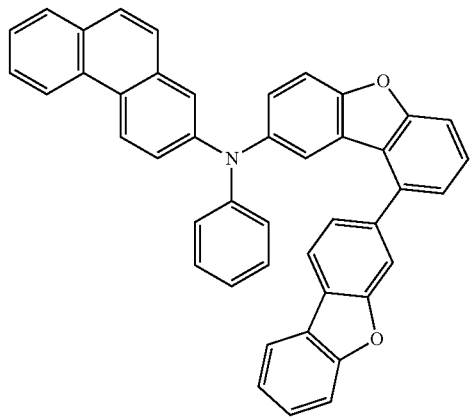
N-21
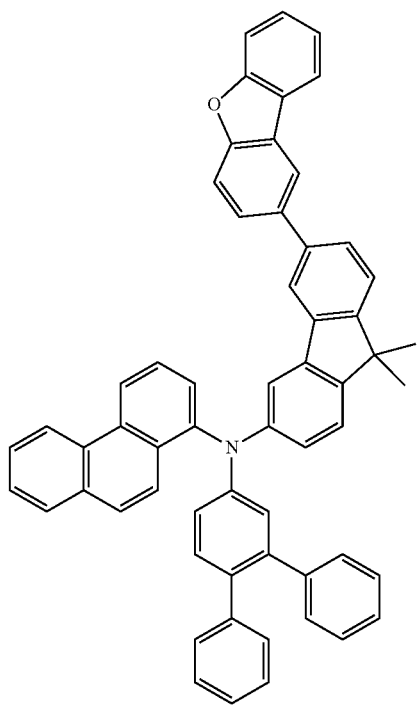

-continued
N-22
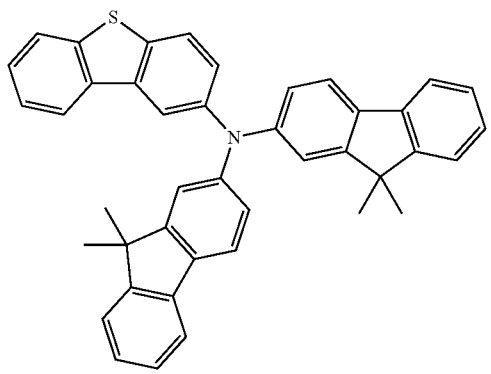
N-23
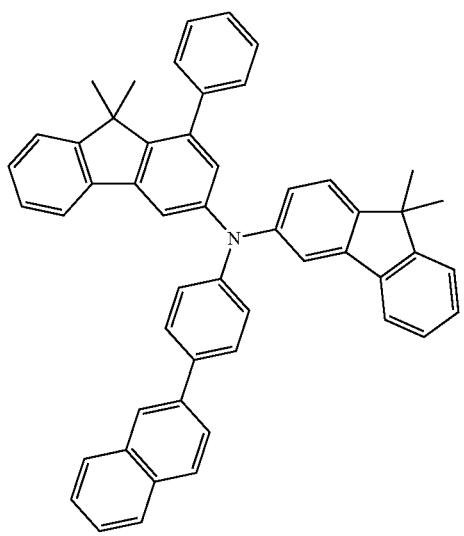
N-24
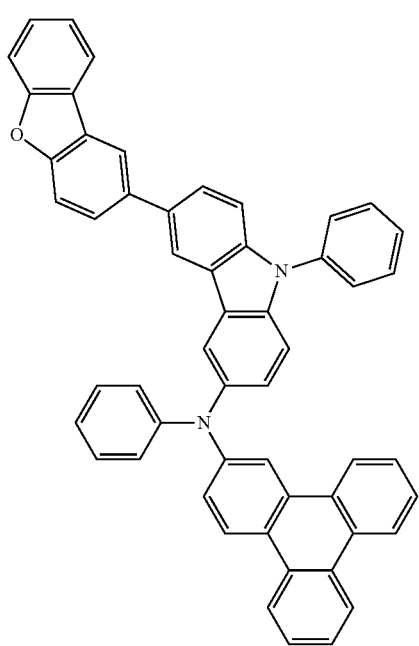
-continued
N-25
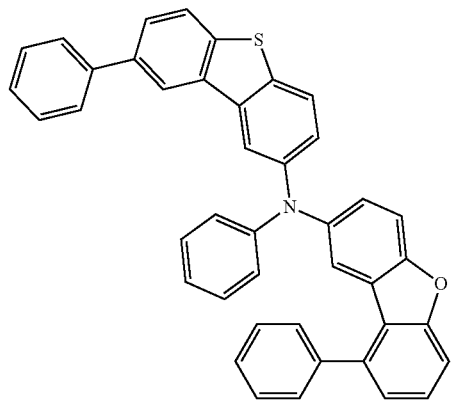
N-26
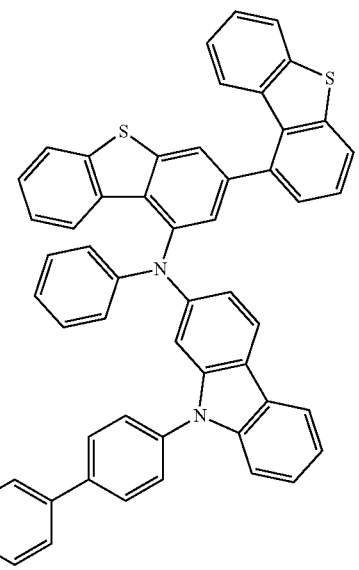
N-27
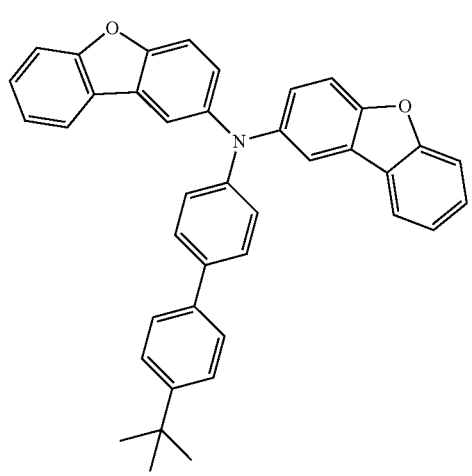

N-28
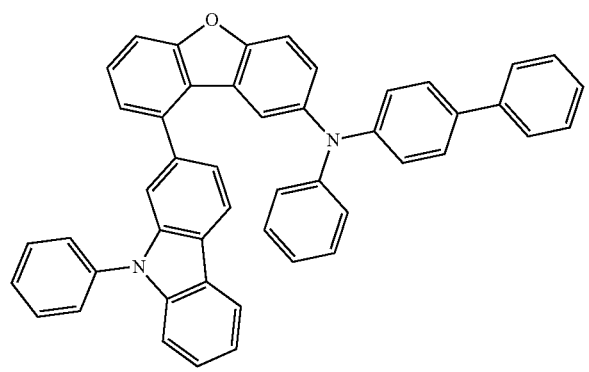
P-29
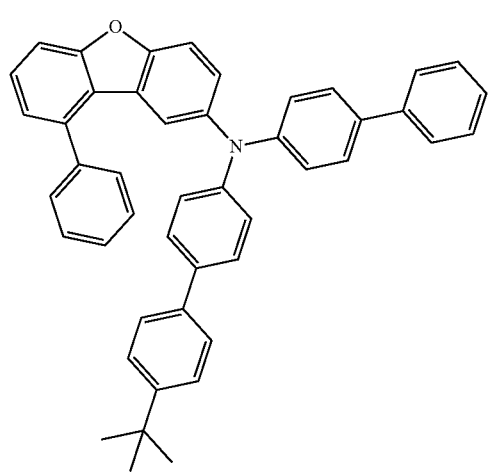
N-30
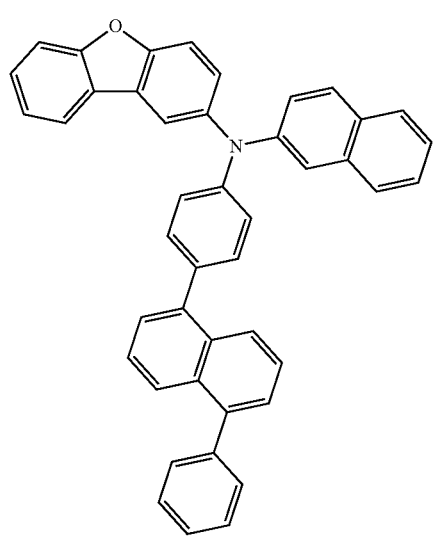
N-31
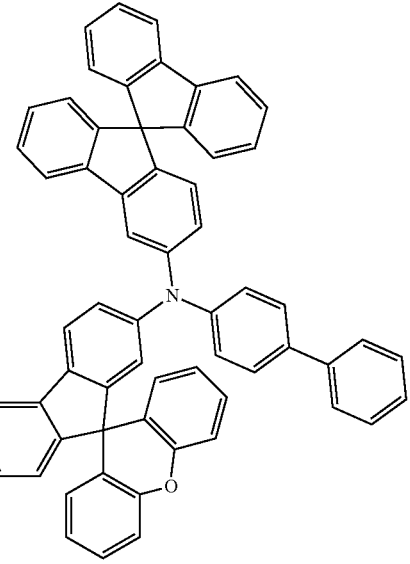
N-32
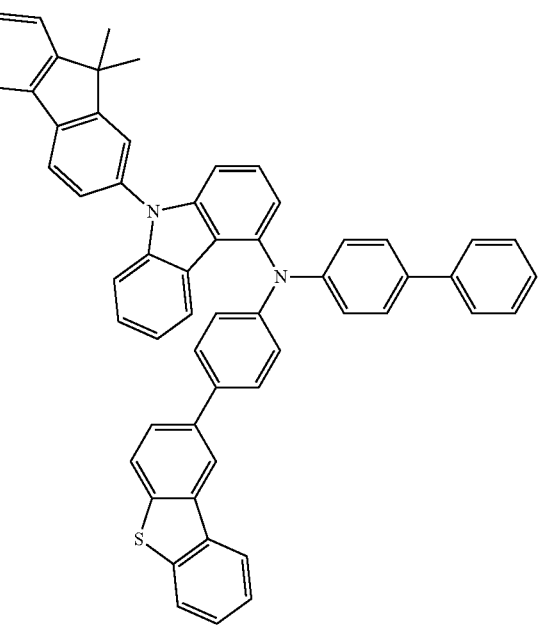
N-33
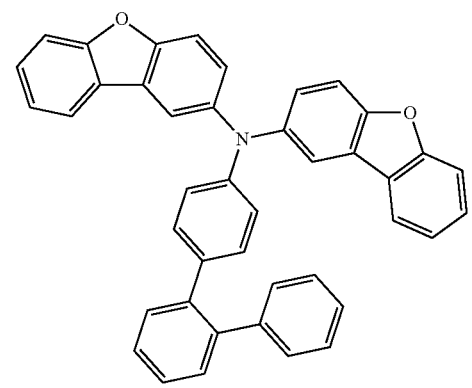

-continued
N-34
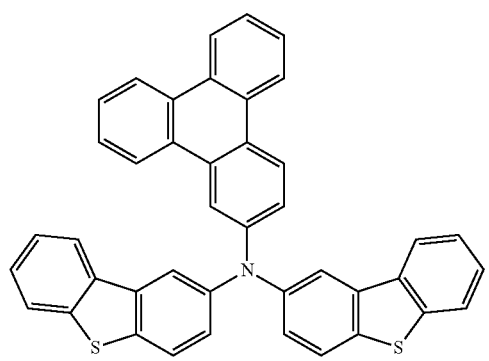
N-35
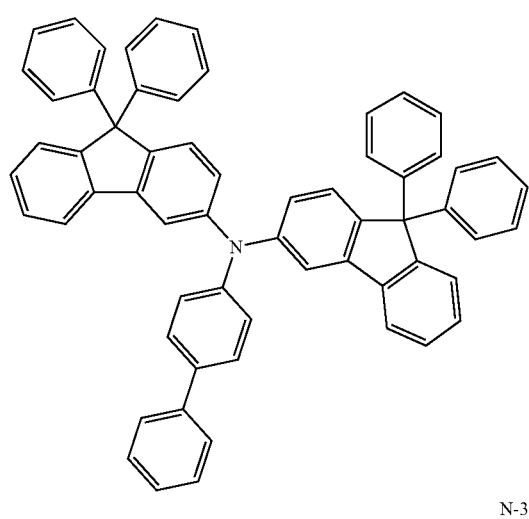
N-36
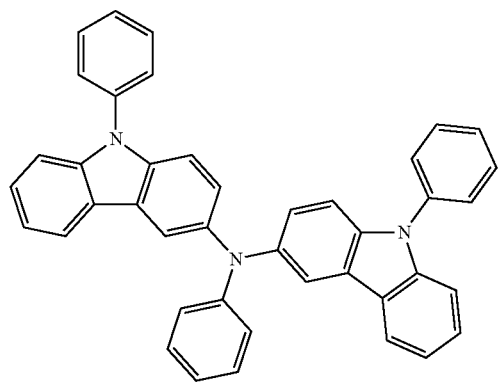
N-37
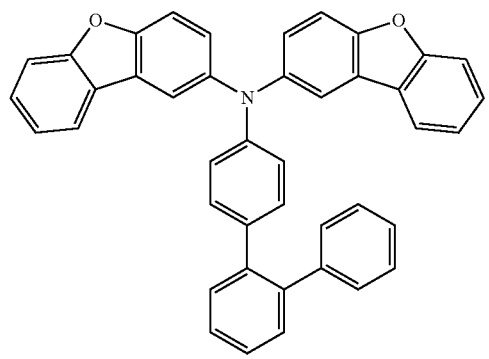
N-38
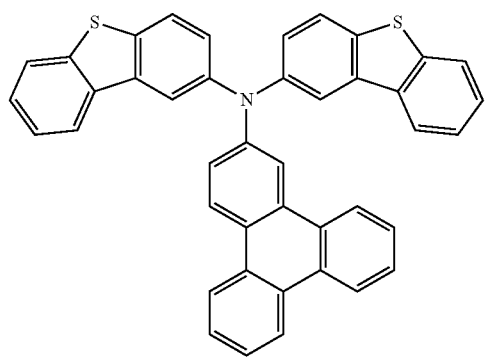
N-39
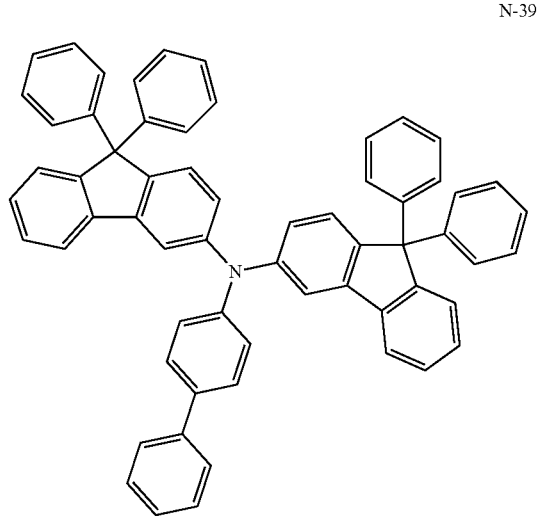
N-40
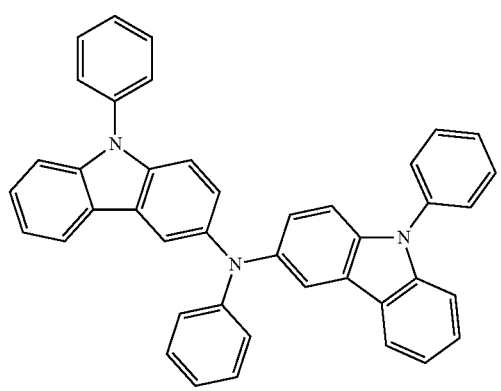

N-41
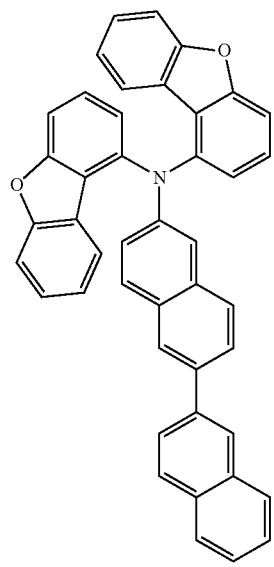
N-42
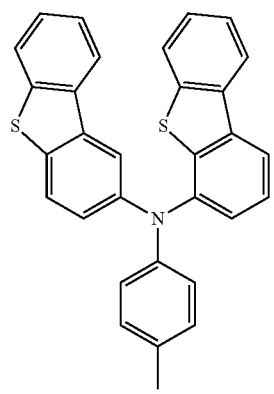
N-43
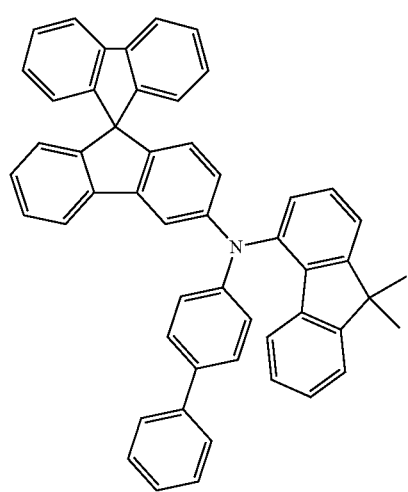
N-44
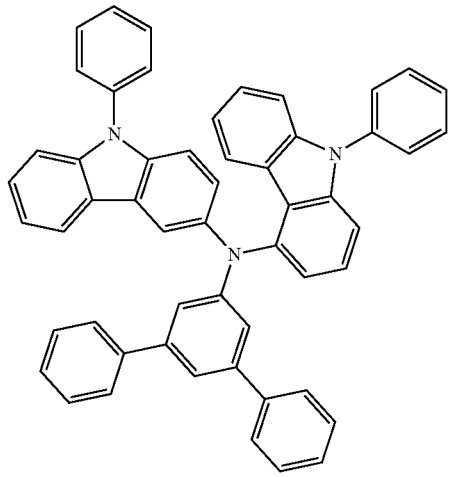
N-45
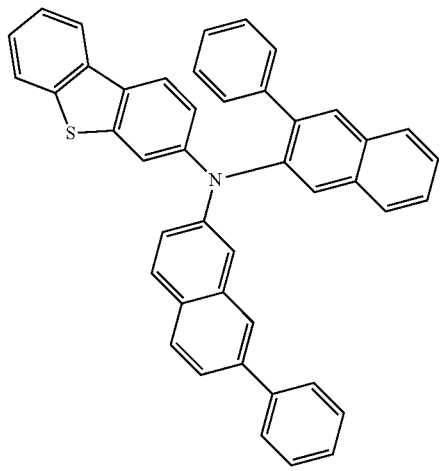
N-46
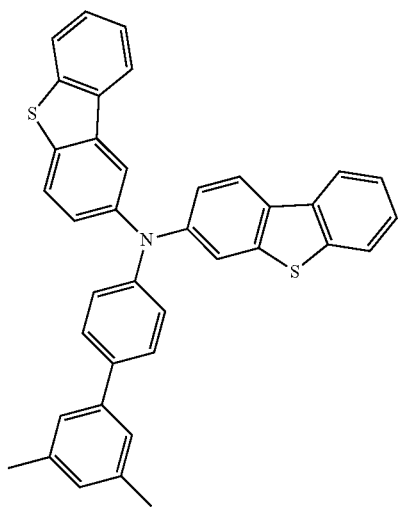

N-47
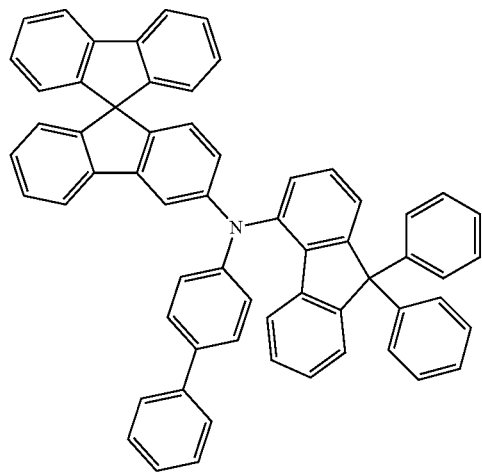
N-48
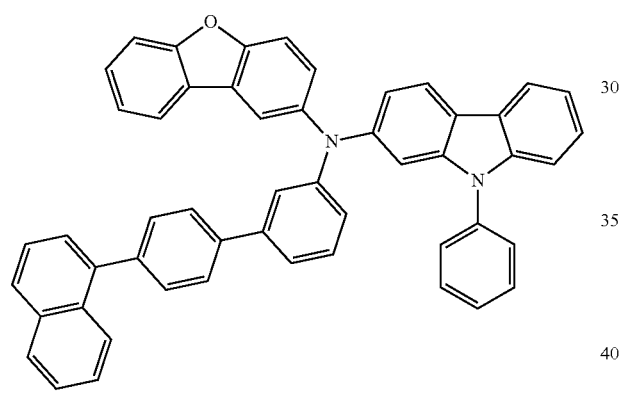
N-49
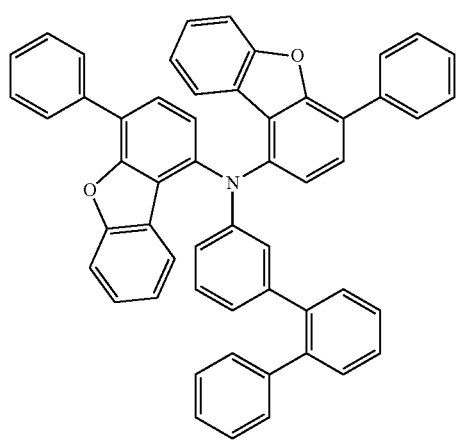
N-50
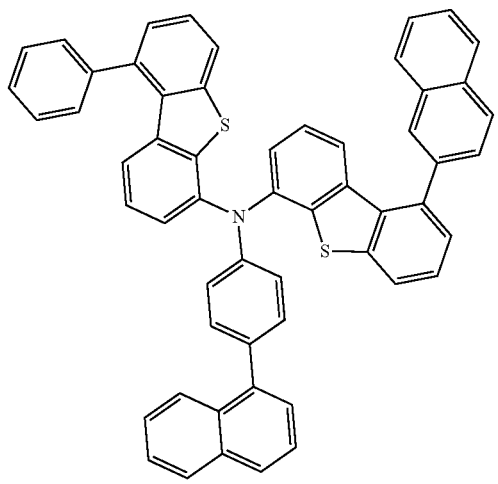
N-51
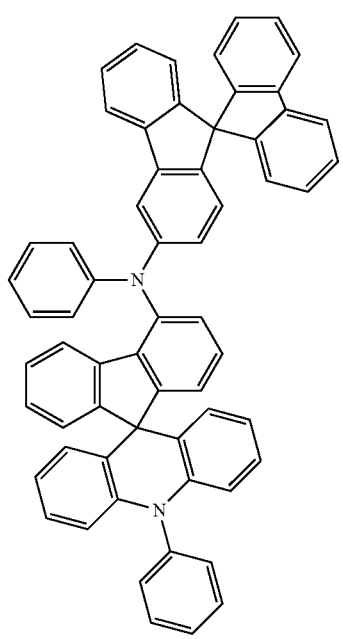

N-52
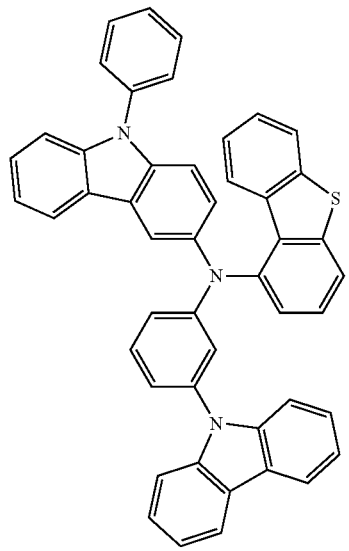
N-55
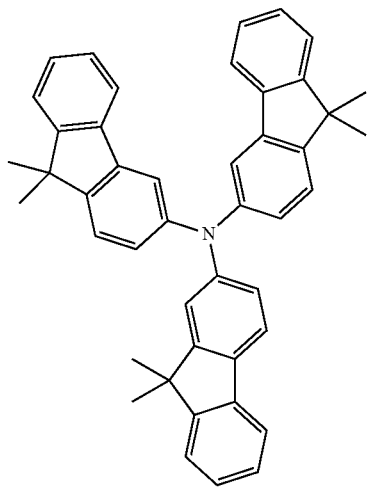
N-53
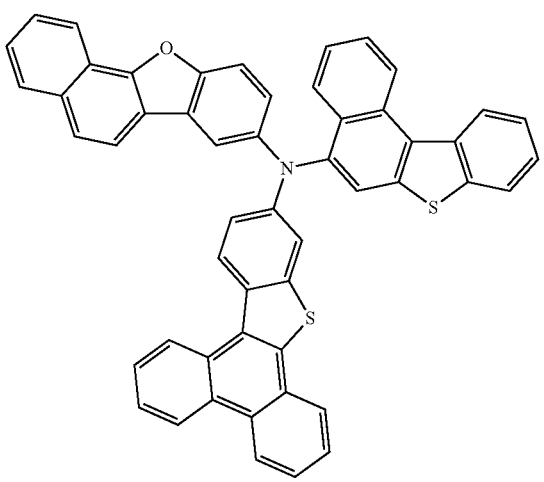
N-56
N-54
N-57
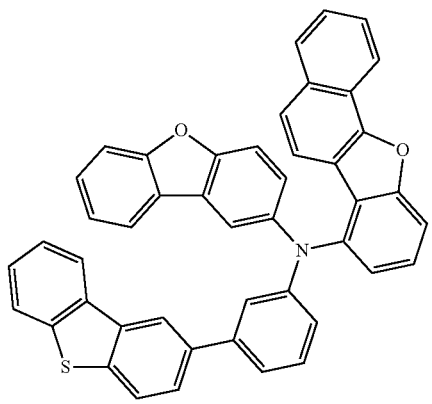

-continued
N-58
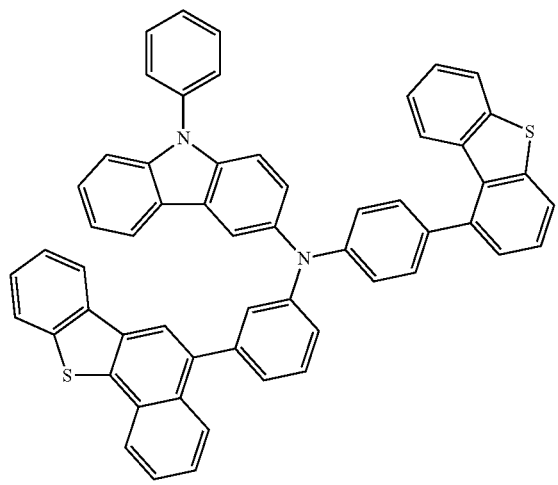
N-59
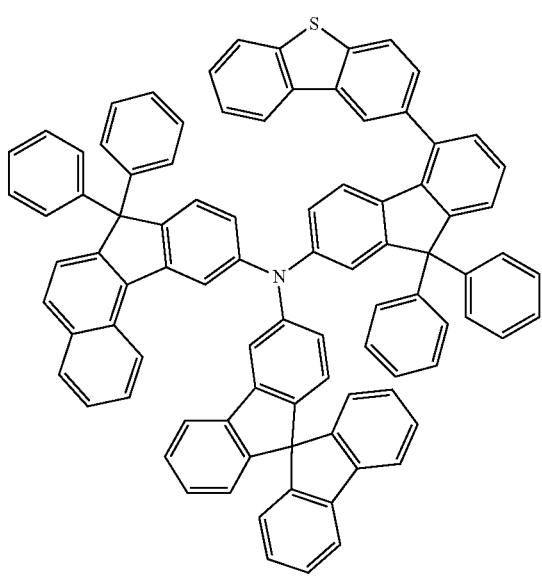
N-60
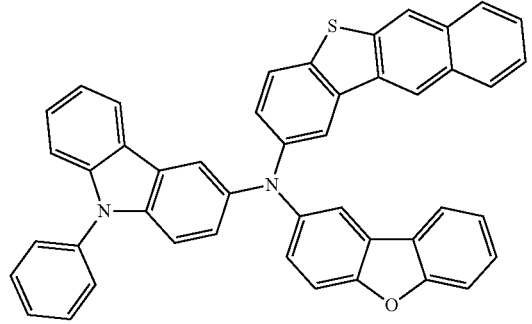
-continued
N-61
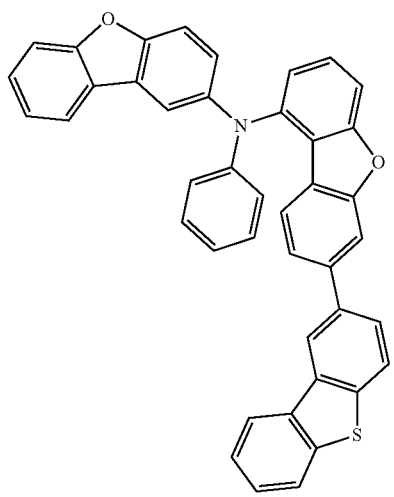
N-62
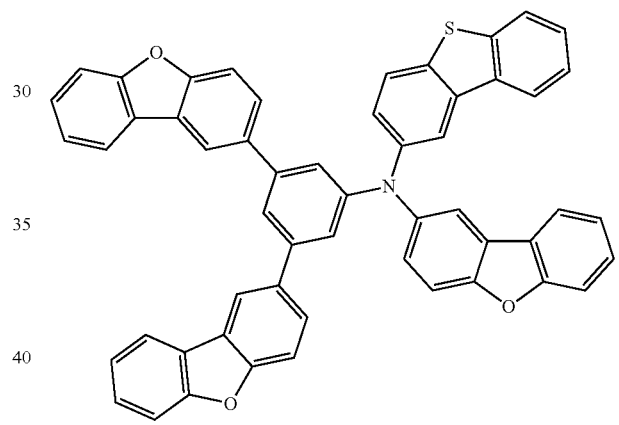
N-63
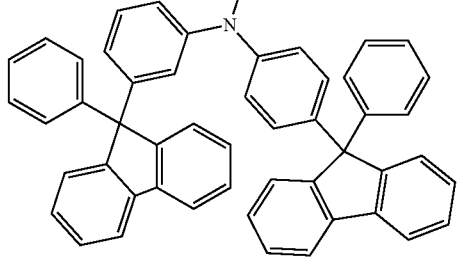

-continued
N-64
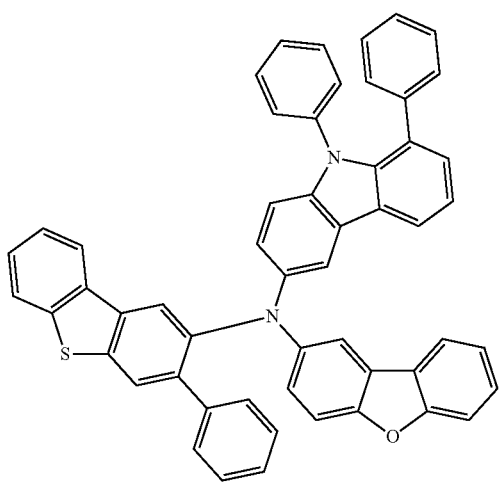
N-65
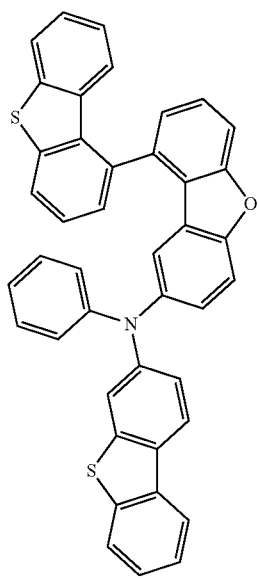
N-66
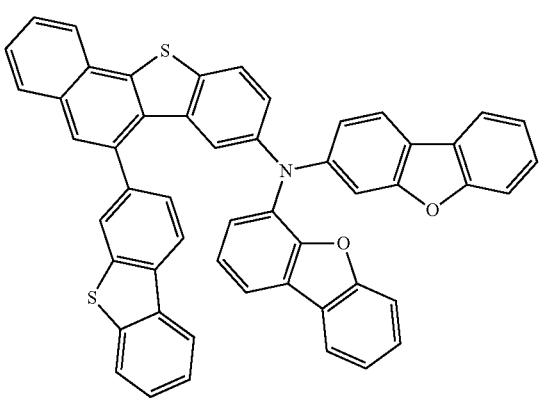
-continued
N-67
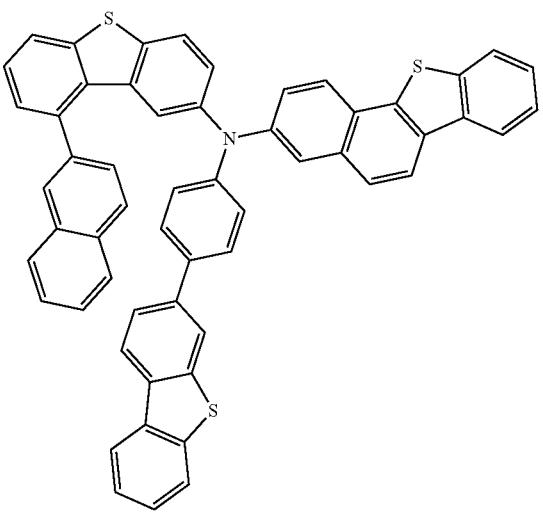
N-68
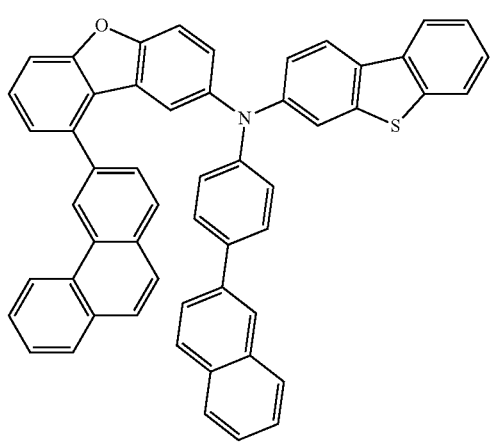
N-69
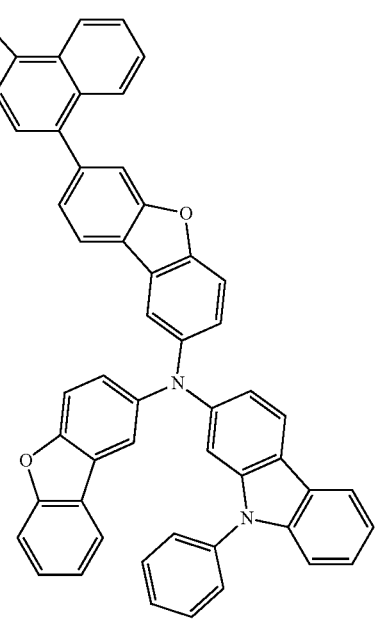

N-70
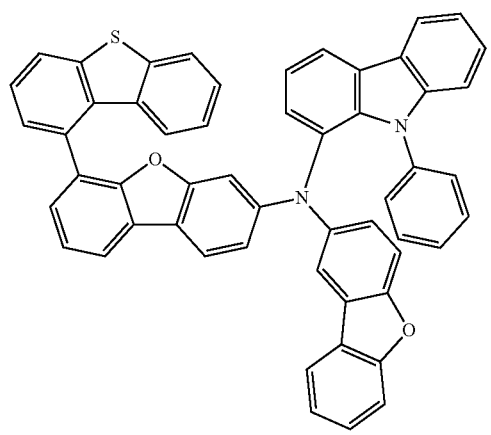
N-71
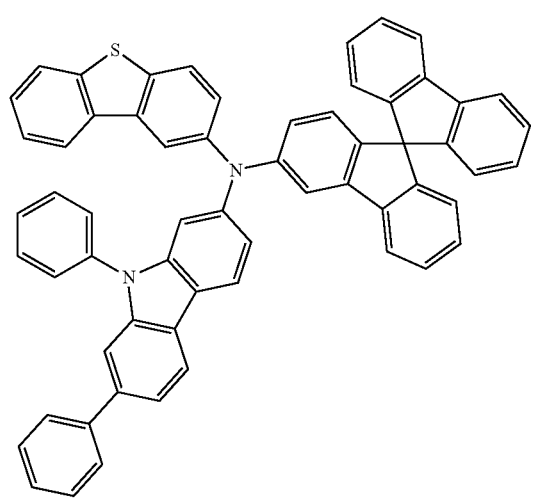
N-73
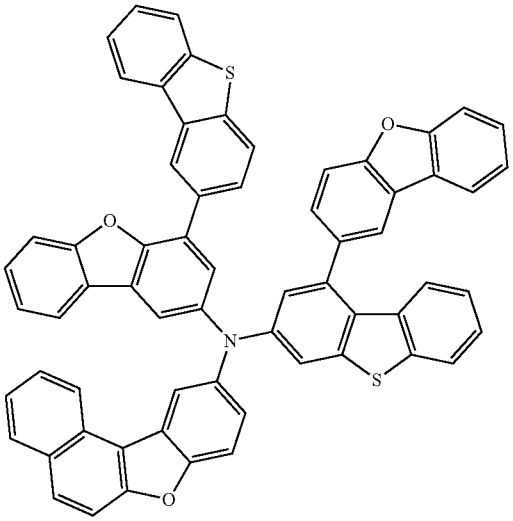
N-72
N-74
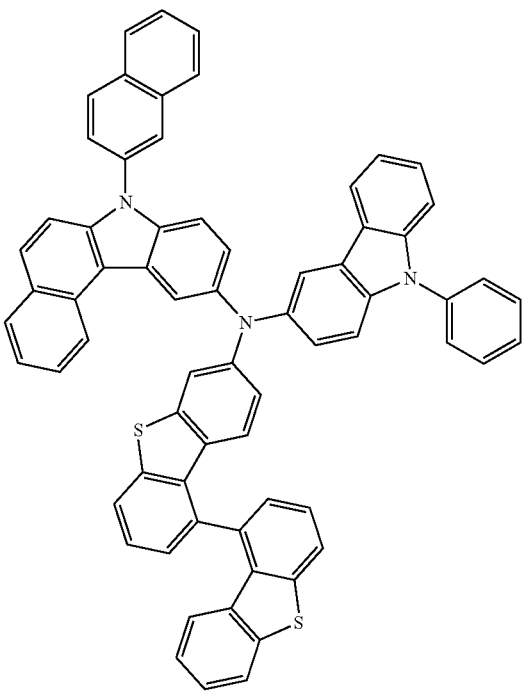

N-75
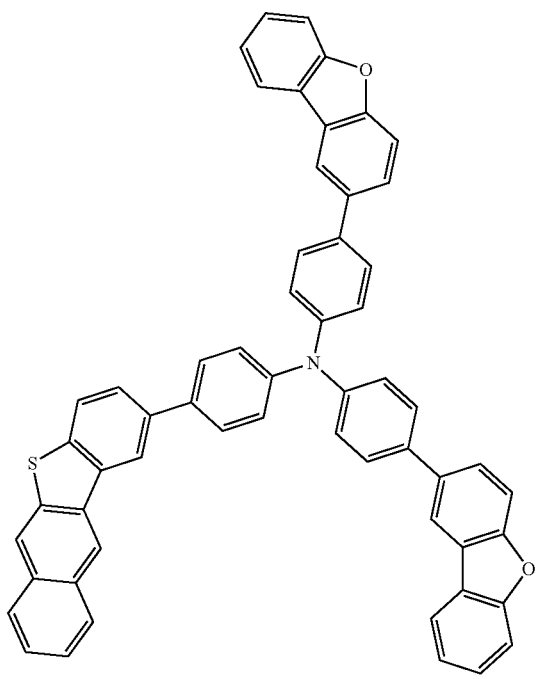
N-77
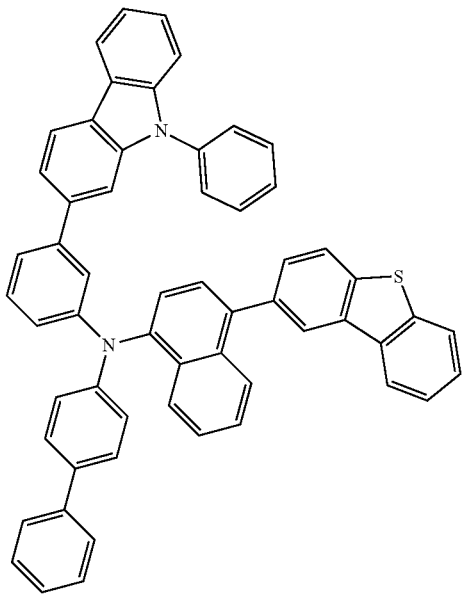
N-76
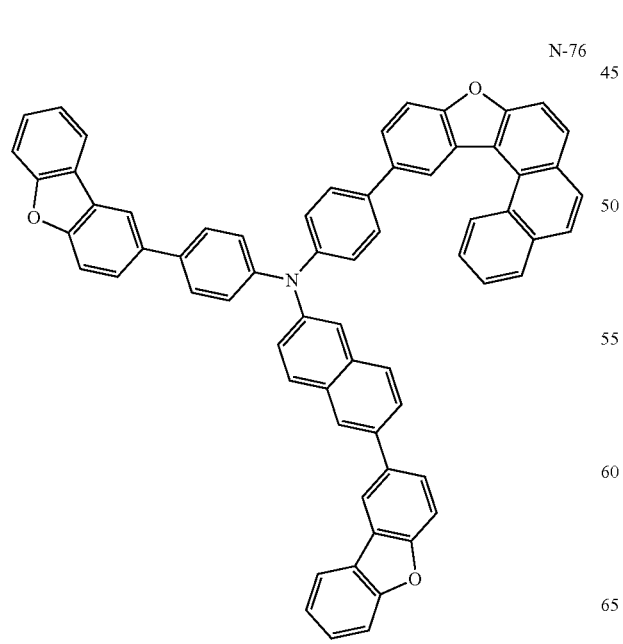
N-78
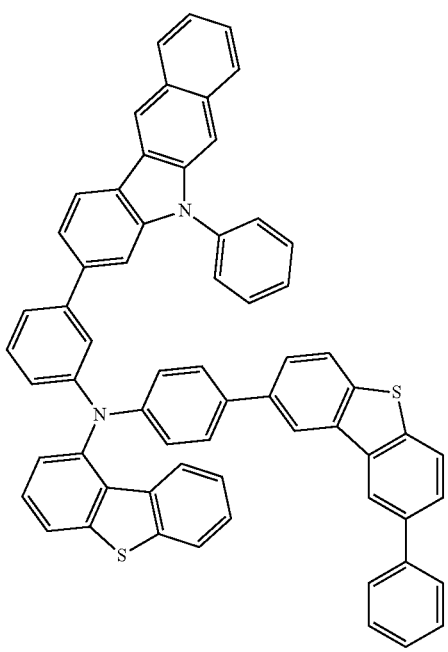

N-79
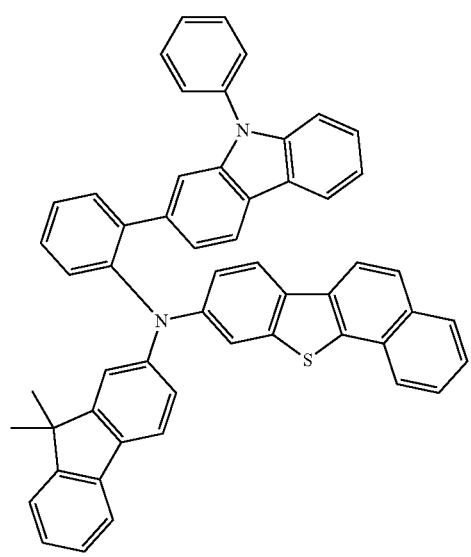
N-81
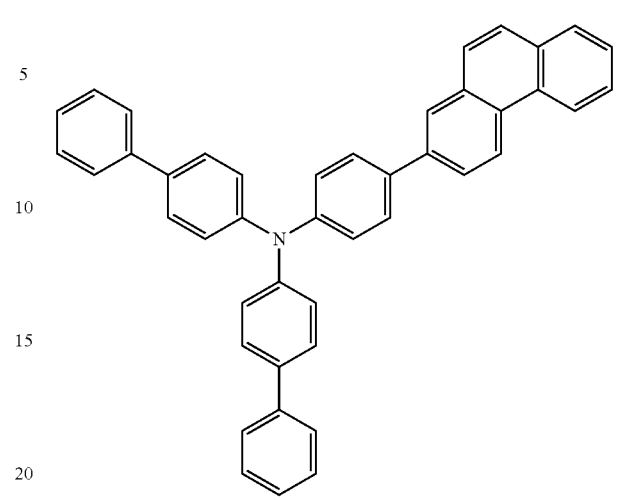
N-80
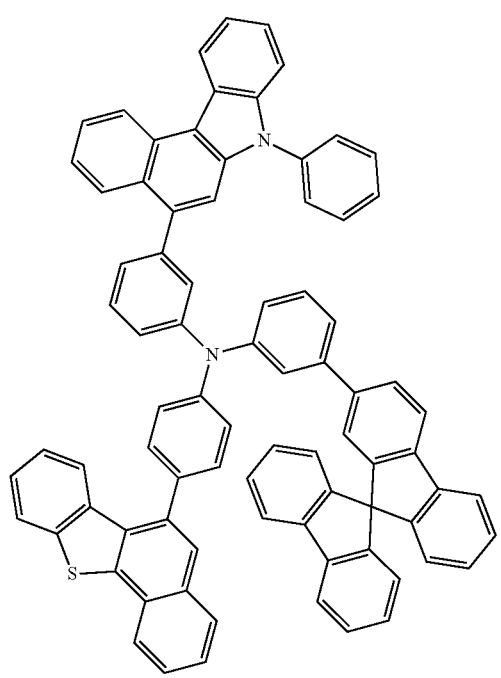
N-82
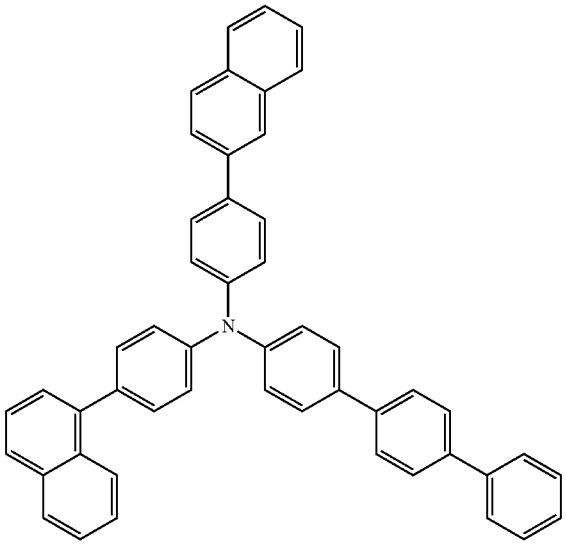

N-83
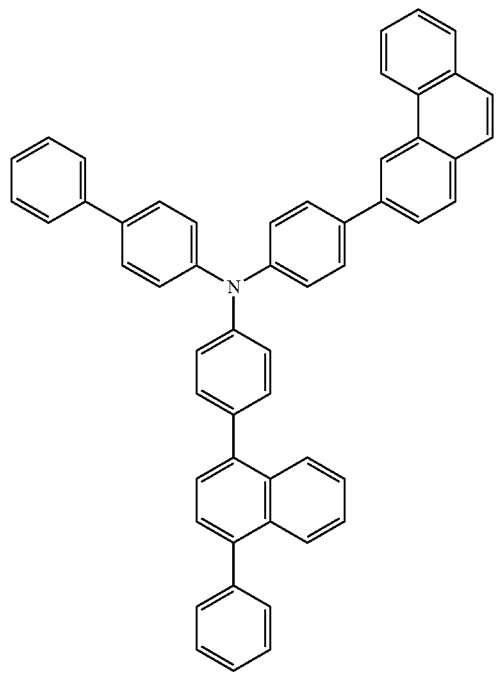
N-85
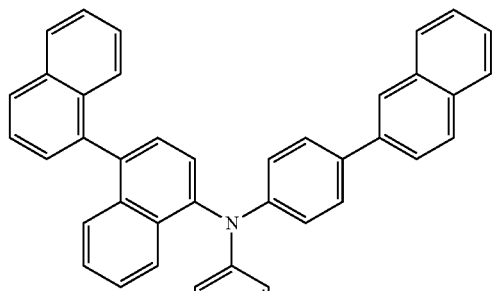
N-86
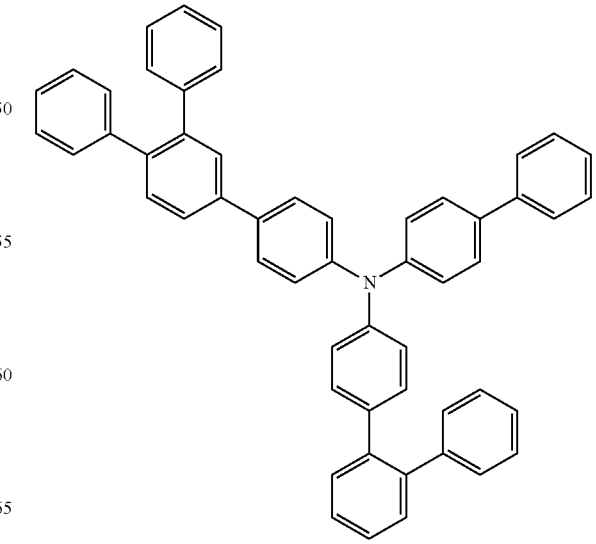
N-84
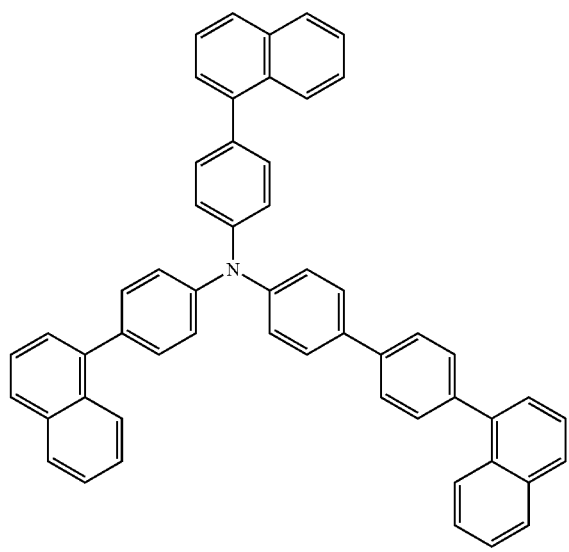
N-87
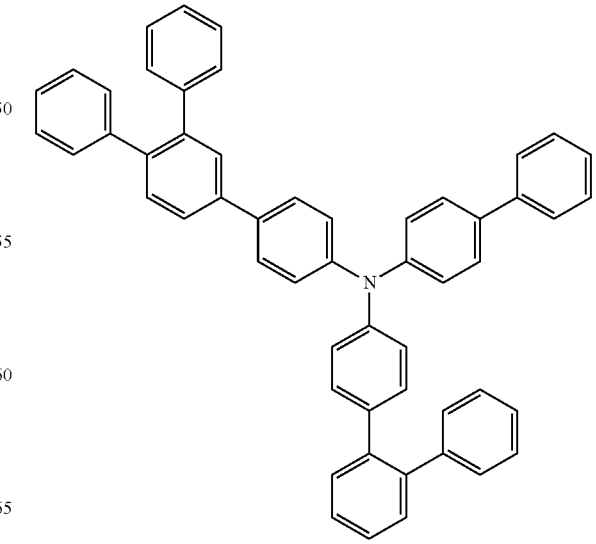

N-88
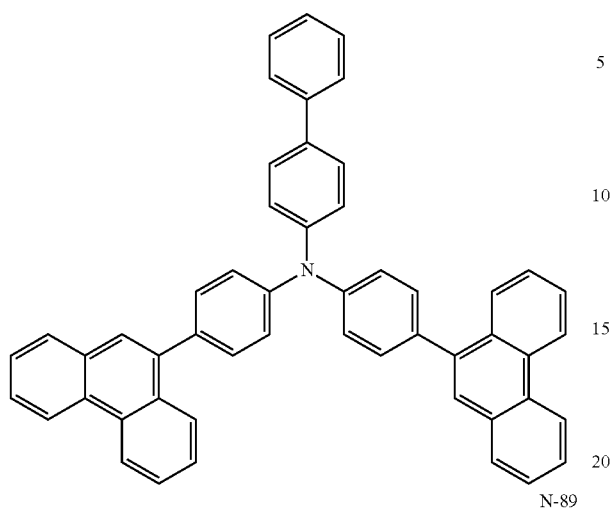
N-91
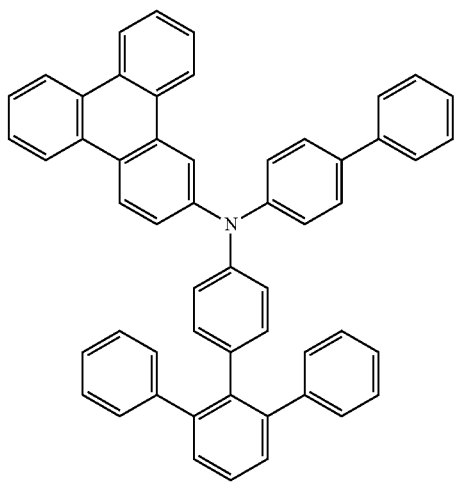
N-89
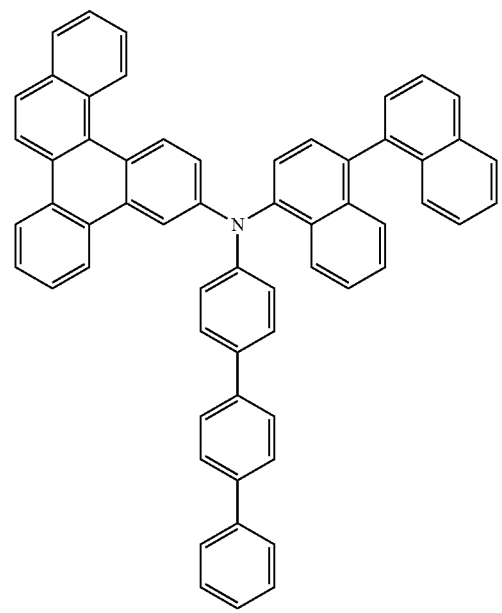
N-92
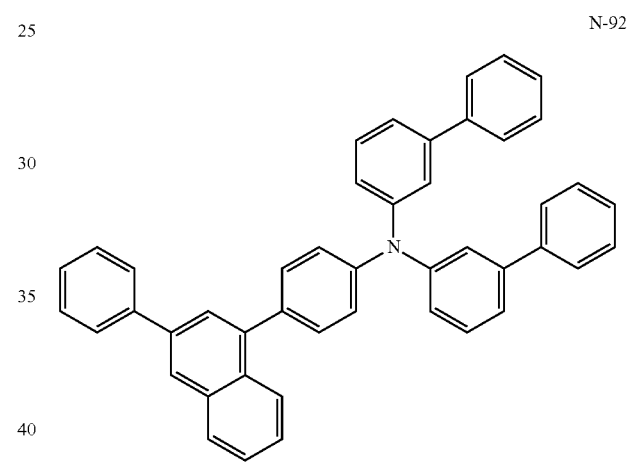
N-90
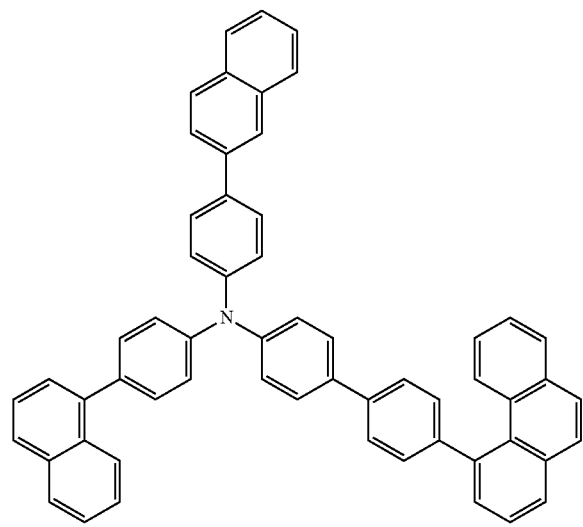
N-93

-continued
N-94
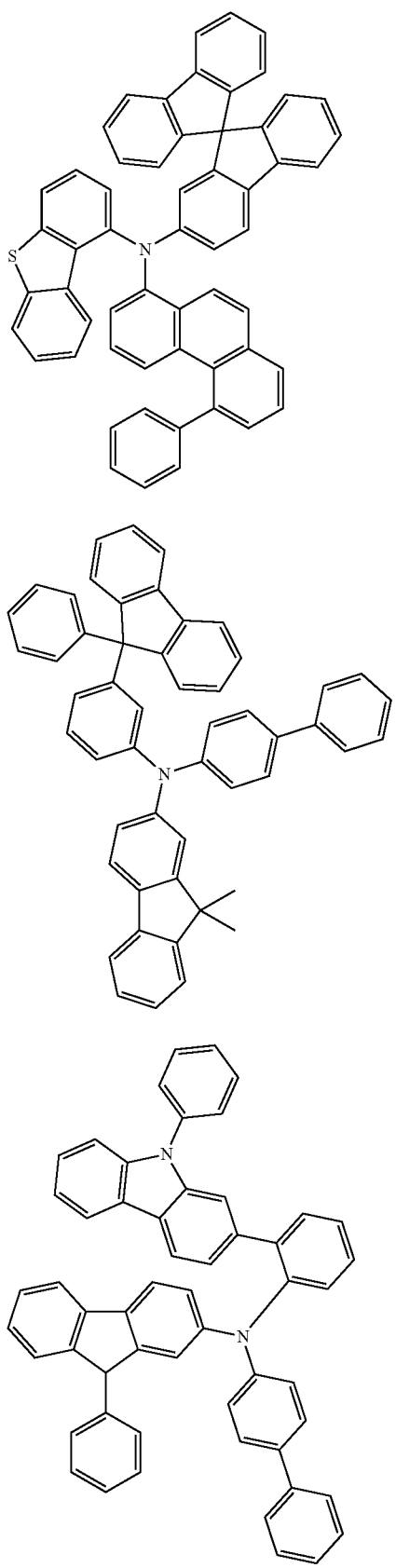
N-95
N-96
Also, the compound represented by Formula 3 is any one of the following compounds S-1 to S-108.
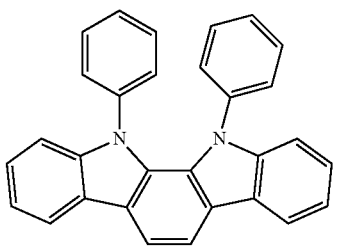
S-1
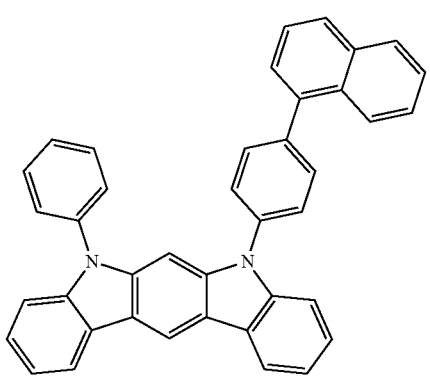
S-2
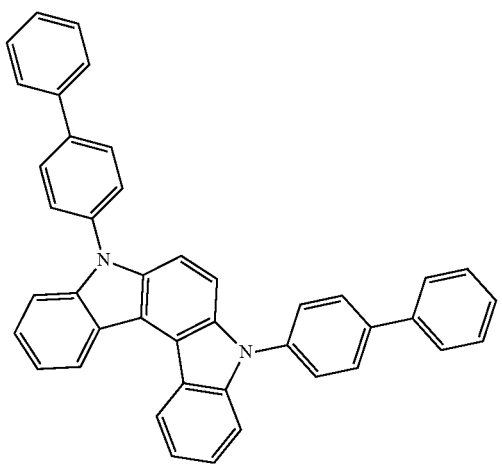
S-3
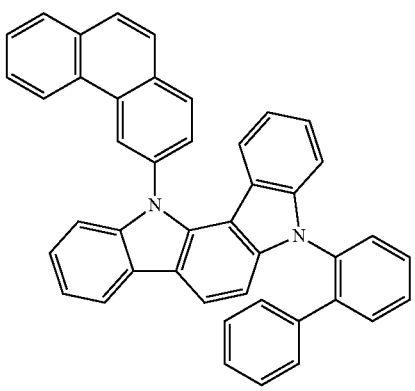
S-4

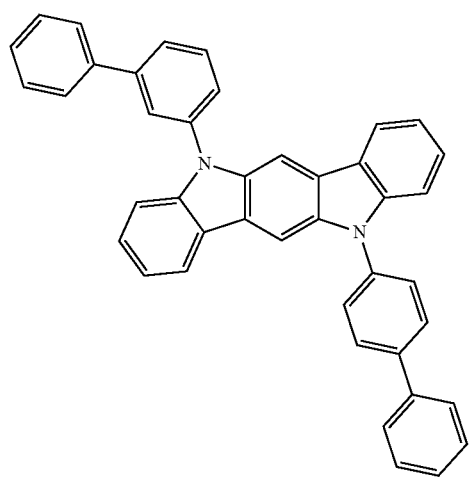
S-5
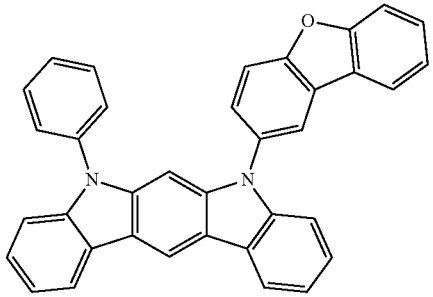
S-8
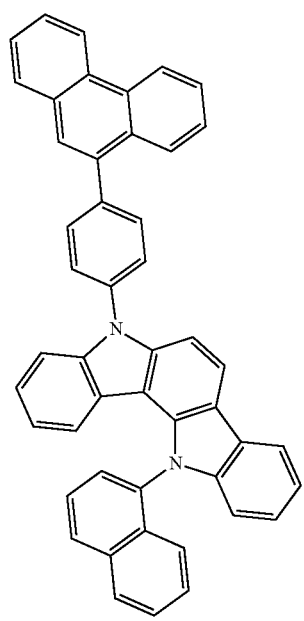
S-6
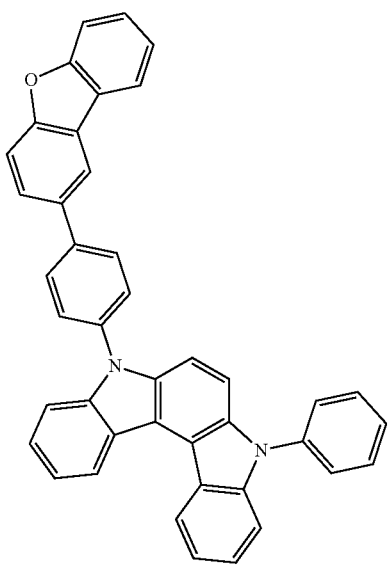
S-9
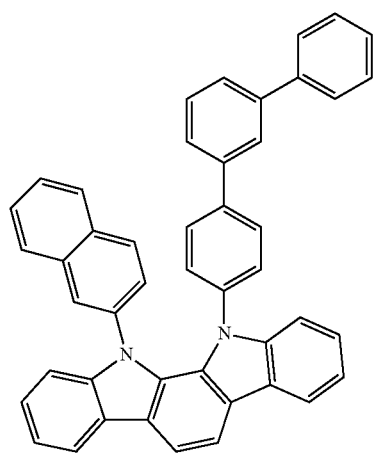
S-7
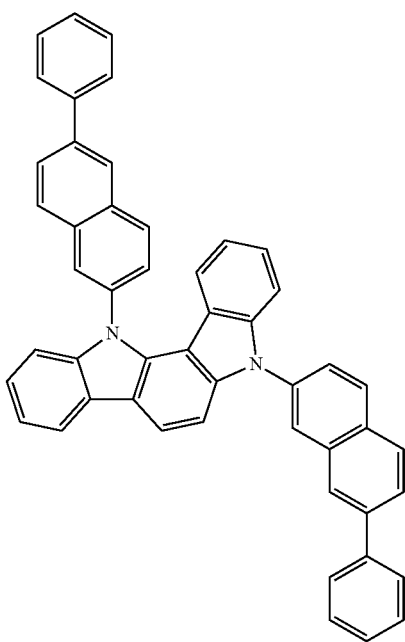
S-10

S-11
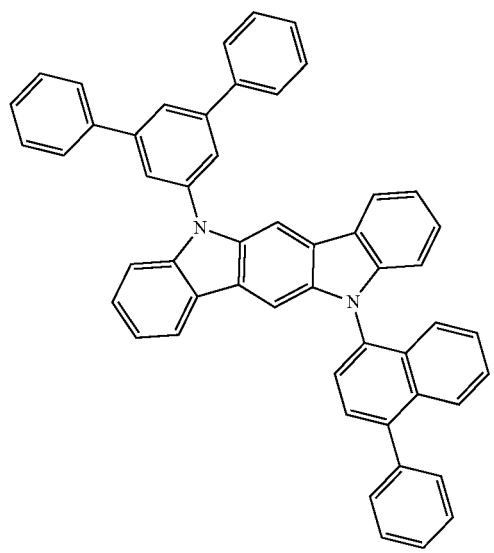
S-12
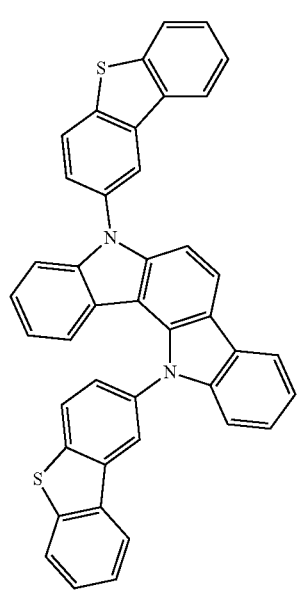
S-13
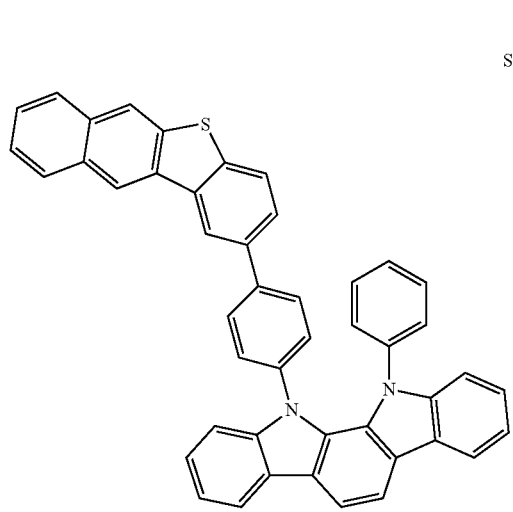
S-14
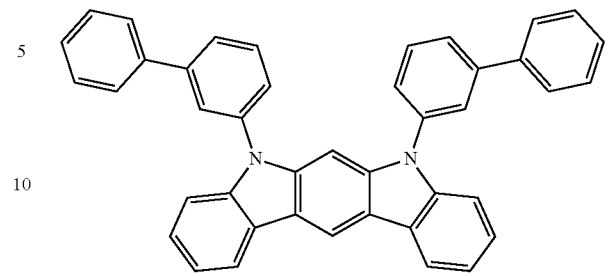
S-15
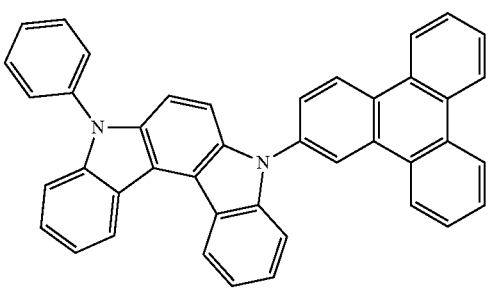
S-16
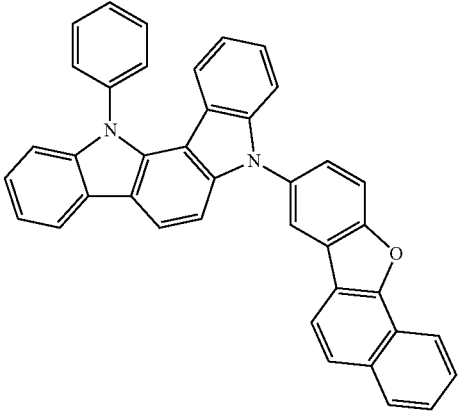
S-17
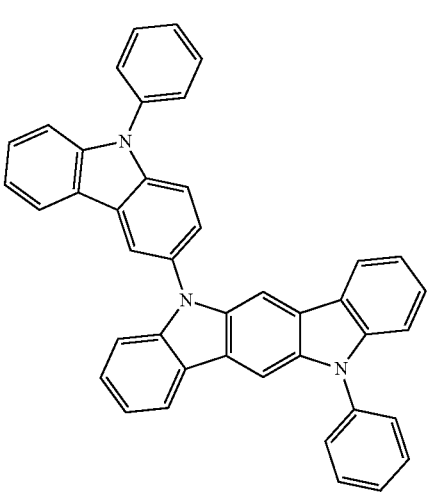

-continued
S-18
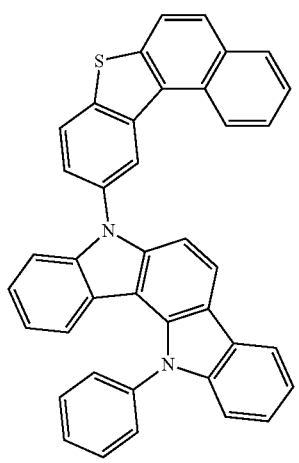
S-19
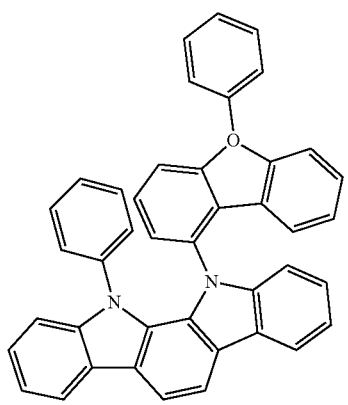
S-20
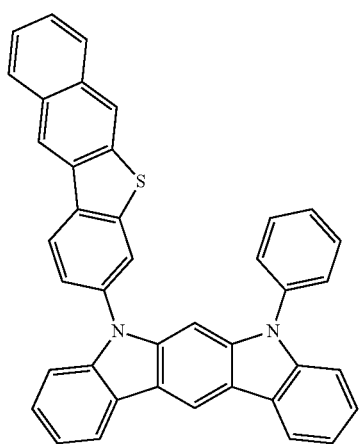
S-21
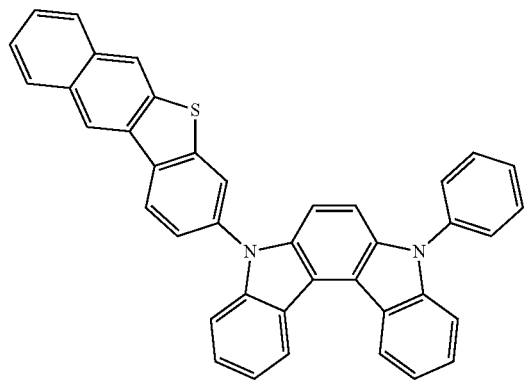
S-22
S-23
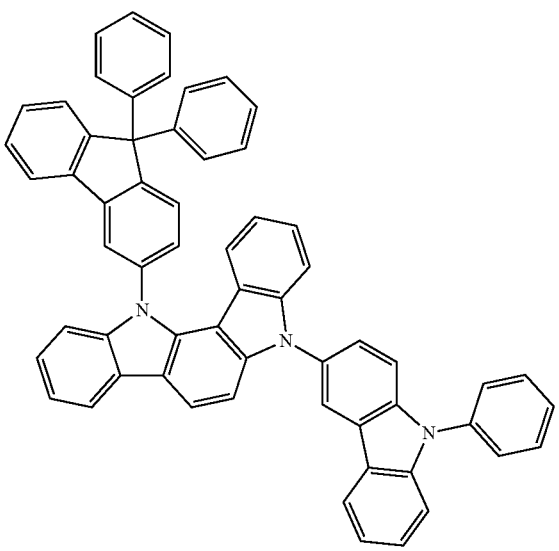

S-24
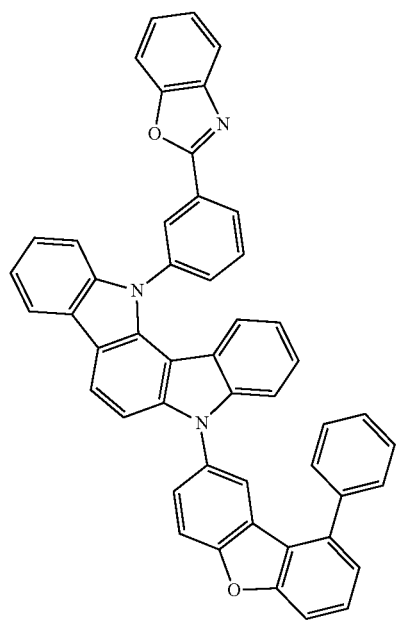
S-25
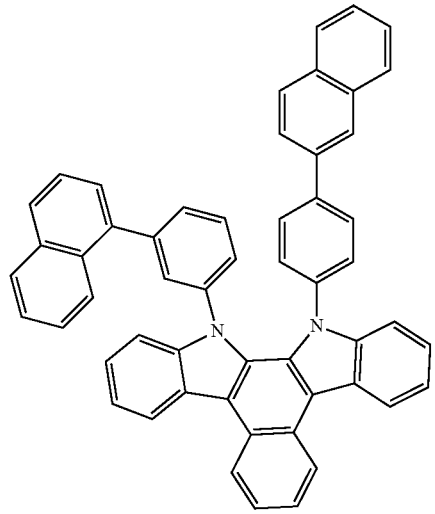
S-26
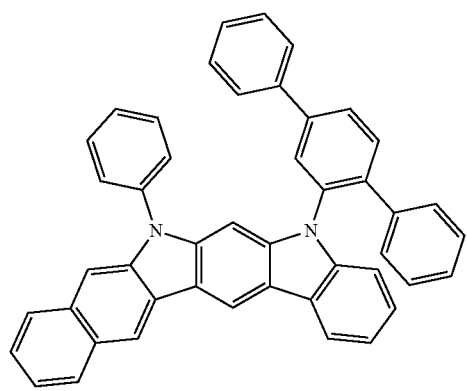
S-27
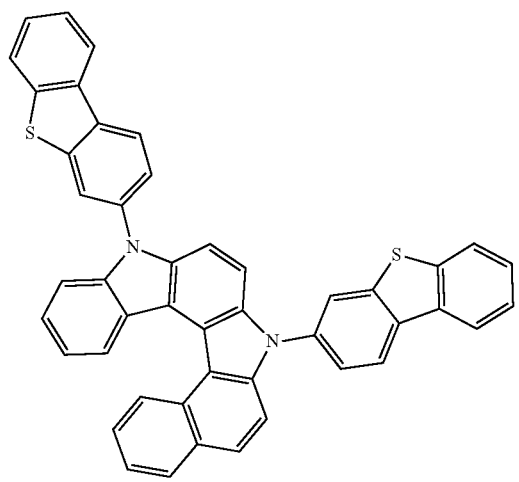
S-28
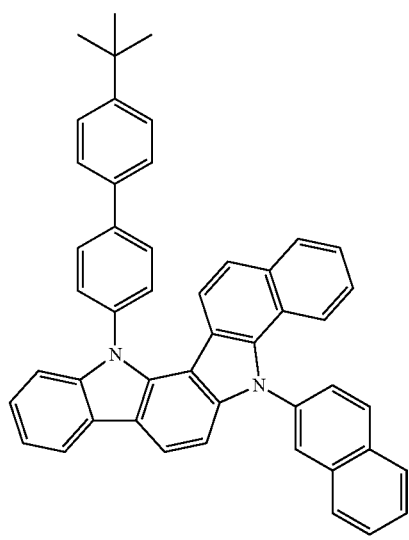
S-29
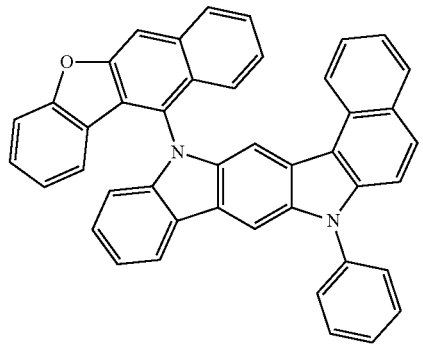

S-30
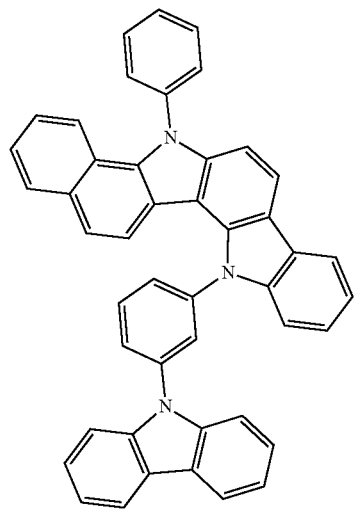
S-31
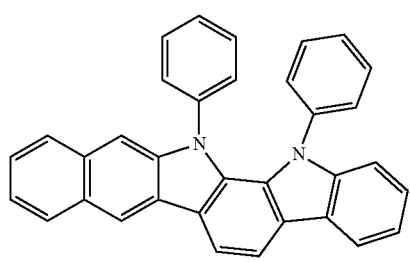
S-32
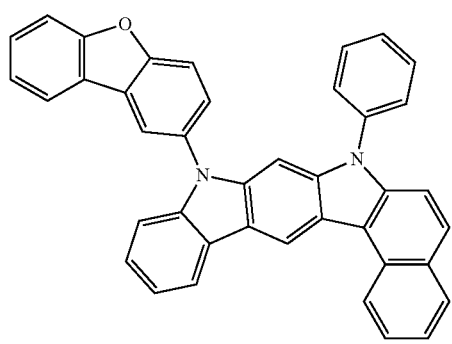
S-33
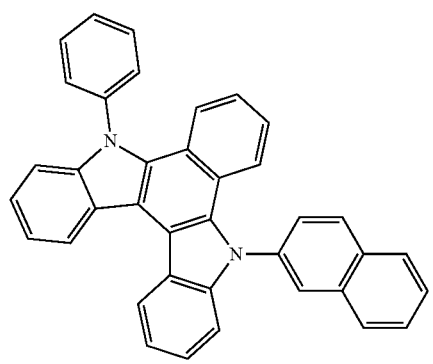
S-34
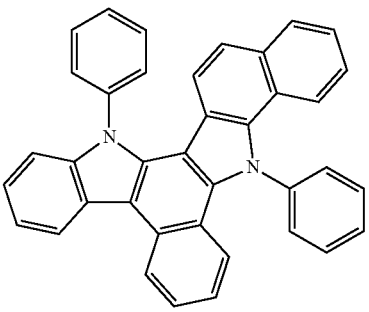
S-35
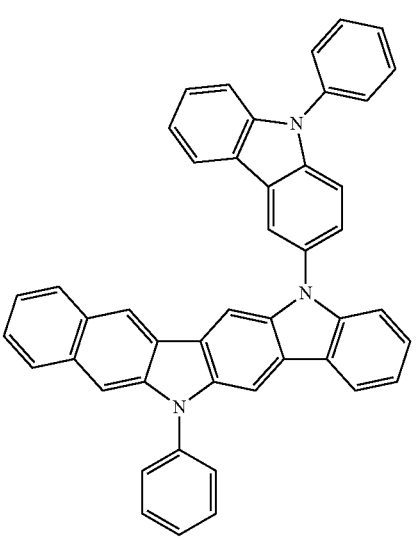
S-36
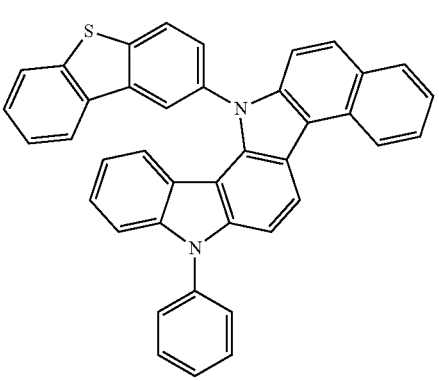
S-37
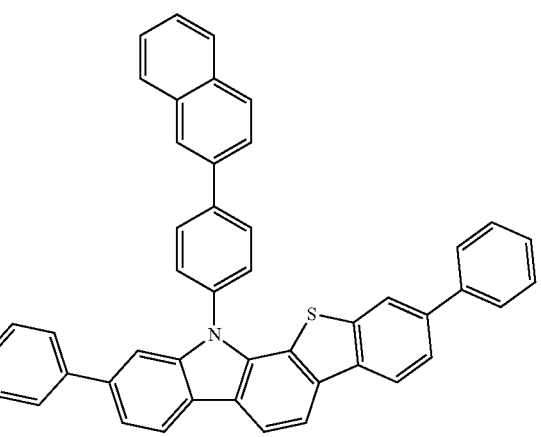

S-38
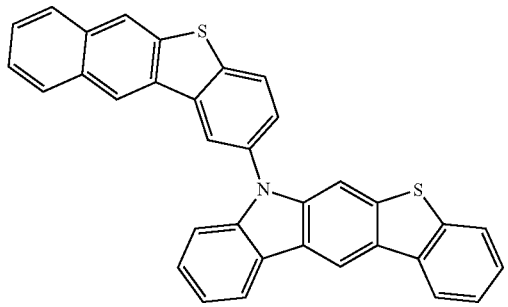
S-39
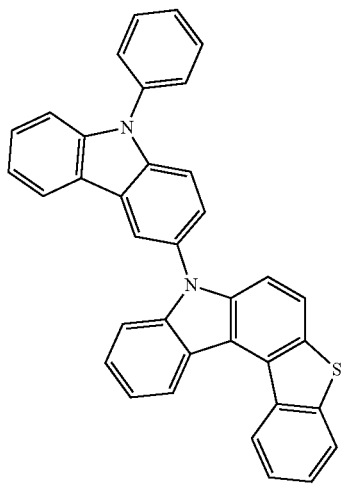
S-40
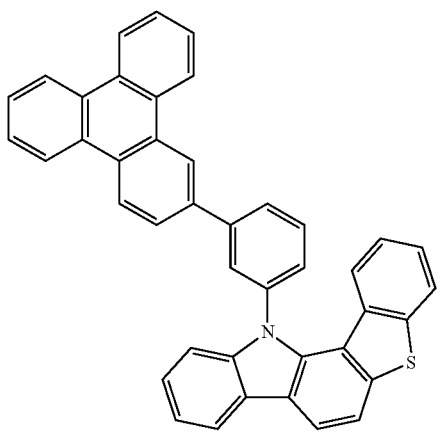
S-41
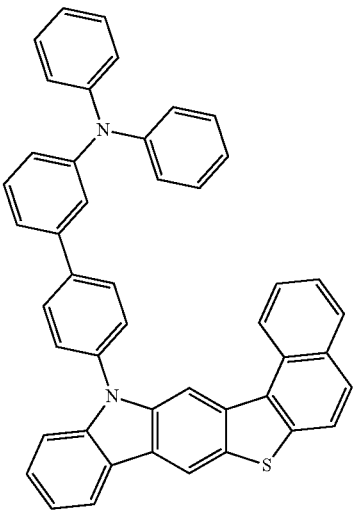
S-42
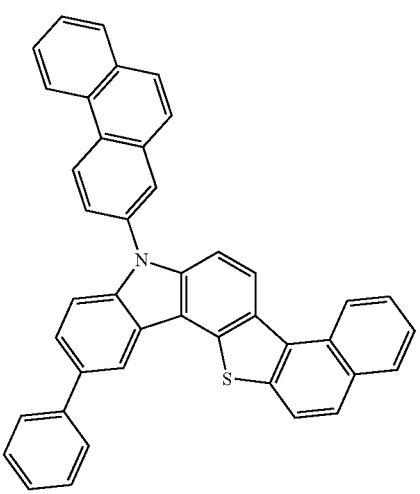
S-43
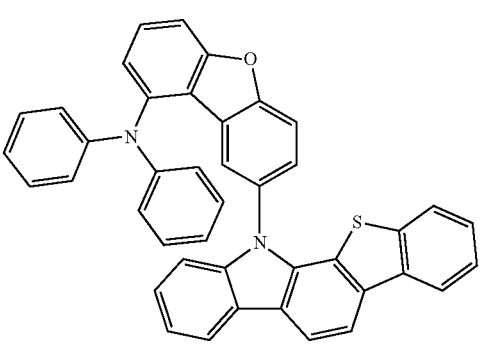

-continued
S-44
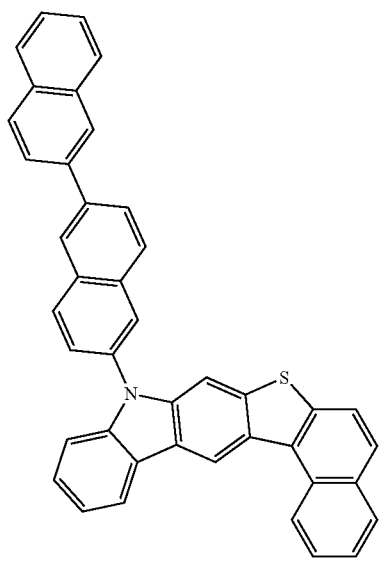
S-45
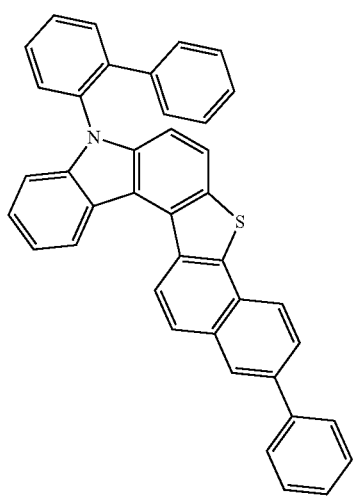
S-46
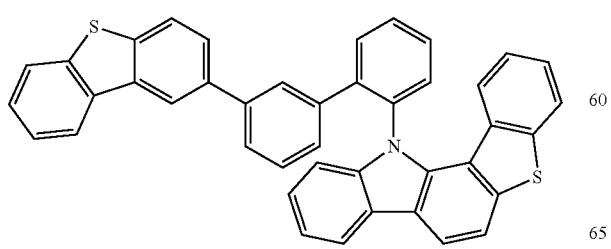
-continued
S-47
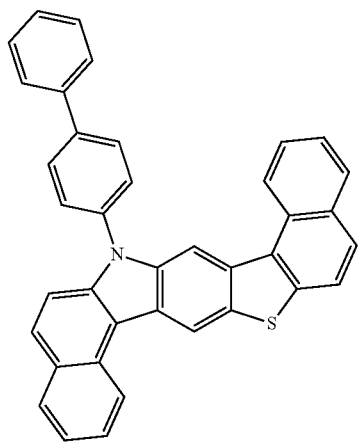
S-48
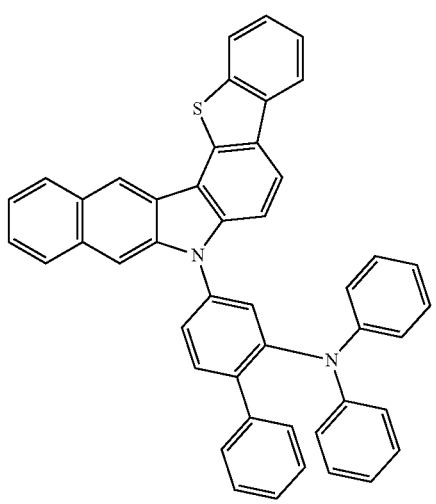
S-49
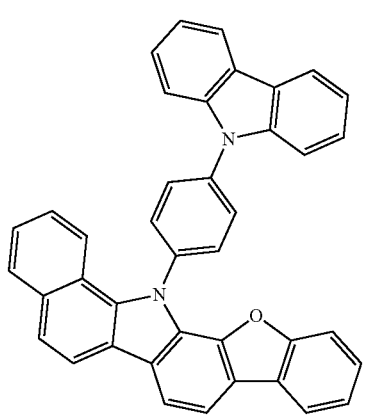

-continued
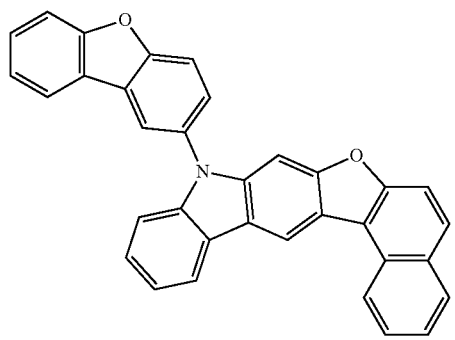
S-50
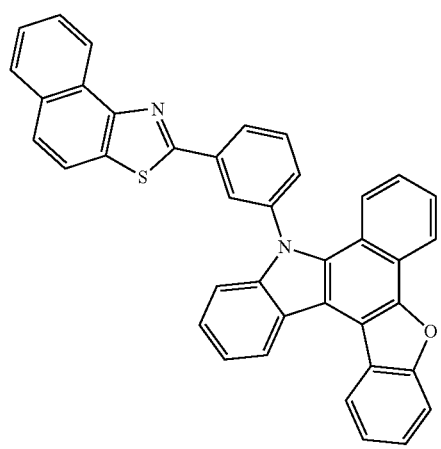
S-51
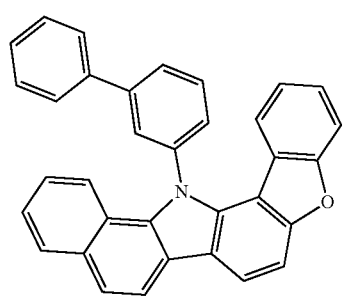
S-52
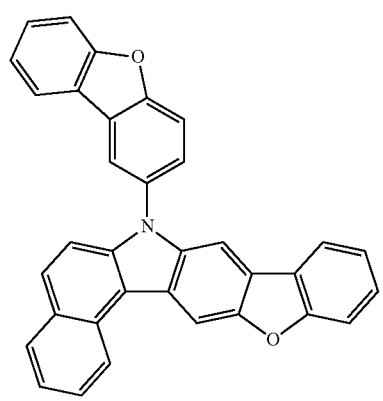
S-53
-continued
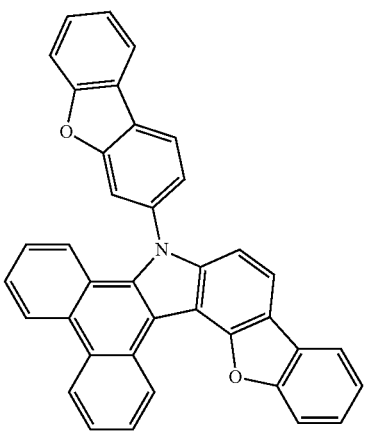
S-54
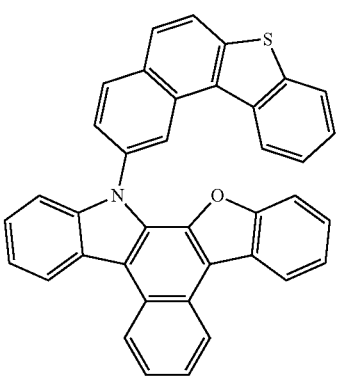
S-55
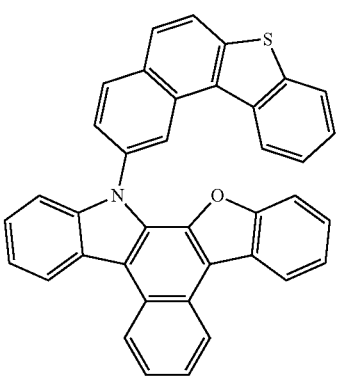
S-56
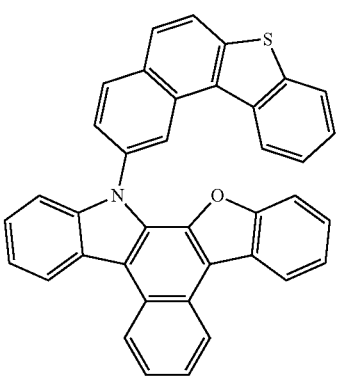
S-57

101
-continued
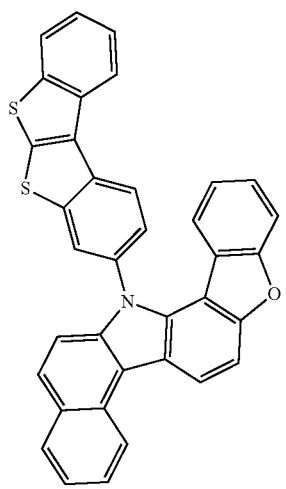
S-58
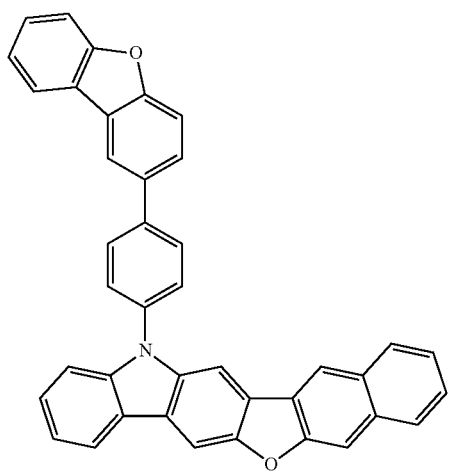
S-59
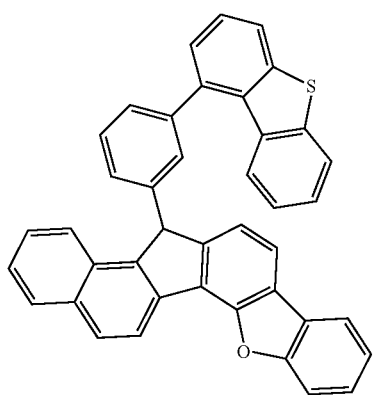
S-60
102
-continued
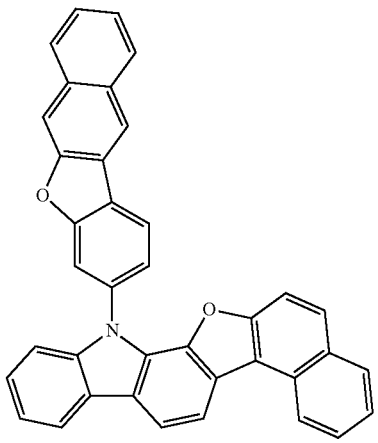
S-61
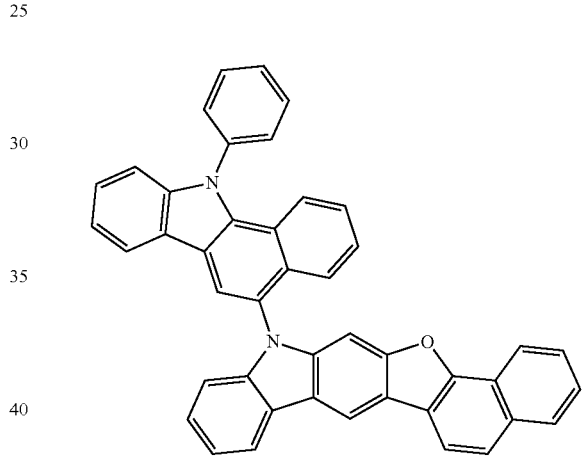
S-62
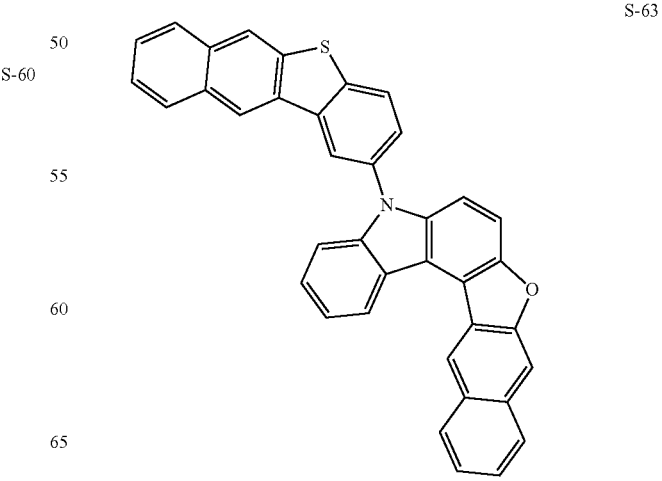
S-63

S-64
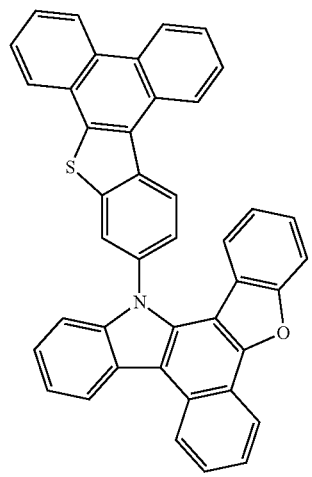
S-65
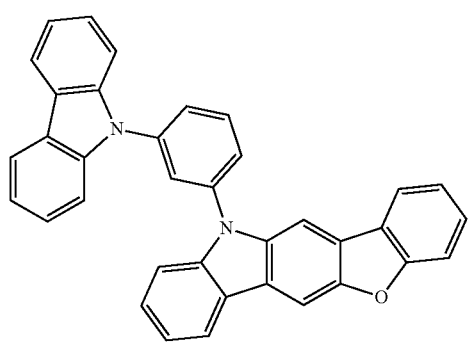
S-66
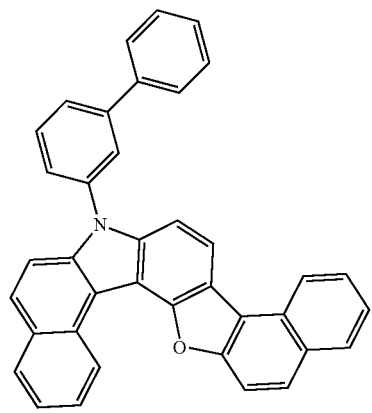
S-67
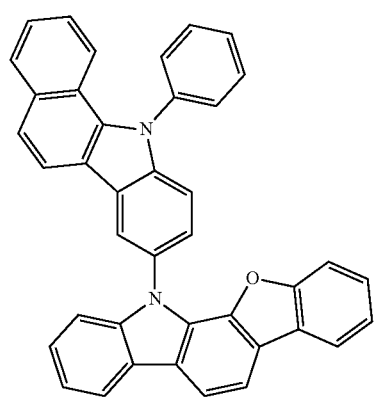
S-68
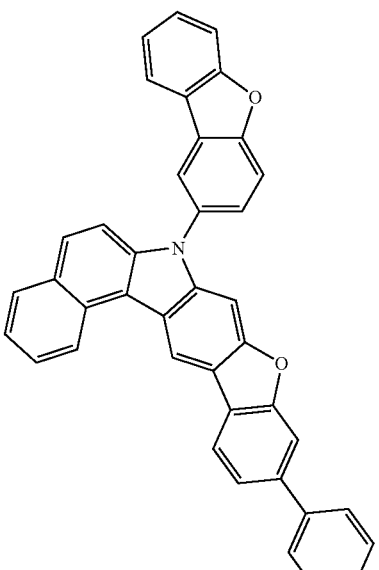
S-69
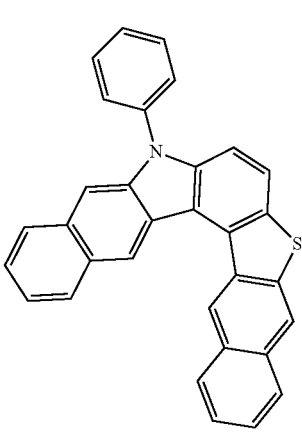
S-70
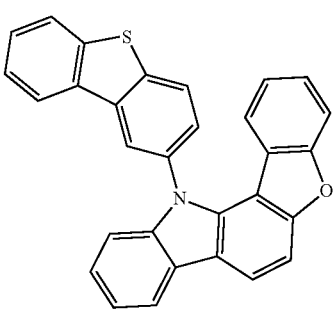

S-71
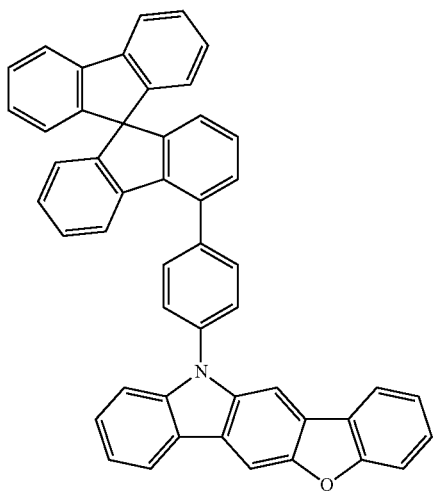
S-74
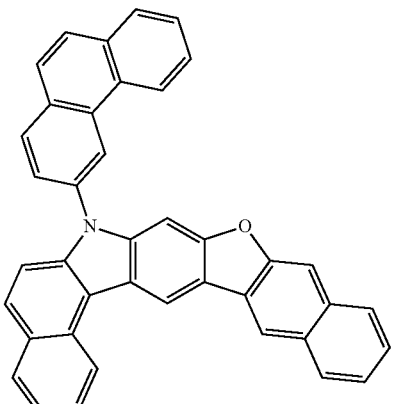
S-72
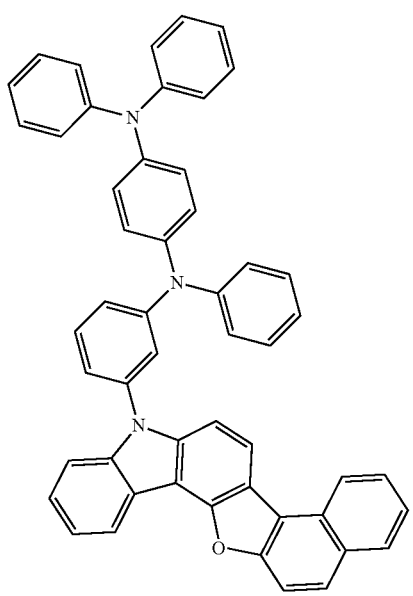
S-75
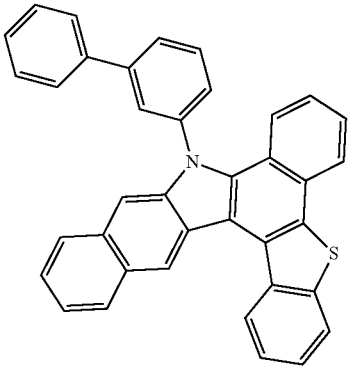
S-76
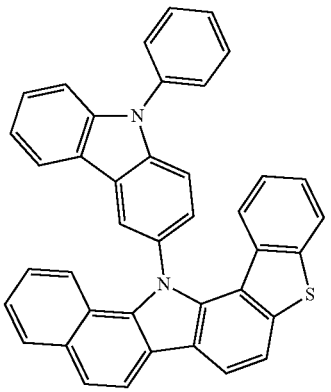
S-73
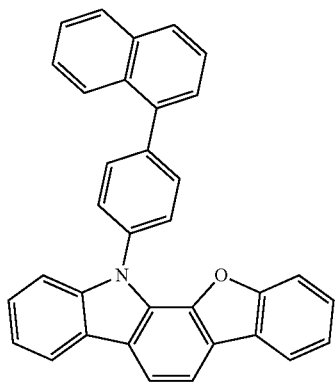
S-77
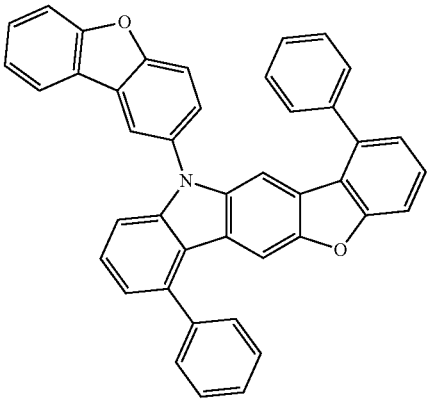

-continued
S-78
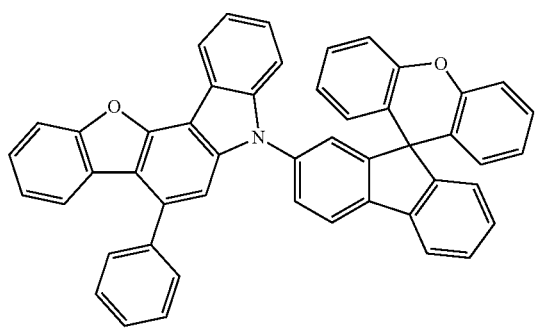
S-79
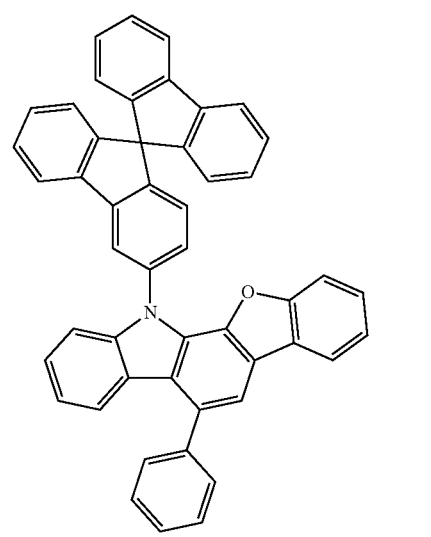
S-80
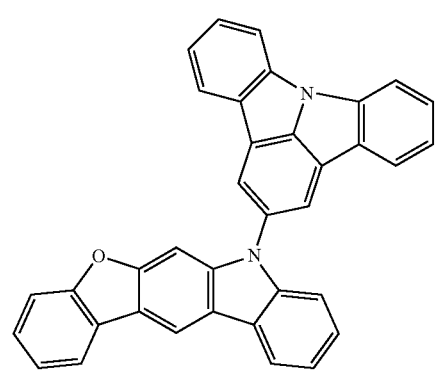
S-81
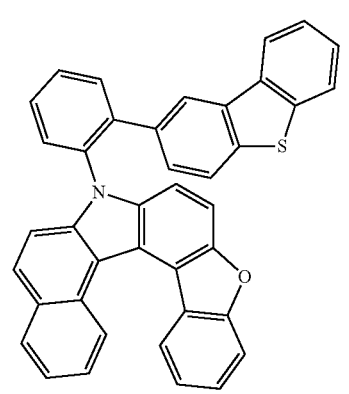
-continued
S-82
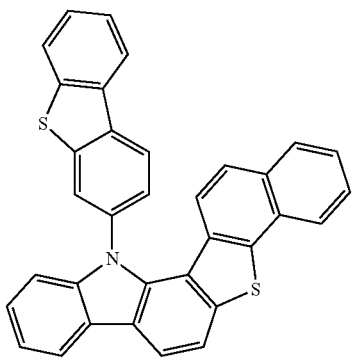
S-83
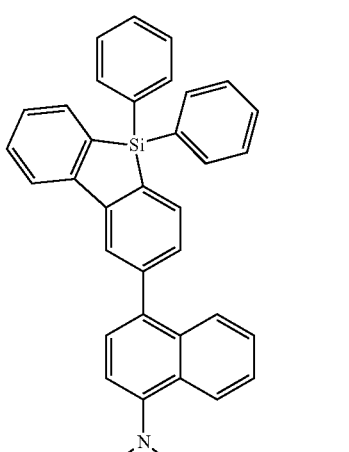
S-84
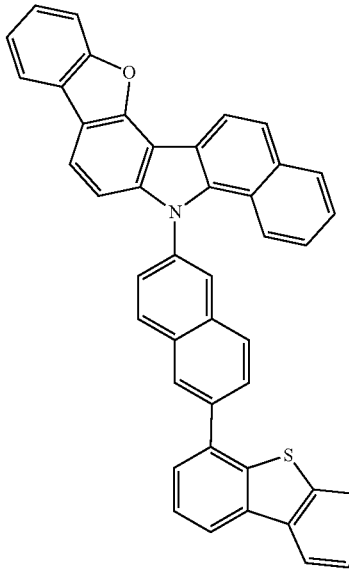

-continued
S-85
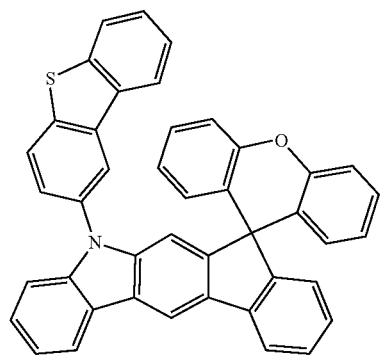
S-86
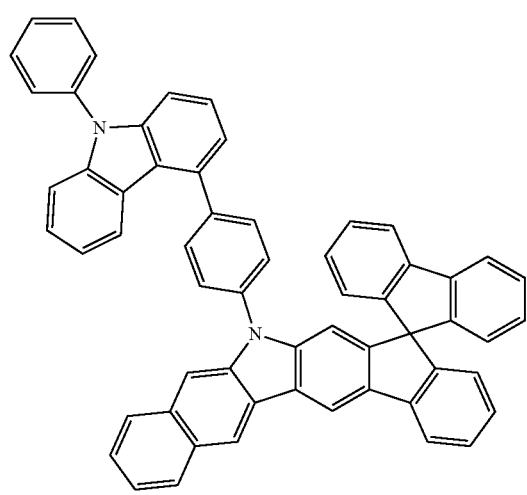
S-87
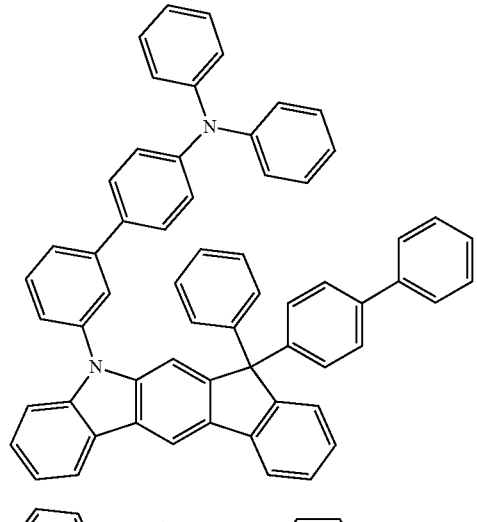
S-88
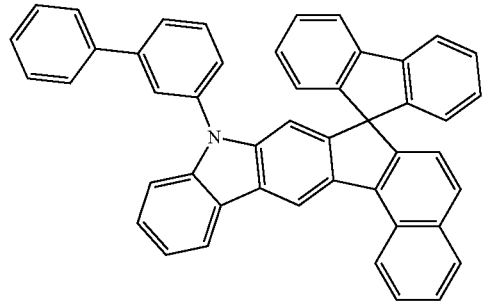
-continued
S-89
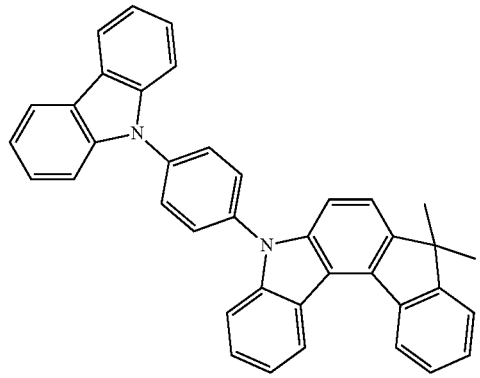
S-90
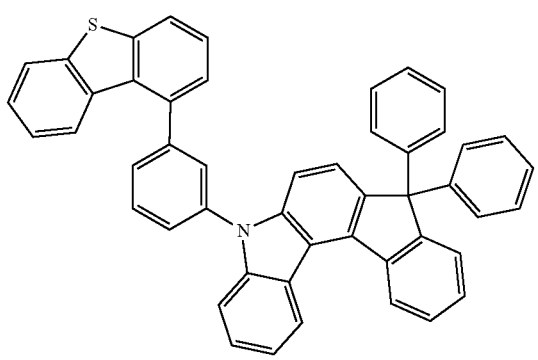
S-91
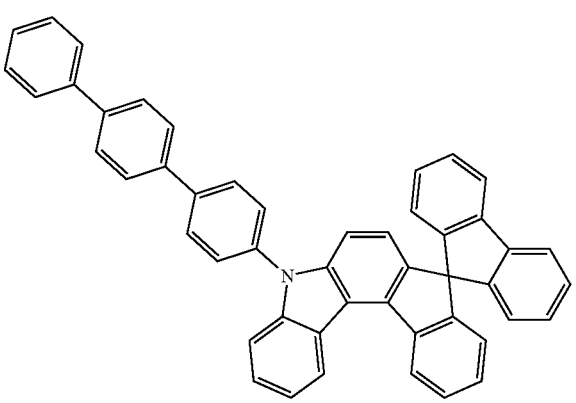

-continued
S-92
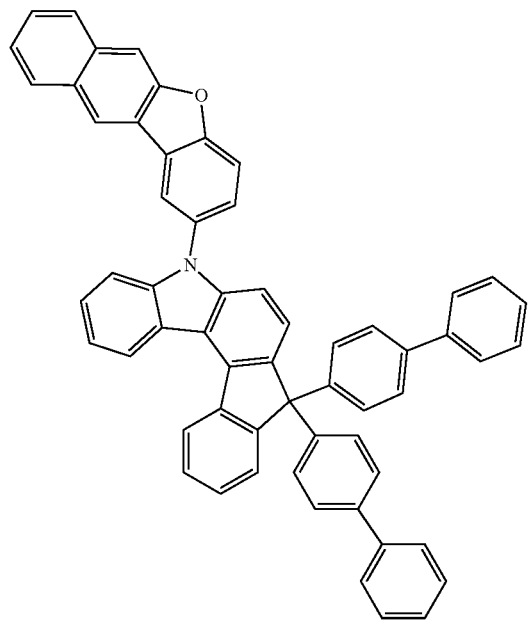
S-93
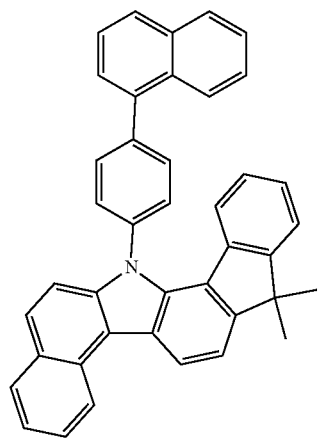
S-94
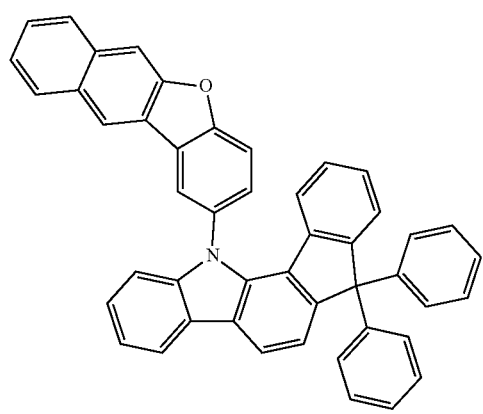
-continued
S-95
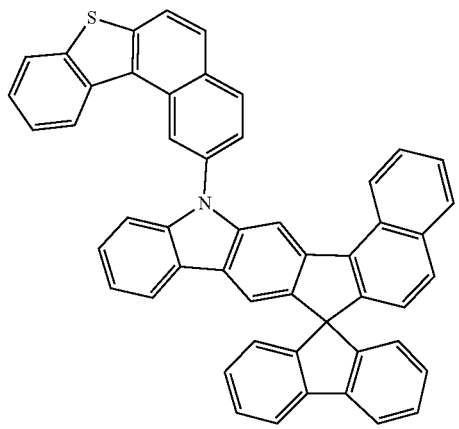
S-96
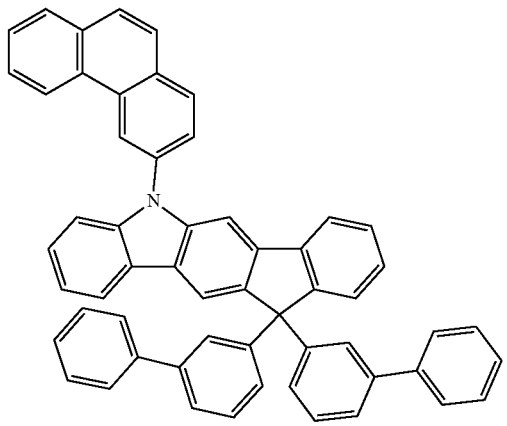
S-97
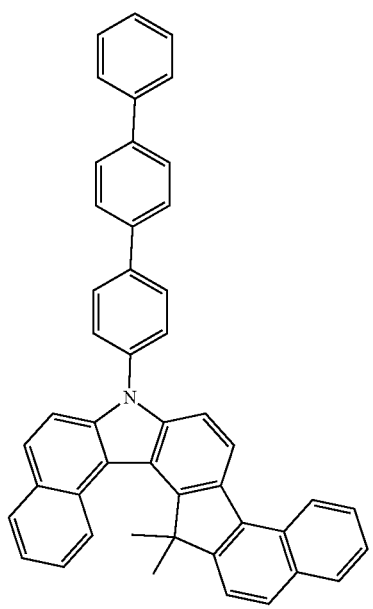

S-98
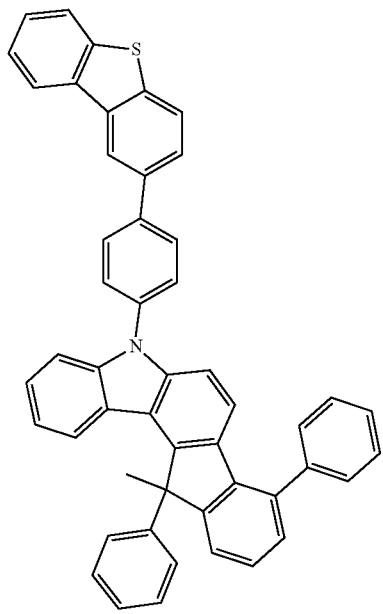
S-99
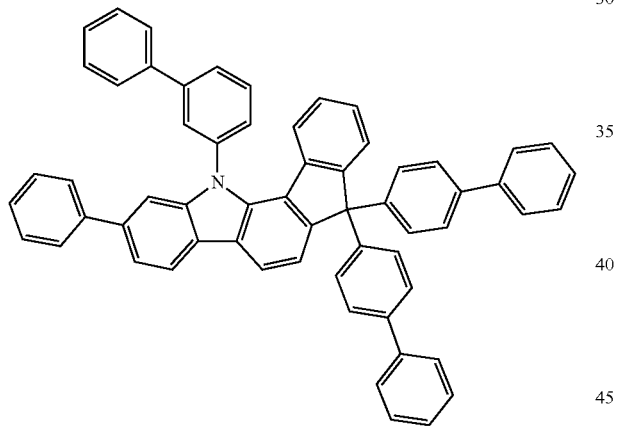
S-100
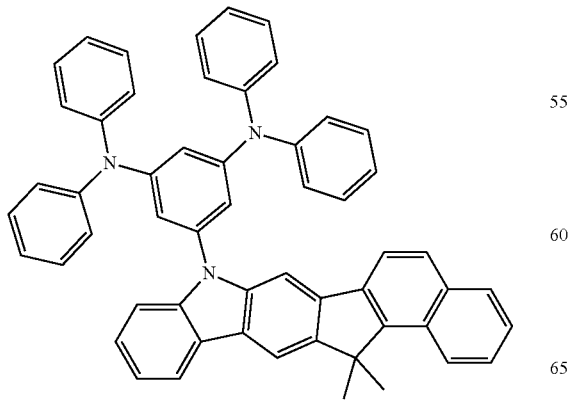
S-101
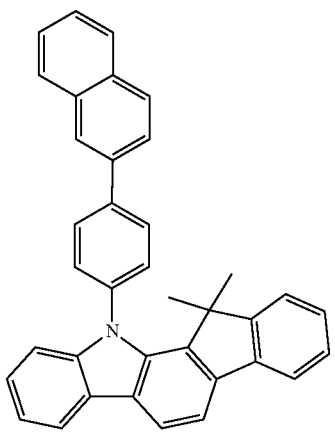
S-102
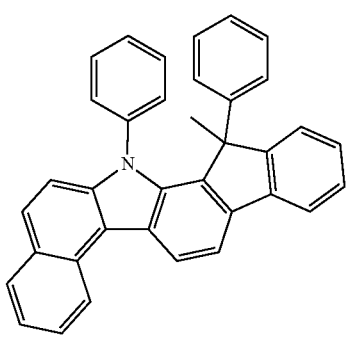
S-103
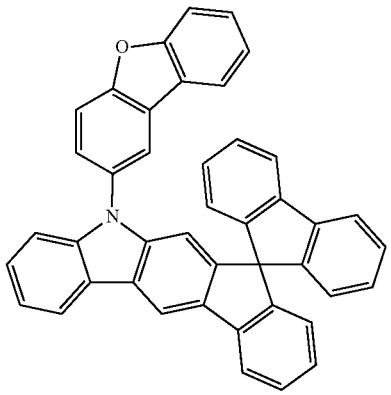
S-104
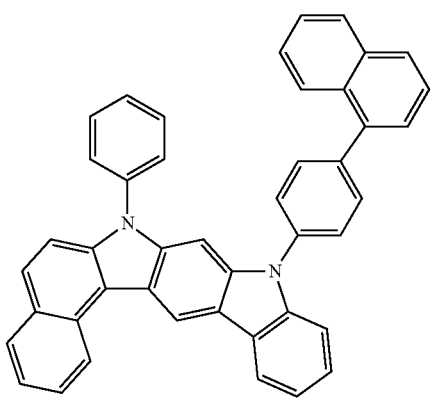

-continued

S-105
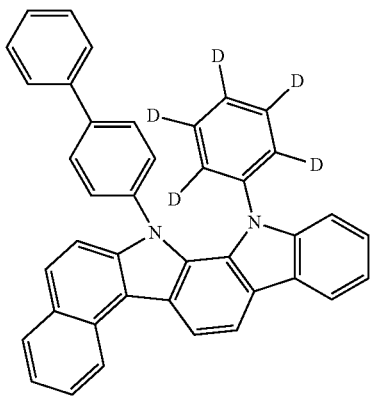

S-106
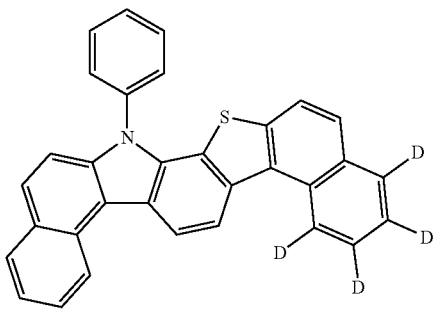

S-107
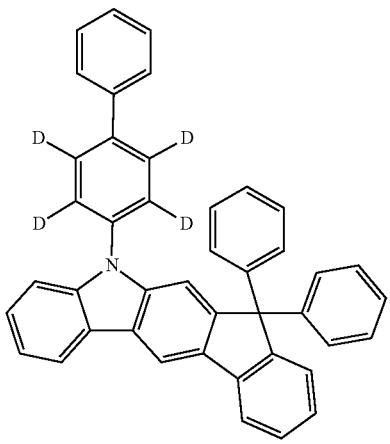

S-108
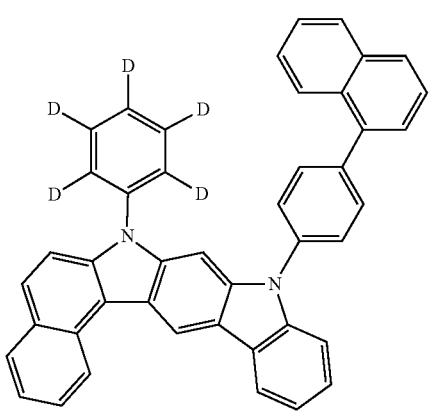

The present invention may further include a light efficiency enhancing layer formed on at least one surface of the first electrode and the second electrode opposite to the organic material layer.

Also, the organic material layer may include 2 or more stacks including a hole transport layer, an emitting layer, and an electron transport layer sequentially formed on the anode, and the organic material layer may further include a charge generation layer formed between the 2 or more stacks.

In another aspect, the present invention provides an electronic device comprising a display device including the organic electronic element; and a control unit for driving the display device; here, the organic electronic element is at least one of an OLED, an organic solar cell, an organic photo conductor, an organic transistor and an element for monochromic or white illumination.

Hereinafter, Synthesis Examples of the compound represented by Formula according to the present invention and preparation examples of the organic electronic element according to the present invention will be described in detail by way of example, but are not limited to the following examples of the invention.

Synthesis Example

The compound (final products) represented by Formula (1) according to the present invention is synthesized by reacting Sub1 and Sub2 as shown in Scheme 1, but is not limited thereto.

<Reaction scheme 1>

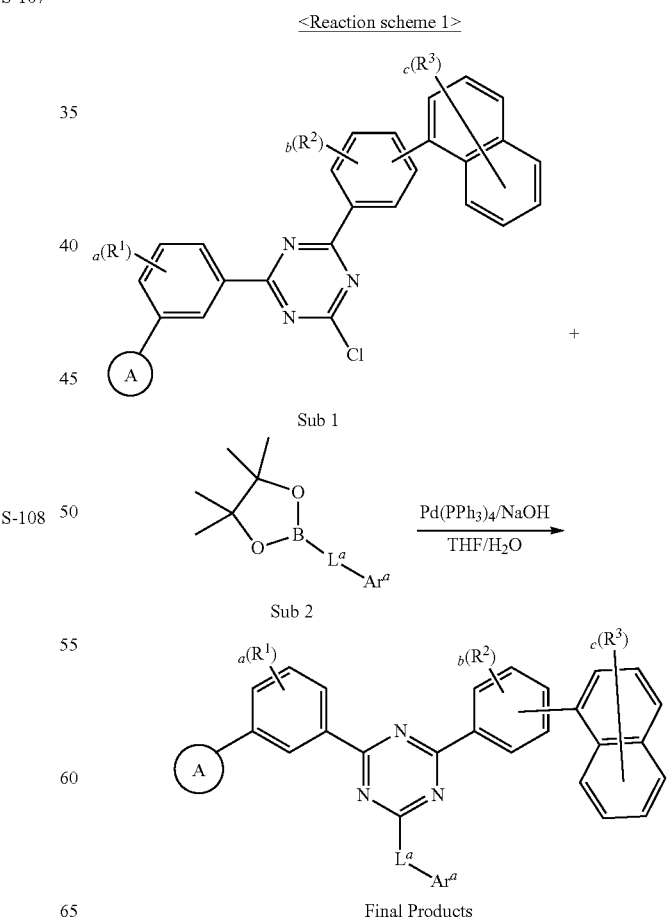

1. Synthesis of Sub 1
Sub 1 of Reaction Scheme 1 may be synthesized by the reaction route of Reaction Scheme 2, but is not limited thereto.
Synthesis examples of specific compounds belonging to Sub 1 are as follows.
1. Synthesis Example of Sub 1-1
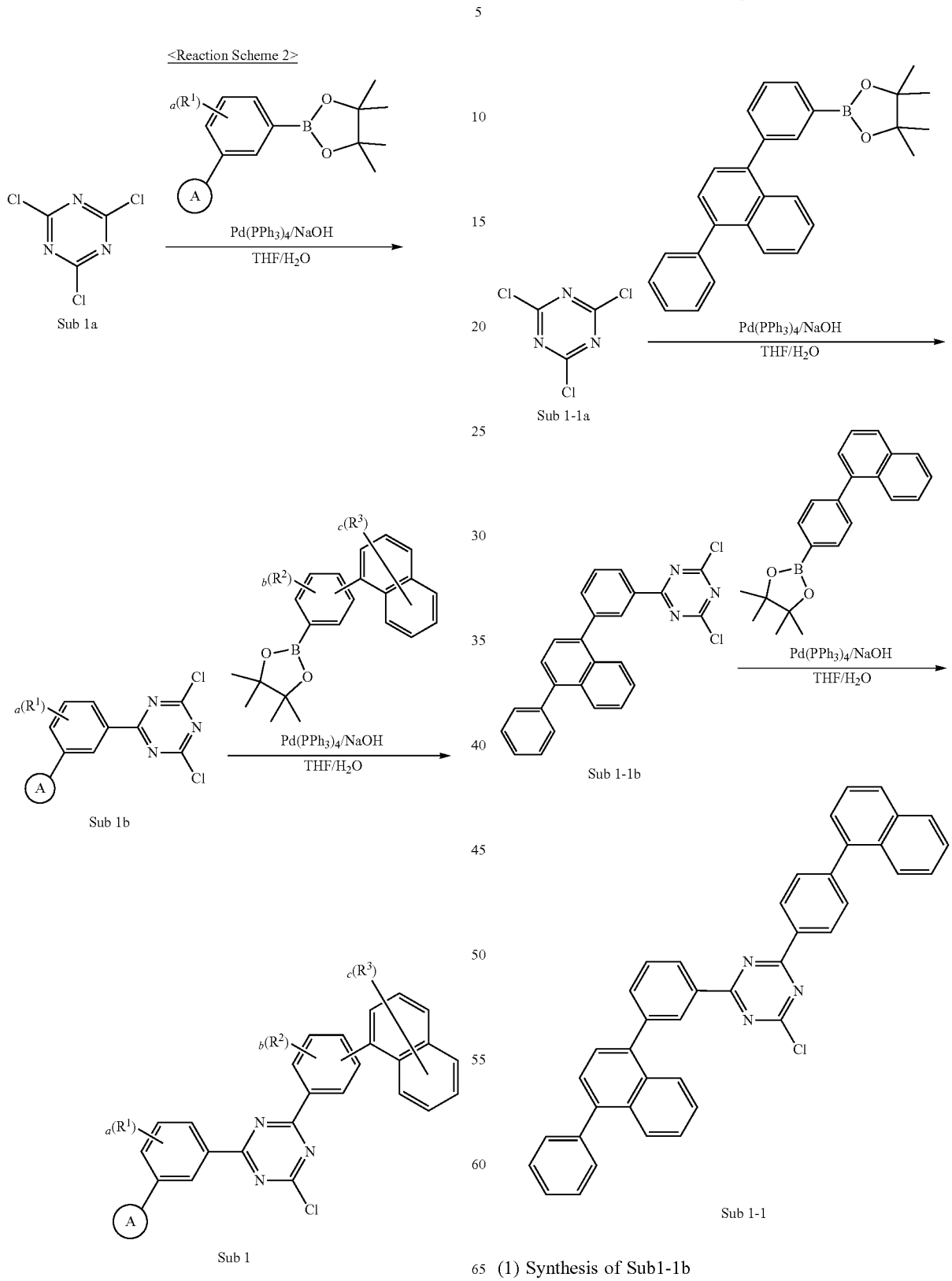
(1) Synthesis of Sub1-1b
Sub1-1a (40.84 g, 221.49 mmol), Sub2-36 (30.00 g, 73.83 mmol), Pd(PPh$_3$)$_4$ (2.56 g, 2.21 mmol), NaOH (5.91 g, 147.66 mmol) were put into a round-bottom flask, and 246 mL of anhydrous THF and 81 mL of water were added and dissolved, followed by refluxing for 12 hours. When the reaction was completed, the reactant was cooled to room temperature, extracted with $CH_2Cl_2$ and water, and then treated with $MgSO_4$. The organic solvent was concentrated and the resulting product was recrystallized using silica gel column to obtain 24.00 g (80%) of Sub1-1b.

(2) Synthesis of Sub1-1

The obtained Sub1-1b (23.93 g, 55.87 mmol) and Sub2-26 (12.30 g, 37.25 mmol), $Pd(PPh_3)_4$ (1.29 g, 1.12 mmol), NaOH (2.98 g, 74.49 mmol) were dissolved in 124 mL of THF and 40 mL of water in a round-bottom flask and stirred at 60° C. for 12 hours.

When the reaction was completed, the reactant was cooled to room temperature, extracted with $CH_2Cl_2$ and water, and then treated with $MgSO_4$. The organic solvent was concentrated and the resulting product was recrystallized using silica gel column to obtain 16.00 g (74%) of Sub1-1.

2. Synthesis Example of Sub 1-2

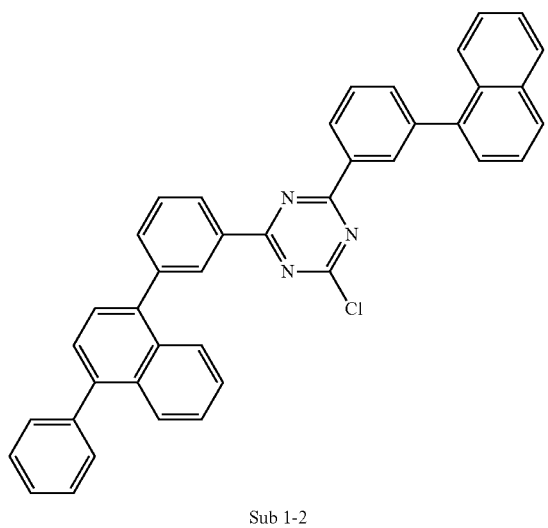

Sub 1-2

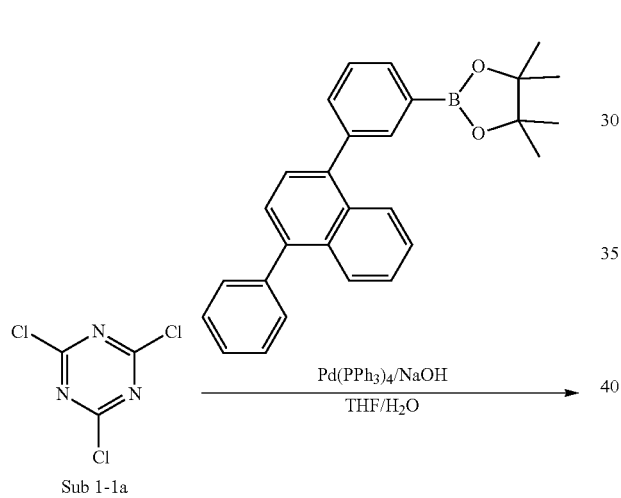

The obtained Sub1-1b (23.93 g, 55.87 mmol) and Sub2-37 (12.30 g, 37.25 mmol), $Pd(PPh_3)_4$ (1.29 g, 1.12 mmol), NaOH (2.98 g, 74.49 mmol) were dissolved in 124 mL of THF and 40 mL of water in a round-bottom flask and stirred at 60° C. for 12 hours. When the reaction was completed, the reactant was cooled to room temperature, extracted with $CH_2Cl_2$ and water, and then treated with $MgSO_4$. The organic solvent was concentrated and the resulting product was recrystallized using silica gel column to obtain 14.43 g (65%) of Sub1-2.

3. Synthesis Example of Sub 1-3

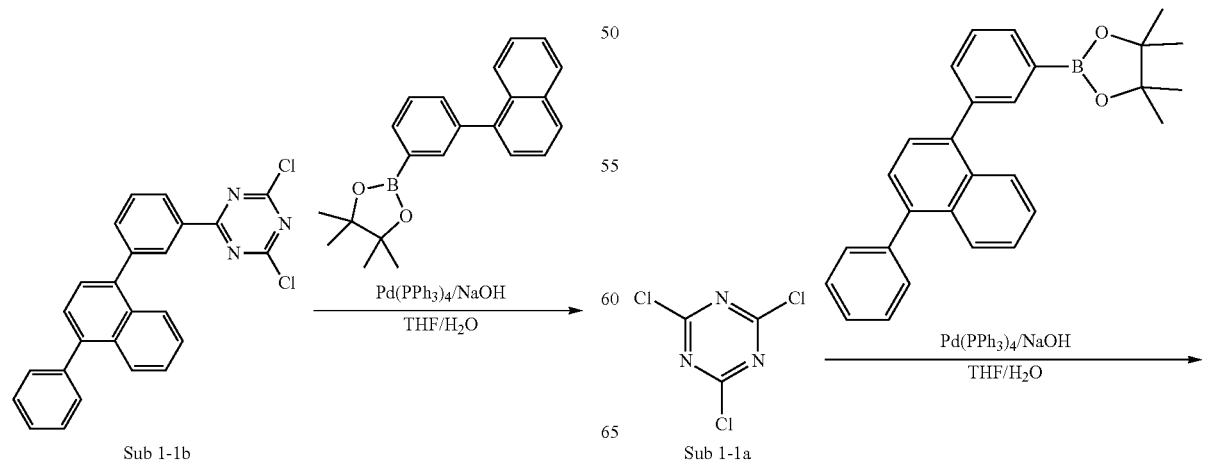

-continued

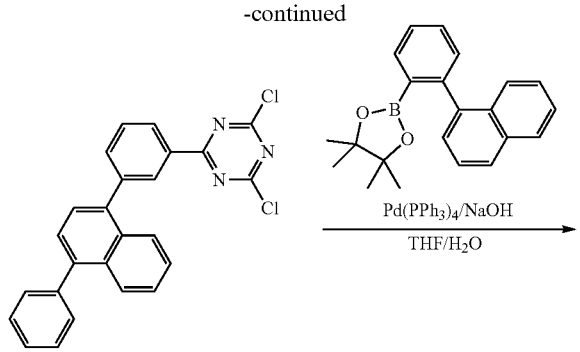

Sub 1-1b

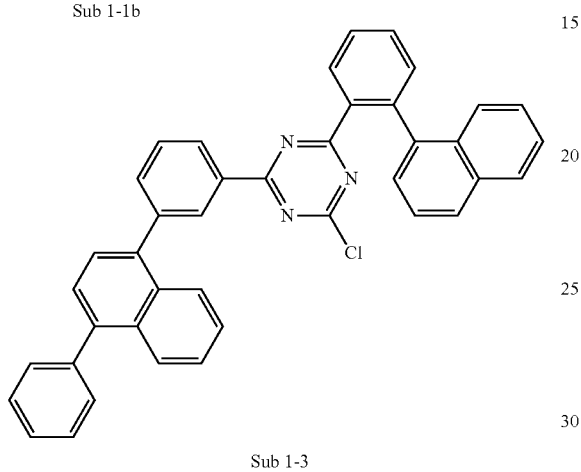

Sub 1-3

The obtained Sub1-1b (23.93 g, 55.87 mmol) and Sub2-38 (12.30 g, 37.25 mmol), Pd(PPh$_3$)$_4$ (1.29 g, 1.12 mmol), NaOH (2.98 g, 74.49 mmol) were dissolved in 124 mL of THF and 40 mL of water in a round-bottom flask and stirred at 60° C. for 12 hours. When the reaction was completed, the reactant was cooled to room temperature, extracted with CH$_2$Cl$_2$ and water, and then treated with MgSO$_4$. The organic solvent was concentrated and the resulting product was recrystallized using silica gel column to obtain 8.88 g (40%) of Sub1-3.

4. Synthesis Example of Sub 1-5

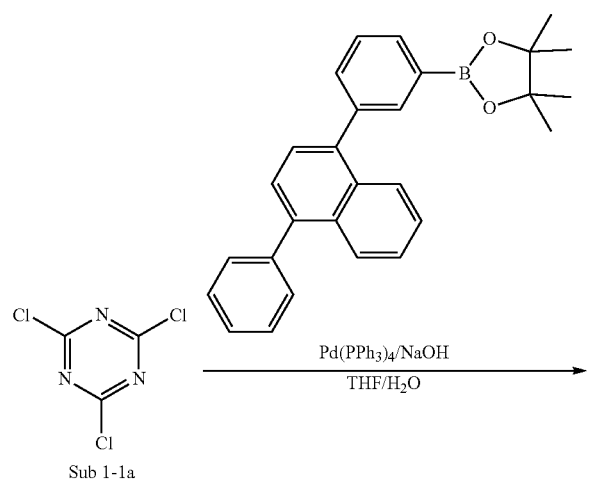

Sub 1-1a

-continued

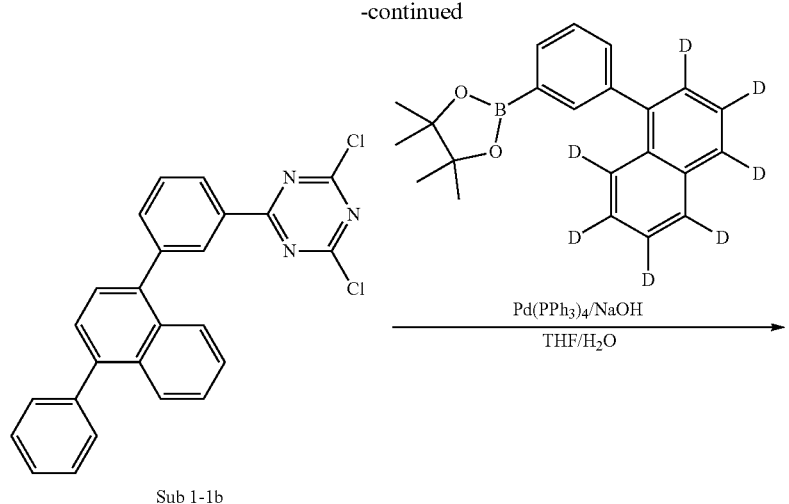

Sub 1-1b

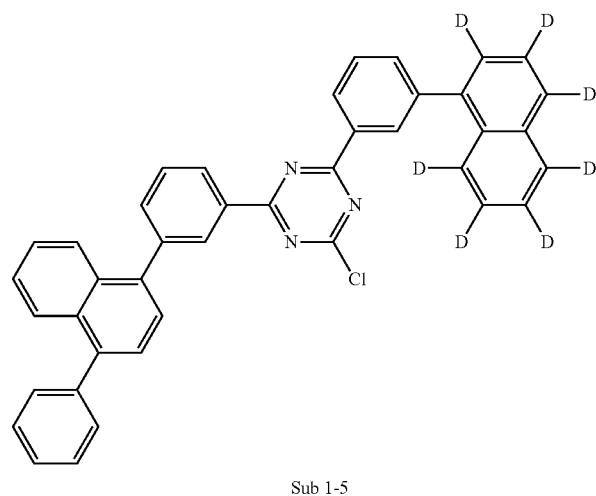

Sub 1-5

The obtained Sub1-1b (20.95 g, 48.92 mmol) and Sub2-44 (11.00 g, 32.61 mmol), Pd(PPh$_3$)$_4$ (1.13 g, 0.98 mmol), NaOH (2.61 g, 65.23 mmol) were dissolved in 109 mL of THF and 35 mL of water in a round-bottom flask and stirred at 60° C. for 12 hours. When the reaction was completed, the reactant was cooled to room temperature, extracted with CH$_2$Cl$_2$ and water, and then treated with MgSO$_4$. The organic solvent was concentrated and the resulting product was recrystallized using silica gel column to obtain 15.74 g (80%) of Sub1-5.

5. Synthesis Example of Sub 1-7

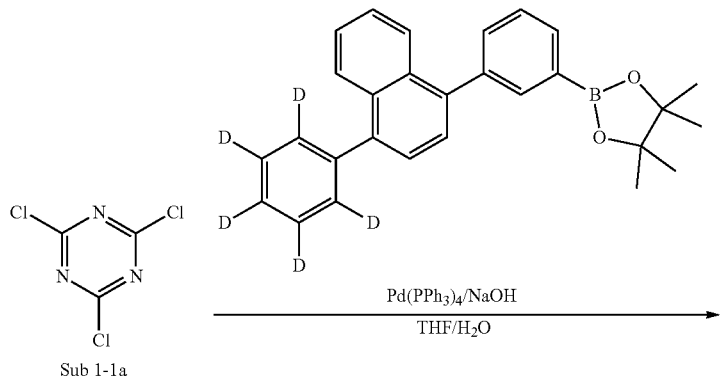

-continued

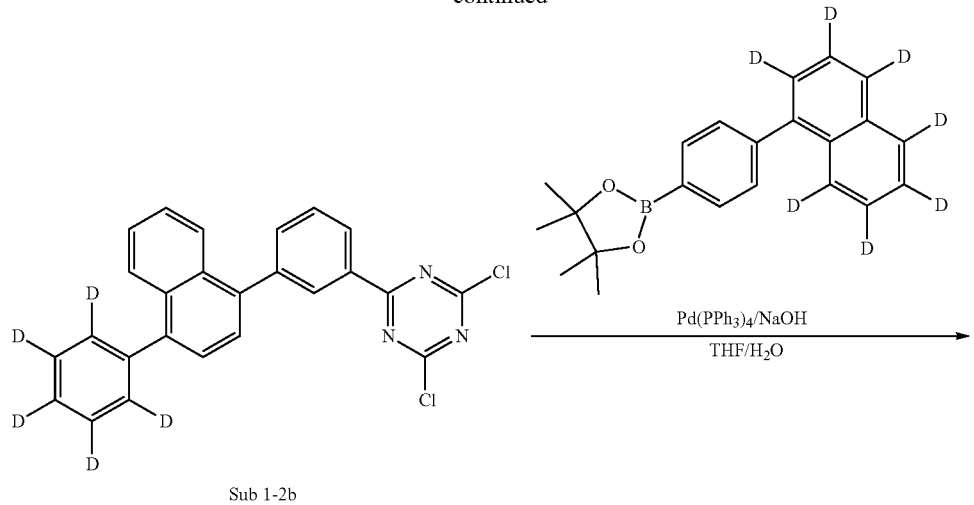
Sub 1-2b

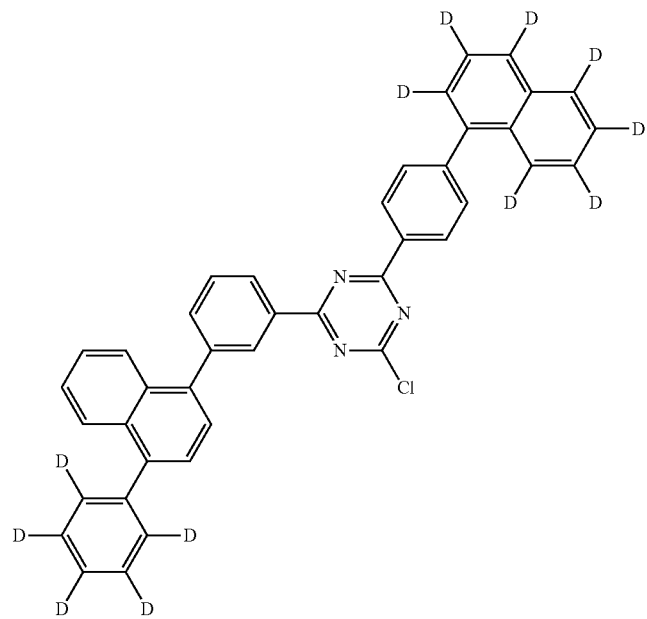
Sub1-7

(1) Synthesis of Sub1-2b

Put Sub1-1a (53.79 g, 291.72 mmol), Sub2-40 (40.00 g, 97.24 mmol), Pd(PPh$_3$)$_4$ (3.37 g, 2.92 mmol), NaOH (7.78 g, 194.48 mmol) in a round-bottom flask, add 324 mL of anhydrous THF and 108 mL of water to dissolve, and reflux for 12 hours. When the reaction was completed, the reactant was cooled to room temperature, extracted with CH$_2$Cl$_2$ and water, and then treated with MgSO$_4$. The organic solvent was concentrated and the resulting product was recrystallized using silica gel column to obtain 27.39 g (64%) of Sub1-2b.

(2) Synthesis of Sub1-7

The obtained Sub1-2b (19.27 g, 44.47 mmol) and Sub2-43 (10.00 g, 29.65 mmol), Pd(PPh$_3$)$_4$ (1.03 g, 0.89 mmol), NaOH (2.37 g, 59.30 mmol) were dissolved in 99 mL of THF and 33 mL of water in a round-bottom flask and stirred at 60° C. for 12 hours. When the reaction was completed, the reactant was cooled to room temperature, extracted with CH$_2$Cl$_2$ and water, and then treated with MgSO$_4$. The organic solvent was concentrated and the resulting product was recrystallized using silica gel column to obtain 14.43 g (81%) of Sub1-7.

6. Synthesis Example of Sub 1-9

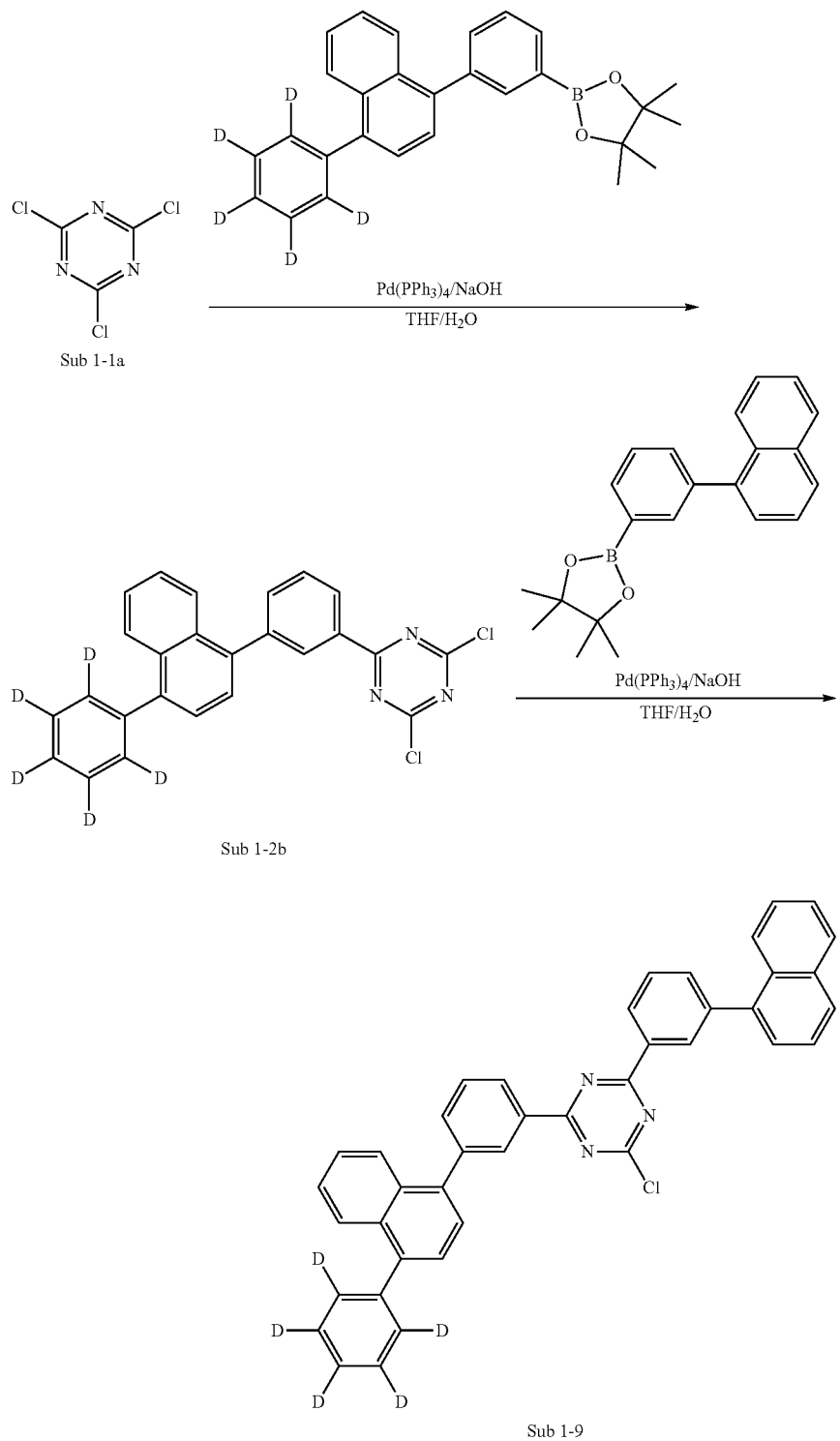

The obtained Sub1-2b (25.59 g, 59.05 mmol) and Sub2-37 (13.00 g, 39.37 mmol), Pd(PPh$_3$)$_4$ (1.37 g, 1.18 mmol), NaOH (3.15 g, 78.73 mmol) were dissolved in 131 mL of THF and 41 mL of water in a round-bottom flask and stirred at 60° C. for 12 hours. When the reaction was completed, the reactant was cooled to room temperature, extracted with CH$_2$Cl$_2$ and water, and then treated with MgSO$_4$. The organic solvent was concentrated and the resulting product was recrystallized using silica gel column to obtain 17.75 g (74%) of Sub1-9.

7. Synthesis Example of Sub 1-11

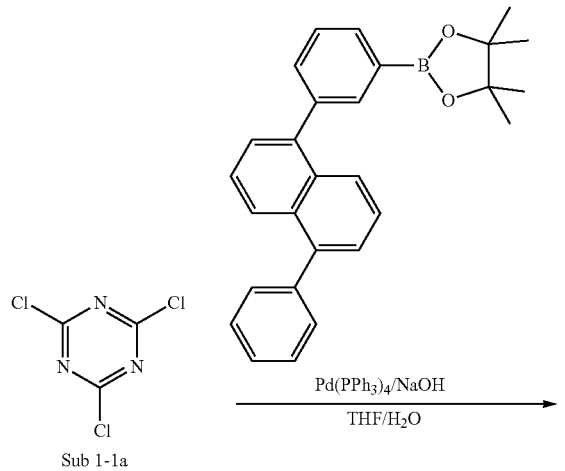

Sub 1-1a

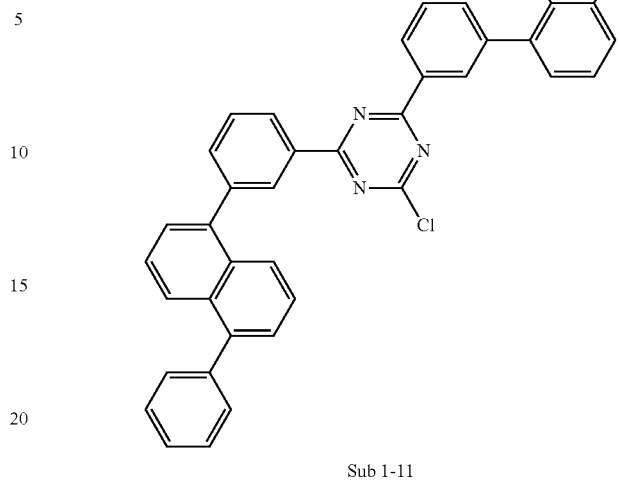

Sub 1-11

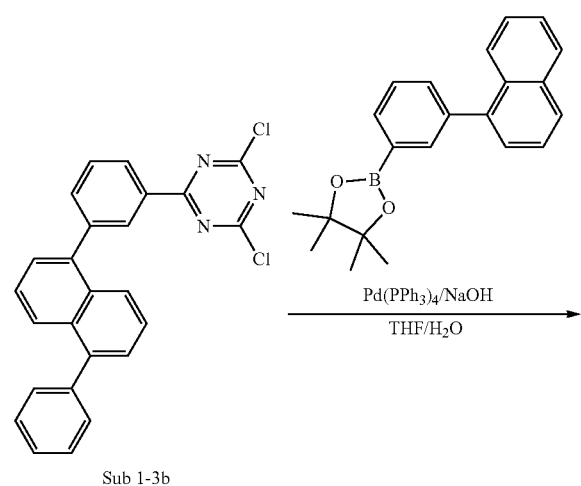

Sub 1-3b (1) Synthesis of Sub1-3b

Put Sub1-1a (47.65 g, 258.41 mmol), Sub2-46 (35.00 g, 86.14 mmol), Pd(PPh$_3$)$_4$ (2.99 g, 2.58 mmol), NaOH (6.89 g, 172.27 mmol) in a round-bottom flask, add 290 mL of anhydrous THF and 96 mL of water to dissolve, and reflux for 12 hours. When the reaction was completed, the reactant was cooled to room temperature, extracted with CH$_2$Cl$_2$ and water, and then treated with MgSO$_4$. The organic solvent was concentrated and the resulting product was recrystallized using silica gel column to obtain 29.52 g (80%) of Sub1-3b (2) Synthesis of Sub1-11

The obtained Sub1-3b (27.24 g, 63.59 mmol) and Sub2-37 (14.00 g, 42.39 mmol), Pd(PPh$_3$)$_4$ (1.47 g, 1.27 mmol), NaOH (3.39 g, 84.79 mmol) were dissolved in 141 mL of THF and 50 mL of water in a round-bottom flask and stirred at 60° C. for 12 hours. When the reaction was completed, the reactant was cooled to room temperature, extracted with CH$_2$Cl$_2$ and water, and then treated with MgSO$_4$. The organic solvent was concentrated and the resulting product was recrystallized using silica gel column to obtain 19.21 g (76%) of Sub1-11.

8. Synthesis Example of Sub 1-13

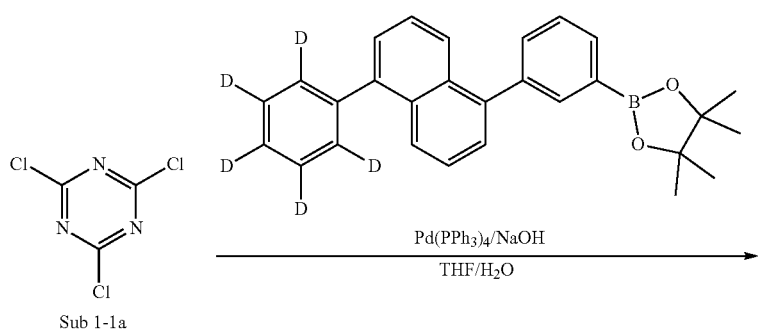

Sub 1-1a

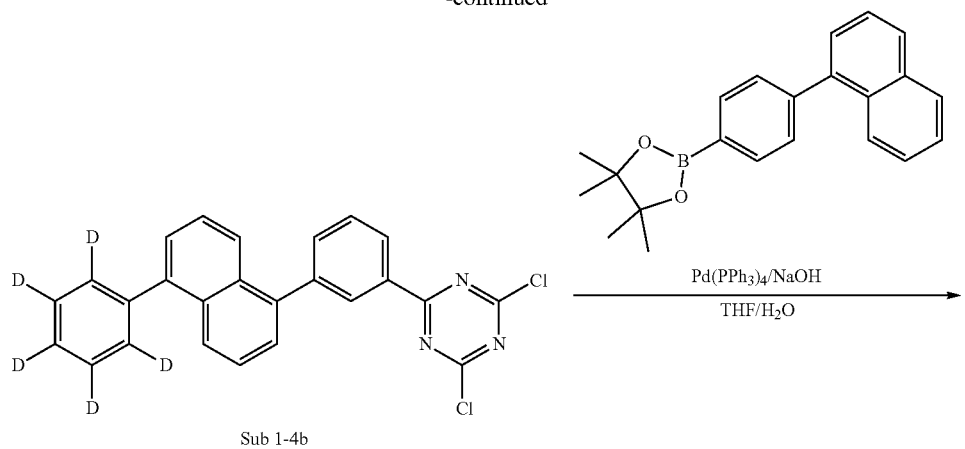

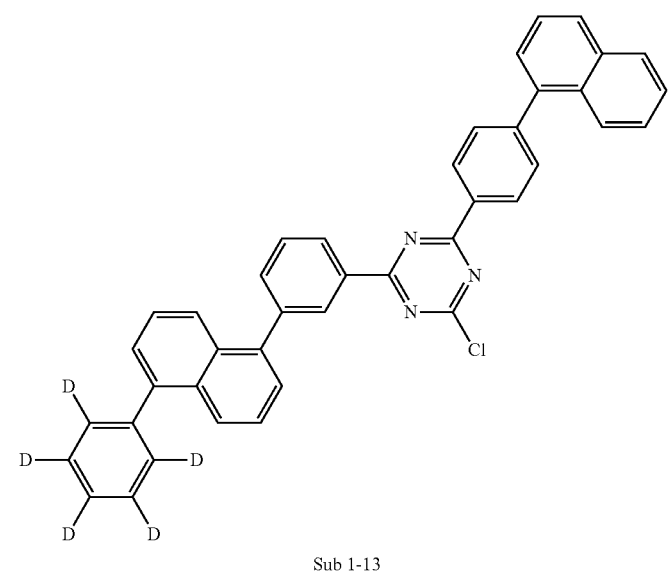

(1) Synthesis of Sub1-4b

Put Sub1-1a (40.34 g, 218.79 mmol), Sub2-47 (30.00 g, 72.93 mmol), Pd(PPh₃)₄ (2.53 g, 2.19 mmol), NaOH (5.83 g, 145.86 mmol) in a round-bottom flask, add 243 mL of anhydrous THF and 81 mL of water to dissolve, and reflux for 12 hours. When the reaction was completed, the reactant was cooled to room temperature, extracted with CH₂Cl₂ and water, and then treated with MgSO₄. The organic solvent was concentrated and the resulting product was recrystallized using silica gel column to obtain 19.59 g (62%) of Sub1-4b.

(2) Synthesis of Sub1-13

The obtained Sub1-4b (15.75 g, 36.34 mmol) and Sub2-26 (8.00 g, 24.23 mmol), Pd(PPh₃)₄ (0.84 g, 0.73 mmol), NaOH (1.94 g, 48.45 mmol) were dissolved in 80 mL of THF and 26 mL of water in a round-bottom flask and stirred at 60° C. for 12 hours. When the reaction was completed, the reactant was cooled to room temperature, extracted with CH₂Cl₂ and water, and then treated with MgSO₄. The organic solvent was concentrated and the resulting product was recrystallized using silica gel column to obtain 8.01 g (55%) of Sub1-13.

9. Synthesis Example of Sub 1-14

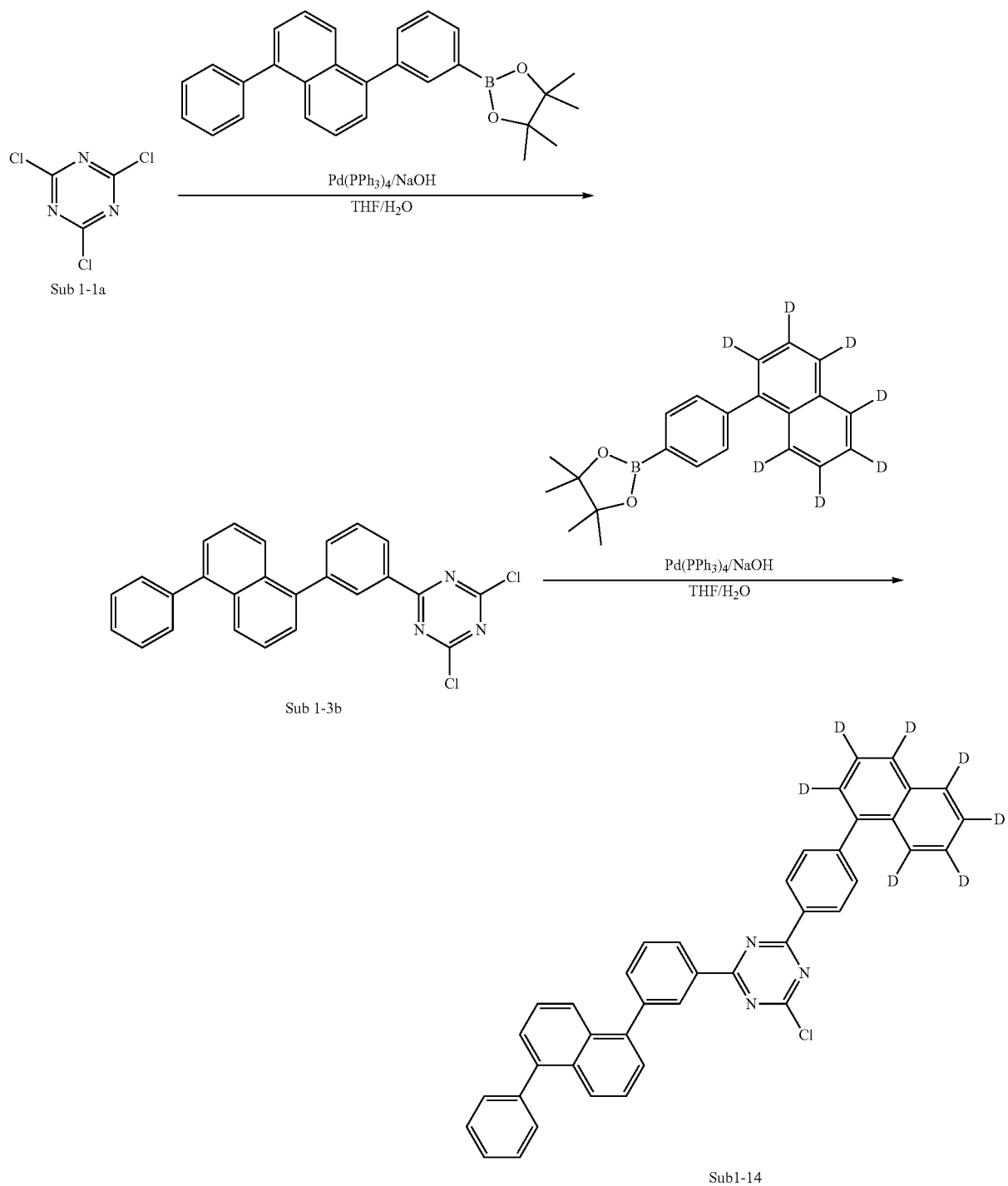

The obtained Sub1-3b (26.67 g, 62.26 mmol) and Sub2-43 (14.00 g, 41.51 mmol), Pd(PPh₃)₄ (1.44 g, 1.25 mmol), NaOH (3.32 g, 83.02 mmol) were dissolved in 138 mL of THF and 46 mL of water in a round-bottom flask and stirred at 60° C. for 12 hours. When the reaction was completed, the reactant was cooled to room temperature, extracted with CH₂Cl₂ and water, and then treated with MgSO₄. The organic solvent was concentrated and the resulting product was recrystallized using silica gel column to obtain 17.17 g (68%) of Sub1-14.

Otherwise, the compound belonging to Sub 1 may be the following compounds, but is not limited thereto, and Table 1 shows FD-MS (Field Desorption-Mass Spectrometry) values of the compounds belonging to Sub 1.

Sub1-1
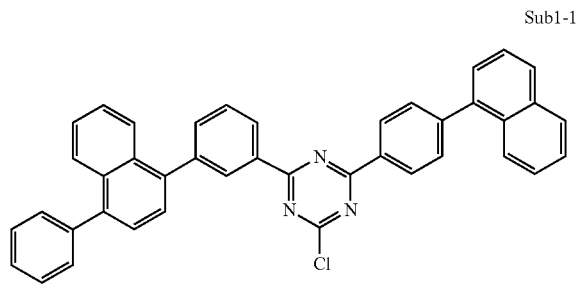
Sub1-2
Sub1-3
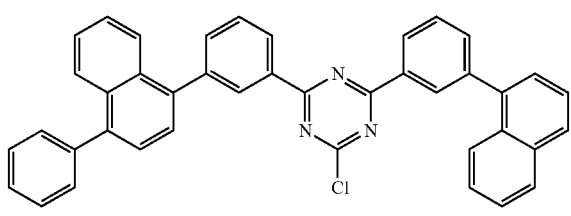
Sub1-4
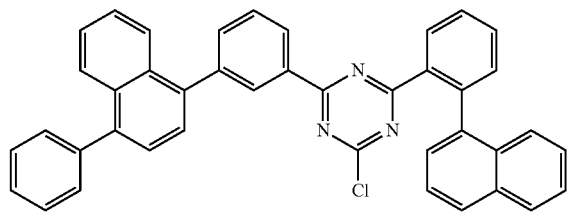
Sub1-5
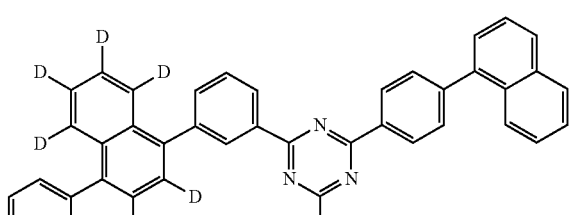
Sub1-6
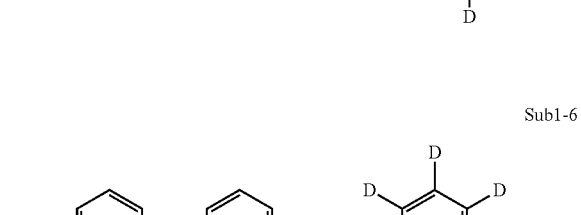
Sub1-7
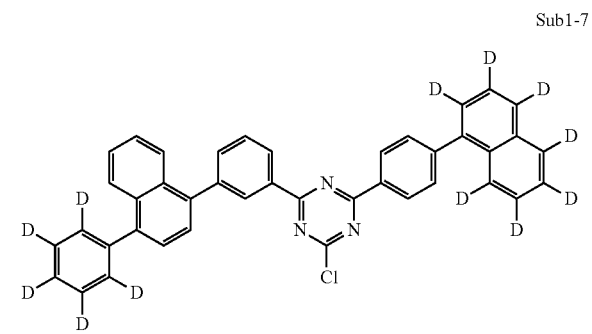
Sub1-8
Sub1-9
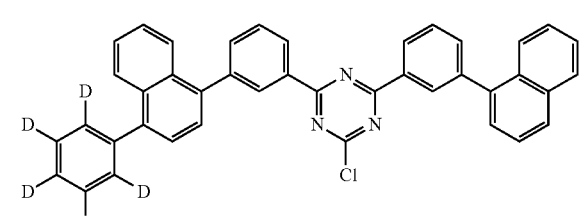
Sub1-10
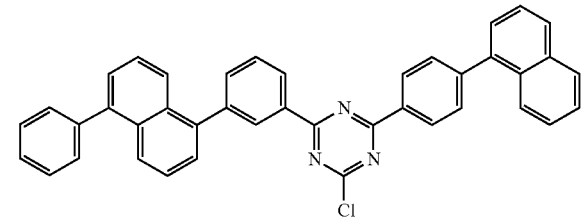
Sub1-11
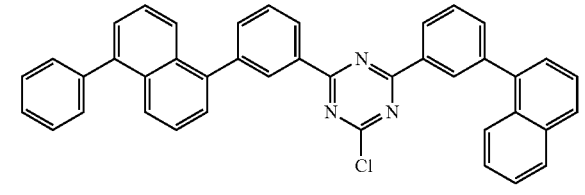
Sub1-12
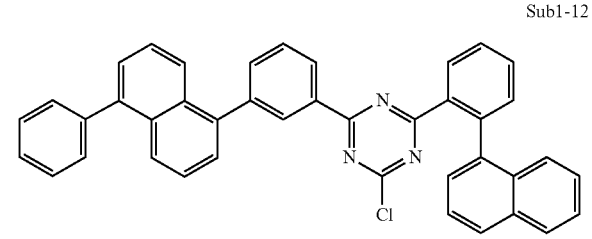

Sub1-13

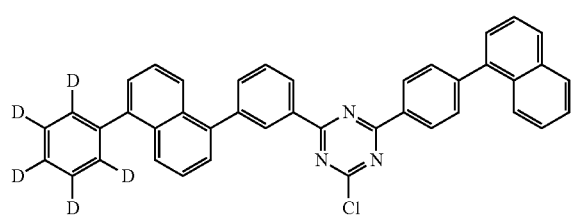

Sub1-16

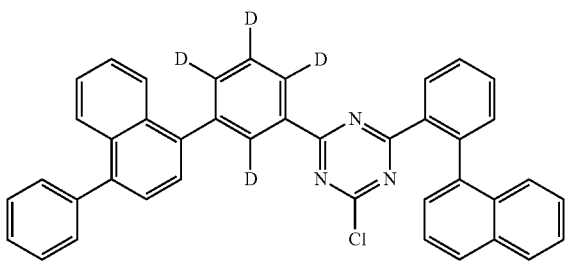

Sub1-14

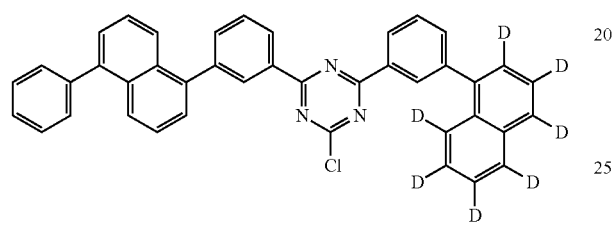

Sub1-15

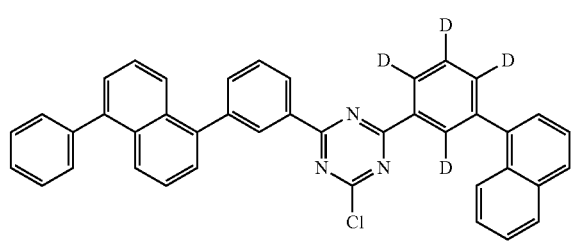

Sub1-17

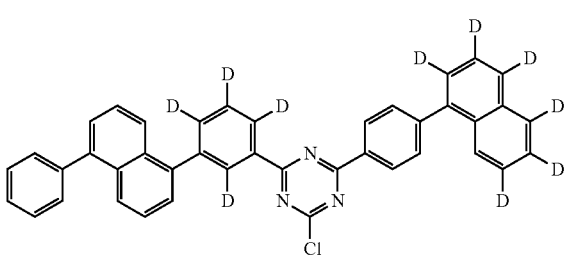

TABLE 1

| Cpd. | FD-MS | Cpd. | FD-MS |
|---|---|---|---|
| Sub1-1 | m/z = 595.18($C_{41}H_{26}ClN_3$ = 596.13) | Sub1-2 | m/z = 595.18($C_{41}H_{26}ClN_3$ = 596.13) |
| Sub1-3 | m/z = 595.18($C_{41}H_{26}ClN_3$ = 596.13) | Sub1-4 | m/z = 601.22($C_{41}H_{20}D_6ClN_3$ = 602.17) |
| Sub1-5 | m/z = 602.23($C_{41}H_{19}D_7ClN_3$ = 603.17) | Sub1-6 | m/z = 599.21($C_{41}H_{22}D_4ClN_3$ = 600.15) |
| Sub1-7 | m/z = 606.25($C_{41}H_{15}D_{11}ClN_3$ = 607.2) | Sub1-8 | m/z = 600.21($C_{41}H_{21}D_5ClN_3$ = 601.16) |
| Sub1-9 | m/z = 600.21($C_{41}H_{21}D_5ClN_3$ = 601.16) | Sub1-10 | m/z = 595.18($C_{41}H_{26}ClN_3$ = 596.13) |
| Sub1-11 | m/z = 595.18($C_{41}H_{26}ClN_3$ = 596.13) | Sub1-12 | m/z = 595.18($C_{41}H_{26}ClN_3$ = 596.13) |
| Sub1-13 | m/z = 600.21($C_{41}H_{21}D_5ClN_3$ = 601.16) | Sub1-14 | m/z = 602.23($C_{41}H_{19}D_7ClN_3$ = 603.17) |
| Sub1-15 | m/z = 599.21($C_{41}H_{22}D_4ClN_3$ = 600.15) | Sub1-16 | m/z = 599.21($C_{41}H_{22}D_4ClN_3$ = 600.15) |
| Sub1-17 | m/z = 605.24($C_{41}H_{16}D_{10}ClN_3$ = 606.19) | | |

II. Synthesis of Sub 2

Sub 2 of Scheme 1 may be synthesized by the route of Reaction Scheme 3, but is not limited thereto. Hal1=Cl, Br <Reaction Scheme 3>

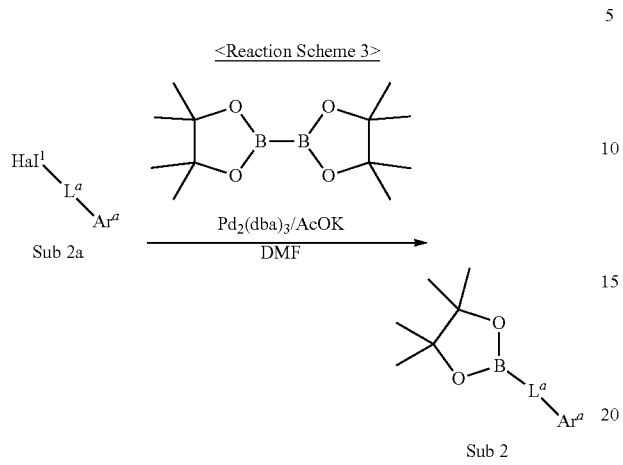

Sub 2

Synthesis examples of specific compounds belonging to Sub 2 are as follows.

1. Synthesis Example of Sub 2-1

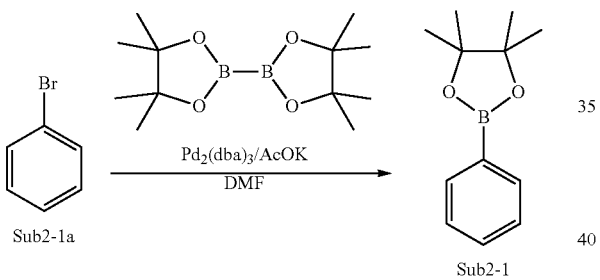

Sub2-1a (10.00 g, 63.69 mmol), 4,4,4',4',5,5,5',5'-octamethyl-2,2'-bi(1,3,2-dioxaborolane) (21.03 g, 82.80 mmol), Pd$_2$(dba)$_3$ (1.75 g, 1.91 mmol), AcOK (12.50 g, 127.38 mmol) were added to DMF (212 mL) and stirred at 160° C. for 4 h. After the reaction was completed, the reaction solvent was removed and the concentrated organic material was subjected to silicagel column or recrystallization to obtain 8.45 g (65%) of the product Sub2-1.

2. Synthesis Example of Sub 2-2

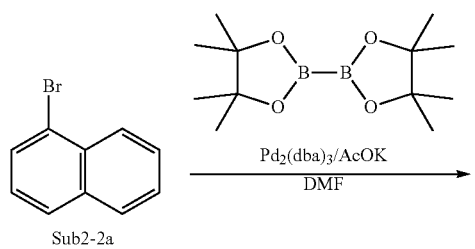

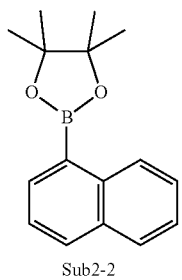

Sub2-2

Sub2-2a (10.00 g, 48.29 mmol), 4,4,4',4',5,5,5',5'-octamethyl-2,2'-bi(1,3,2-dioxaborolane) (15.94 g, 62.78 mmol), Pd$_2$(dba)$_3$ (1.33 g, 1.45 mmol), AcOK (9.48 g, 96.59 mmol) were added to DMF (161 mL) and stirred at 160° C. for 4 h. After the reaction was completed, the reaction solvent was removed and the concentrated organic material was subjected to silicagel column or recrystallization to obtain 7.36 g (60%) of the product Sub2-2.

3. Synthesis Example of Sub 2-7

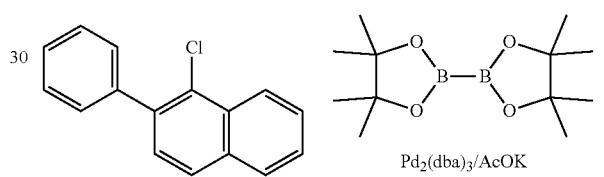

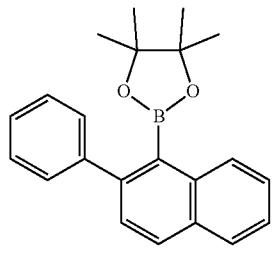

Sub2-7

Sub2-7a (10.00 g, 41.89 mmol)$^{0-}$|| 4,4,4',4',5,5,5',5'-octamethyl-2,2'-bi(1,3,2-dioxaborolane) (13.83 g, 54.46 mmol), Pd$_2$(dba)$_3$ (1.15 g, 1.26 mmol), AcOK (8.22 g, 83.78 mmol) were added to DMF (140 mL) and stirred at 160° C. for 4 h. After the reaction was completed, the reaction solvent was removed and the concentrated organic material was subjected to silicagel column or recrystallization to obtain 9.41 g (68%) of the product Sub2-7.

4. Synthesis Example of Sub 2-26

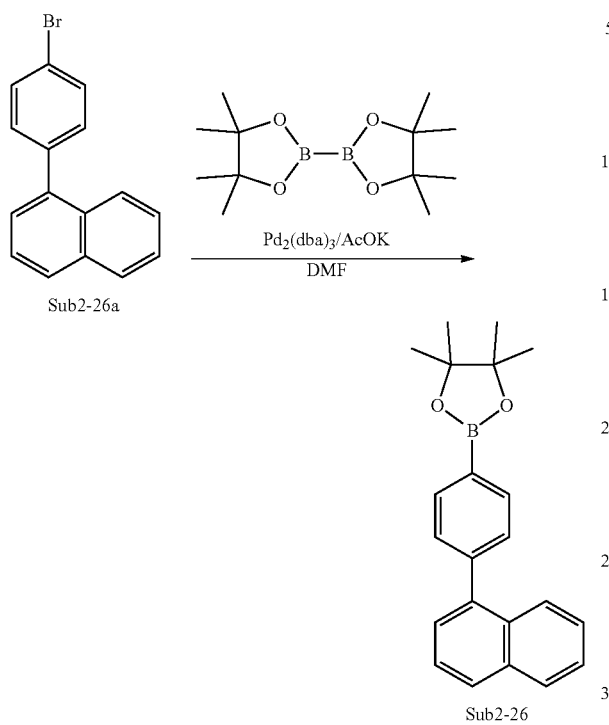

Sub2-26a (10.00 g, 35.31 mmol)$^{0-}$|| 4,4,4',4',5,5,5',5'-octamethyl-2,2'-bi(1,3,2-dioxaborolane) (11.66 g, 45.91 mmol), Pd$_2$(dba)$_3$ (0.97 g, 1.06 mmol), AcOK (6.93 g, 70.63 mmol) were added to DMF (117 mL) and stirred at 160° C. for 4 h. After the reaction was completed, the reaction solvent was removed and the concentrated organic material was subjected to silicagel column or recrystallization to obtain 7.35 g (63%) of the product Sub2-26.

5. Synthesis Example of Sub 2-29

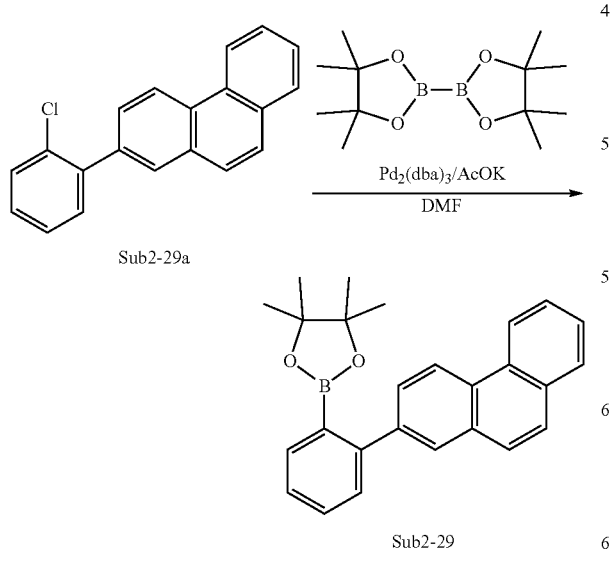

Sub2-29a (10.00 g, 34.63 mmol), 4,4,4',4',5,5,5',5'-octamethyl-2,2'-bi(1,3,2-dioxaborolane) (11.43 g, 45.02 mmol), Pd$_2$(dba)$_3$ (0.95 g, 1.04 mmol), AcOK (6.80 g, 69.26 mmol) were added to DMF (115 mL) and stirred at 160° C. for 4 h. After the reaction was completed, the reaction solvent was removed and the concentrated organic material was subjected to silicagel column or recrystallization to obtain 10.27 g (78%) of the product Sub2-29.

6. Synthesis Example of Sub 2-30

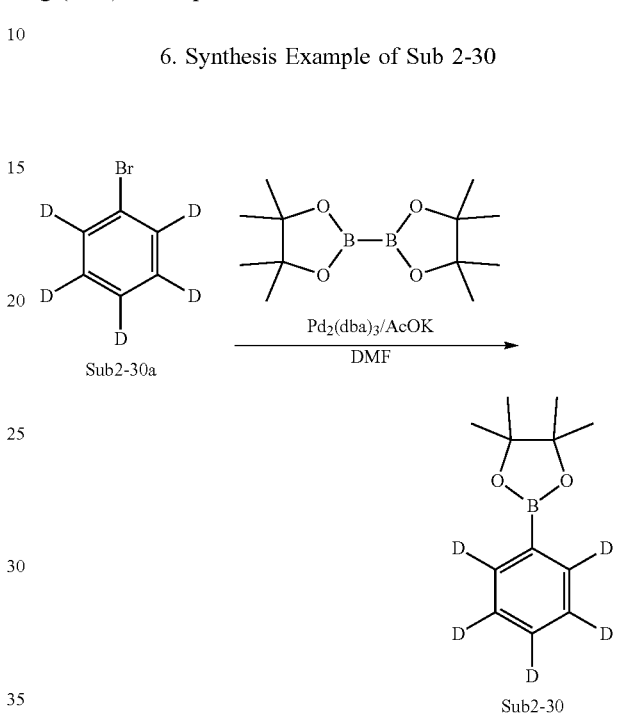

Sub2-30a (10.00 g, 61.71 mmol), 4,4,4',4',5,5,5',5'-octamethyl-2,2'-bi(1,3,2-dioxaborolane) (20.37 g, 80.23 mmol), Pd$_2$(dba)$_3$ (1.70 g, 1.85 mmol), AcOK (1.11 g, 123.43 mmol) were added to DMF (206 mL) and stirred at 160° C. for 4 h. After the reaction was completed, the reaction solvent was removed and the concentrated organic material was subjected to silicagel column or recrystallization to obtain 9.68 g (75%) of the product Sub2-30.

7. Synthesis Example of Sub 2-36

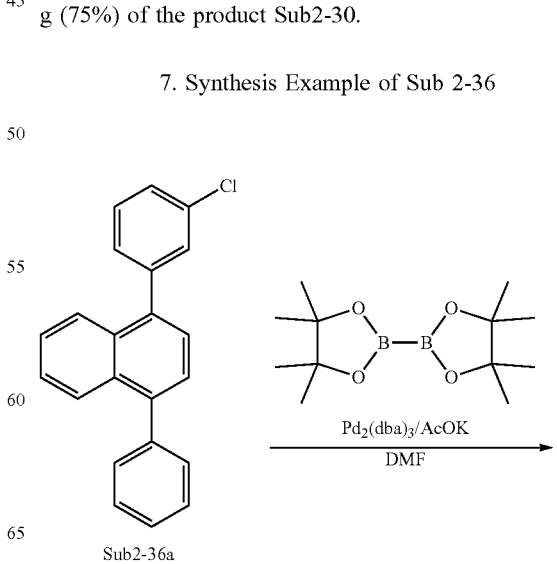

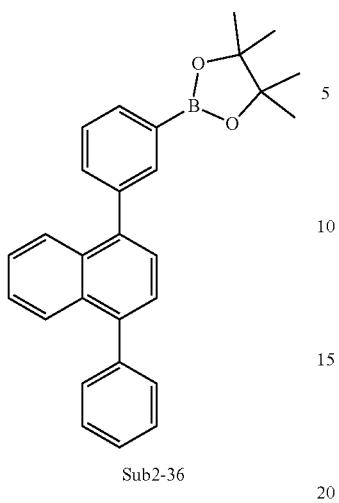

Sub2-36

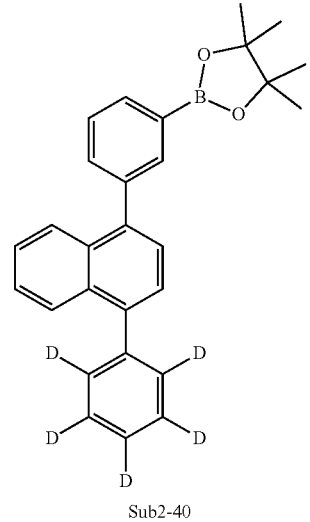

Sub2-40

Sub2-36a (10.00 g, 31.77 mmol), 4,4,4',4',5,5,5',5'-octamethyl-2,2'-bi(1,3,2-dioxaborolane) (10.49 g, 41.29 mmol), Pd$_2$(dba)$_3$ (0.87 g, 0.95 mmol), AcOK (6.23 g, 63.53 mmol) were added to DMF (106 mL) and stirred at 160° C. for 4 h. After the reaction was completed, the reaction solvent was removed and the concentrated organic material was subjected to silicagel column or recrystallization to obtain 10.33 g (80%) of the product Sub2-36.

Sub2-40a (10.00 g, 31.27 mmol), 4,4,4',4',5,5,5',5'-octamethyl-2,2'-bi(1,3,2-dioxaborolane) (10.32 g, 40.65 mmol), Pd$_2$(dba)$_3$ (0.86 g, 0.94 mmol), AcOK (6.14 g, 62.53 mmol) were added to DMF (105 mL) and stirred at 160° C. for 4 h. After the reaction was completed, the reaction solvent was removed and the concentrated organic material was subjected to silicagel column or recrystallization to obtain 9.00 g (70%) of the product Sub2-40.

9. Synthesis Example of Sub 2-43

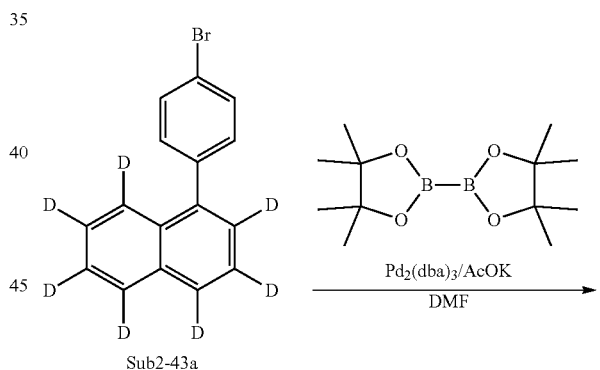

Sub2-43a

8. Synthesis Example of Sub 2-40

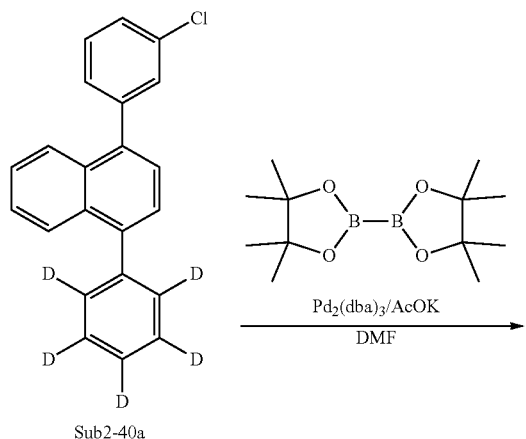

Sub2-40a

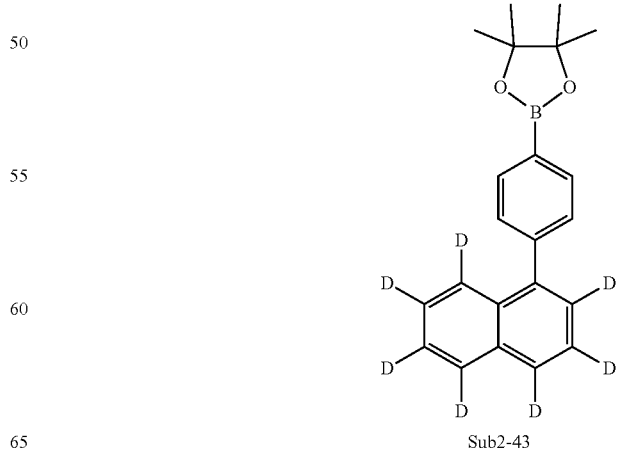

Sub2-43

Sub2-43a (10.00 g, 34.46 mmol), 4,4,4',4',5,5,5',5'-octamethyl-2,2'-bi(1,3,2-dioxaborolane) (11.38 g, 44.80 mmol), Pd₂(dba)₃ (0.95 g, 1.03 mmol), AcOK (6.76 g, 68.92 mmol) were added to DMF (115 mL) and stirred at 160° C. for 4 h. After the reaction was completed, the reaction solvent was removed and the concentrated organic material was subjected to silicagel column or recrystallization to obtain 8.60 g (74%) of the product Sub2-43.

10. Synthesis Example of Sub 2-46

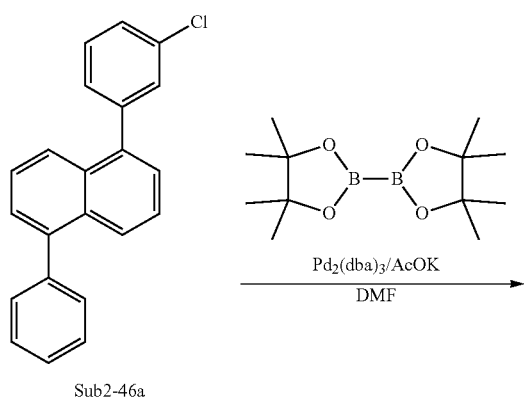

Sub2-46a

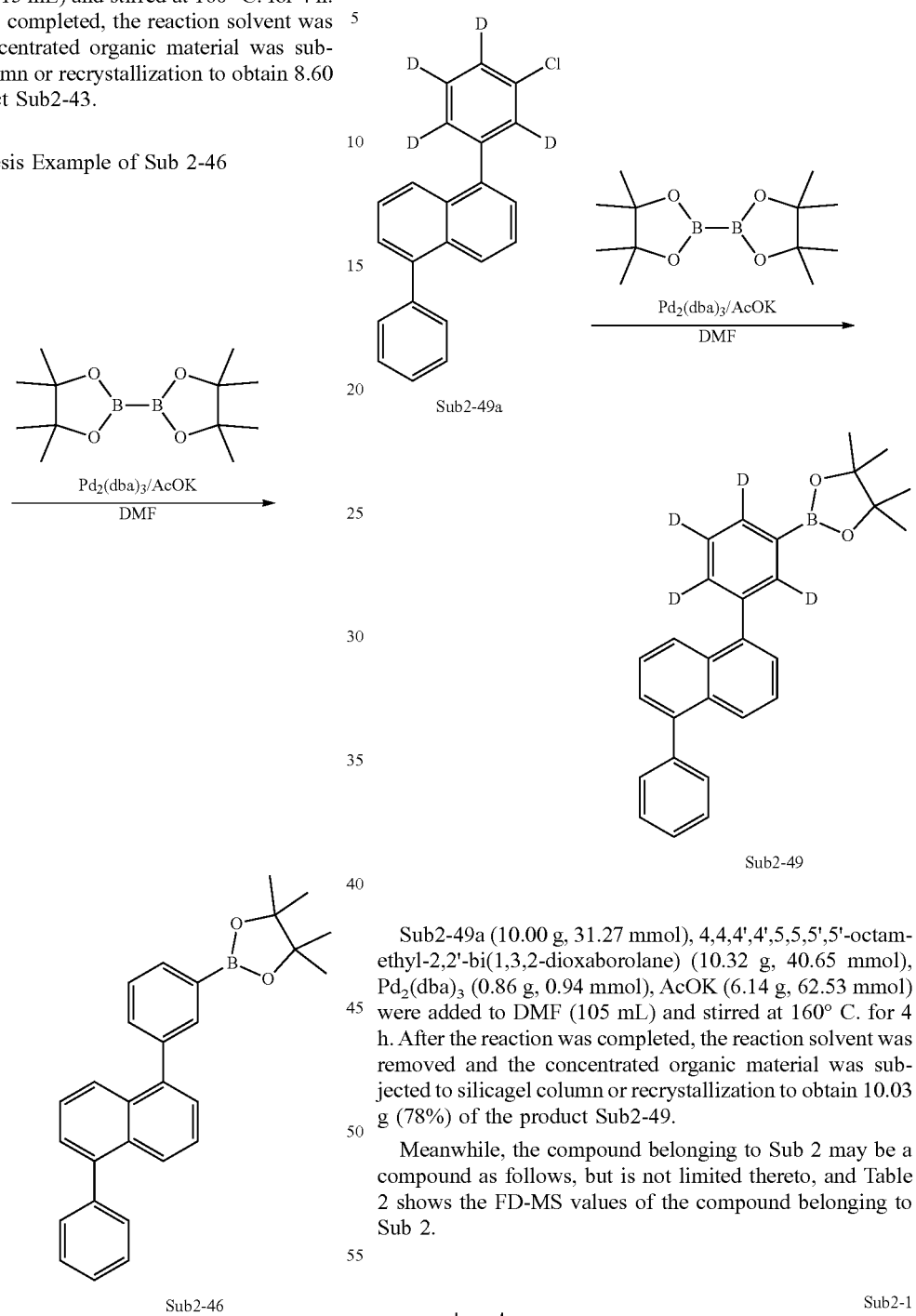

Sub2-46

Sub2-46a (10.00 g, 31.77 mmol), 4,4,4',4',5,5,5',5'-octamethyl-2,2'-bi(1,3,2-dioxaborolane) (10.49 g, 41.29 mmol), Pd₂(dba)₃ (0.87 g, 0.95 mmol), AcOK (6.23 g, 63.53 mmol) were added to DMF (106 mL) and stirred at 160° C. for 4 h. After the reaction was completed, the reaction solvent was removed and the concentrated organic material was subjected to silicagel column or recrystallization to obtain 9.03 g (70%) of the product Sub2-46.

11. Synthesis Example of Sub 2-49

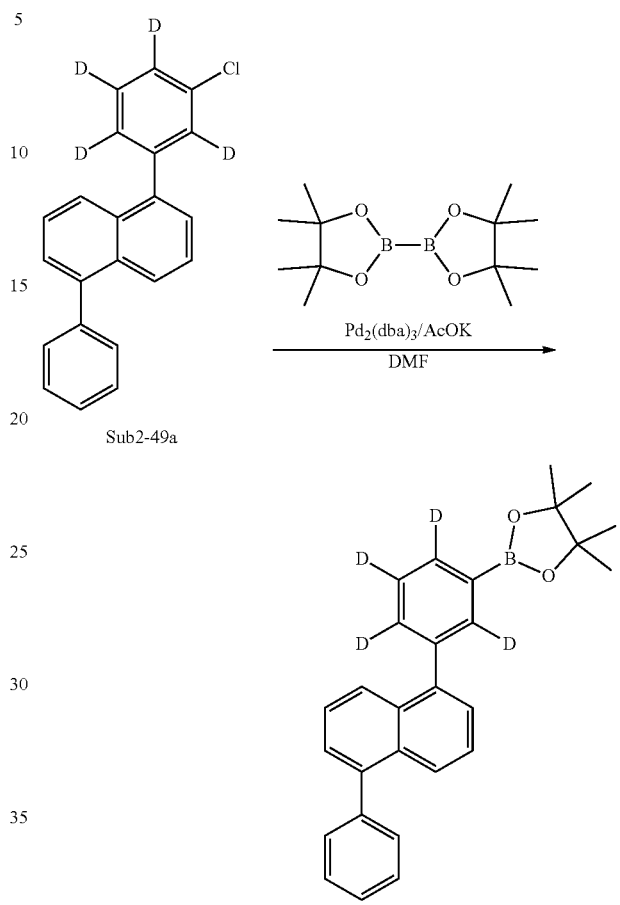

Sub2-49a (10.00 g, 31.27 mmol), 4,4,4',4',5,5,5',5'-octamethyl-2,2'-bi(1,3,2-dioxaborolane) (10.32 g, 40.65 mmol), Pd₂(dba)₃ (0.86 g, 0.94 mmol), AcOK (6.14 g, 62.53 mmol) were added to DMF (105 mL) and stirred at 160° C. for 4 h. After the reaction was completed, the reaction solvent was removed and the concentrated organic material was subjected to silicagel column or recrystallization to obtain 10.03 g (78%) of the product Sub2-49.

Meanwhile, the compound belonging to Sub 2 may be a compound as follows, but is not limited thereto, and Table 2 shows the FD-MS values of the compound belonging to Sub 2.

Sub2-1

Sub2-2 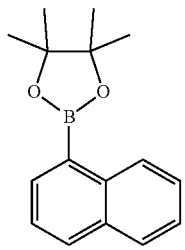
Sub2-3 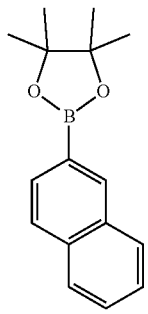
Sub2-4 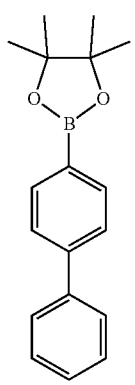
Sub2-5 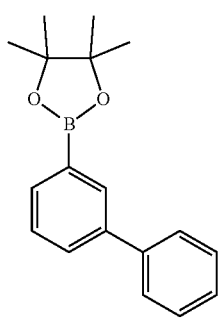
Sub2-6 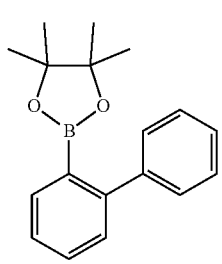
Sub2-7 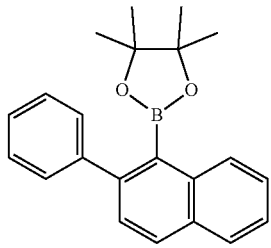
Sub2-8 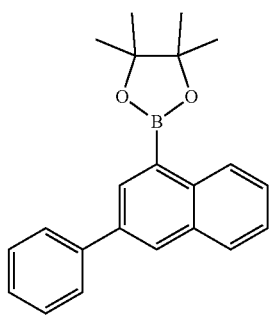
Sub2-9 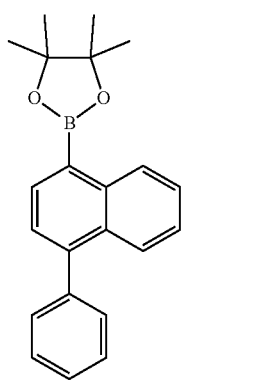
Sub2-10 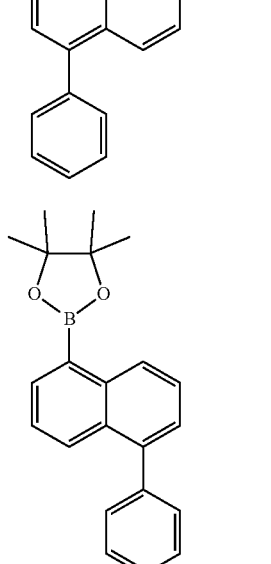
Sub2-11 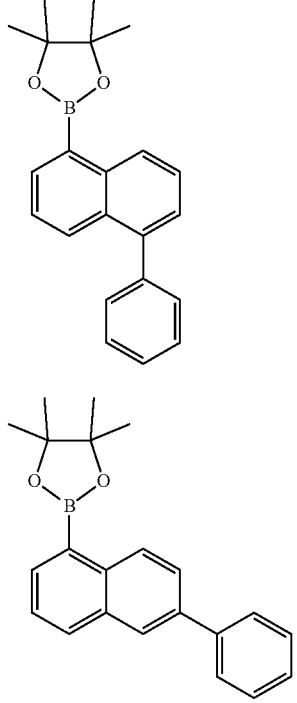

Sub2-12
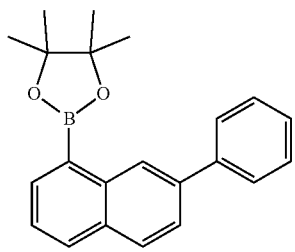
Sub2-13
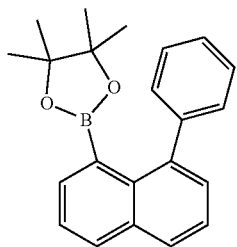
Sub2-14
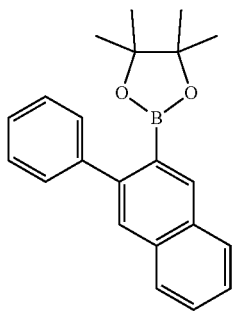
Sub2-15
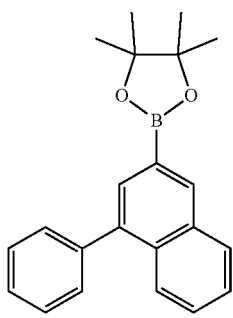
Sub2-16
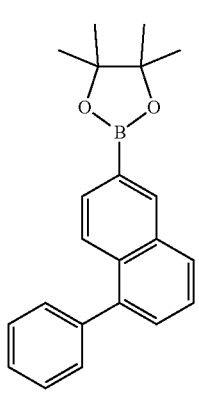
Sub2-17
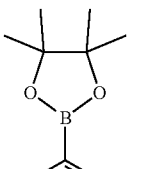
Sub2-18
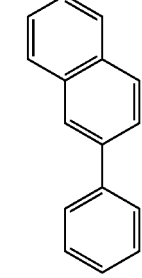
Sub2-19
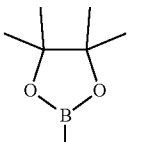
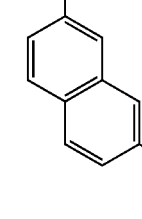
Sub2-20
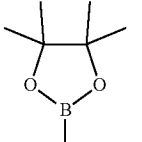
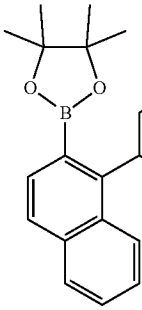

151
-continued
Sub2-21
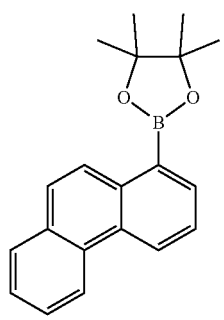
Sub2-22
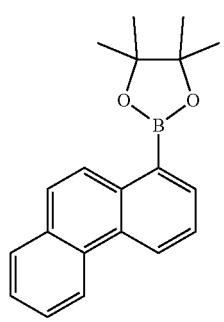
Sub2-23
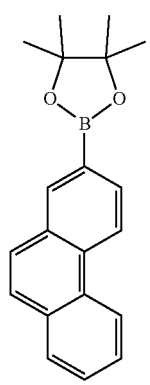
Sub2-24
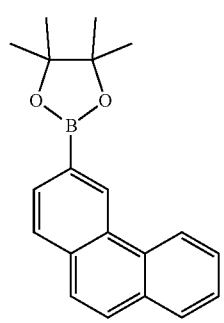
152
-continued
Sub2-25
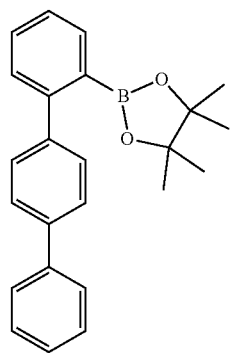
Sub2-26
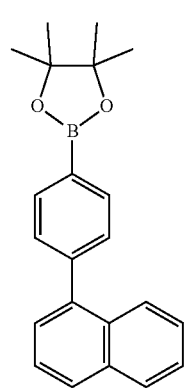
Sub2-27
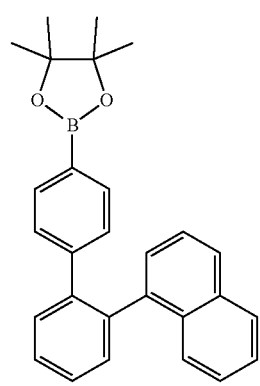
Sub2-29
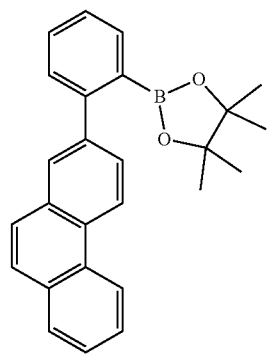

Sub2-30 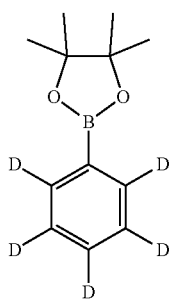
Sub2-31 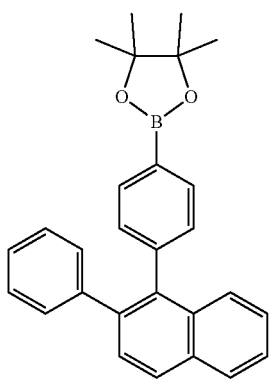
Sub2-32 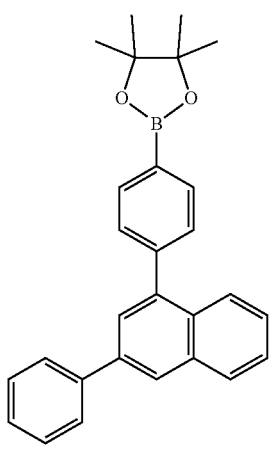
Sub2-33 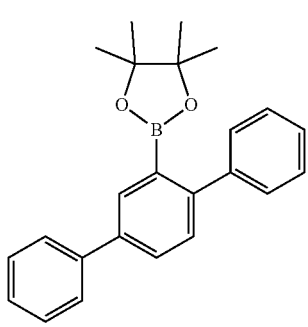
Sub2-34 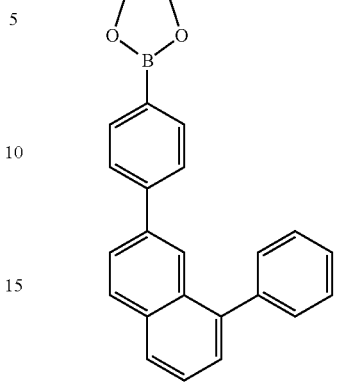
Sub2-35 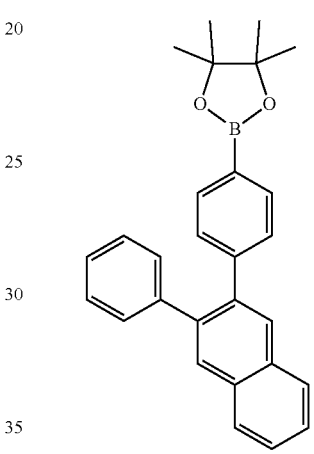
Sub2-36 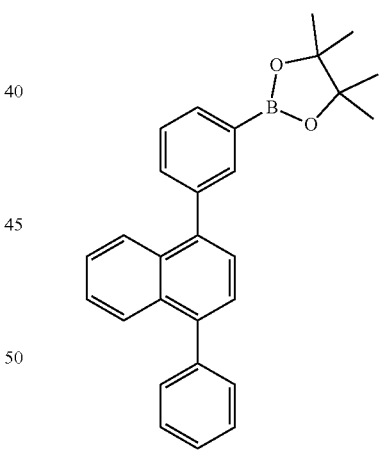
Sub2-37 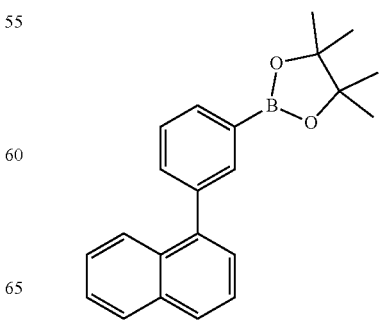

Sub2-38
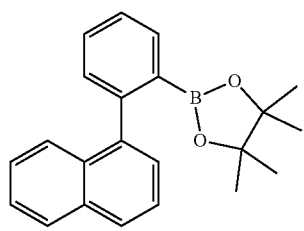
Sub2-39
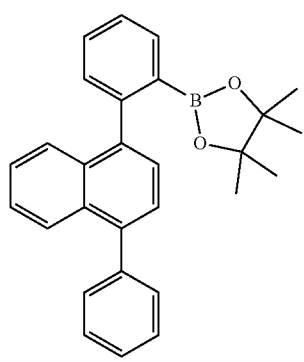
Sub2-40
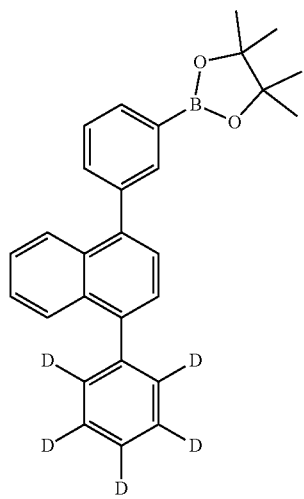
Sub2-41
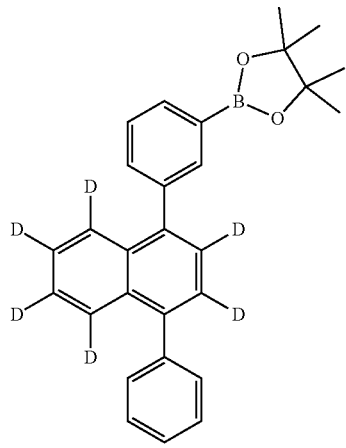
Sub2-42
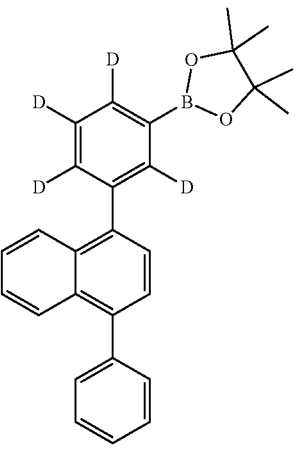
Sub2-43
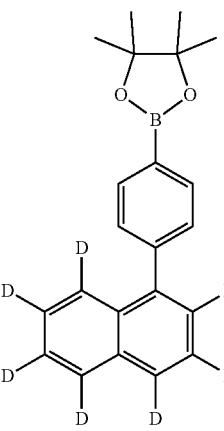
Sub2-44
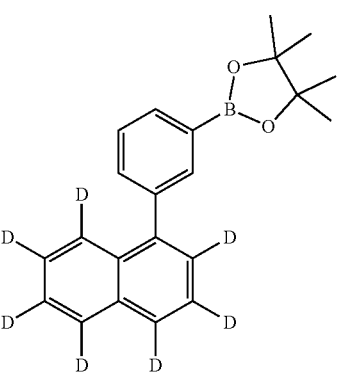
Sub2-45
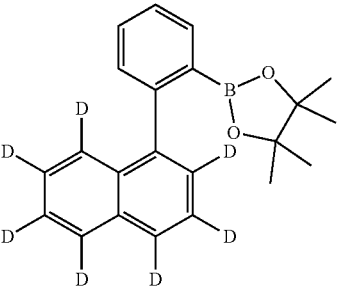

Sub2-46
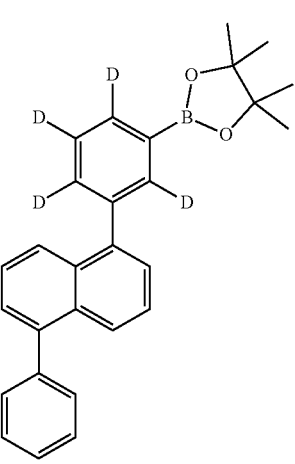
Sub2-47
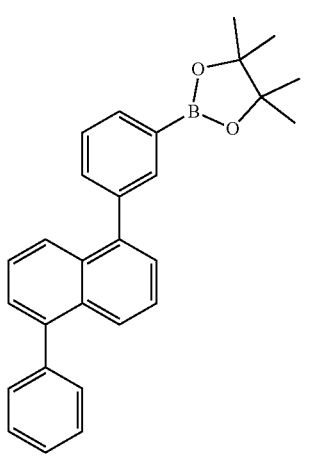
Sub2-48
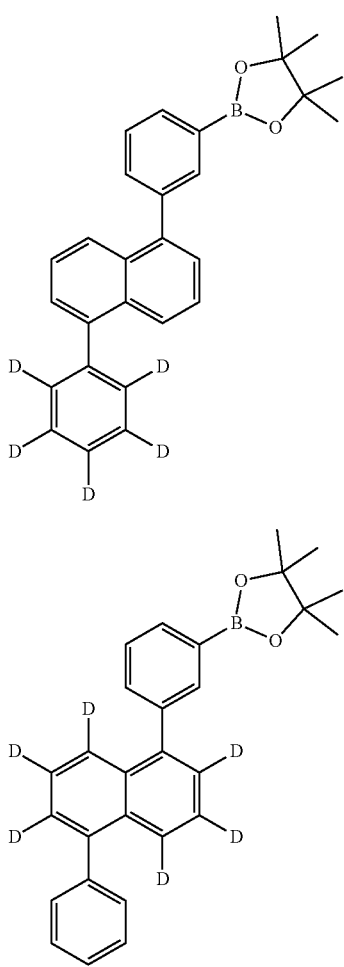
Sub2-49
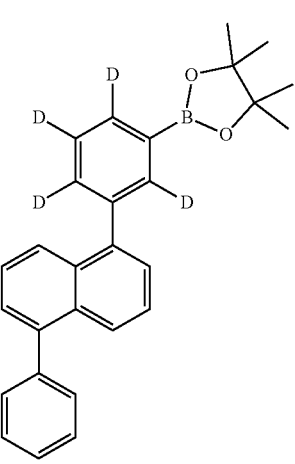
Sub2-50
TABLE 2
| Cpd. | FD-MS | Cpd. | FD-MS |
|---|---|---|---|
| Sub2-1 | m/z = 204.13($C_{12}H_{17}BO_2$ = 204.08) | Sub2-2 | m/z = 254.15($C_{18}H_{19}BO_2$ = 254.14) |
| Sub2-3 | m/z = 254.15($C_{16}H_{19}BO_2$ = 254.14) | Sub2-4 | m/z = 280.16($C_{18}H_{21}BO_2$ = 280.17) |
| Sub2-5 | m/z = 280.16($C_{18}H_{21}BO_2$ = 280.17) | Sub2-6 | m/z = 280.16($C_{18}H_{21}BO_2$ = 280.17) |
| Sub2-7 | m/z = 330.18($C_{22}H_{23}BO_2$ = 330.23) | Sub2-8 | m/z = 330.18($C_{22}H_{23}BO_2$ = 330.23) |
| Sub2-9 | m/z = 330.18($C_{22}H_{23}BO_2$ = 330.23) | Sub2-10 | m/z = 330.18($C_{22}H_{23}BO_2$ = 330.23) |
| Sub2-11 | m/z = 330.18($C_{22}H_{23}BO_2$ = 330.23) | Sub2-12 | m/z = 330.18($C_{22}H_{23}BO_2$ = 330.23) |
| Sub2-13 | m/z = 330.18($C_{22}H_{23}BO_2$ = 330.23) | Sub2-14 | m/z = 330.18($C_{22}H_{23}BO_2$ = 330.23) |

TABLE 2-continued

| Cpd. | FD-MS | Cpd. | FD-MS |
|---|---|---|---|
| Sub2-15 | m/z = 330.18($C_{22}H_{23}BO_2$ = 330.23) | Sub2-16 | m/z = 330.18($C_{22}H_{23}BO_2$ = 330.23) |
| Sub2-17 | m/z = 330.18($C_{22}H_{23}BO_2$ = 330.23) | Sub2-18 | m/z = 330.18($C_{22}H_{23}BO_2$ = 330.23) |
| Sub2-19 | m/z = 330.18($C_{22}H_{23}BO_2$ = 330.23) | Sub2-20 | m/z = 330.18($C_{22}H_{23}BO_2$ = 330.23) |
| Sub2-21 | m/z = 304.16($C_{20}H_{21}BO_2$ = 304.2) | Sub2-22 | m/z = 304.16($C_{20}H_{21}BO_2$ = 304.2) |
| Sub2-23 | m/z = 304.16($C_{20}H_{21}BO_2$ = 304.2) | Sub2-24 | m/z = 304.16($C_{20}H_{21}BO_2$ = 304.2) |
| Sub2-25 | m/z = 356.19($C_{24}H_{25}BO_2$ = 356.27) | Sub2-26 | m/z = 330.18($C_{22}H_{23}BO_2$ = 330.23) |
| Sub2-27 | m/z = 406.21($C_{28}H_{27}BO_2$ = 406.33) | Sub2-28 | m/z = 406.21($C_{28}H_{27}BO_2$ = 406.33) |
| Sub2-29 | m/z = 380.19($C_{26}H_{25}BO_2$ = 380.29) | Sub2-30 | m/z = 209.16($C_{12}H_{12}D_5BO_2$ = 209.11) |
| Sub2-31 | m/z = 406.21($C_{28}H_{27}BO_2$ = 406.33) | Sub2-32 | m/z = 406.21($C_{28}H_{27}BO_2$ = 406.33) |
| Sub2-33 | m/z = 356.19($C_{24}H_{25}BO_2$ = 356.27) | Sub2-34 | m/z = 406.21($C_{28}H_{27}BO_2$ = 406.33) |
| Sub2-35 | m/z = 406.21($C_{28}H_{27}BO_2$ = 406.33) | Sub2-36 | m/z = 406.21($C_{28}H_{27}BO_2$ = 406.33) |
| Sub2-37 | m/z = 330.18($C_{22}H_{23}BO_2$ = 330.23) | Sub2-38 | m/z = 330.18($C_{22}H_{23}BO_2$ = 330.23) |
| Sub2-39 | m/z = 406.21($C_{28}H_{27}BO_2$ = 406.33) | Sub2-40 | m/z = 411.24($C_{28}H_{22}D_5BO_2$ = 411.36) |
| Sub2-41 | m/z = 412.25($C_{28}H_{21}D_6BO_2$ = 412.37) | Sub2-42 | m/z = 410.24($C_{28}H_{23}D_4BO_2$ = 410.36) |
| Sub2-43 | m/z = 337.22($C_{22}H_{16}D_7BO_2$ = 337.28) | Sub2-44 | m/z = 337.22($C_{22}H_{16}D_7BO_2$ = 337.28) |
| Sub2-45 | m/z = 337.22($C_{22}H_{16}D_7BO_2$ = 337.28) | Sub2-46 | m/z = 406.21($C_{28}H_{27}BO_2$ = 406.33) |
| Sub2-47 | m/z = 411.24($C_{28}H_{22}D_5BO_2$ = 411.36) | Sub2-48 | m/z = 412.25($C_{28}H_{21}D_6BO_2$ = 412.37) |
| Sub2-49 | m/z = 410.24($C_{28}H_{23}D_4BO_2$ = 410.36) | Sub2-50 | m/z = 415.27($C_{28}H_{18}D_9BO_2$ = 415.39) |

III. Synthesis of Final Product

1. Synthesis Example of P-1

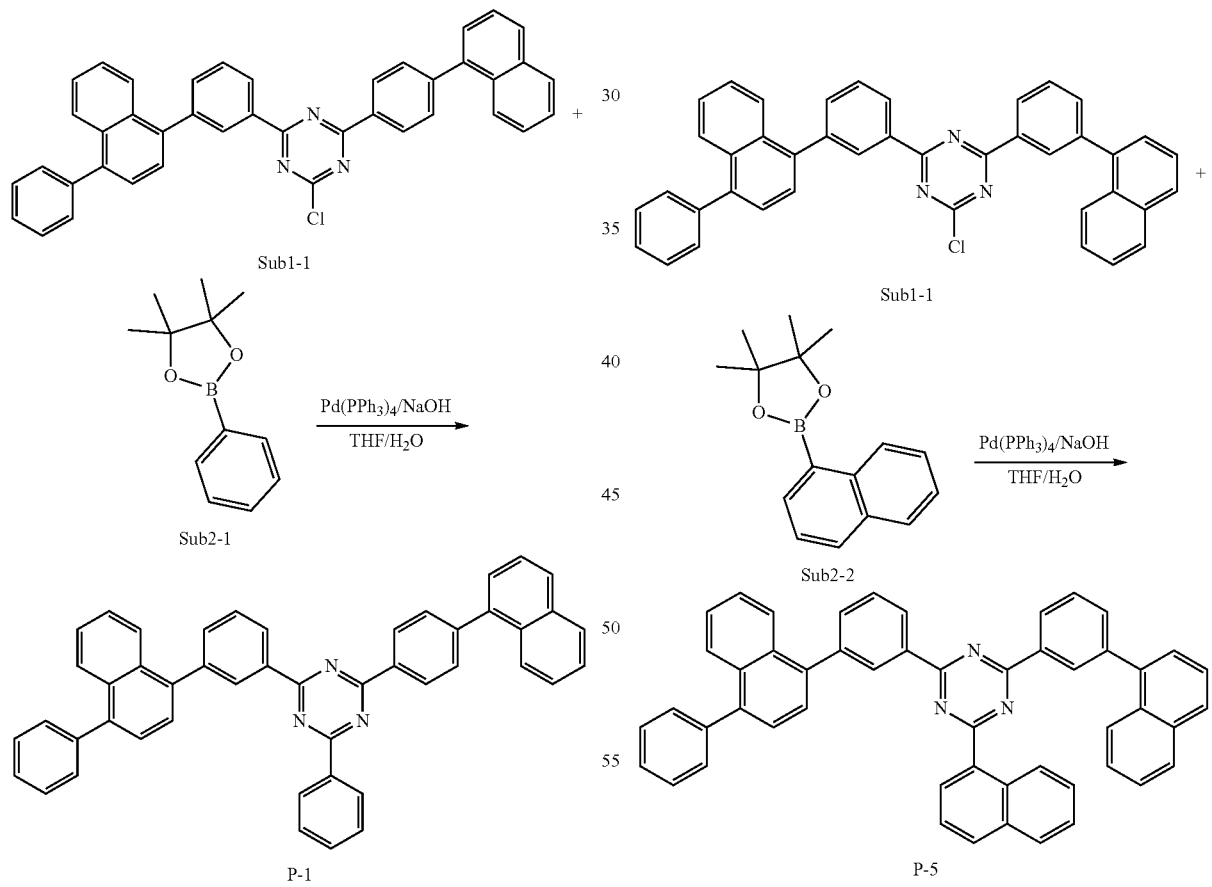

Sub1-1 (29.21 g, 49.00 mmol), Sub2-1 (10.00 g, 49.00 mmol), Pd(PPh$_3$)$_4$ (1.70 g, 1.47 mmol), NaOH (3.92 g, 98.00 mmol), 164 mL of THF, and 53 mL of water were added to a round-bottom flask, and reacted at 75° C. for 8 hours. When the reaction was completed, the temperature of the reactant was cooled to room temperature, and the reaction solvent was removed. Then, the concentrated reactant was subjected to silicagel column and recrystallization to obtain 25.20 g (81%) of product P-1.

2. Synthesis Example of P-5

Sub1-2 (25.80 g, 43.28 mmol), Sub2-2 (11.00 g, 43.28 mmol), Pd(PPh$_3$)$_4$ (1.50 g, 1.30 mmol), NaOH (3.46 g, 86.57 mmol), 145 mL of THF, and 46 mL of water were added and reacted at 75° C. for 8 hours. When the reaction was completed, 22.63 g (76%) of product P-5 was obtained by using the separation method of P-1.

3. Synthesis Example of P-9

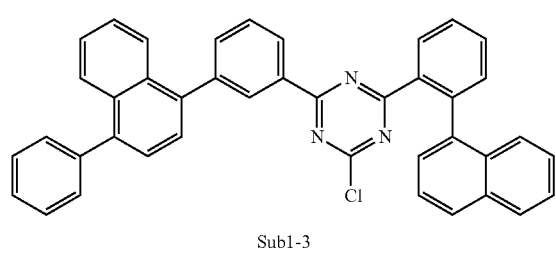

Sub1-3

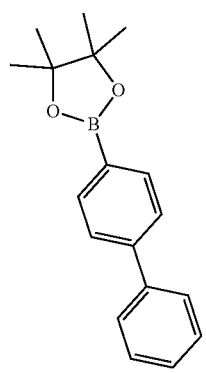

Sub2-4

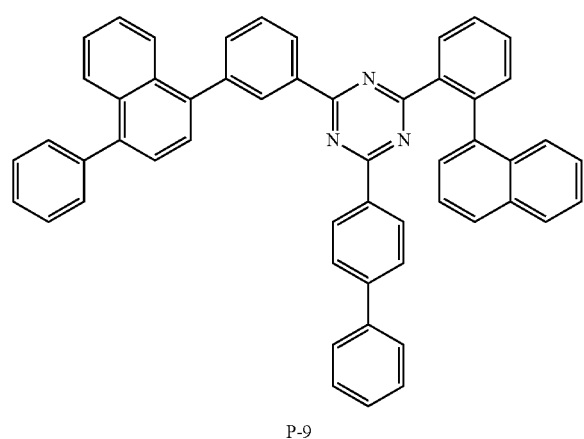

P-9

Sub1-3 (17.02 g, 28.55 mmol), Sub2-4 (8.00 g, 28.55 mmol), Pd(PPh₃)₄ (0.99 g, 0.86 mmol), NaOH (2.28 g, 57.11 mmol), 96 mL of THF, and 32 mL of water were added and reacted at 75° C. for 8 hours. When the reaction was completed, 17.12 g (84%) of product P-9 was obtained by using the separation method of P-1.

4. Synthesis Example of P-27

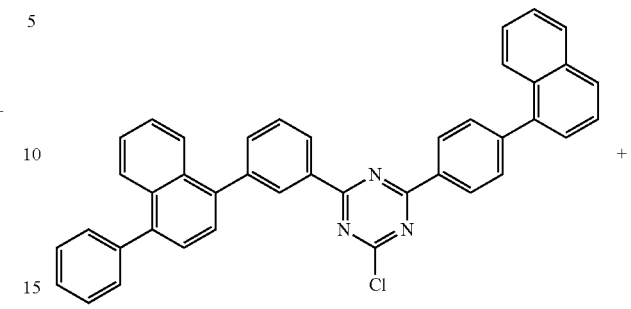

Sub1-1

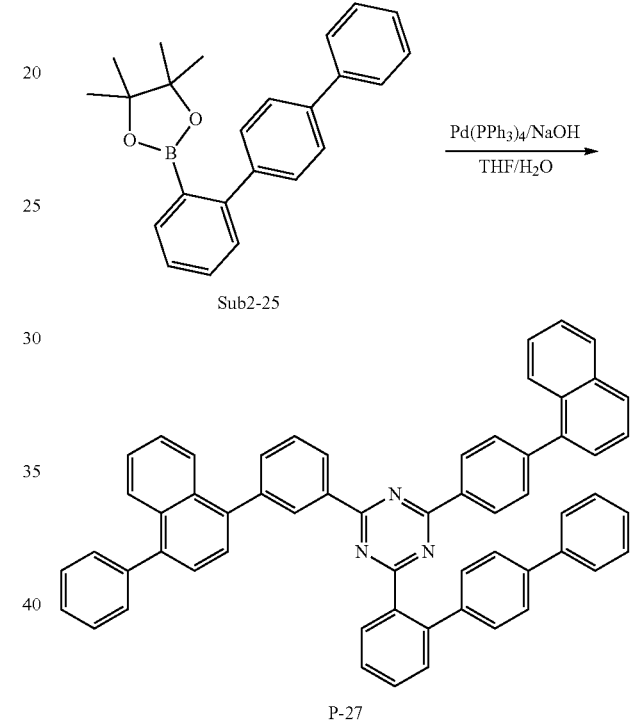

Sub2-25

P-27

Sub1-1 (15.06 g, 25.26 mmol), Sub2-25 (9.00 g, 25.26 mmol), Pd(PPh₃)₄ (0.88 g, 0.76 mmol), NaOH (2.02 g, 50.52 mmol), 84 mL of THF, and 28 mL of water were added and reacted at 75° C. for 8 hours. When the reaction was completed, 17.56 g (88%) of product P-27 was obtained by using the separation method of P-1.

5. Synthesis Example of P-57

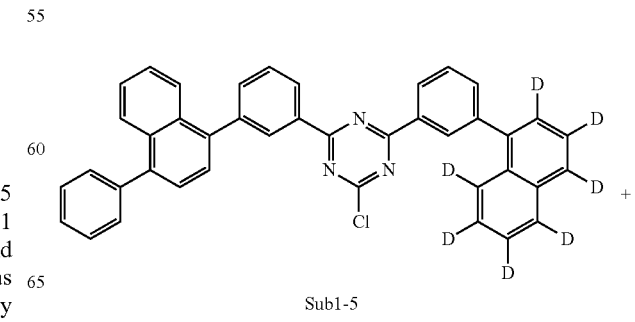

Sub1-5

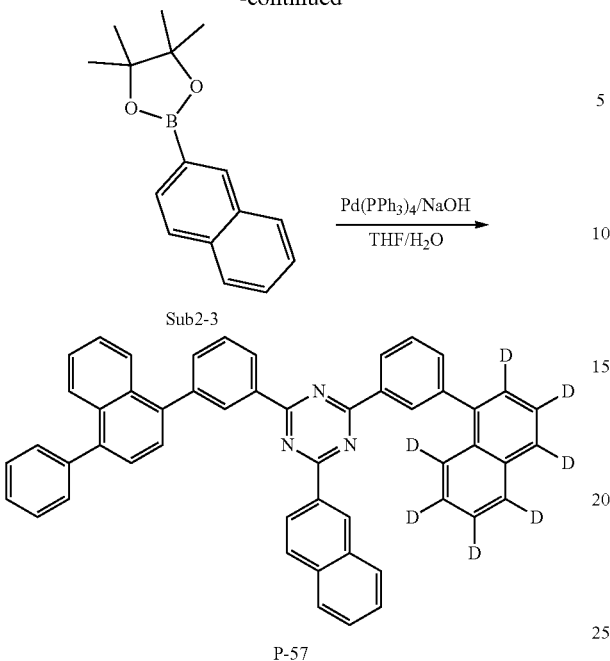

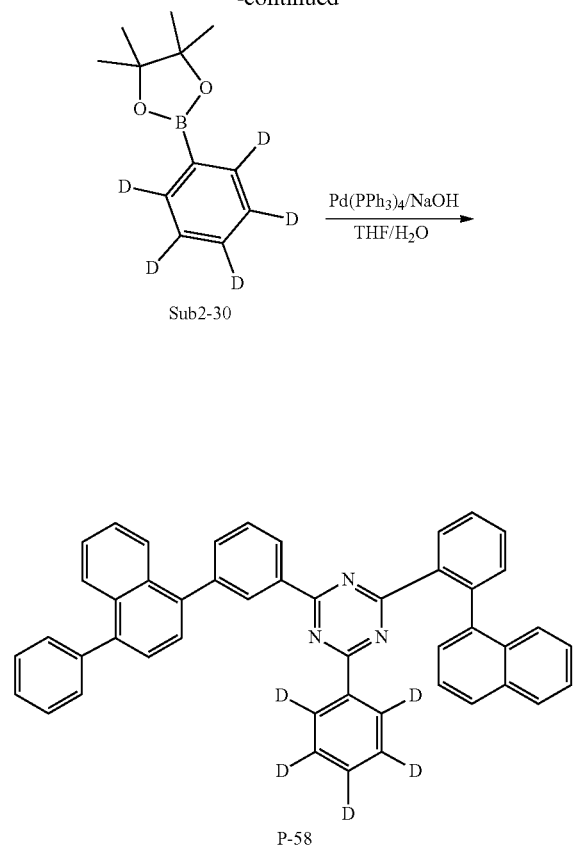

Sub1-5 (18.99 g, 31.48 mmol), Sub2-3 (8.00 g, 31.48 mmol), Pd(PPh$_3$)$_4$ (1.09 g, 0.94 mmol), NaOH (2.52 g, 62.96 mmol), 105 mL of THF, and 34 mL of water were added and reacted at 75° C. for 8 hours. When the reaction was completed, 18.36 g (84%) of product P-57 was obtained by using the separation method of P-1.

6. Synthesis Example of P-58

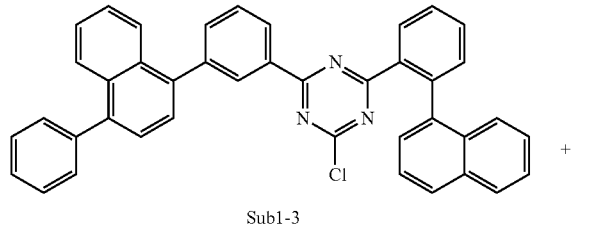

Sub1-3 (19.96 g, 33.48 mmol), Sub2-30 (7.00 g, 33.48 mmol), Pd(PPh$_3$)$_4$ (1.16 g, 1.00 mmol), NaOH (2.68 g, 66.95 mmol), 112 mL of THF, and 37 mL of water were added and reacted at 75° C. for 8 hours. When the reaction was completed, 16.78 g (78%) of product P-58 was obtained by using the separation method of P-1.

7. Synthesis Example of P-62

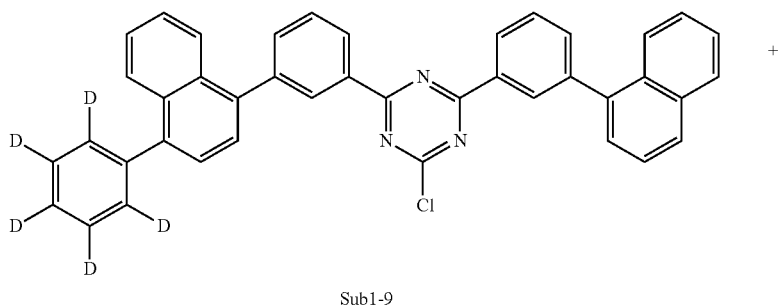

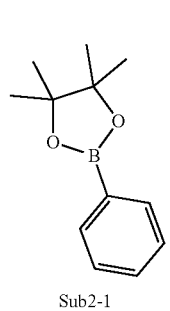 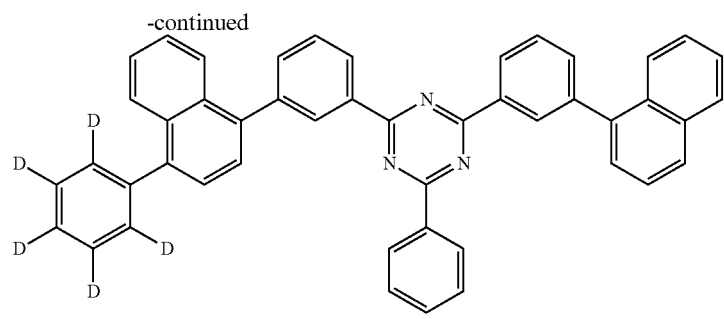
Sub1-9 (17.67 g, 29.40 mmol), Sub2-1 (6.00 g, 29.40 mmol), Pd(PPh₃)₄ (1.02 g, 0.88 mmol), NaOH (2.35 g, 58.80 mmol), 98 mL of THF, and 32 mL of water were added and reacted at 75° C. for 8 hours. When the reaction was completed, 15.57 g (82%) of product P-62 was obtained by using the separation method of P-1.
8. Synthesis Example of P-63
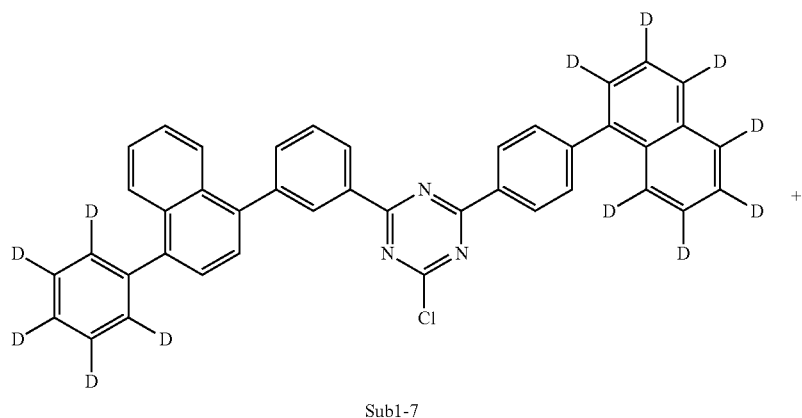
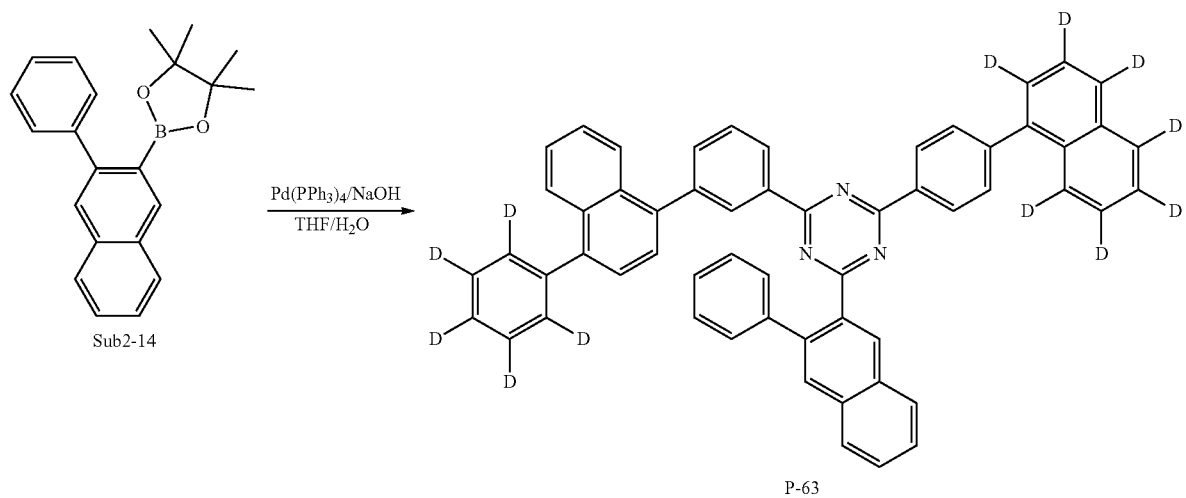

Sub1-7 (12.89 g, 21.20 mmol), Sub2-14 (7.00 g, 21.20 mmol), Pd(PPh₃)₄ (0.74 g, 0.64 mmol), NaOH (1.70 g, 42.39 mmol), 70 mL of THF, and 23 mL of water were added and reacted at 75° C. for 8 hours. When the reaction was completed, 13.98 g (85%) of product P-63 was obtained by using the separation method of P-1.

9. Synthesis Example of P-80

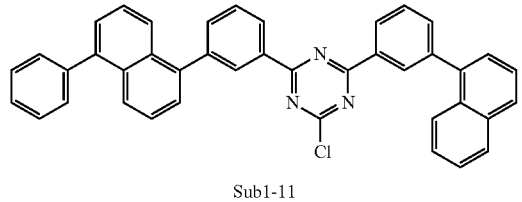

Sub1-11

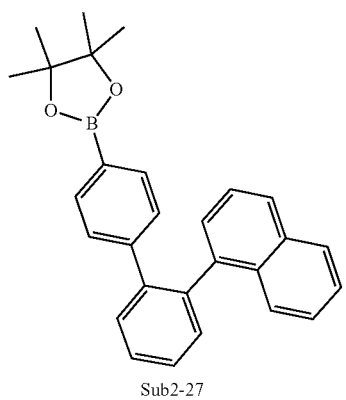

Sub2-27

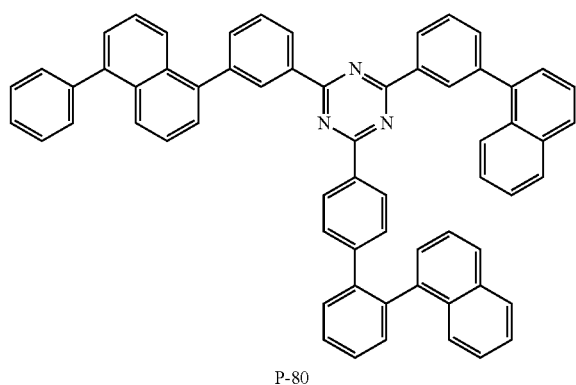

P-80

Sub1-11 (8.80 g, 14.77 mmol), Sub2-27 (6.00 g, 14.77 mmol), Pd(PPh₃)₄ (0.51 g, 0.44 mmol), NaOH (1.18 g, 29.53 mmol), 50 mL of THF, and 16 mL of water were added and reacted at 75° C. for 8 hours. When the reaction was completed, 8.06 g (65%) of product P-80 was obtained by using the separation method of P-1.

10. Synthesis Example of P-84

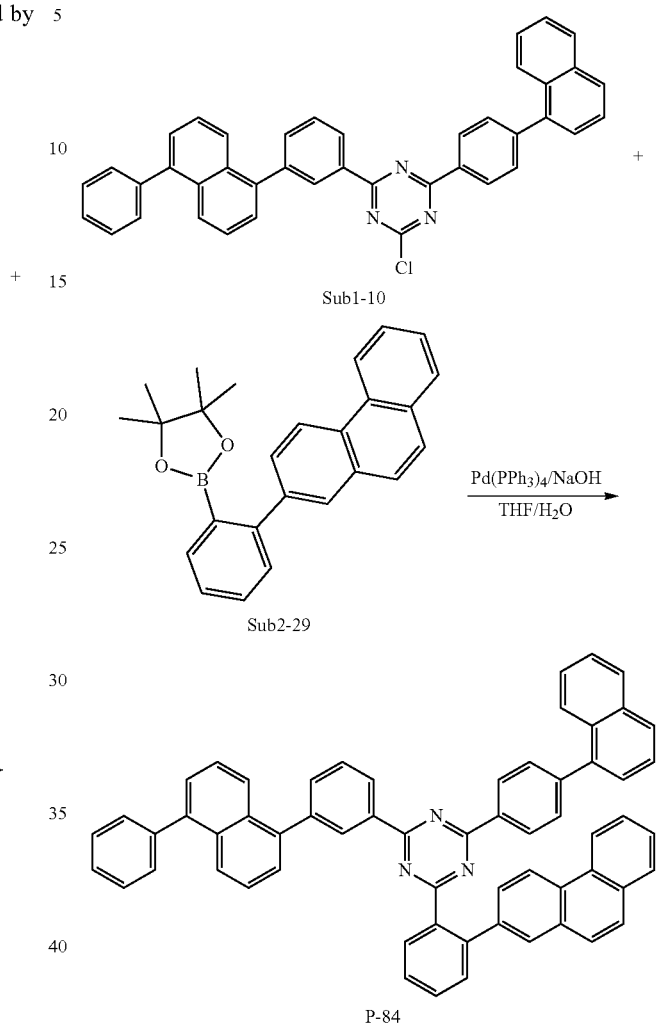

Sub1-10 (12.54 g, 21.04 mmol), Sub2-29 (8.00 g, 21.04 mmol), Pd(PPh₃)₄ (0.73 g, 0.63 mmol), NaOH (1.68 g, 42.07 mmol), 70 mL of THF, and 23 mL of water were added and reacted at 75° C. for 8 hours. When the reaction was completed, 11.98 g (70%) of product P-84 was obtained by using the separation method of P-1.

11. Synthesis Example of P-85

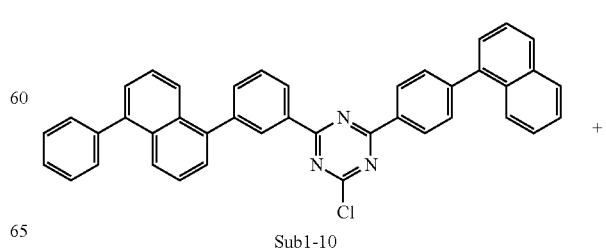

Sub1-10

-continued

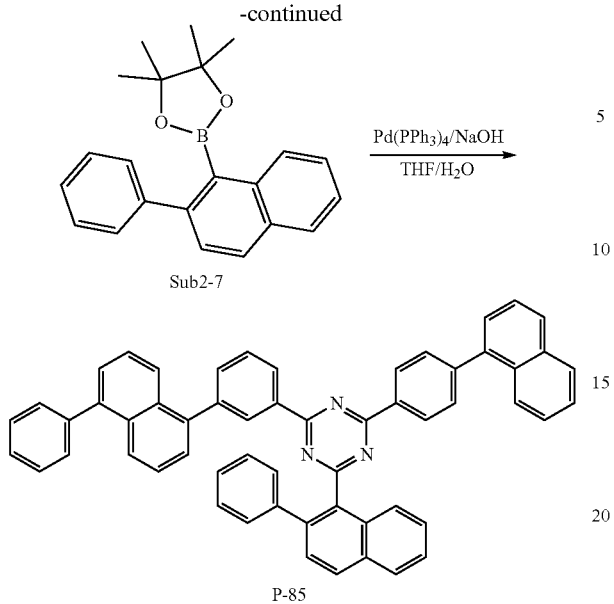

Sub1-10 (9.03 g, 15.14 mmol), Sub2-7 (5.00 g, 15.14 mmol), Pd(PPh$_3$)$_4$ (0.53 g, 0.45 mmol), NaOH (1.21 g, 30.28 mmol), 51 mL of THF, and 17 mL of water were added and reacted at 75° C. for 8 hours. When the reaction was completed, 9.48 g (82%) of product P-85 was obtained by using the separation method of P-1.

12. Synthesis Example of P-96

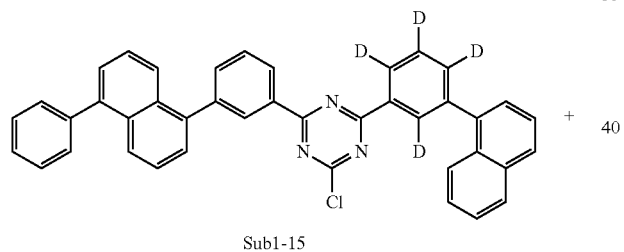

-continued

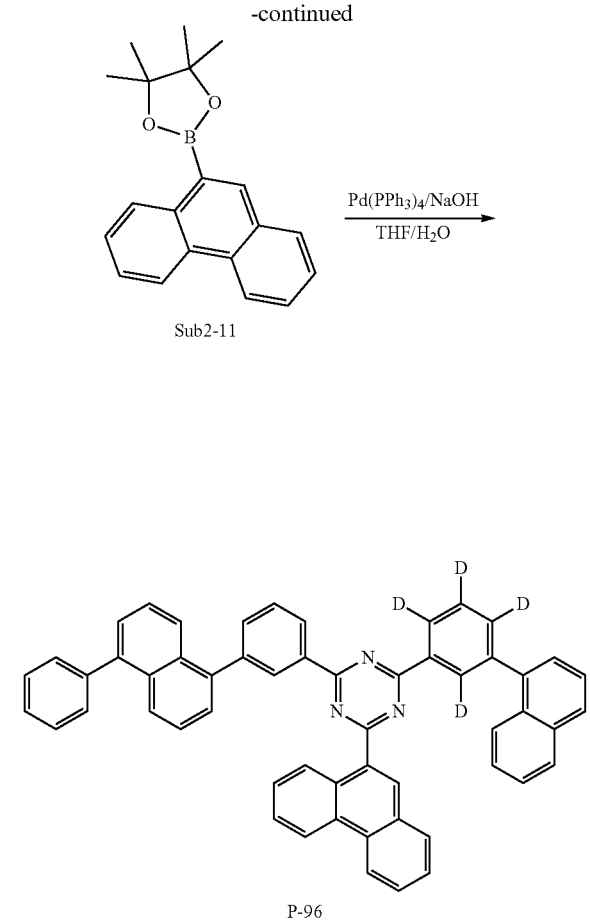

Sub1-15 (11.84 g, 19.72 mmol), Sub2-11 (6.00 g, 19.72 mmol), Pd(PPh$_3$)$_4$ (0.68 g, 0.59 mmol), NaOH (1.58 g, 39.45 mmol), 65 mL of THF, and 22 mL of water were added and reacted at 75° C. for 8 hours. When the reaction was completed, 11.26 g (77%) of product P-96 was obtained by using the separation method of P-1.

Meanwhile, the FD-MS values of the compounds P-1 to P-98 of the present invention prepared according to the above synthesis examples are shown in Table 3.

TABLE 3

| Cpd. | FD-MS | Cpd. | FD-MS |
|---|---|---|---|
| P-1 | m/z = 637.25($C_{47}H_{31}N_3$ = 637.79) | P-2 | m/z = 637.25($C_{47}H_{31}N_3$ = 637.79) |
| P-3 | m/z = 637.25($C_{47}H_{31}N_3$ = 637.79) | P-4 | m/z = 687.27($C_{51}H_{33}N_3$ = 687.85) |
| P-5 | m/z = 687.27($C_{51}H_{33}N_3$ = 687.85) | P-6 | m/z = 687.27($C_{51}H_{33}N_3$ = 687.85) |
| P-7 | m/z = 687.27($C_{51}H_{33}N_3$ = 687.85) | P-8 | m/z = 713.28($C_{53}H_{35}N_3$ = 713.88) |
| P-9 | m/z = 713.28($C_{53}H_{35}N_3$ = 713.88) | P-10 | m/z = 737.28($C_{55}H_{35}N_3$ = 737.91) |
| P-11 | m/z = 737.28($C_{55}H_{35}N_3$ = 737.91) | P-12 | m/z = 737.28($C_{55}H_{35}N_3$ = 737.91) |
| P-13 | m/z = 713.28($C_{53}H_{35}N_3$ = 713.88) | P-14 | m/z = 713.28($C_{53}H_{35}N_3$ = 713.88) |
| P-15 | m/z = 713.28($C_{53}H_{35}N_3$ = 713.88) | P-16 | m/z = 713.28($C_{53}H_{35}N_3$ = 713.88) |
| P-17 | m/z = 789.31($C_{59}H_{39}N_3$ = 789.98) | P-18 | m/z = 789.31($C_{59}H_{39}N_3$ = 789.98) |
| P-19 | m/z = 789.31($C_{59}H_{39}N_3$ = 789.98) | P-20 | m/z = 789.31($C_{59}H_{39}N_3$ = 789.98) |
| P-21 | m/z = 789.31($C_{59}H_{39}N_3$ = 789.98) | P-22 | m/z = 789.31($C_{59}H_{39}N_3$ = 789.98) |
| P-23 | m/z = 839.33($C_{63}H_{41}N_3$ = 840.04) | P-24 | m/z = 839.33($C_{63}H_{41}N_3$ = 840.04) |
| P-25 | m/z = 839.33($C_{63}H_{41}N_3$ = 840.04) | P-26 | m/z = 839.33($C_{63}H_{41}N_3$ = 840.04) |
| P-27 | m/z = 789.31($C_{59}H_{39}N_3$ = 789.98) | P-28 | m/z = 789.31($C_{59}H_{39}N_3$ = 789.98) |
| P-29 | m/z = 789.31($C_{59}H_{39}N_3$ = 789.98) | P-30 | m/z = 865.35($C_{65}H_{43}N_3$ = 866.08) |
| P-31 | m/z = 763.3($C_{57}H_{37}N_3$ = 763.94) | P-32 | m/z = 813.31($C_{61}H_{39}N_3$ = 814.00) |
| P-33 | m/z = 813.31($C_{61}H_{39}N_3$ = 814.00) | P-34 | m/z = 763.3($C_{57}H_{37}N_3$ = 763.94) |
| P-35 | m/z = 763.3($C_{57}H_{37}N_3$ = 763.94) | P-36 | m/z = 763.3($C_{57}H_{37}N_3$ = 763.94) |
| P-37 | m/z = 763.3($C_{57}H_{37}N_3$ = 763.94) | P-38 | m/z = 763.3($C_{57}H_{37}N_3$ = 763.94) |
| P-39 | m/z = 763.3($C_{57}H_{37}N_3$ = 763.94) | P-40 | m/z = 763.3($C_{57}H_{37}N_3$ = 763.94) |

TABLE 3-continued

| Cpd. | FD-MS | Cpd. | FD-MS |
| --- | --- | --- | --- |
| P-41 | m/z = 763.3($C_{57}H_{37}N_3$ = 763.94) | P-42 | m/z = 763.3($C_{57}H_{37}N_3$ = 763.94) |
| P-43 | m/z = 763.3($C_{57}H_{37}N_3$ = 763.94) | P-44 | m/z = 763.3($C_{57}H_{37}N_3$ = 763.94) |
| P-45 | m/z = 839.33($C_{63}H_{41}N_3$ = 840.04) | P-46 | m/z = 839.33($C_{63}H_{41}N_3$ = 840.04) |
| P-47 | m/z = 839.33($C_{63}H_{41}N_3$ = 840.04) | P-48 | m/z = 839.33($C_{63}H_{41}N_3$ = 840.04) |
| P-49 | m/z = 839.33($C_{63}H_{41}N_3$ = 840.04) | P-50 | m/z = 839.33($C_{63}H_{41}N_3$ = 840.04) |
| P-51 | m/z = 839.33($C_{63}H_{41}N_3$ = 840.04) | P-52 | m/z = 642.28($C_{47}H_{26}D_5N_3$ = 642.82) |
| P-53 | m/z = 643.29($C_{47}H_{25}D_6N_3$ = 643.82) | P-54 | m/z = 644.3($C_{47}H_{24}D_7N_3$ = 644.83) |
| P-55 | m/z = 641.28($C_{47}H_{27}D_4N_3$ = 641.81) | P-56 | m/z = 642.28($C_{47}H_{26}D_5N_3$ = 642.82) |
| P-57 | m/z = 694.31($C_{51}H_{26}D_7N_3$ = 694.89) | P-58 | m/z = 642.28($C_{47}H_{26}D_5N_3$ = 642.82) |
| P-59 | m/z = 646.31($C_{47}H_{22}D_9N_3$ = 646.84) | P-60 | m/z = 649.33($C_{47}H_{19}D_{12}N_3$ = 649.86) |
| P-61 | m/z = 648.32($C_{47}H_{20}D_{11}N_3$ = 648.85) | P-62 | m/z = 642.28($C_{47}H_{26}D_5N_3$ = 642.82) |
| P-63 | m/z = 642.28($C_{47}H_{26}D_5N_3$ = 642.82) | P-64 | m/z = 775.37($C_{57}H_{25}D_{12}N_3$ = 776.02) |
| P-65 | m/z = 775.37($C_{57}H_{25}D_{12}N_3$ = 776.02) | P-66 | m/z = 722.34($C_{53}H_{26}D_9N_3$ = 722.94) |
| P-67 | m/z = 637.25($C_{47}H_{31}N_3$ = 637.79) | P-68 | m/z = 637.25($C_{47}H_{31}N_3$ = 637.79) |
| P-69 | m/z = 637.25($C_{47}H_{31}N_3$ = 637.79) | P-70 | m/z = 687.27($C_{51}H_{33}N_3$ = 687.85) |
| P-71 | m/z = 687.27($C_{51}H_{33}N_3$ = 687.85) | P-72 | m/z = 713.28($C_{53}H_{35}N_3$ = 713.88) |
| P-73 | m/z = 737.28($C_{55}H_{35}N_3$ = 737.91) | P-74 | m/z = 713.28($C_{53}H_{35}N_3$ = 713.88) |
| P-75 | m/z = 713.28($C_{53}H_{35}N_3$ = 713.88) | P-76 | m/z = 789.31($C_{59}H_{39}N_3$ = 789.98) |
| P-77 | m/z = 789.31($C_{59}H_{39}N_3$ = 789.98) | P-78 | m/z = 789.31($C_{59}H_{39}N_3$ = 789.98) |
| P-79 | m/z = 789.31($C_{59}H_{39}N_3$ = 789.98) | P-80 | m/z = 839.33($C_{63}H_{41}N_3$ = 840.04) |
| P-81 | m/z = 839.33($C_{63}H_{41}N_3$ = 840.04) | P-82 | m/z = 763.3($C_{57}H_{37}N_3$ = 763.94) |
| P-83 | m/z = 813.31($C_{61}H_{39}N_3$ = 814.00) | P-84 | m/z = 813.31($C_{61}H_{39}N_3$ = 814.00) |
| P-85 | m/z = 763.3($C_{57}H_{37}N_3$ = 763.94) | P-86 | m/z = 763.3($C_{57}H_{37}N_3$ = 763.94) |
| P-87 | m/z = 763.3($C_{57}H_{37}N_3$ = 763.94) | P-88 | m/z = 839.33($C_{63}H_{41}N_3$ = 840.04) |
| P-89 | m/z = 839.33($C_{63}H_{41}N_3$ = 840.04) | P-90 | m/z = 839.33($C_{63}H_{41}N_3$ = 840.04) |
| P-91 | m/z = 641.28($C_{47}H_{27}D_4N_3$ = 641.81) | P-92 | m/z = 641.28($C_{47}H_{27}D_4N_3$ = 641.81) |
| P-93 | m/z = 642.28($C_{47}H_{26}D_5N_3$ = 642.82) | P-94 | m/z = 642.28($C_{47}H_{26}D_5N_3$ = 642.82) |
| P-95 | m/z = 691.29($C_{51}H_{29}D_4N_3$ = 691.87) | P-96 | m/z = 741.31($C_{55}H_{31}D_4N_3$ = 741.93) |
| P-97 | m/z = 741.31($C_{55}H_{31}D_4N_3$ = 741.93) | P-98 | m/z = 847.38($C_{63}H_{33}D_8N_3$ = 848.09) |

Synthesis Example 2

1. Synthesis Example of N-12

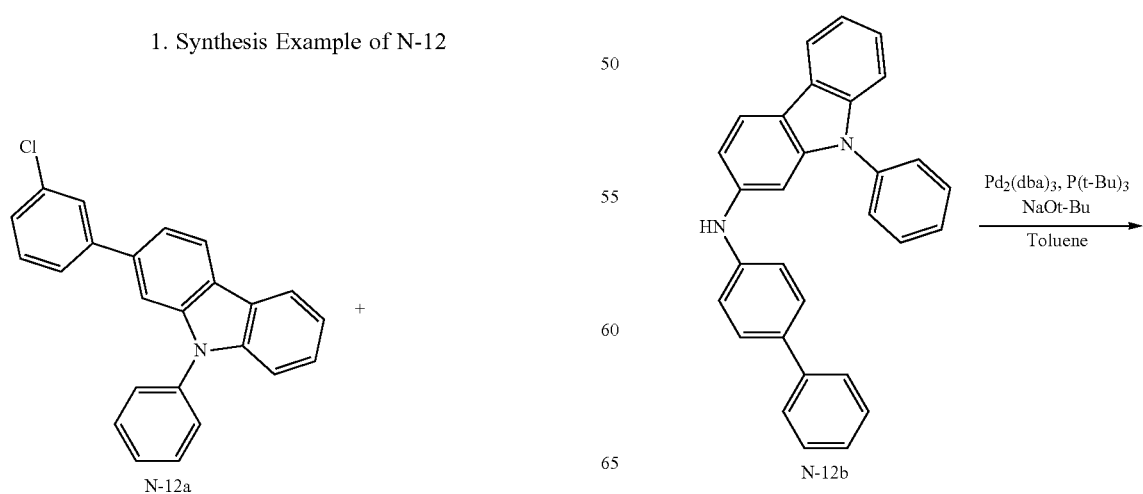

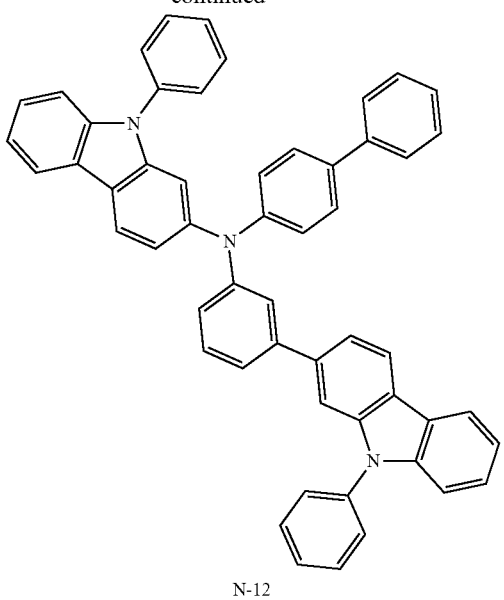

N-12

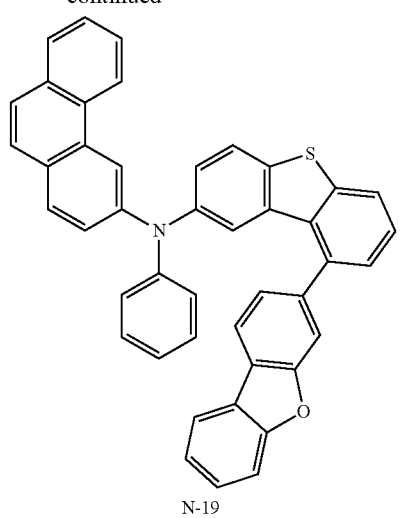

N-19

N-12a (30 g, 0.08 mol), N-12b (34.8 g, 0.08 mol), Pd$_2$(dba)$_3$ (2.3 g, 0.003 mol), NaOt-Bu (24.5 g, 0.25 mol), P(t-Bu)$_3$ (2.1 g, 0.005 mol), Toluene (170 mL) were added and reacted at 135° C. for 6 hours. When the reaction was completed, 53 g (85.8%) of the product N-12 was obtained by using the separation method for P-1.

N-19a (50 g, 0.13 mol), N-19b (35 g, 0.13 mol), Pd$_2$(dba)$_3$ (3.6 g, 0.004 mol), NaOt-Bu (37.6 g, 0.40 mol), P(t-Bu)$_3$ (3.2 g, 0.008 mol), Toluene (260 mL) were added and reacted at 135° C. for 6 hours. When the reaction was completed, 67 g (83.4%) of the product N-19 was obtained by using the separation method for P-1.

2. Synthesis Example of N-19

3. Synthesis Example of S-32

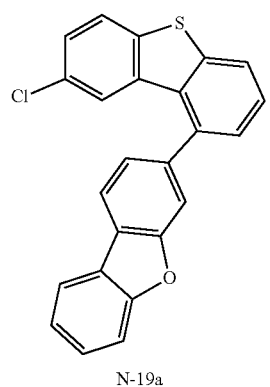

N-19a

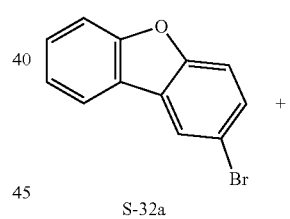

S-32a

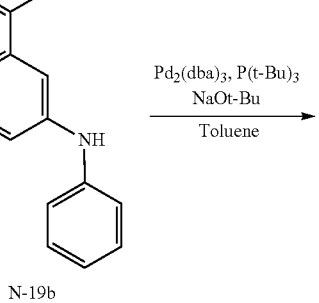

N-19b

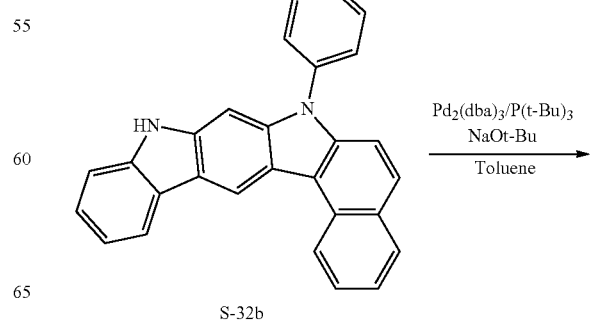

S-32b

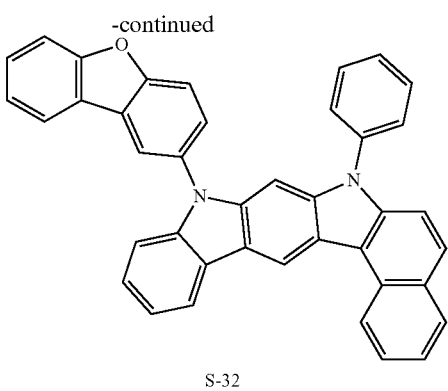

S-32

S-32a (10 g, 0.04 mol), S-32b (15.6 g, 0.04 mol), Pd$_2$(dba)$_3$ (1.1 g, 0.001 mol), NaOt-Bu (11.7 g, 0.12 mol), P(t-Bu)$_3$ (1.0 g, 0.002 mol), Toluene (80 mL) were added and reacted at 135° C. for 6 hours. When the reaction was completed, 18 g (80.8%) of the product S-32 was obtained by using the separation method for P-1.

4. Synthesis Example of S-74

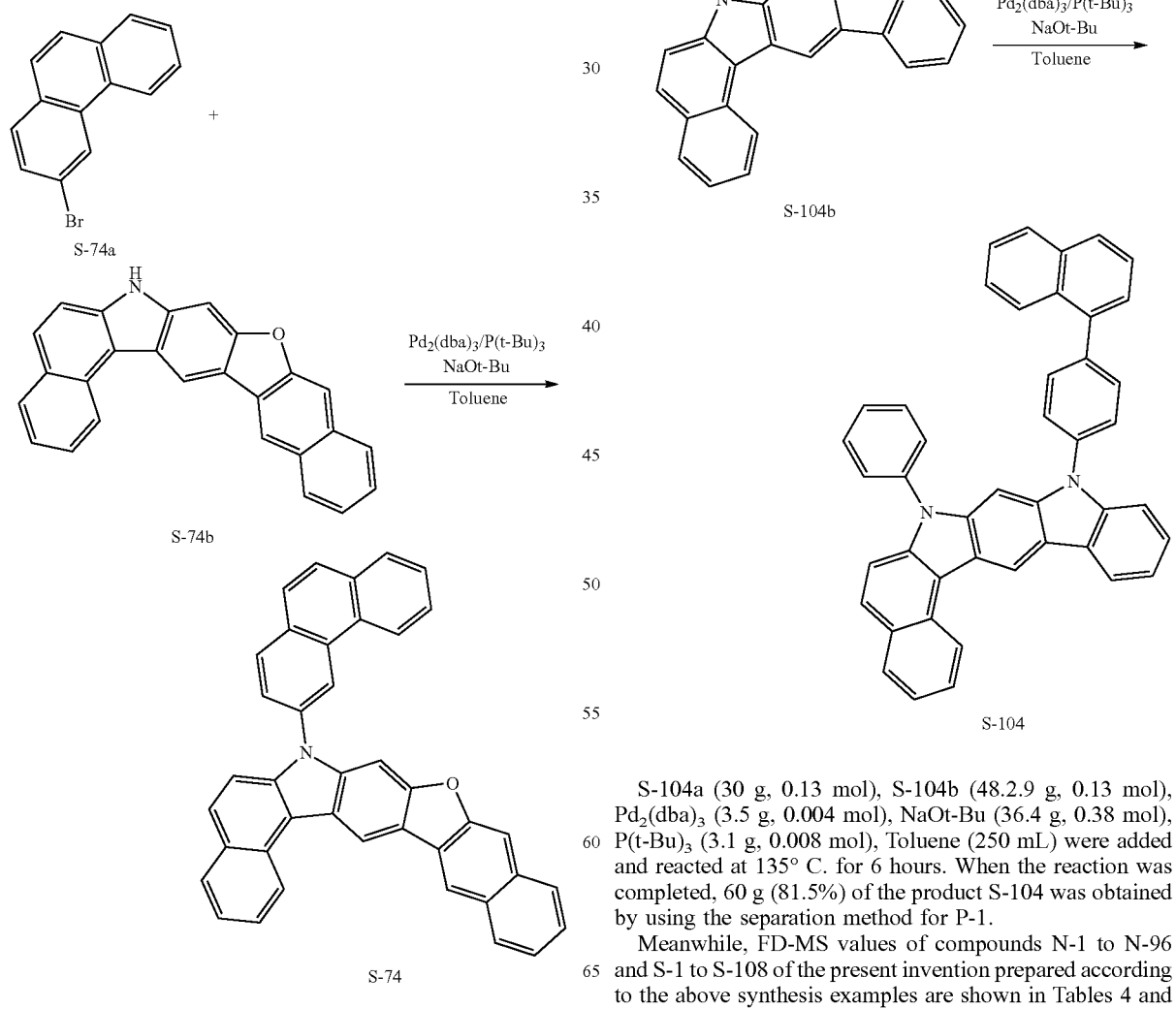

S-74a (15 g, 0.06 mol), S-74b (20.9 g, 0.06 mol), Pd$_2$(dba)$_3$ (1.6 g, 0.002 mol), NaOt-Bu (16.9 g, 0.18 mol), P(t-Bu)$_3$ (1.4 g, 0.004 mol), Toluene (120 mL) were added and reacted at 135° C. for 6 hours. When the reaction was completed, 27 g (86.4%) of the product S-74 was obtained by using the separation method for P-1.

5. Synthesis Example of S-104

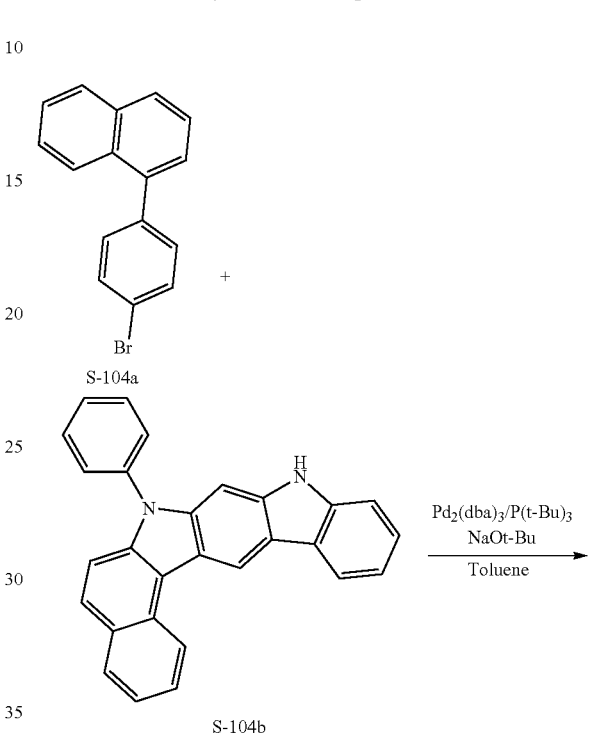

S-104a (30 g, 0.13 mol), S-104b (48.2.9 g, 0.13 mol), Pd$_2$(dba)$_3$ (3.5 g, 0.004 mol), NaOt-Bu (36.4 g, 0.38 mol), P(t-Bu)$_3$ (3.1 g, 0.008 mol), Toluene (250 mL) were added and reacted at 135° C. for 6 hours. When the reaction was completed, 60 g (81.5%) of the product S-104 was obtained by using the separation method for P-1.

Meanwhile, FD-MS values of compounds N-1 to N-96 and S-1 to S-108 of the present invention prepared according to the above synthesis examples are shown in Tables 4 and 5.

TABLE 4

| Cpd. | FD-MS | Cpd. | FD-MS |
| --- | --- | --- | --- |
| N-1 | m/z = 487.19($C_{36}H_{25}NO$ = 487.6) | N-2 | m/z = 553.19($C_{40}H_{27}NS$ = 553.72) |
| N-3 | m/z = 563.26($C_{43}H_{33}N$ = 563.74) | N-4 | m/z = 602.27($C_{45}H_{34}N_2$ = 602.78) |
| N-5 | m/z = 517.15($C_{36}H_{23}NOS$ = 517.65) | N-6 | m/z = 603.2($C_{44}H_{29}NS$ = 603.78) |
| N-7 | m/z = 735.29($C_{57}H_{37}N$ = 735.93) | N-8 | m/z = 562.24($C_{42}H_{30}N_2$ = 562.72) |
| N-9 | m/z = 565.17($C_{40}H_{23}NO_3$ = 565.63) | N-10 | m/z = 581.14($C_{40}H_{23}NO_2S$ = 581.69) |
| N-11 | m/z = 823.24($C_{59}H_{37}NS_2$ = 824.07) | N-12 | m/z = 727.3($C_{54}H_{37}N_3$ = 727.91) |
| N-13 | m/z = 627.22($C_{46}H_{29}NO_2$ = 627.74) | N-14 | m/z = 633.16($C_{44}H_{27}NS_2$ = 633.83) |
| N-15 | m/z = 675.29($C_{52}H_{37}N$ = 675.88) | N-16 | m/z = 678.3($C_{51}H_{38}N_2$ = 678.88) |
| N-17 | m/z = 669.21($C_{48}H_{31}NOS$ = 669.84) | N-18 | m/z = 785.22($C_{56}H_{35}NS_2$ = 786.02) |
| N-19 | m/z = 617.18($C_{44}H_{27}NOS$ = 617.77) | N-20 | m/z = 601.2($C_{44}H_{27}NO_2$ = 601.71) |
| N-21 | m/z = 779.32($C_{59}H_{41}NO$ = 779.98) | N-22 | m/z = 583.23($C_{42}H_{33}NS$ = 583.79) |
| N-23 | m/z = 679.32($C_{52}H_{41}N$ = 679.91) | N-24 | m/z = 726.27($C_{54}H_{34}N_2O$ = 726.88) |
| N-25 | m/z = 593.18($C_{42}H_{27}NOS$ = 593.74) | N-26 | m/z = 774.22($C_{54}H_{34}N_2S_2$ = 775) |
| N-27 | m/z = 557.24($C_{40}H_{31}NO_2$ = 557.69) | N-28 | m/z = 652.25($C_{48}H_{32}N_2O$ = 652.8) |
| N-29 | m/z = 619.29($C_{46}H_{37}NO$ = 619.81) | N-30 | m/z = 603.2($C_{44}H_{29}NS$ = 603.78) |
| N-31 | m/z = 813.3($C_{62}H_{39}NO$ = 814) | N-32 | m/z = 784.29($C_{57}H_{40}N_2S$ = 785.02) |
| N-33 | m/z = 577.2($C_{42}H_{27}NO_2$ = 577.68) | N-34 | m/z = 607.14($C_{42}H_{25}NS_2$ = 607.79) |
| N-35 | m/z = 801.34($C_{62}H_{43}N$ = 802.03) | N-36 | m/z = 575.24($C_{42}H_{29}N_3$ = 575.72) |
| N-37 | m/z = 577.2($C_{42}H_{27}NO_2$ = 577.68) | N-38 | m/z = 607.14($C_{42}H_{25}NS_2$ = 607.79) |
| N-39 | m/z = 801.34($C_{62}H_{43}N$ = 802.03) | N-40 | m/z = 575.24($C_{42}H_{29}N_3$ = 575.72) |
| N-41 | m/z = 601.2($C_{44}H_{27}NO_2$ = 601.71) | N-42 | m/z = 471.11($C_{31}H_{21}NS_2$ = 471.64) |
| N-43 | m/z = 675.29($C_{52}H_{37}N$ = 675.88) | N-44 | m/z = 727.3($C_{54}H_{37}N_3$ = 727.91) |
| N-45 | m/z = 603.2($C_{44}H_{29}NS$ = 603.78) | N-46 | m/z = 561.16($C_{38}H_{27}NS_2$ = 561.76) |
| N-47 | m/z = 799.32($C_{62}H_{41}N$ = 800.02) | N-48 | m/z = 702.27($C_{52}H_{34}N_2O$ = 702.86) |
| N-49 | m/z = 729.27($C_{54}H_{35}NO_2$ = 729.88) | N-50 | m/z = 785.22($C_{56}H_{35}NS_2$ = 786.02) |
| N-51 | m/z = 812.32($C_{62}H_{40}N_2$ = 81 3.02) | N-52 | m/z = 681.22($C_{48}H_{31}N_3S$ = 681.86) |
| N-53 | m/z = 615.18($C_{44}H_{25}NO_3$ = 615.69) | N-54 | m/z = 763.15($C_{52}H_{29}NS_3$ = 763.99) |
| N-55 | m/z = 593.31($C_{45}H_{39}N$ = 593.81) | N-56 | m/z = 840.33($C_{62}H_{40}N_4$ = 841.03) |
| N-57 | m/z = 657.18($C_{46}H_{27}NO_2S$ = 657.79) | N-58 | m/z = 824.23($C_{58}H_{36}N_2S_2$ = 825.06) |
| N-59 | m/z = 1195.42($C_{91}H_{57}NS$ = 1196.52) | N-60 | m/z = 656.19($C_{46}H_{28}N_2OS$ = 656.8) |
| N-61 | m/z = 607.16($C_{42}H_{25}NO_2S$ = 607.73) | N-62 | m/z = 773.2($C_{54}H_{31}NO_3S$ = 773.91) |
| N-63 | m/z = 1013.4($C_{79}H_{51}N$ = 1014.28) | N-64 | m/z = 758.24($C_{54}H_{34}N_2OS$ = 758.94) |
| N-65 | m/z = 623.14($C_{42}H_{25}NOS_2$ = 623.79) | N-66 | m/z = 763.16($C_{52}H_{29}NO_2S_2$ = 763.93) |
| N-67 | m/z = 799.2($C_{56}H_{33}NOS_2$ = 800.01) | N-68 | m/z = 743.23($C_{54}H_{33}NOS$ = 743.92) |
| N-69 | m/z = 872.25($C_{62}H_{36}N_2O_2S$ = 873.04) | N-70 | m/z = 772.22($C_{54}H_{32}N_2O_2S$ = 772.92) |
| N-71 | m/z = 830.28($C_{61}H_{38}N_2S$ = 831.05) | N-72 | m/z = 808.25($C_{58}H_{33}FN_2O_2$ = 808.91) |
| N-73 | m/z = 929.21($C_{64}H_{35}NO_3S_2$ = 930.11) | N-74 | m/z = 963.27($C_{68}H_{41}N_3S_2$ = 964.22) |
| N-75 | m/z = 809.24($C_{58}H_{35}NO_2S$ = 809.98) | N-76 | m/z = 893.29($C_{66}H_{39}NO_3$ = 894.04) |
| N-77 | m/z = 794.28($C_{58}H_{38}N_2S$ = 795.02) | N-78 | m/z = 900.26($C_{64}H_{40}N_2S_2$ = 901.16) |
| N-79 | m/z = 758.28($C_{55}H_{38}N_2S$ = 758.98) | N-80 | m/z = 1082.37($C_{51}H_{50}N_2S$ = 1083.37) |
| N-81 | m/z = 573.25($C_{44}H_{31}N$ = 573.74) | N-82 | m/z = 649.28($C_{50}H_{35}N$ = 649.84) |
| N-83 | m/z = 699.29($C_{54}H_{37}N$ = 699.9) | N-84 | m/z = 699.29($C_{54}H_{37}N$ = 699.9) |
| N-85 | m/z = 673.28($C_{52}H_{35}N$ = 673.86) | N-86 | m/z = 649.28($C_{50}H_{35}N$ = 649.84) |
| N-87 | m/z = 625.28($C_{48}H_{35}N$ = 625.82) | N-88 | m/z = 673.28($C_{52}H_{35}N$ = 673.86) |
| N-89 | m/z = 773.31($C_{60}H_{39}N$ = 773.98) | N-90 | m/z = 749.31($C_{58}H_{39}N$ = 749.96) |
| N-91 | m/z = 699.29($C_{54}H_{37}N$ = 699.9) | N-92 | m/z = 599.26($C_{46}H_{33}N$ = 599.78) |
| N-93 | m/z = 639.26($C_{48}H_{33}NO$ = 639.8) | N-94 | m/z = 765.25($C_{57}H_{35}N_3$ = 765.97) |
| N-95 | m/z = 677.31($C_{52}H_{39}N$ = 677.89) | N-96 | m/z = 727.3($C_{54}H_{37}N_3$ = 727.91) |

TABLE 5

| Cpd. | FD-MS | Cpd. | FD-MS |
| --- | --- | --- | --- |
| S-1 | m/z = 408.16($C_{30}H_{20}N_2$ = 408.5) | S-2 | m/z = 534.21($C_{40}H_{26}N_2$ = 534.66) |
| S-3 | m/z = 560.23($C_{42}H_{28}N_2$ = 560.7) | S-4 | m/z = 584.23($C_{44}H_{28}N_2$ = 584.72) |
| S-5 | m/z = 560.23($C_{42}H_{28}N_2$ = 560.7) | S-6 | m/z = 634.24($C_{48}H_{30}N_2$ = 634.78) |
| S-7 | m/z = 610.24($C_{46}H_{30}N_2$ = 610.76) | S-8 | m/z = 498.17($C_{36}H_{22}N_2O$ = 498.59) |
| S-9 | m/z = 574.2($C_{42}H_{26}N_2O$ = 574.68) | S-10 | m/z = 660.26($C_{50}H_{32}N_2$ = 660.82) |
| S-11 | m/z = 686.27($C_{52}H_{34}N_2$ = 686.86) | S-12 | m/z = 620.14($C_{42}H_{24}N_2S_2$ = 620.79) |
| S-13 | m/z = 640.2($C_{46}H_{28}N_2S$ = 640.8) | S-14 | m/z = 560.23($C_{42}H_{28}N_2$ = 560.7) |
| S-15 | m/z = 558.21($C_{42}H_{26}N_2$ = 558.68) | S-16 | m/z = 548.19($C_{40}H_{24}N_2O$ = 548.65) |
| S-17 | m/z = 573.22($C_{42}H_{27}N_3$ = 573.7) | S-18 | m/z = 564.17($C_{40}H_{24}N_2S$ = 564.71) |
| S-19 | m/z = 574.2($C_{42}H_{26}N_2O$ = 574.68) | S-20 | m/z = 564.17($C_{40}H_{24}N_2S$ = 564.71) |
| S-21 | m/z = 564.17($C_{40}H_{24}N_2S$ = 564.71) | S-22 | m/z = 813.31($C_{61}H_{39}N_3$ = 814) |
| S-23 | m/z = 696.26($C_{53}H_{32}N_2$ = 696.85) | S-24 | m/z = 691.23($C_{49}H_{29}N_3O_2$ = 691.79) |
| S-25 | m/z = 710.27($C_{54}H_{34}N_2$ = 710.88) | S-26 | m/z = 610.24($C_{46}H_{30}N_2$ = 610.76) |
| S-27 | m/z = 670.15($C_{46}H_{26}N_2S_2$ = 670.85) | S-28 | m/z = 640.29($C_{48}H_{36}N_2$ = 640.83) |
| S-29 | m/z = 598.2($C_{44}H_{26}N_2O$ = 598.71) | S-30 | m/z = 623.24($C_{46}H_{29}N_3$ = 623.76) |
| S-31 | m/z = 458.18($C_{34}H_{22}N_2$ = 458.56) | S-32 | m/z = 548.19($C_{40}H_{24}N_2O$ = 548.65) |
| S-33 | m/z = 508.19($C_{38}H_{24}N_2$ = 508.62) | S-34 | m/z = 508.19($C_{38}H_{24}N_2$ = 508.62) |
| S-35 | m/z = 623.24($C_{46}H_{29}N_3$ = 623.76) | S-36 | m/z = 564.17($C_{40}H_{24}N_2S$ = 564.71) |
| S-37 | m/z = 627.2($C_{46}H_{29}NS$ = 627.81) | S-38 | m/z = 505.1($C_{34}H_{19}NS_2$ = 505.65) |
| S-39 | m/z = 514.15($C_{36}H_{22}N_2S$ = 514.65) | S-40 | m/z = 575.17($C_{42}H_{25}NS$ = 575.73) |
| S-41 | m/z = 642.21($C_{46}H_{30}N_2S$ = 642.82) | S-42 | m/z = 575.17($C_{42}H_{25}NS$ = 575.73) |

TABLE 5-continued

| Cpd. | FD-MS | Cpd. | FD-MS |
|---|---|---|---|
| S-43 | m/z = 606.18($C_{42}H_{26}N_2OS$ = 606.74) | S-44 | m/z = 575.17($C_{42}H_{25}NS$ = 575.73) |
| S-45 | m/z = 551.17($C_{40}H_{25}NS$ = 551.71) | S-46 | m/z = 607.14($C_{42}H_{25}NS_2$ = 607.79) |
| S-47 | m/z = 525.16($C_{38}H_{23}NS$ = 525.67) | S-48 | m/z = 642.21($C_{46}H_{30}N_2S$ = 642.82) |
| S-49 | m/z = 548.19($C_{40}H_{24}N_2O$ = 548.65) | S-50 | m/z = 473.14($C_{34}H_{19}NO_2$ = 473.53) |
| S-51 | m/z = 566.15($C_{39}H_{22}N_2OS$ = 566.68) | S-52 | m/z = 459.16($C_{34}H_{21}NO$ = 459.55) |
| S-53 | m/z = 473.14($C_{34}H_{19}NO_2$ = 473.53) | S-54 | m/z = 523.16($C_{38}H_{21}NO_2$ = 523.59) |
| S-55 | m/z = 539.13($C_{38}H_{21}NOS$ = 539.65) | S-56 | m/z = 548.19($C_{40}H_{24}N_2O$ = 548.65) |
| S-57 | m/z = 489.12($C_{34}H_{19}NOS$ = 489.59) | S-58 | m/z = 545.09($C_{36}H_{19}NOS_2$ = 545.67) |
| S-59 | m/z = 549.17($C_{40}H_{23}NO_2$ = 549.63) | S-60 | m/z = 565.15($C_{40}H_{23}NOS$ = 565.69) |
| S-61 | m/z = 523.16($C_{38}H_{21}NO_2$ = 523.59) | S-62 | m/z = 598.2($C_{44}H_{26}N_2O$ = 598.71) |
| S-63 | m/z = 539.13($C_{38}H_{21}NOS$ = 539.65) | S-64 | m/z = 589.15($C_{42}H_{23}NOS$ = 589.71) |
| S-65 | m/z = 498.17($C_{36}H_{22}N_2O$ = 498.59) | S-66 | m/z = 509.18($C_{38}H_{23}NO$ = 509.61) |
| S-67 | m/z = 548.19($C_{40}H_{24}N_2O$ = 548.65) | S-68 | m/z = 549.17($C_{40}H_{23}NO_2$ = 549.63) |
| S-69 | m/z = 449.12($C_{32}H_{19}NS$ = 449.57) | S-70 | m/z = 439.1($C_{30}H_{17}NOS$ = 439.53) |
| S-71 | m/z = 647.22($C_{49}H_{29}NO$ = 647.78) | S-72 | m/z = 717.28($C_{52}H_{35}N_3O$ = 717.87) |
| S-73 | m/z = 459.16($C_{34}H_{21}NO$ = 459.55) | S-74 | m/z = 533.18($C_{40}H_{23}NO$ = 533.63) |
| S-75 | m/z = 525.16($C_{38}H_{23}NS$ = 525.67) | S-76 | m/z = 564.17($C_{40}H_{24}N_2S$ = 564.71) |
| S-77 | m/z = 575.19($C_{42}H_{25}NO_2$ = 575.67) | S-78 | m/z = 663.22($C_{49}H_{29}NO_2$ = 663.78) |
| S-79 | m/z = 647.22($C_{49}H_{29}NO$ = 647.78) | S-80 | m/z = 496.16($C_{36}H_{20}N_2O$ = 496.57) |
| S-81 | m/z = 565.15($C_{40}H_{23}NOS$ = 565.69) | S-82 | m/z = 505.1($C_{34}H_{19}NS_2$ = 505.65) |
| S-83 | m/z = 765.25($C_{56}H_{35}NOSi$ = 765.99) | S-84 | m/z = 615.17($C_{44}H_{25}NOS$ = 615.75) |
| S-85 | m/z = 603.17($C_{43}H_{25}NOS$ = 603.74) | S-86 | m/z = 772.29($C_{59}H_{36}N_2$ = 772.95) |
| S-87 | m/z = 802.33($C_{61}H_{42}N_2$ = 803.02) | S-88 | m/z = 607.23($C_{47}H_{29}N$ = 607.76) |
| S-89 | m/z = 524.23($C_{39}H_{28}N_2$ = 524.67) | S-90 | m/z = 665.22($C_{49}H_{31}NS$ = 665.85) |
| S-91 | m/z = 633.25($C_{49}H_{31}N$ = 633.79) | S-92 | m/z = 775.29($C_{59}H_{37}NO$ = 775.95) |
| S-93 | m/z = 535.23($C_{41}H_{29}N$ = 535.69) | S-94 | m/z = 623.22($C_{47}H_{29}NO$ = 623.76) |
| S-95 | m/z = 687.2($C_{51}H_{29}NS$ = 687.86) | S-96 | m/z = 735.29($C_{57}H_{37}N$ = 735.93) |
| S-97 | m/z = 611.26($C_{47}H_{33}N$ = 611.79) | S-98 | m/z = 679.23($C_{50}H_{33}NS$ = 679.88) |
| S-99 | m/z = 787.32($C_{61}H_{41}N$ = 788.01) | S-100 | m/z = 743.33($C_{55}H_{41}N_3$ = 743.95) |
| S-101 | m/z = 485.21($C_{37}H_{27}N$ = 485.63) | S-102 | m/z = 471.2($C_{36}H_{25}N$ = 471.6) |
| S-103 | m/z = 571.19($C_{43}H_{25}NO$ = 571.68) | S-104 | m/z = 584.23($C_{44}H_{28}N_2$ = 584.72) |
| S-105 | m/z = 539.24($C_{40}H_{21}D_5N_2$ = 539.69) | S-106 | m/z = 453.15($C_{32}H_{15}NS$ = 471.6) |
| S-107 | m/z = 563.26($C_{43}H_{26}D_4NO$ = 563.74) | S-108 | m/z = 589.26($C_{44}H_{23}D_5N_2$ = 584.72) |

[Element Data]

[Example 1] Red Organic Light Emitting Device (Phosphorescent Host)

An organic electroluminescent device was manufactured according to a conventional method by using the compound obtained through synthesis as a light emitting host material of the emitting layer. First, N1-(naphthalen-2-yl)-N4, N4-bis (4-(naphthalen-2-yl(phenyl)amino)phenyl)-N1-phenylbenzene-1,4-diamine (hereinafter, 2-TNANA) film was vacuum-deposited on the ITO layer (anode) formed on a glass substrate to form a hole injection layer having a thickness of 60 nm, and then on the hole injection layer, 4,4-bis[N-(1-naphthyl)-N-phenylamino]biphenyl (hereinafter, NPB) as a hole transport compound was vacuum-deposited to a thickness of 50 nm to form a hole transport layer. Tris(4-(9H-carbazol-9-yl)phenyl)amine (hereinafter, TCTA) was vacuum-deposited to a thickness of 10 nm as an emitting auxiliary layer material on the hole transport layer to form a emitting auxiliary layer. After forming the emitting auxiliary layer, on the emitting auxiliary layer, the compound P-1 of the present invention represented by Formula (1) and the compound N-12 of the present invention represented by Formula (2) were used in a weight ratio (5:5) as a host, and an emitting layer was deposited to a thickness of 30 nm by doping (piq)$_2$r(acac) as a dopant material at a weight ratio of 95:5. Then, as a hole blocking layer, (1,1'-bisphenyl)-4-oleato)bis(2-methyl-8-quinolineoleato)aluminum (hereinafter, BAlq) was vacuum-deposited to a thickness of 10 nm, and as an electron transport layer, bis(10-hydroxybenzo[h]quinolinato)beryllium (hereinafter, BeBq$_2$) was deposited to a thickness of 20 nm. Thereafter, LiF, which is an alkali metal halide, was deposited as an electron injection layer to a thickness of 0.2 nm, and then Al was deposited to a thickness of 150 nm and used as a cathode, thereby manufacturing an organic electroluminescent device.

[Example 2] to [Example 29]

An organic electroluminescent device was manufactured in the same manner as in Example 1 by using the compounds of the present invention shown in Table 6 instead of the compounds P-1 and N-12 of the present invention as the host material of the emitting layer of Example 1.

[Comparative Example 1] to [Comparative Example 2]

An organic electroluminescent device was manufactured in the same manner as in Example 1, except that Comparative Compound A or Comparative Compound B was used instead of Compound P-1 of the present invention as a host material for the emitting layer.

<comparative example A>

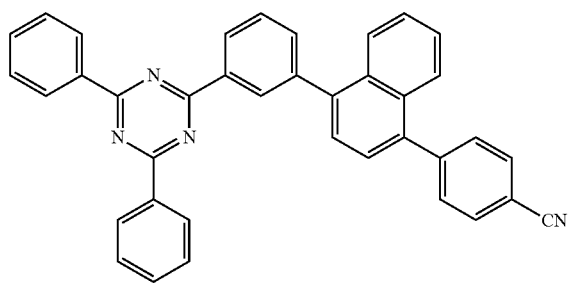

<comparative example B>

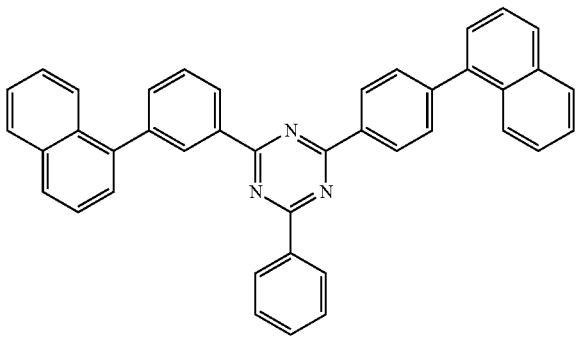

By applying a forward bias DC voltage to the organic electroluminescent devices manufactured by Examples 1 to 29, Comparative Examples 1 and Comparative Example 2, Electroluminescence (EL) characteristics were measured with PR-650 from Photoresearch, and the T95 lifetime was measured using a lifetime measuring device manufactured by McScience at 2500 cd/m$^2$ standard luminance, and the measurement results are shown in Table 6.

TABLE 6

| | First compound | Second compound | Voltage (V) | Current Density (mA/cm$^2$) | Efficiency (cd/A) | T (95) | CIE x | CIE y |
|---|---|---|---|---|---|---|---|---|
| comparative example1 | comparative compoundA | compound (N-12) | 5.5 | 10.4 | 24.1 | 98.8 | 0.636 | 0.322 |
| comparative example2 | comparative compoundB | compound (N-12) | 5.3 | 9.9 | 25.2 | 101.6 | 0.640 | 0.335 |
| example1 | compound (P-1) | compound (N-12) | 5.0 | 8.2 | 30.5 | 114.0 | 0.651 | 0.342 |
| example2 | compound (P-2) | compound (N-12) | 5.0 | 8.1 | 31.0 | 117.6 | 0.646 | 0.344 |
| example3 | compound (P-3) | compound (N-12) | 5.1 | 8.5 | 29.5 | 108.4 | 0.650 | 0.335 |
| example4 | compound (P-4) | compound (N-12) | 5.0 | 8.5 | 29.5 | 112.6 | 0.645 | 0.348 |
| example5 | compound (P-10) | compound (N-12) | 5.0 | 8.3 | 30.2 | 112.0 | 0.654 | 0.337 |
| example6 | compound (P-52) | compound (N-12) | 5.0 | 8.1 | 30.8 | 121.1 | 0.652 | 0.340 |
| example7 | compound (P-54) | compound (N-12) | 5.0 | 8.2 | 30.6 | 118.3 | 0.646 | 0.339 |
| example8 | compound (P-57) | compound (N-12) | 4.9 | 8.3 | 30.2 | 120.2 | 0.650 | 0.333 |
| example9 | compound (P-62) | compound (N-12) | 4.9 | 8.0 | 31.3 | 124.2 | 0.654 | 0.341 |
| example10 | compound (P-67) | compound (N-12) | 5.1 | 8.9 | 28.0 | 120.2 | 0.650 | 0.349 |
| example11 | compound (P-68) | compound (N-12) | 5.0 | 8.8 | 28.5 | 123.7 | 0.649 | 0.325 |
| example12 | compound (P-69) | compound (N-12) | 5.2 | 9.2 | 27.1 | 114.3 | 0.653 | 0.335 |
| example13 | compound (P-94) | compound (N-12) | 5.0 | 8.9 | 28.2 | 127.1 | 0.655 | 0.345 |
| example14 | compound (P-2) | compound (N-17) | 4.7 | 7.7 | 32.6 | 124.4 | 0.646 | 0.333 |
| example15 | compound (P-2) | compound (N-82) | 4.8 | 8.0 | 31.3 | 121.6 | 0.647 | 0.325 |

TABLE 6-continued

| | First compound | Second compound | Voltage (V) | Current Density (mA/cm²) | Efficiency (cd/A) | T (95) | CIE x | CIE y |
|---|---|---|---|---|---|---|---|---|
| example16 | compound (P-2) | compound (S-32) | 4.9 | 7.8 | 32.2 | 128.8 | 0.650 | 0.338 |
| example17 | compound (P-2) | compound (S-108) | 4.8 | 7.5 | 33.5 | 132.6 | 0.646 | 0.325 |
| example18 | compound (P-52) | compound (N-17) | 4.7 | 7.7 | 32.3 | 127.7 | 0.647 | 0.330 |
| example19 | compound (P-52) | compound (N-82) | 4.8 | 8.1 | 31.0 | 125.7 | 0.646 | 0.342 |
| example20 | compound (P-52) | compound (S-32) | 4.9 | 7.8 | 31.9 | 132.6 | 0.651 | 0.331 |
| example21 | compound (P-52) | compound (S-108) | 4.8 | 7.5 | 33.2 | 136.5 | 0.645 | 0.340 |
| example22 | compound (P-62) | compound (N-17) | 4.7 | 7.6 | 32.8 | 131.5 | 0.654 | 0.325 |
| example23 | compound (P-62) | compound (N-82) | 4.8 | 7.9 | 31.7 | 129.6 | 0.651 | 0.322 |
| example24 | compound (P-62) | compound (S-32) | 4.8 | 7.7 | 32.5 | 136.8 | 0.654 | 0.342 |
| example25 | compound (P-62) | compound (S-108) | 4.7 | 7.4 | 33.9 | 140.2 | 0.647 | 0.333 |
| example26 | compound (P-94) | compound (N-17) | 4.8 | 8.4 | 29.6 | 135.2 | 0.654 | 0.336 |
| example27 | compound (P-94) | compound (N-82) | 4.9 | 8.8 | 28.5 | 132.8 | 0.653 | 0.348 |
| example28 | compound (P-94) | compound (S-32) | 4.9 | 8.5 | 29.3 | 139.7 | 0.646 | 0.342 |
| example29 | compound (P-94) | compound (S-108) | 4.8 | 8.2 | 30.4 | 143.7 | 0.654 | 0.339 |

As can be seen in Table 6, when the compound of the present invention is used as the emitting layer host material, it can be seen that the efficiency is significantly improved compared to the case of using the comparative compound A or the comparative compound B.

As can be seen above, when a plurality of compounds are mixed to form the host of the emitting layer, the characteristics were different depending on the type of the first compound and the second compound, and when the same compound is applied to the second compound, it can be seen that the characteristic difference is remarkably displayed depending on the type of the first compound. Similarly, the second compound shows differences in driving voltage, efficiency, and lifespan depending on the type.

Comparing the comparative compound A and the compound of the present invention, as can be seen in Table 6, it can be confirmed that the compound of the present invention improves overall efficiency and lifespan of the element.

Table 7 is the calculated value of Dipole moment of the comparative compound A and the compound P-2 of the present invention.

TABLE 7

| | Comparative compound A | P-2 |
|---|---|---|
| Dipole moment | 5.5878 | 0.4600 |

Comparing Comparative Compound A and the compound of the present invention, Comparative Compound A has a core in which a cyano group is further substituted with a substituent of -phenyl-naphthyl-phenyl. However, the compound of the present invention has a core that is not further substituted with a cyano group, and additionally has a substituent of -phenyl-naphthyl structure as a substituent of triazine. Due to this structure, the physical properties of the compound are changed, and in particular, as shown in Table 7, in the case of Comparative Compounds A and P-2, there is a large difference in Dipole moment. In other words, it is judged to have a high Dipole moment due to a cyano group with high electronegativity.

Due to this high Dipole moment, the charge in the molecule is biased, and the biased charge can impede the flow of charge. Therefore, it seems that the load is generated in the charge transfer and the driving voltage of the element rapidly increases, which greatly affects the efficiency and lifespan of the element.

Table 8 is data measured using the DFT Method (B3LYP/6-31g(D)) of the Gaussian program of the comparative compound A and the compound P-1 of the present invention

TABLE 8

| | Comparative compound A | P-2 |
|---|---|---|
| HOMO(eV) | −5.866 | −5.448 |
| LUMO(eV) | −1.951 | −1.828 |
| Eg(eV) | 3.914 | 3.620 |
| T1(eV) | 2.520 | 2.536 |
| S1(eV) | 3.460 | 3.187 |

As can be seen in Table 8, comparing the comparative compound A and the compound P-2 of the present invention, it can be seen that T1 is similar but the energy bandgap is reduced, and in particular, that S1 is lowered. Due to this, the wavelength of the energy emitted from the host is increased, and the energy is better transferred to the red dopant. In other words, the low S1 of the compound P-2 of the present invention facilitates the transfer of Foster energy to the dopant, which appears to affect the overall performance improvement of the element.

In addition, when Comparative Compound B is compared with the compound of the present invention, it can be seen that the compound of the present invention improves overall driving voltage and efficiency of the element as shown in Table 6. Comparative compound B has a structure in which -phenyl-naphthyl is substituted with a substituent of triazine, and the compound of the present invention has a structure of -phenyl-naphthyl-phenyl. That is, it seems to affect the efficiency of the element according to the type of the substituent.

The calculated Reorganization Energy values of Comparative Compounds B and P-2 are described in Table 9.

RE values shown in Table 9 mean values calculated by $RE_{elec}$.

TABLE 9

| compound | Reorganization Energy (RE) |
|---|---|
| Comparative compound B | 0.299 |
| P-2 | 0.231 |

Referring to Table 9, RE value is different depending on the substituent of the triazine, the compound P-2 of the present invention has a lower RE value than the comparative compound B. That is, when having a lower RE value, it means high mobility and fast EOD, and the compound of the present invention having a fast EOD value as a whole seems to have a fast driving voltage, high efficiency, and a long lifespan. In particular, when the emitting layer is composed of a plurality of mixtures, driving, efficiency, and lifetime are determined according to the degree of ease of injection of holes and electrons into the dopant, and when the hole and electron ratio (Charge Balance) is properly maintained, the efficiency increases.

In particular, as can be seen in Examples 14 to 29, as a plurality of host compounds, the characteristics were different depending on the type of the first compound and the second compound, and in the end, it is judged that the performance of the element is determined according to the injection characteristics of holes and electrons into the dopant. In the present invention, it can be seen that through the relationship between RE value and mobility, the overall driving reduction effect, efficiency and lifespan increase effect are brought. In addition, the combination of a specific substituent substituted for triazine has a positive effect on overall mobility and acts as a hole-to-electron ratio (e.g. energy balance, stability, etc.), showing an overall improved result. That is, even within the same skeleton, RE value is determined depending on the type and substitution position of the substituent, and it can be seen that the characteristics are very different. Also, in the case of the compound of the present invention, it can be seen that the value of CIEx slightly increased, which indicates that the compound of the present invention as a host may affect the color of the element. That is, as in the present invention, when the phenanthrooxazole structure and the phenanthrene structure at a specific position are simultaneously substituted with the substituent of the triazine, the effect is considered to be maximized as a synergistic effect.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

What is claimed is:

1. A compound represented by Formula (1):

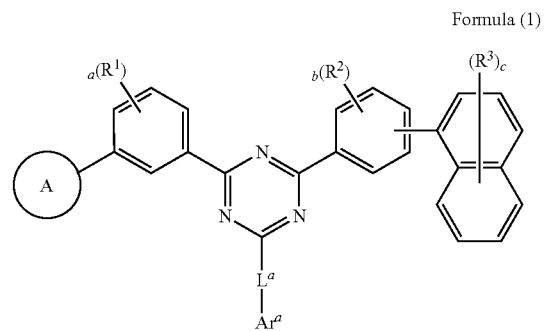

Formula (1)

wherein:

A is a substituent represented by Formula (A-1) or (A-2);

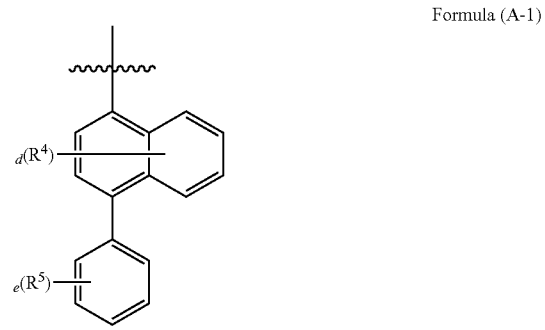

Formula (A-1)

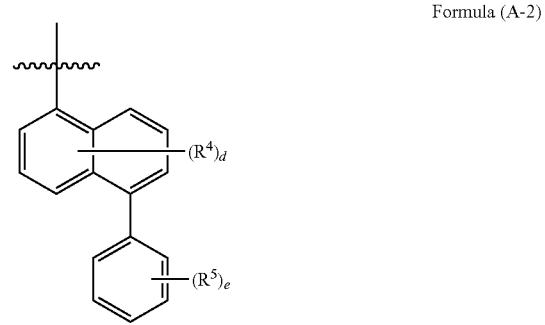

Formula (A-2)

$R^1$, $R^2$, $R^3$, $R^4$ and $R^5$, being the same or different from each other, are hydrogen or deuterium;

a and b are each independently an integer of 0 to 4, c is an integer of 0 to 7, d is an integer of 0 to 6, e is an integer of 0 to 5;

$L^a$ is a direct bond or a $C_6$~$C_{60}$ arylene group;

$Ar^a$ is a $C_6$~$C_{60}$ aryl group;

wherein the aryl group or arylene group may be substituted with one or more substituent(s) selected from the group consisting of deuterium; halogen; silane group; siloxane group; boron group; germanium group; cyano group; nitro group; $C_1$-$C_{20}$ alkylthio group; $C_1$-$C_{20}$ alkoxy group; $C_1$-$C_{20}$ alkyl group; $C_2$-$C_{20}$ alkenyl group; $C_2$-$C_{20}$ alkynyl group; $C_6$-$C_{20}$ aryl group;

$C_6$-$C_{20}$ aryl group substituted with deuterium; a fluorenyl group; $C_2$~$C_{20}$ heterocyclic group; $C_3$-$C_{20}$ cycloalkyl group; $C_7$-$C_{20}$ arylalkyl group; and $C_8$-$C_{20}$ arylalkenyl group; and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by combination thereof.

2. The compound of claim 1, wherein $Ar^a$ is represented by any one of Formulas (A-1) to (A-3):

Formula (A-1)

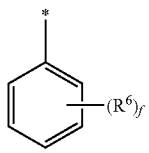

Formula (A-2)

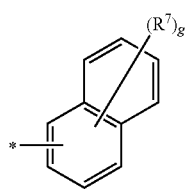

Formula (A-3)

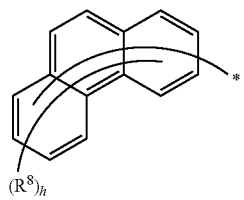

wherein:

\* indicates the bonding position, $R^6$, $R^7$ and $R^6$ are each the same or different, and each independently hydrogen; deuterium; or a $C_6$~$C_{20}$ aryl group;

f is an integer of 0 to 5, g is an integer of 0 to 7, and h is an integer of 0 to 9.

3. The compound of claim 1, wherein $L^a$ is represented by any one of Formulas (L-1) to (L-3):

Formula (L-1)

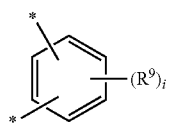

Formula (L-2)

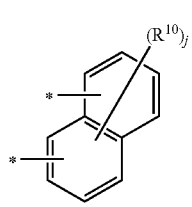

Formula (L-3)

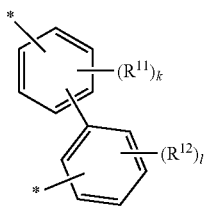

wherein:

\* indicates the bonding position, $R^9$, $R^{10}$, $R^{11}$ and $R^{12}$ are each the same or different, and each independently hydrogen; deuterium; or a $C_6$~$C_{20}$ aryl group, i, k and l are each independently an integer of 0 to 4, and j is an integer of 0 to 6.

4. The compound of claim 1, wherein the compound represented by Formula 1 is represented by any one of P-1 to P-98:

P-1

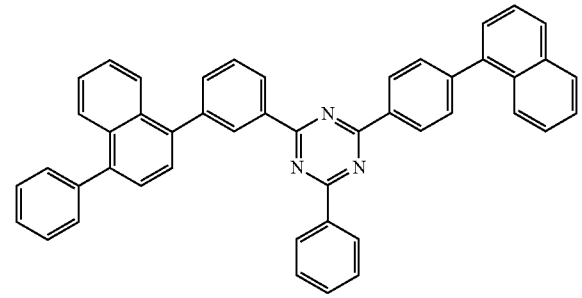

P-2

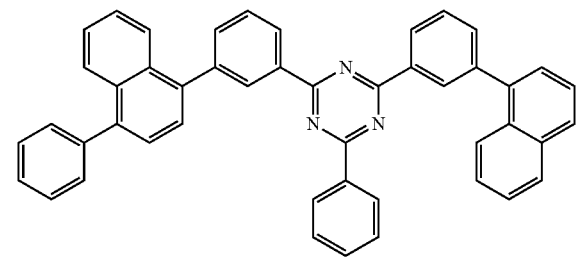

P-3

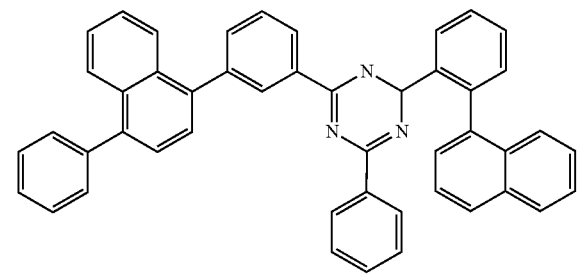

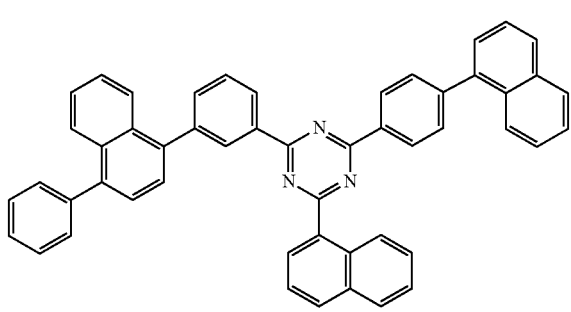
P-4
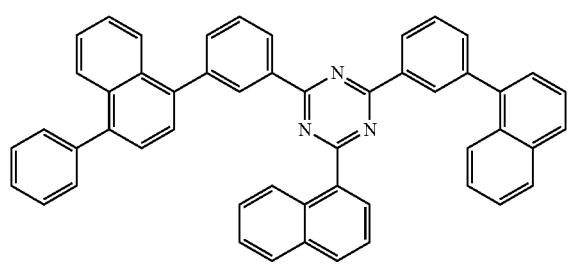
P-5
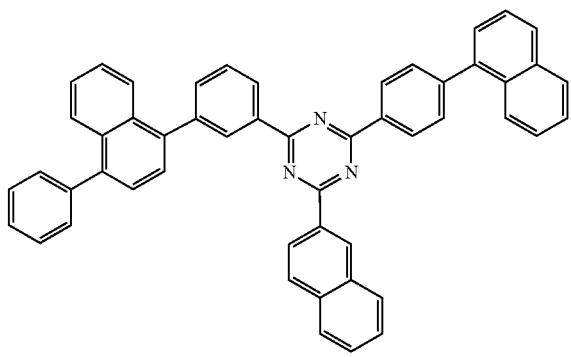
P-6
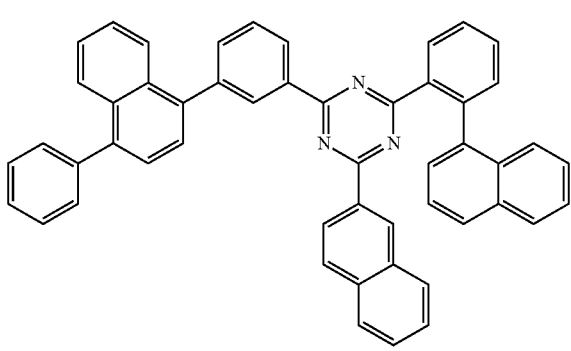
P-7
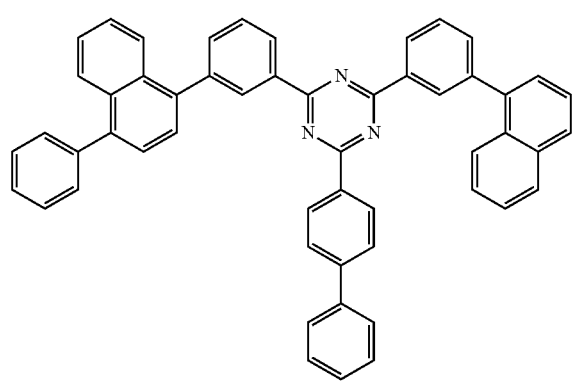
P-8

P-12
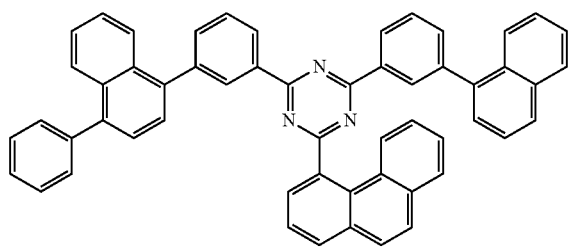
P-13
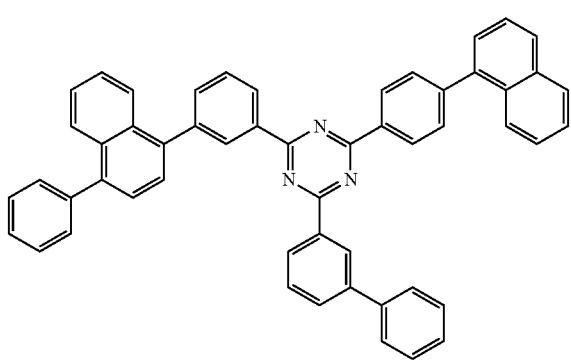
P-14
P-15
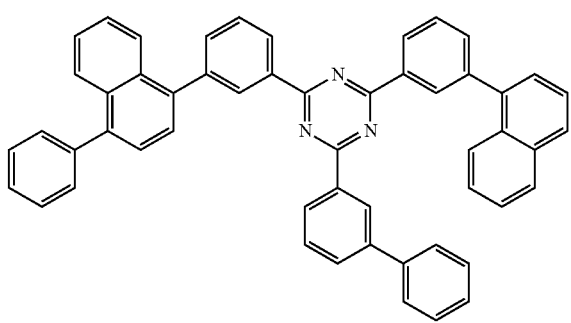
P-16
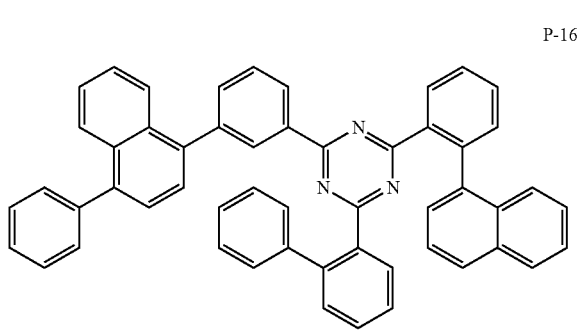
P-17
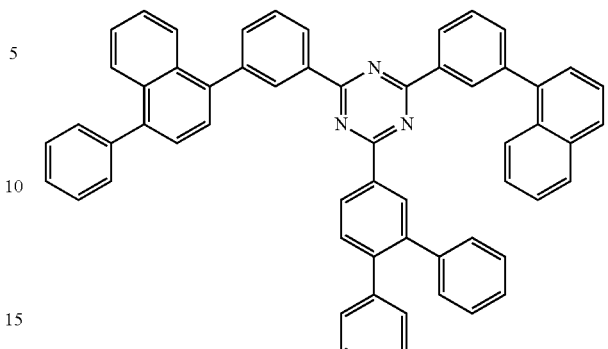
P-18
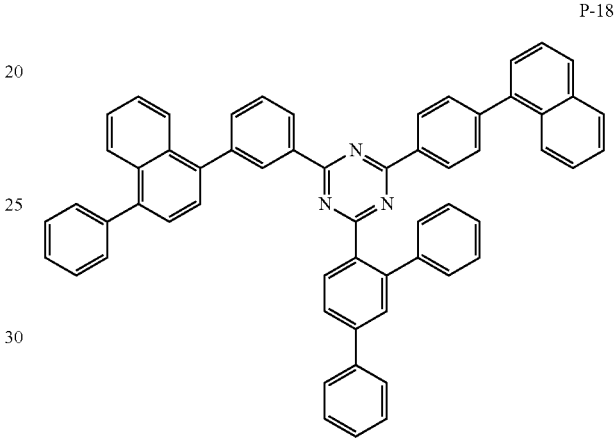
P-19
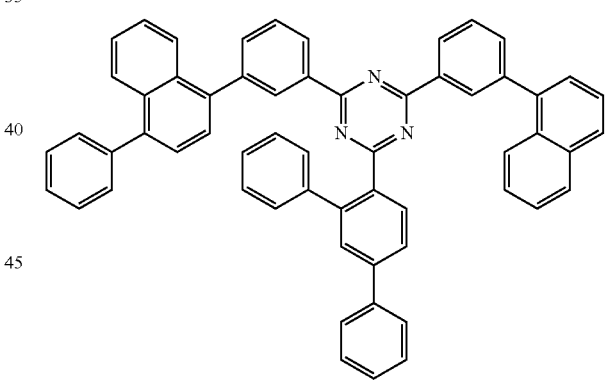
P-20
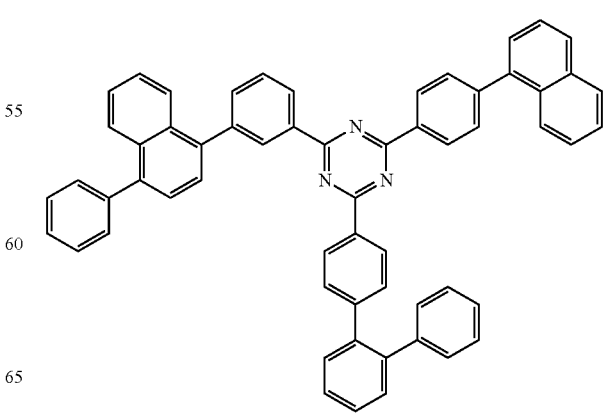

P-21
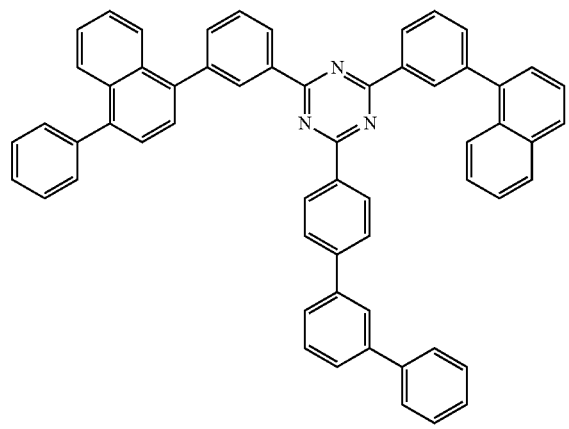
P-22
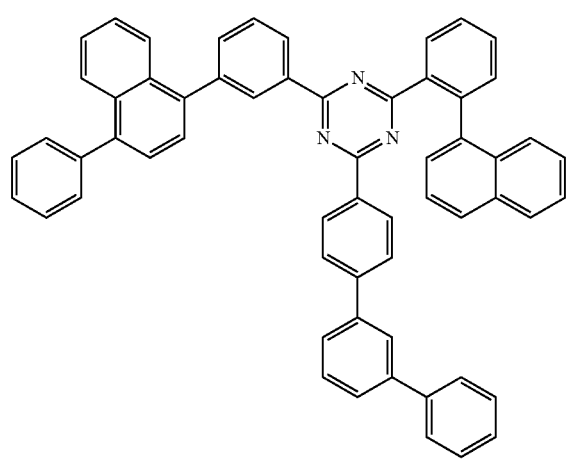
P-23
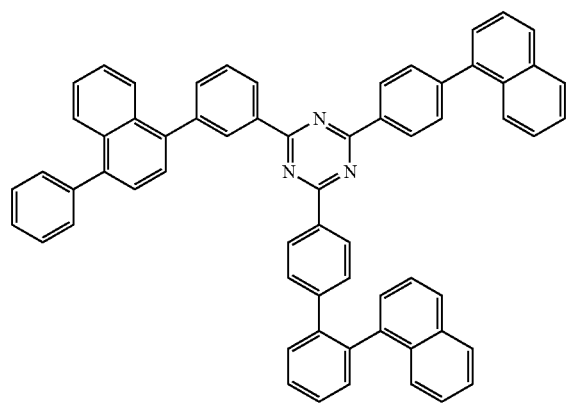
P-24
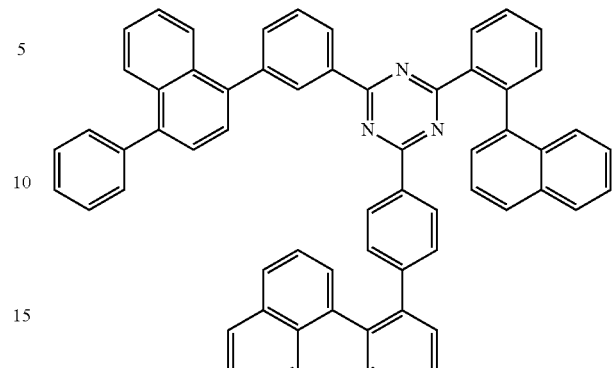
P-25
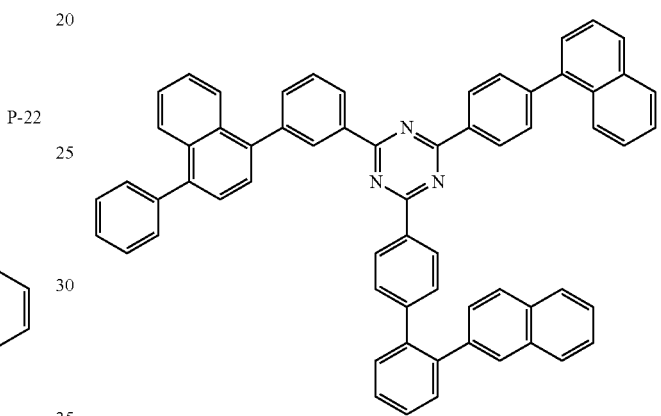
P-26
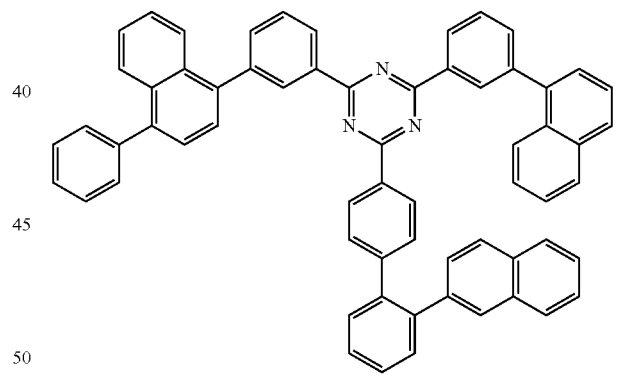
P-27
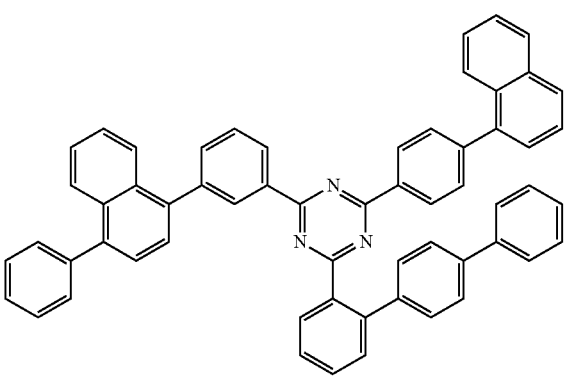

P-28
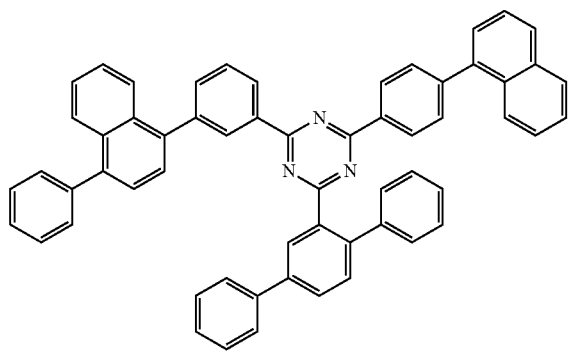
P-29
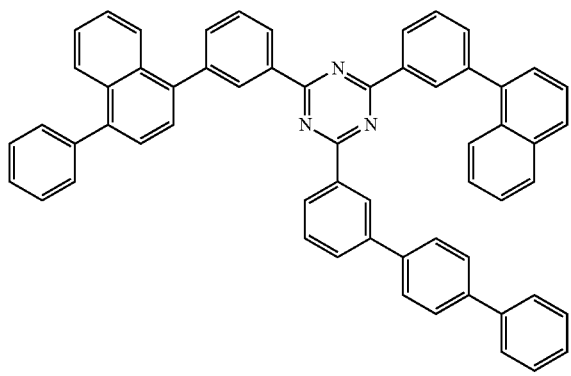
P-30
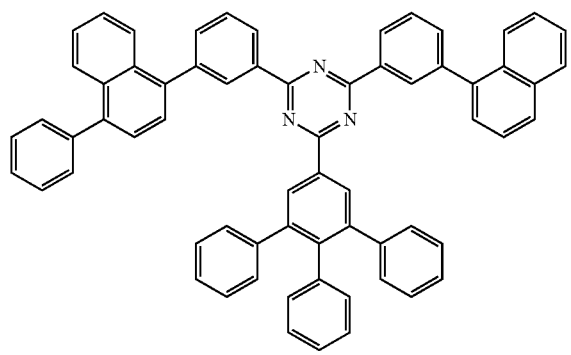
P-31
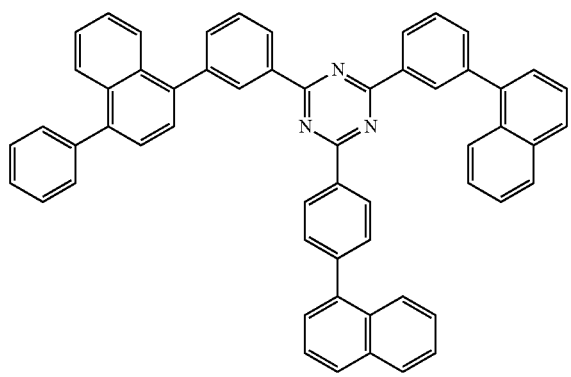
P-32
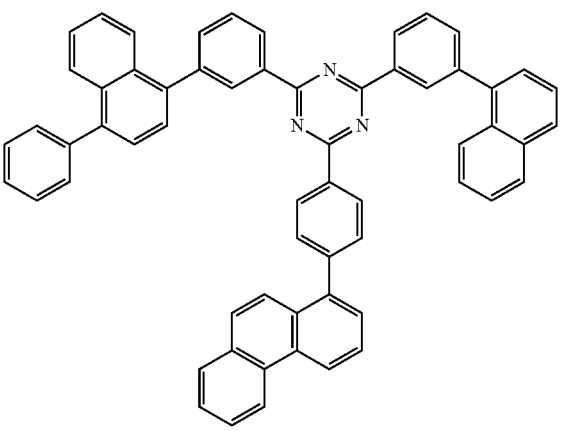
P-33
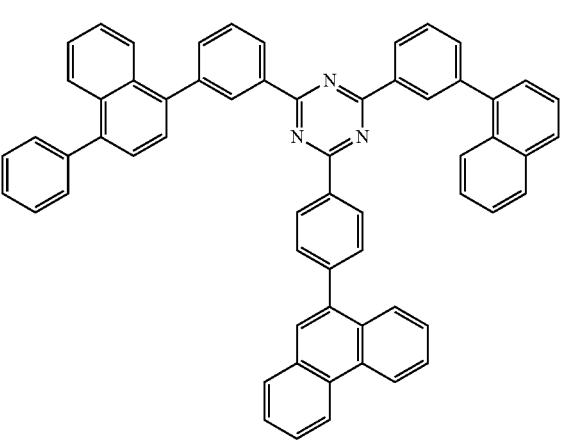
P-34
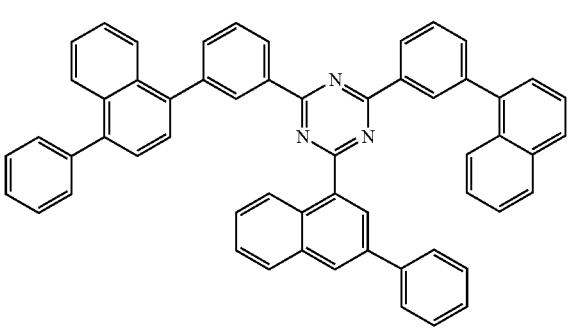
P-35
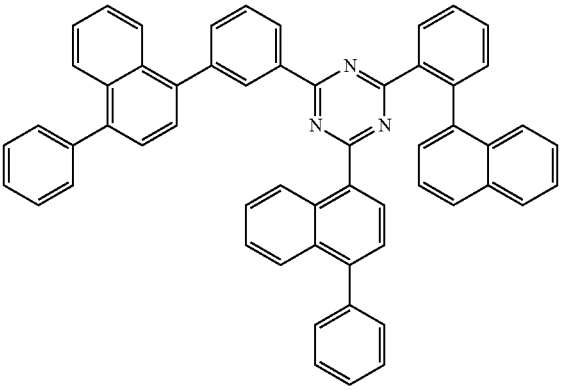

-continued
P-36
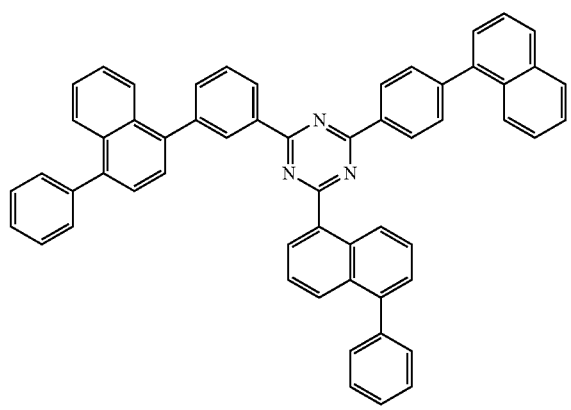
P-37
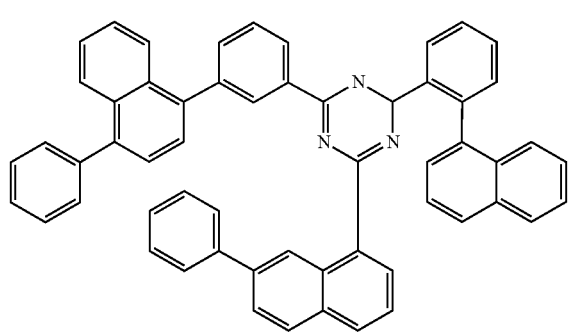
P-38
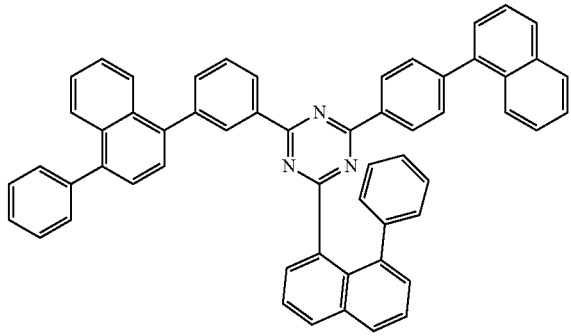
P-39
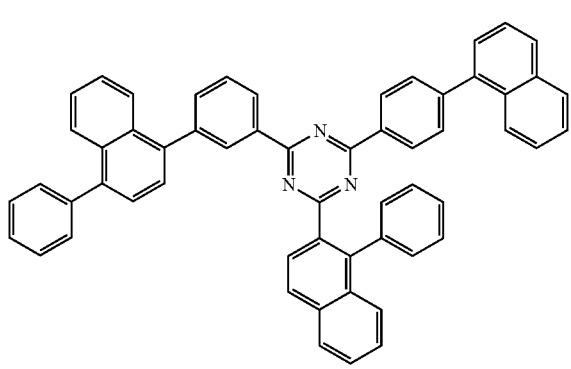
-continued
P-40
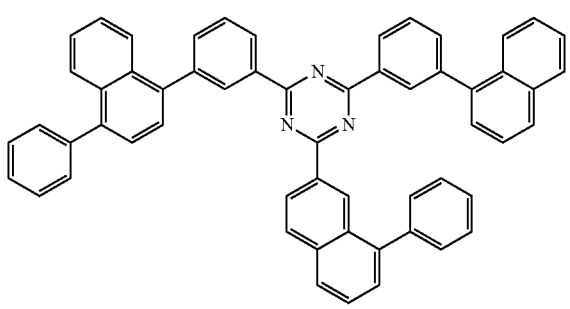
P-41
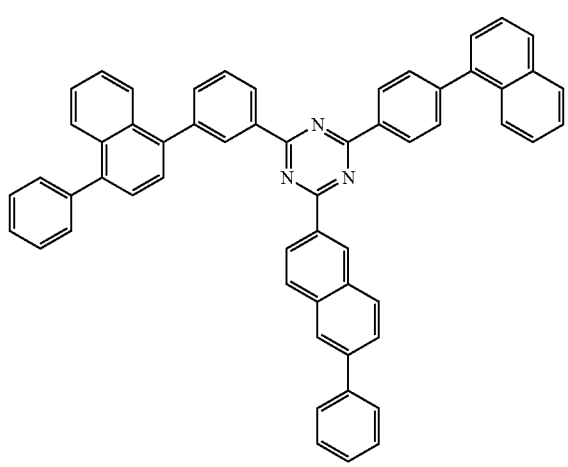
P-42
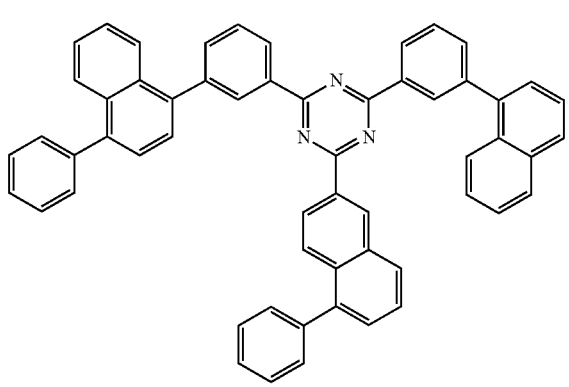
P-43
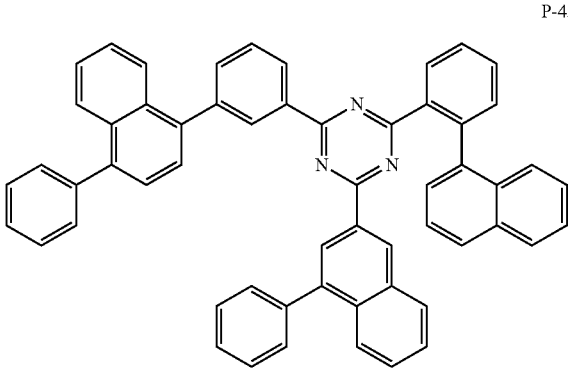

-continued
P-44
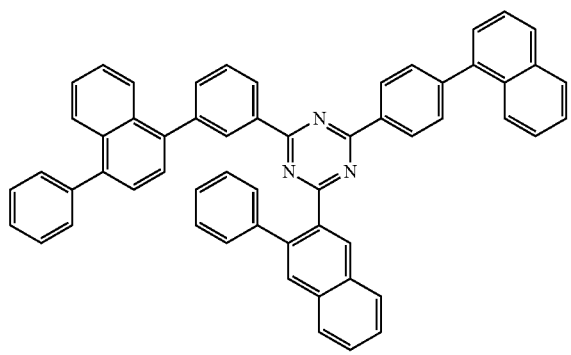
P-45
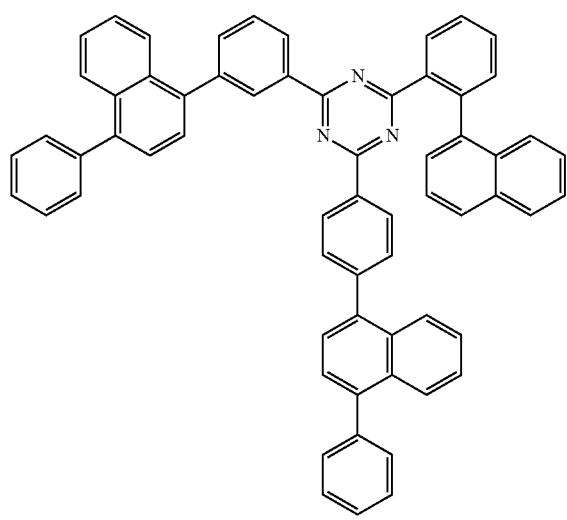
P-46
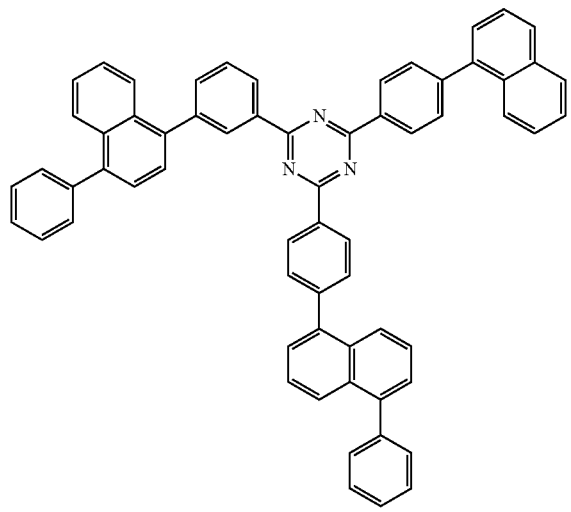
-continued
P-47
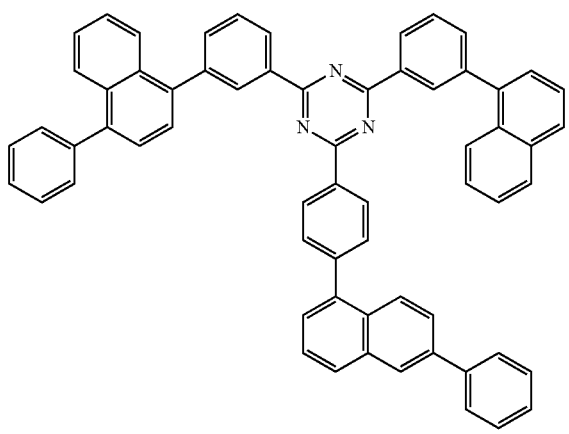
P-48
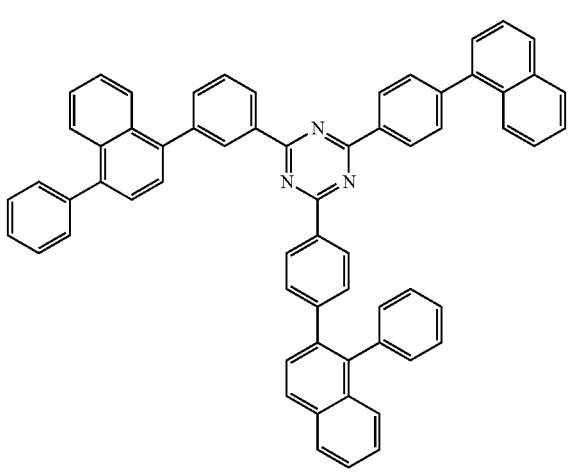
P-49
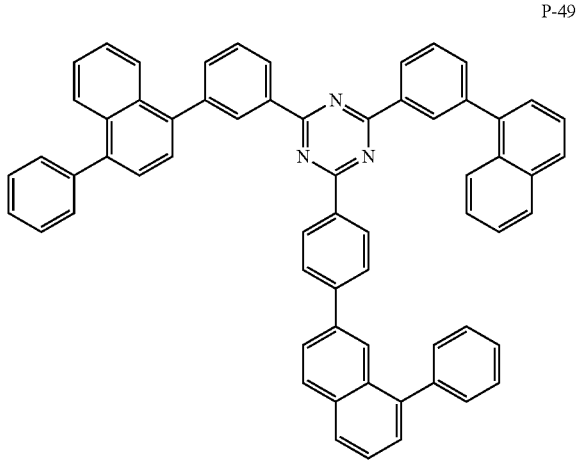

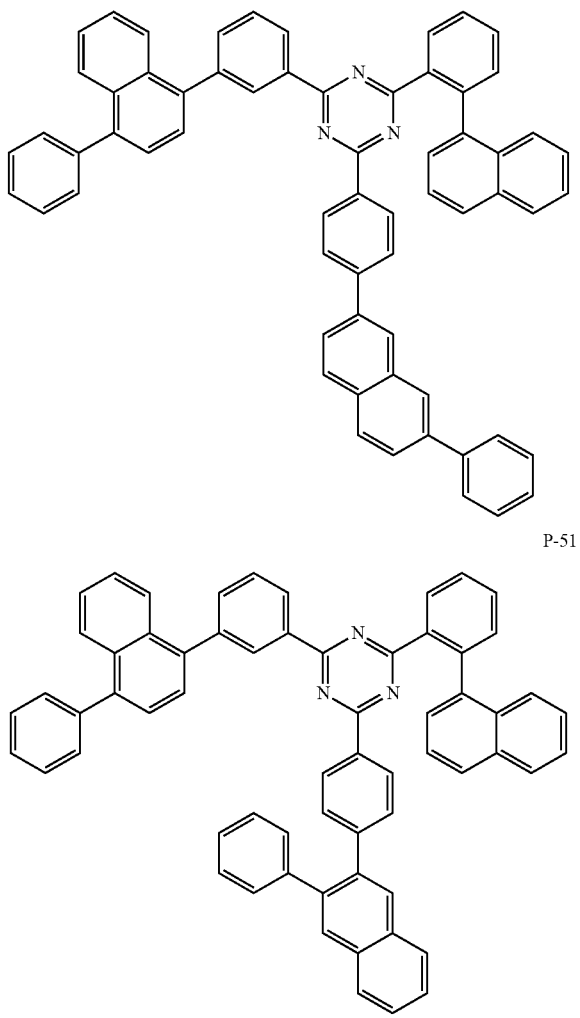
P-50
P-51
P-52
P-53
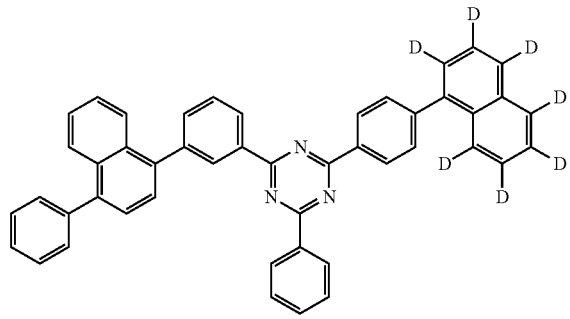
P-54
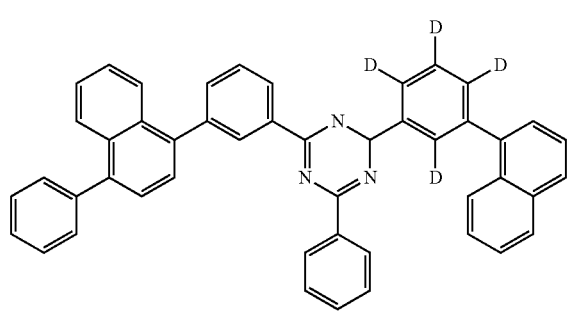
P-55
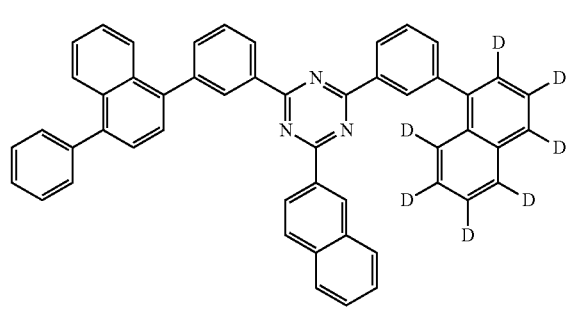
P-56
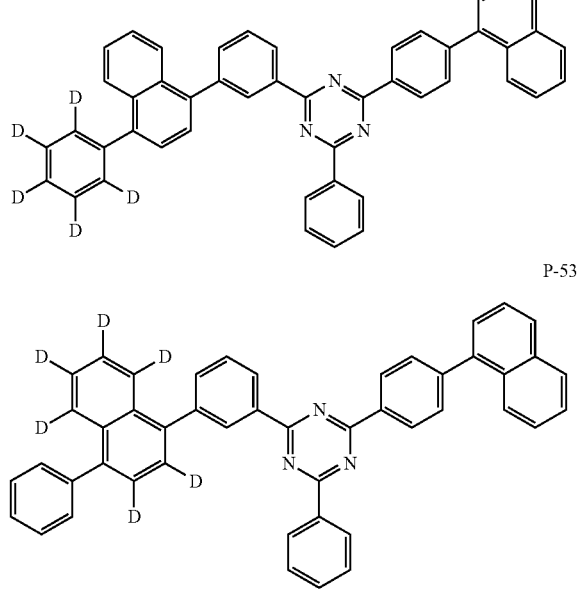
P-57
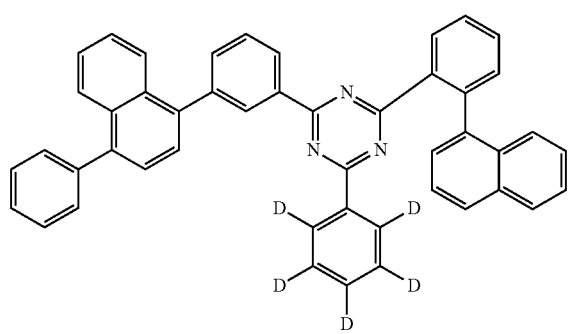
P-58

P-59
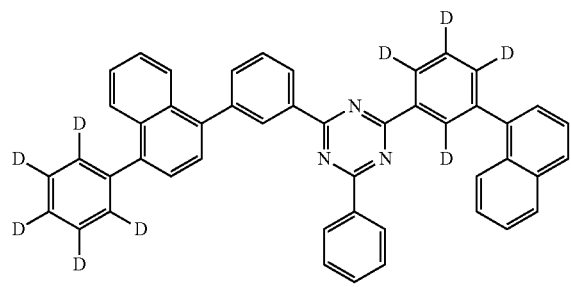
P-60
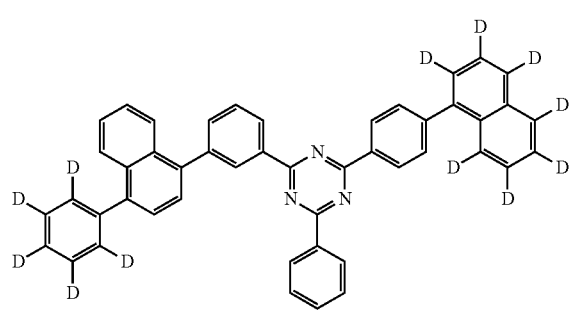
P-61
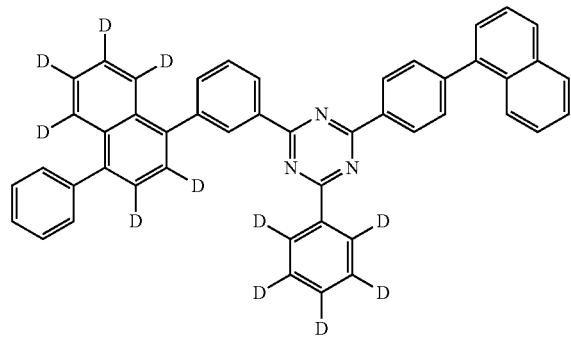
P-62
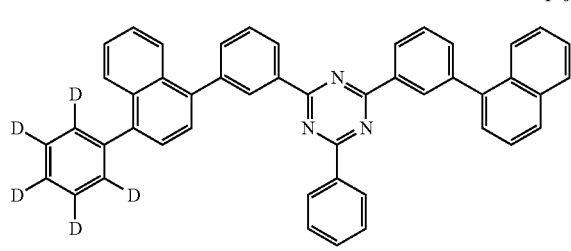
P-63
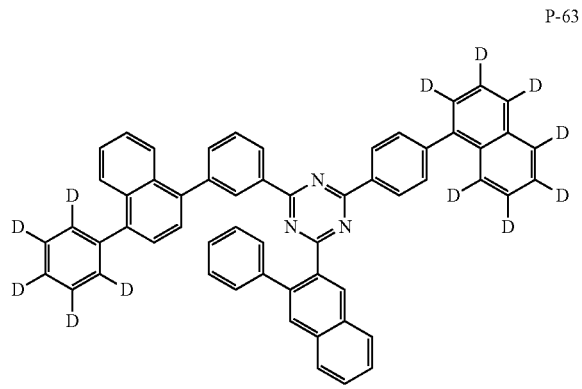
P-64
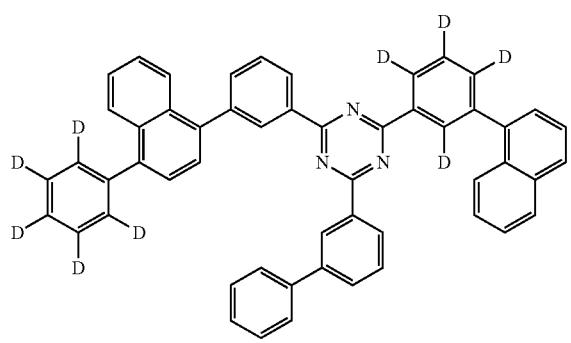
P-65
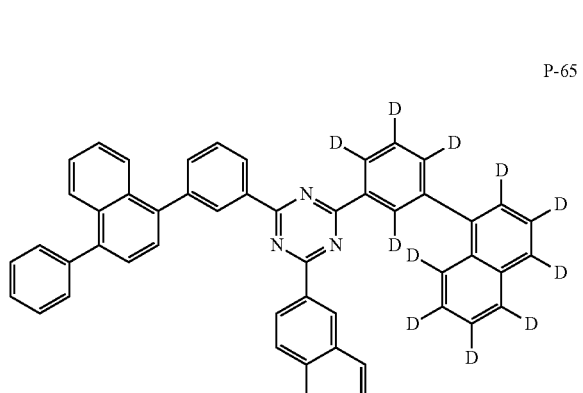
P-66
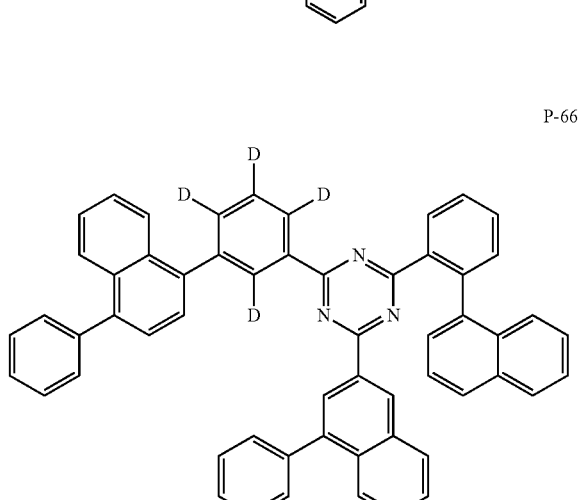
P-67
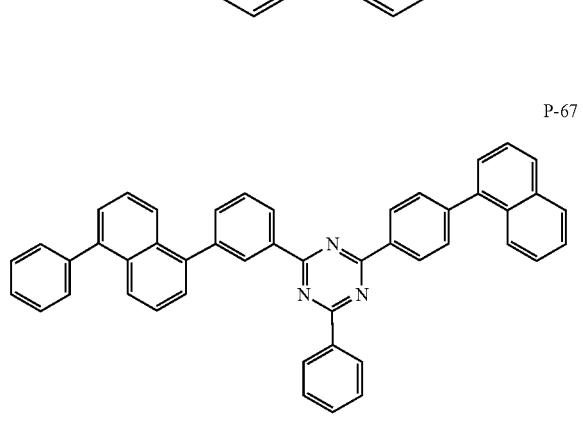

P-68
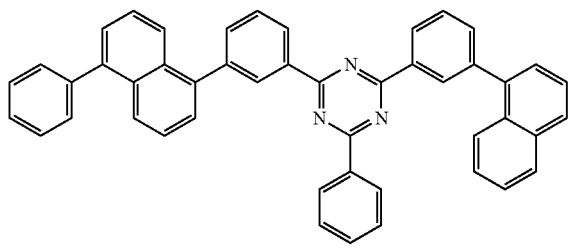
P-69
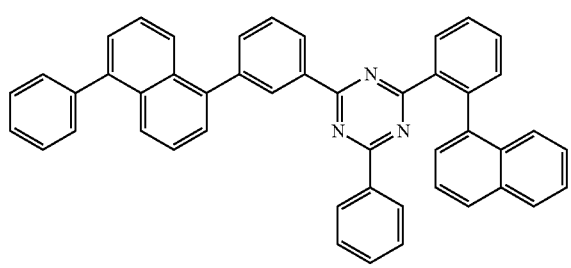
P-70
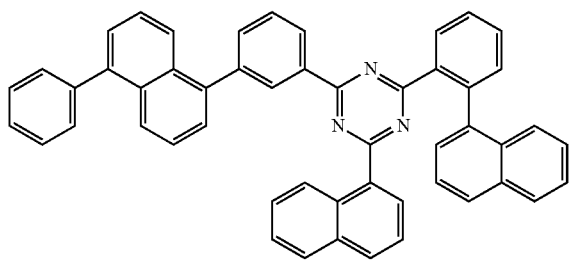
P-71
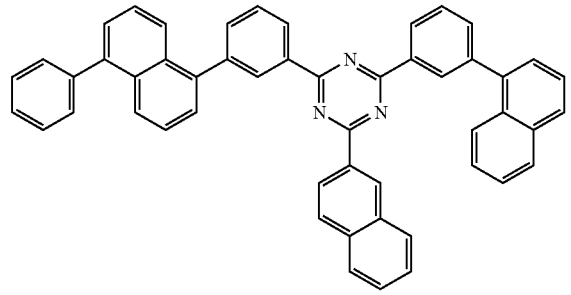
P-72
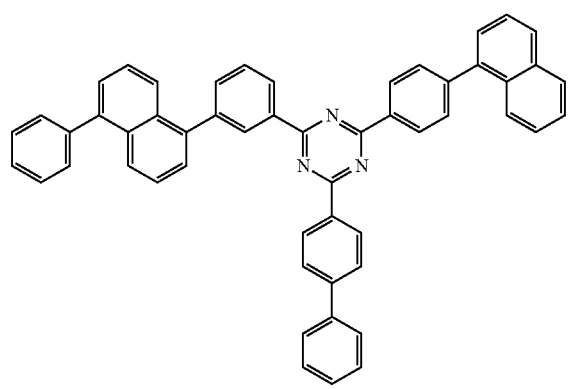
P-73
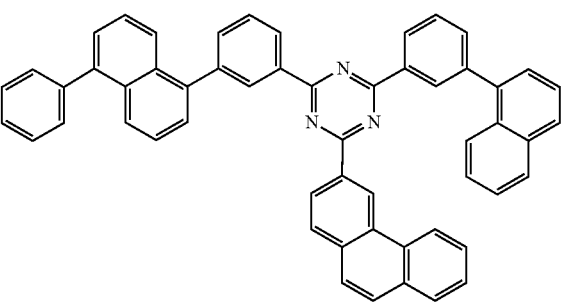
P-74
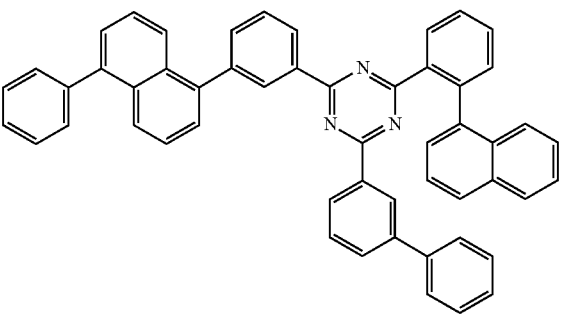
P-75
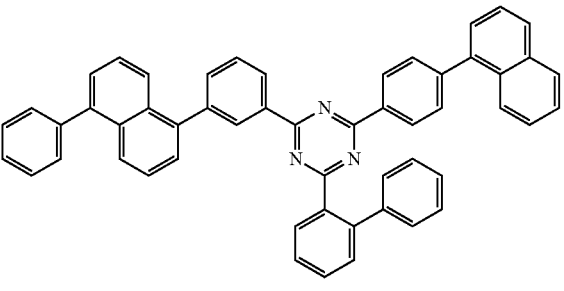
P-76
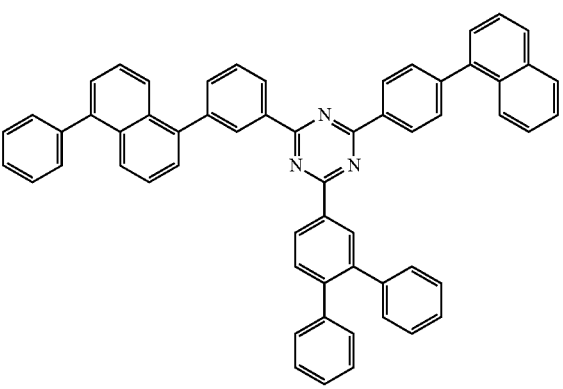

P-77
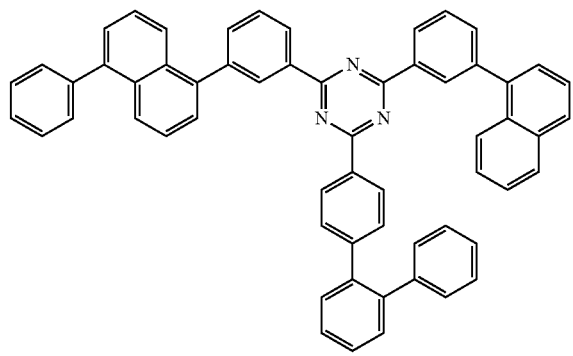
P-78
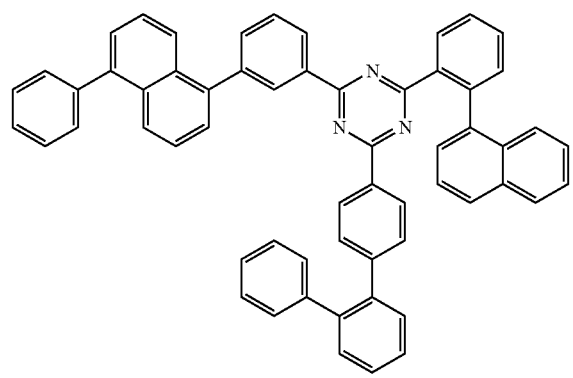
P-79
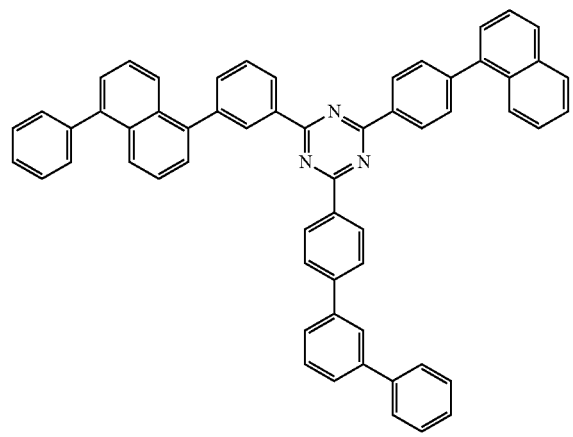
P-80
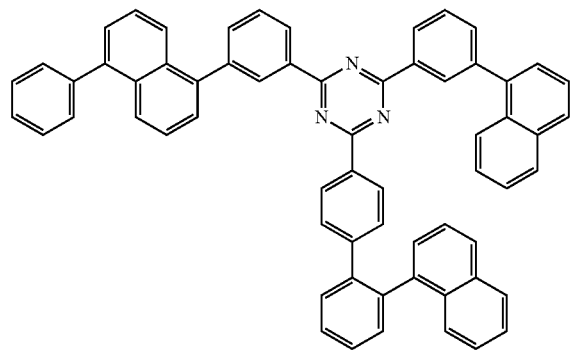
P-81
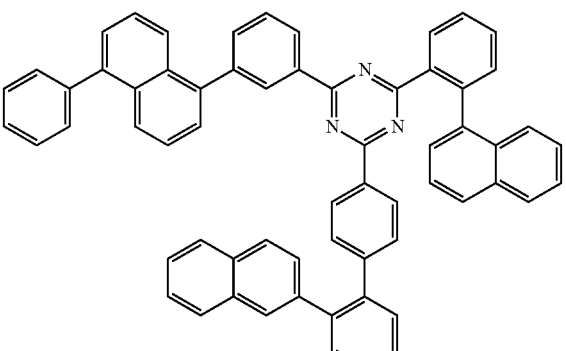
P-82
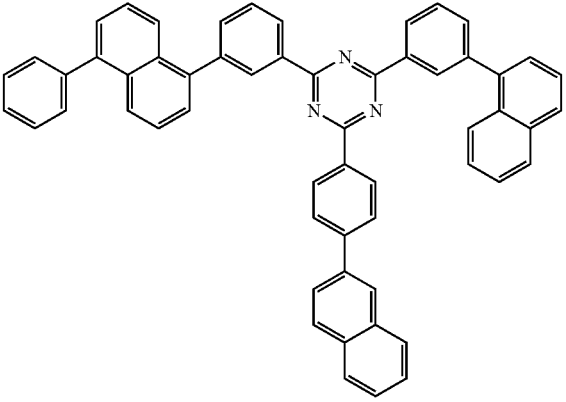
P-83
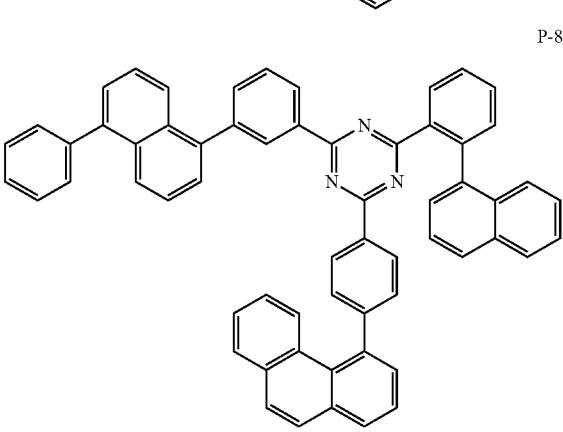
P-84
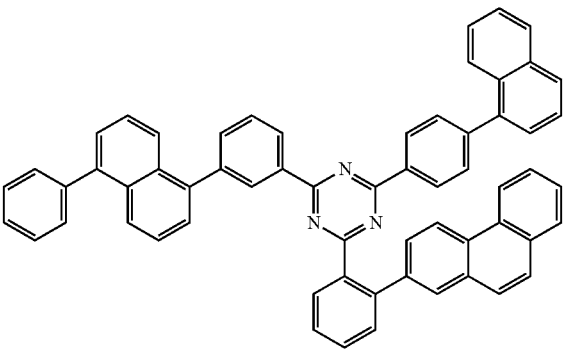

P-85
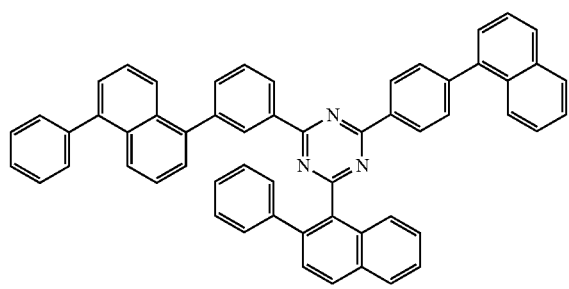
P-86
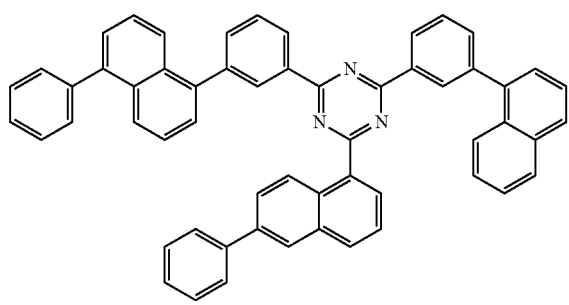
P-87
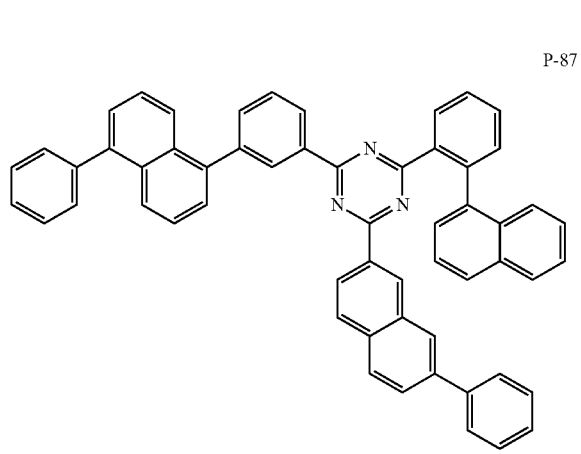
P-88
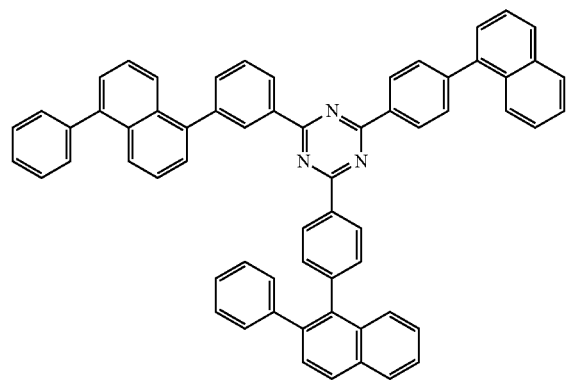
P-89
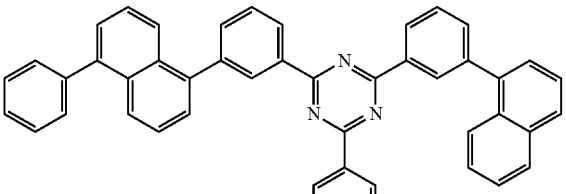
P-90
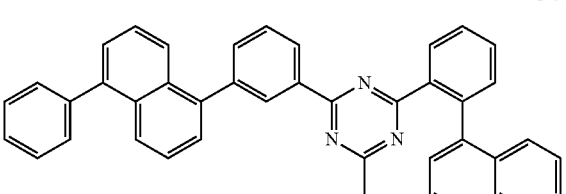
P-91
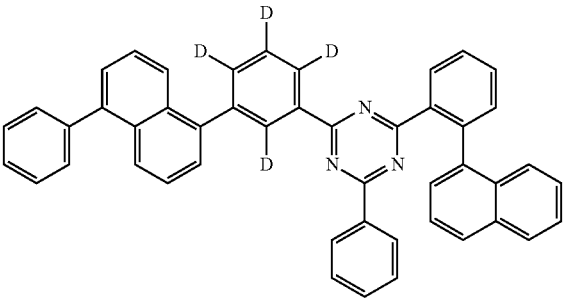
P-92
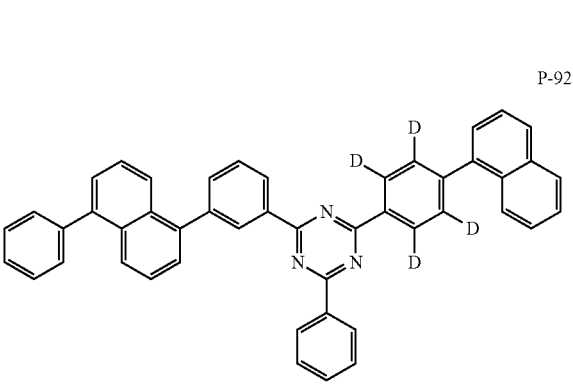

5. An organic electronic element comprising a first electrode, a second electrode, and an organic material layer formed between the first electrode and the second electrode, wherein the organic material layer comprises an emitting layer, wherein the emitting layer is a phosphorescent emitting layer and comprises a first host compound represented by Formula 1 in claim 1 and a second host compound represented by Formula 2 or Formula 3:

<Formula 2>

<Formula 3> wherein:
- $L^4, L^5, L^6$ and $L^7$ are each independently selected from the group consisting of a single bond; a $C_6$-$C_{60}$ arylene group; fluorenylene group; a fused ring group of a $C_3$-$C_{60}$ aliphatic ring and a $C_6$-$C_{60}$ aromatic ring; a $C_2$-$C_{60}$ heterocyclic group;
- $Ar^3, Ar^4$ and $Ar^5$ are each independently selected from the group consisting of a $C_6$-$C_{60}$ aryl group; fluorenyl group; a $C_2$-$C_{60}$ heterocyclic group including at least one heteroatom of O, N, S, Si or P; and a fused ring group of a $C_3$-$C_{60}$ aliphatic ring and a $C_6$-$C_{60}$ aromatic ring;

$Ar^6$ are each independently selected from the group consisting of a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; and -L'-N($R^b$)($R^c$), $L^1$ is selected from the group consisting of a single bond; a $C_6$-$C_{60}$ arylene group; a $C_2$-$C_{60}$ heterocyclic group including at least one heteroatom of O, N, S, Si or P;

$R^b$ and $R^c$ are each independently selected from the group consisting of a $C_6$-$C_{60}$ aryl group; fluorenyl group; a fused ring group of a $C_3$-$C_{60}$ aliphatic ring and a $C_6$-$C_{60}$ aromatic ring; a $C_2$-$C_{60}$ heterocyclic group including at least one heteroatom of O, N, S, Si or P; $C_1$-$C_{60}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group;

Z is O, S, CR'R" or NRa,

B is a $C_6$-$C_{20}$ aryl group,

R' and R" are each independently selected from a group consisting of a $C_6$-$C_{60}$ aryl group; a fluorenyl group; a $C_2$-$C_{60}$ heterocyclic group including at least one hetero atom of O, N, S, Si or P; a fused ring group of a $C_3$-$C_{60}$ aliphatic ring and a $C_6$-$C_{60}$ aromatic ring; a $C_1$-$C_{60}$ alkyl group; a $C_2$-$C_{20}$ alkenyl group; a $C_2$-$C_{20}$ alkynyl group; a $C_1$-$C_{30}$ alkoxyl group; and a $C_6$-$C_{30}$ aryloxy group; or may be bonded to each other to form a ring, $R^{31}$ and $R^{32}$ are each independently the same as or different from each other, and each independently selected from the group consisting of hydrogen; deuterium; halogen; cyano group; nitro group; a $C_6$-$C_{60}$ aryl group; fluorenyl group; a $C_2$-$C_{60}$ heterocyclic group including at least one heteroatom of O, N, S, Si or P; a fused ring group of a $C_3$-$C_{60}$ aliphatic ring and a $C_6$-$C_{60}$ aromatic ring; a $C_1$-$C_6$ alkyl group; a $C_2$-$C_{60}$ alkenyl group; a $C_2$-$C_{60}$ alkynyl group; a $C_1$-$C_{60}$ alkoxy group; a $C_6$-$C_{60}$ aryloxy group; or a plurality of adjacent $R^{31}$ or a plurality of $R^{32}$ may be bonded to each other to form a ring, n and o are each independently an integer from 0 to 4, Ra is a $C_6$-$C_{60}$ aryl group; or a $C_2$-$C_{60}$ heterocyclic group including at least one heteroatom of O, N, S, Si and P, wherein the aryl group, arylene group, heterocyclic group, fluorenyl group, fluorenylene group, fused ring group, alkyl group, alkenyl group, alkynyl group, alkoxy group and aryloxy group may be substituted with one or more substituents selected from the group consisting of deuterium; halogen; silane group; siloxane group; boron group; germanium group; cyano group; nitro group; $C_1$-$C_{20}$ alkylthio group; $C_1$-$C_{20}$ alkoxyl group; $C_1$-$C_{20}$ alkyl group; $C_2$-$C_{20}$ alkenyl group; $C_2$-$C_{20}$ alkynyl group; $C_6$-$C_{20}$ aryl group; $C_6$-$C_{20}$ aryl group substituted with deuterium; a fluorenyl group; $C_2$-$C_{20}$ heterocyclic group; $C_3$-$C_{20}$ cycloalkyl group; $C_7$-$C_{20}$ arylalkyl group; and $C_8$-$C_{20}$ arylalkenyl group; and the substituents may be bonded to each other to form a saturated or unsaturated ring, wherein the term 'ring' means a $C_3$-$C_{60}$ aliphatic ring or a $C_6$-$C_{60}$ aromatic ring or a $C_2$-$C_{60}$ heterocyclic group or a fused ring formed by combination thereof.

6. The organic electronic element of claim 5, wherein the compound represented by Formula 2 is any one of compounds N-1 to N-96:

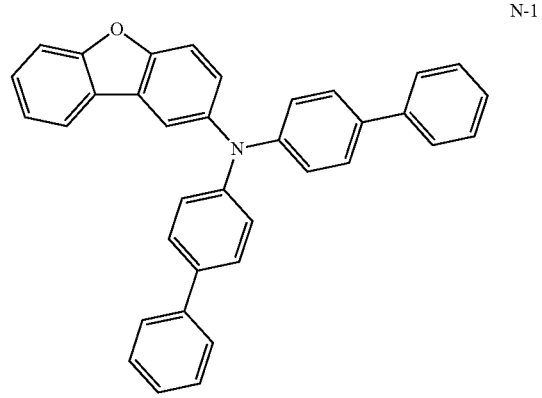

N-1

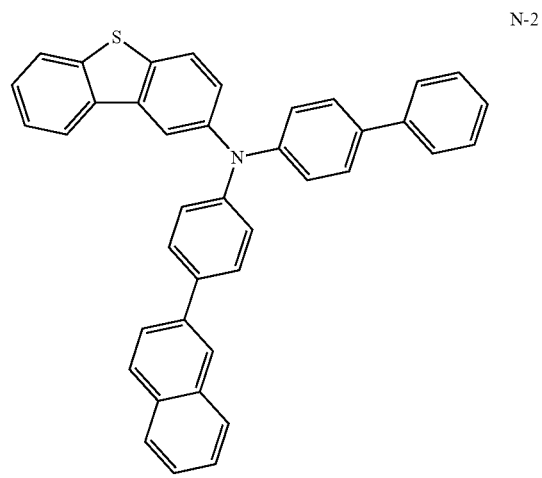

N-2

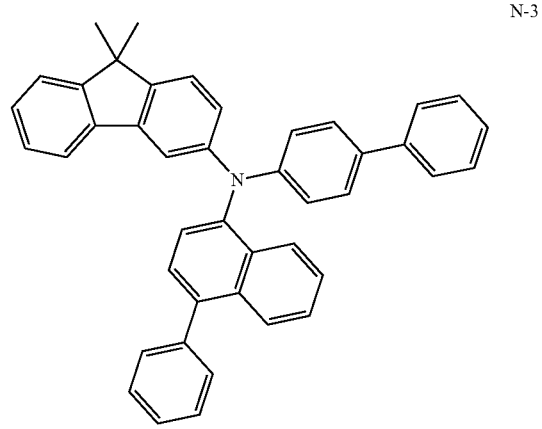

N-3

N-4
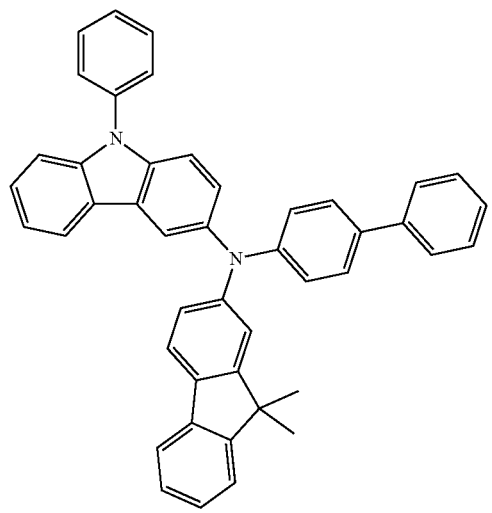
N-7
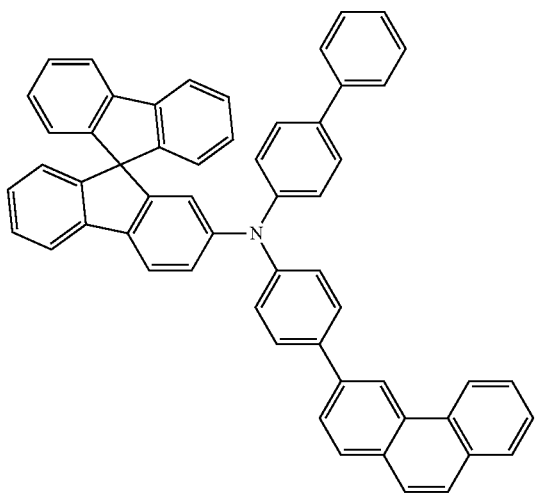
N-5
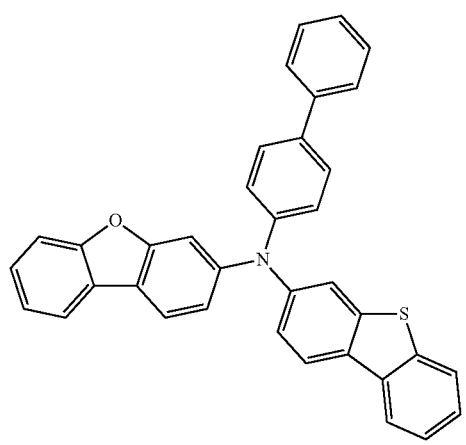
N-8
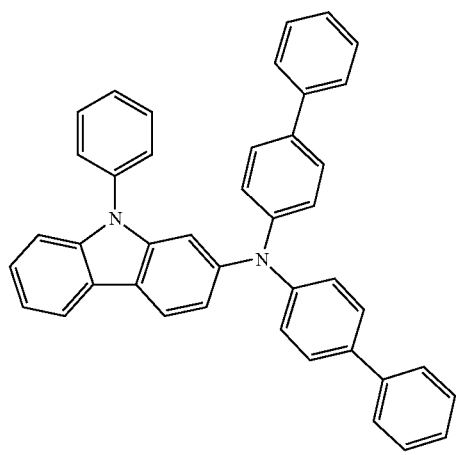
N-6
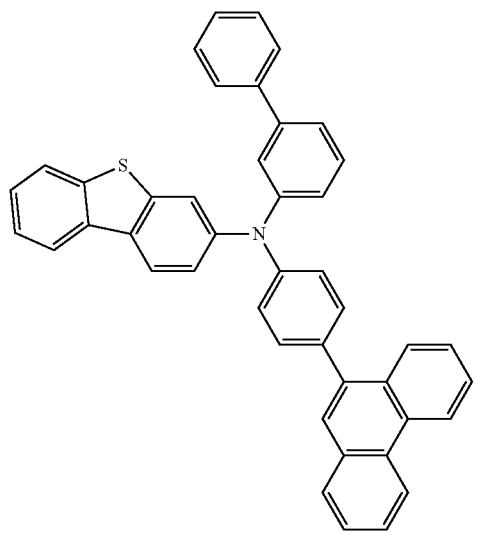
N-9
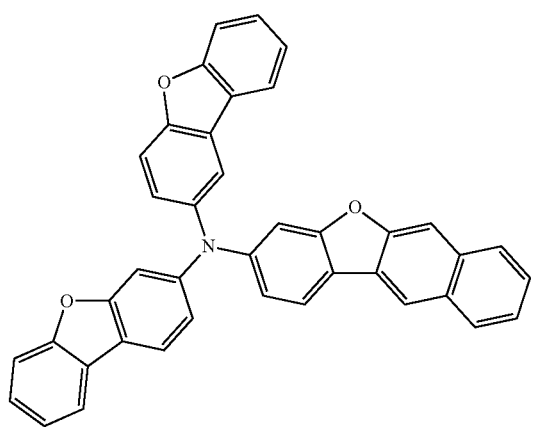

-continued
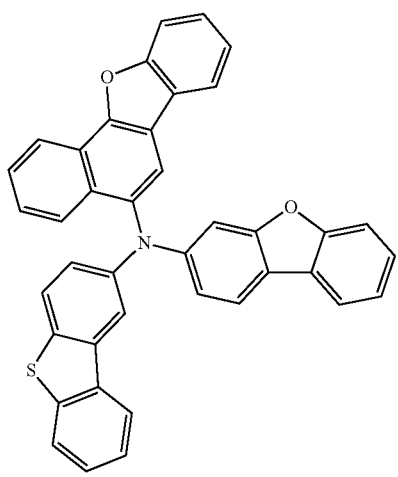
N-10
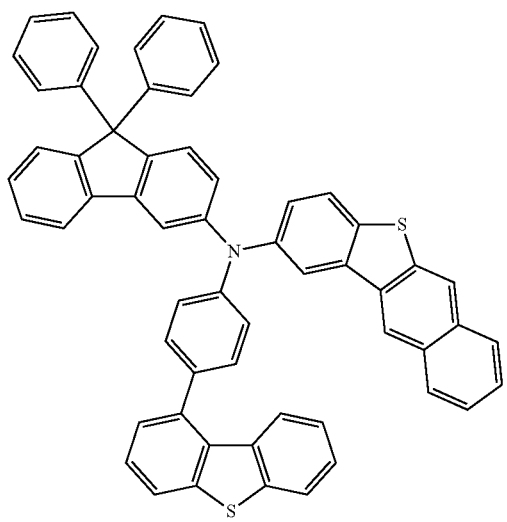
N-11
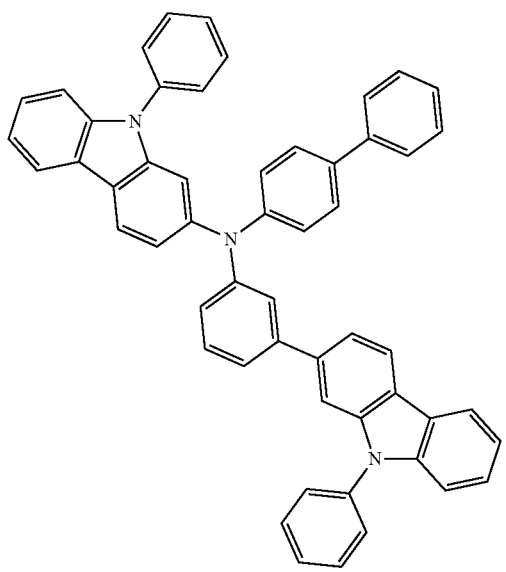
N-12
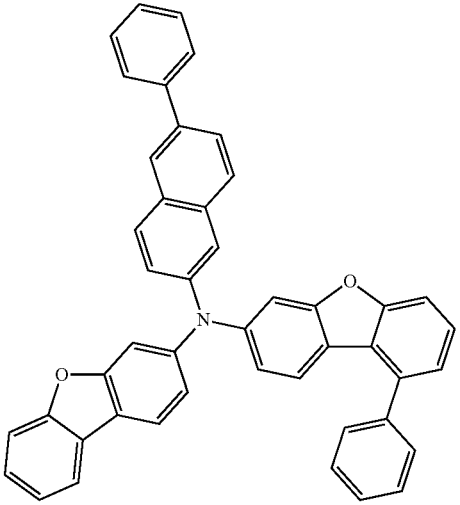
N-13
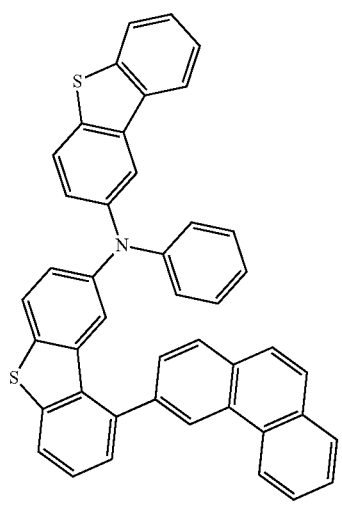
N-14
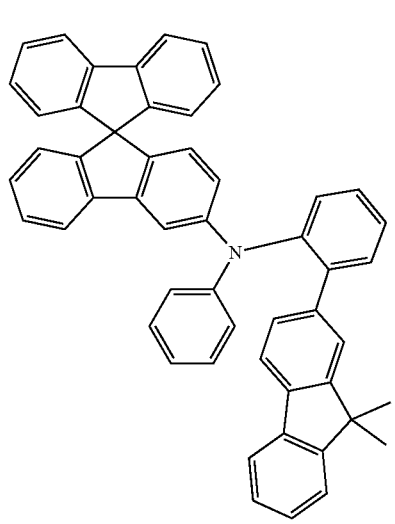
N-15

N-16
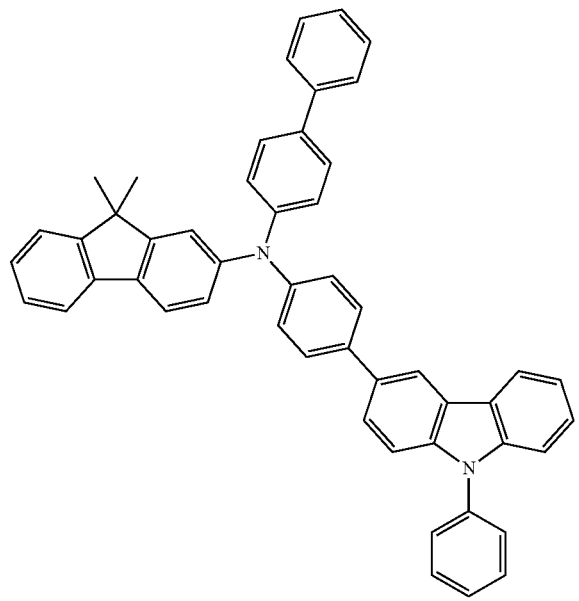
N-17
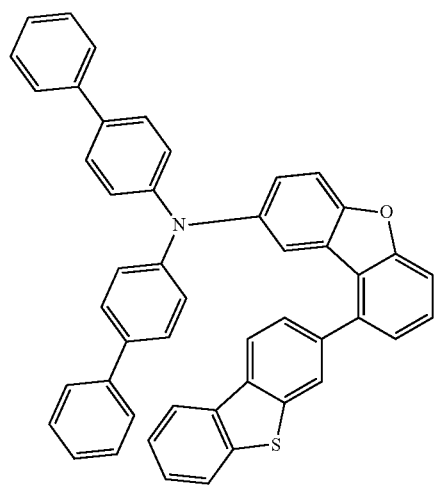
N-18
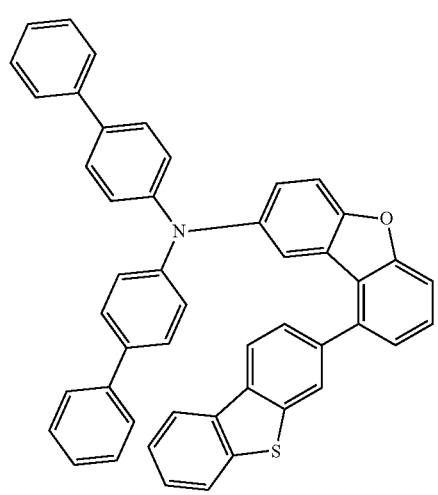
N-19
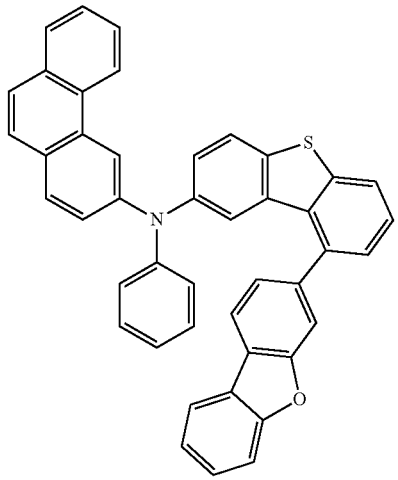
N-20
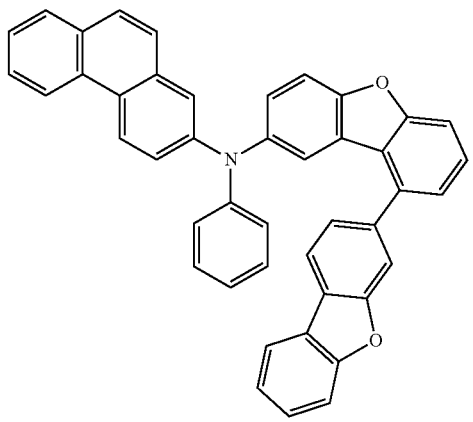
N-21
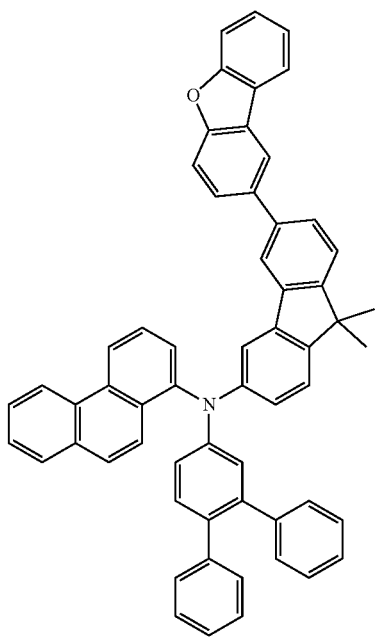

N-22
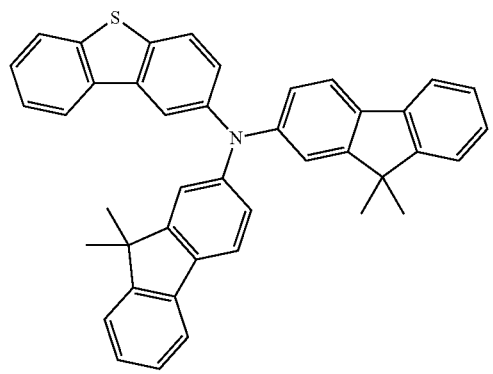
N-23
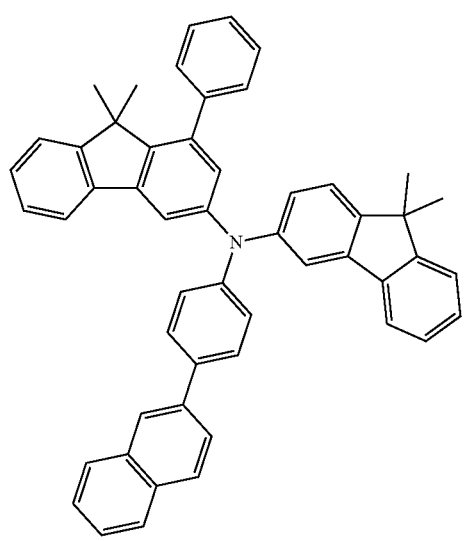
N-24
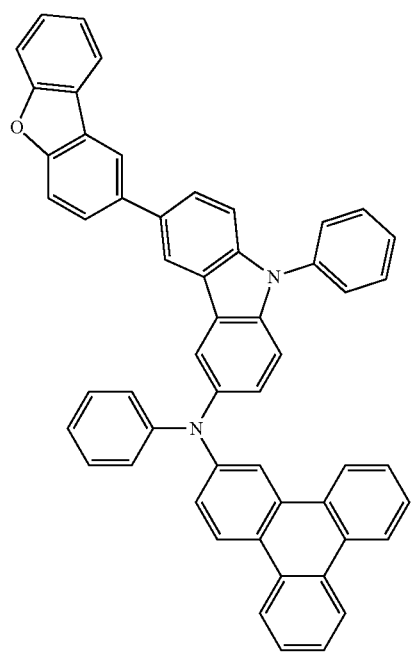
N-25
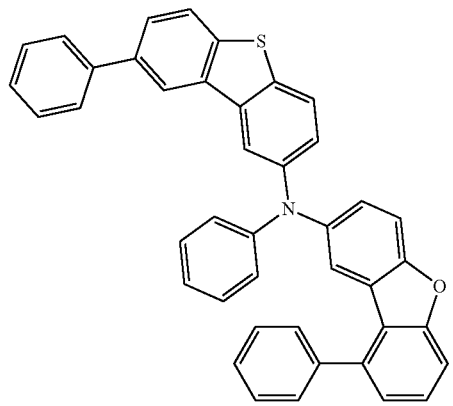
N-26
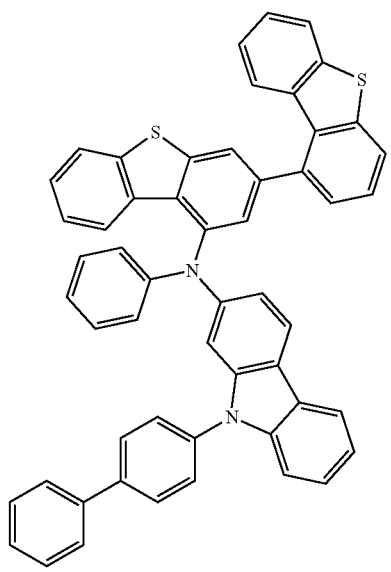
N-27
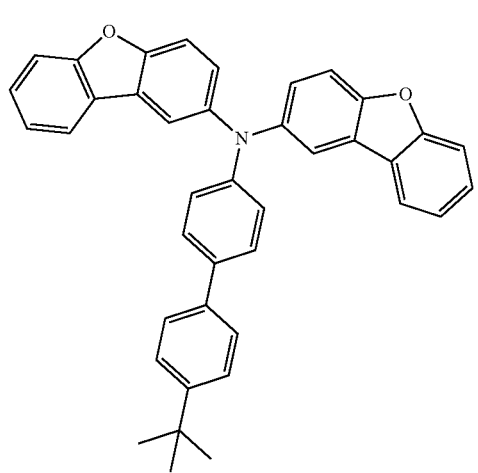

-continued
N-28
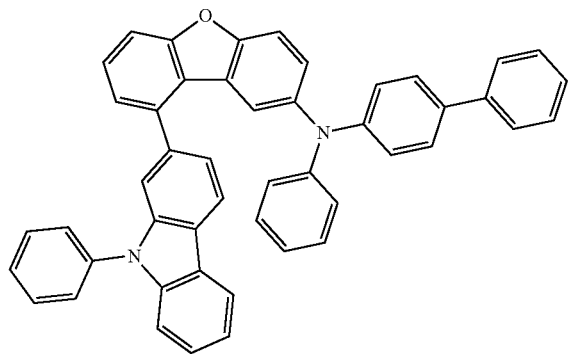
N-29
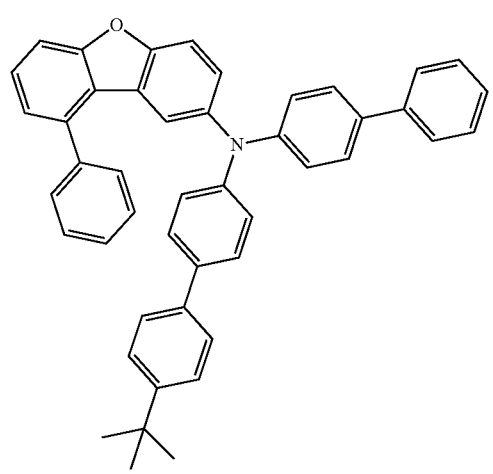
N-30
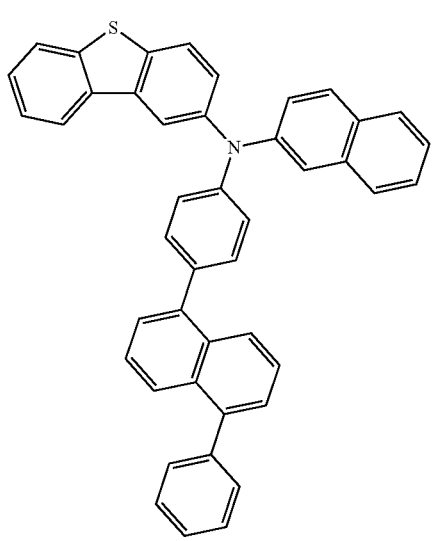
-continued
P-31
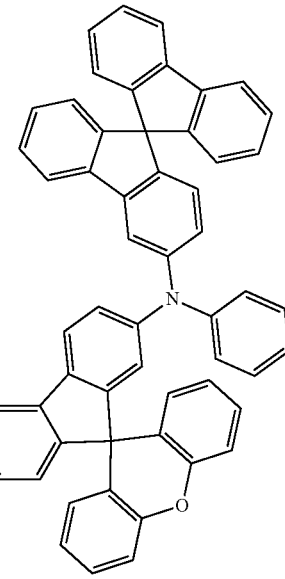
P-32
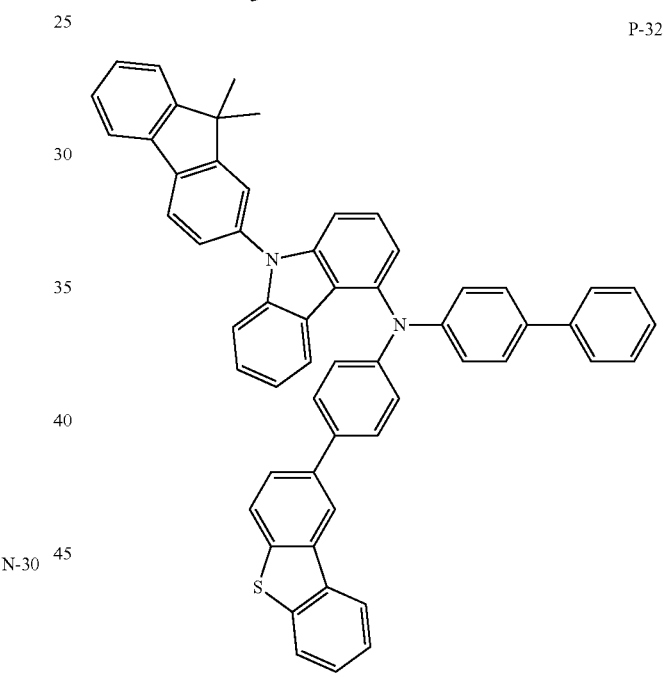
P-33
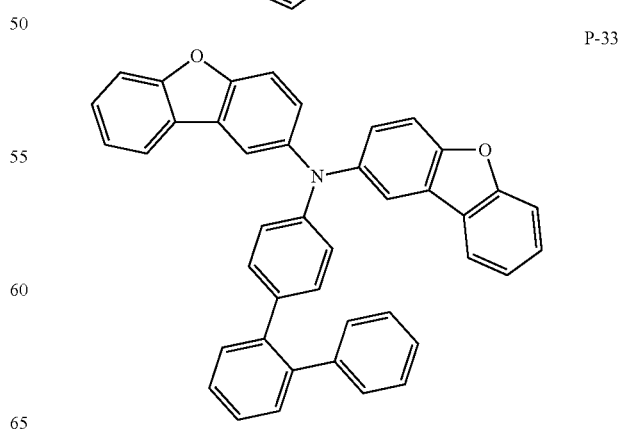

-continued
N-34
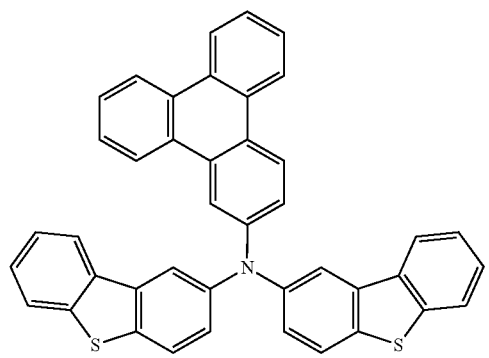
N-35
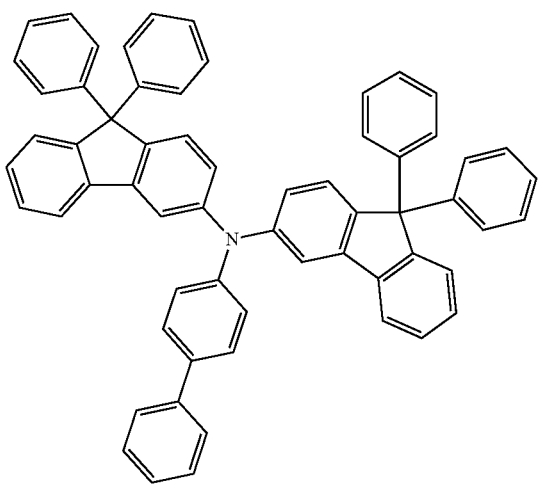
N-36
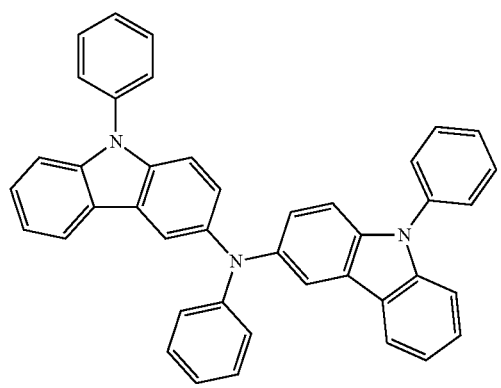
N-37
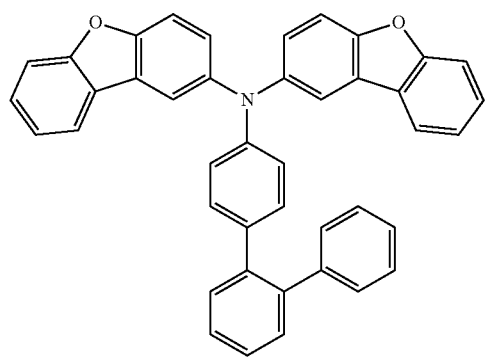
-continued
N-38
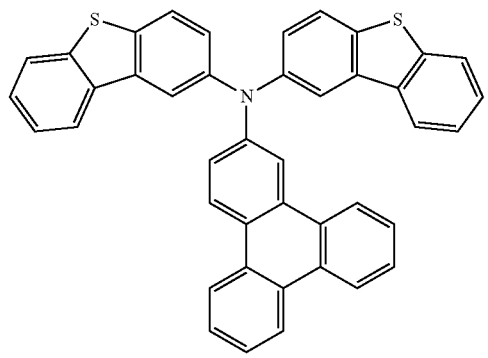
N-39
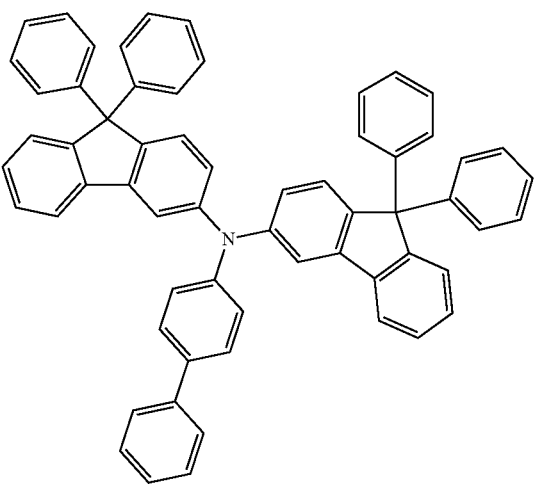
N-40
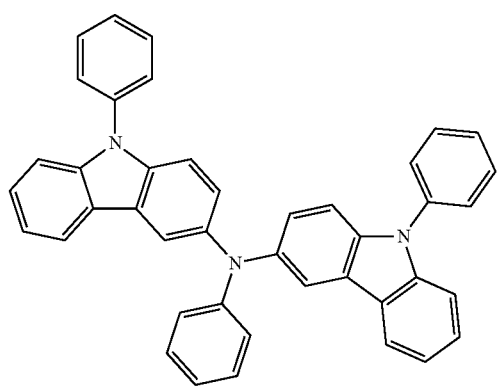

N-41
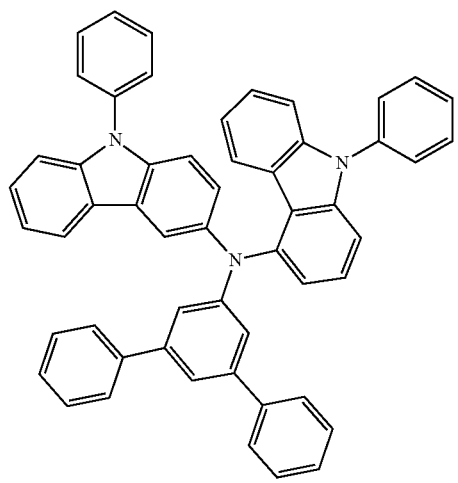
N-44
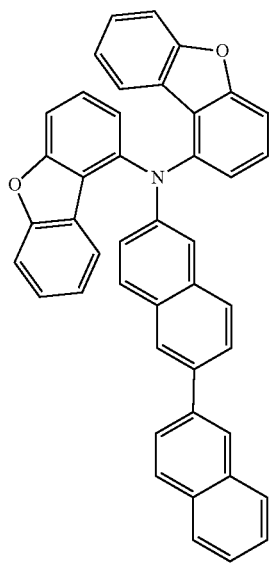
N-42
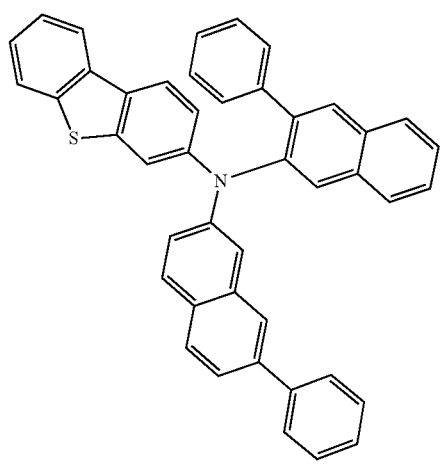
N-45
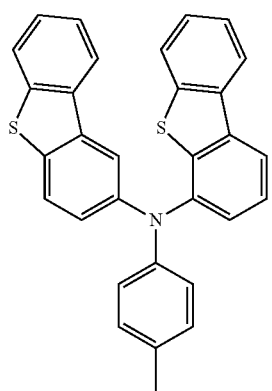
N-43
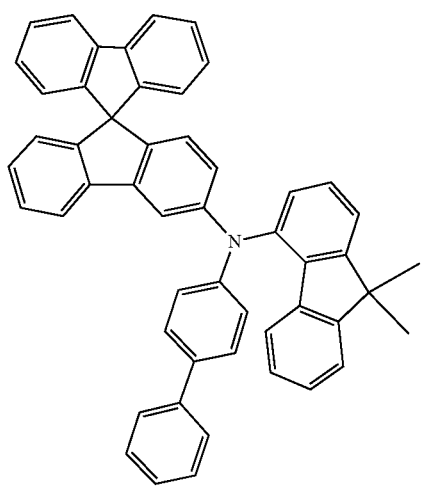
N-46
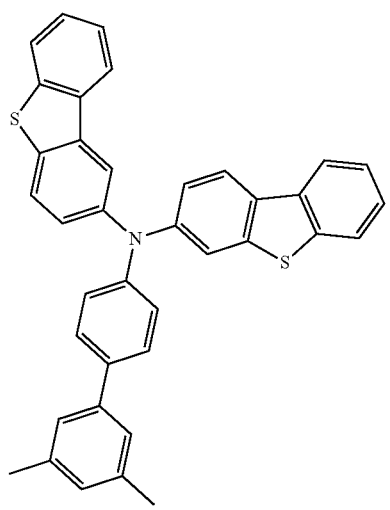

N-47
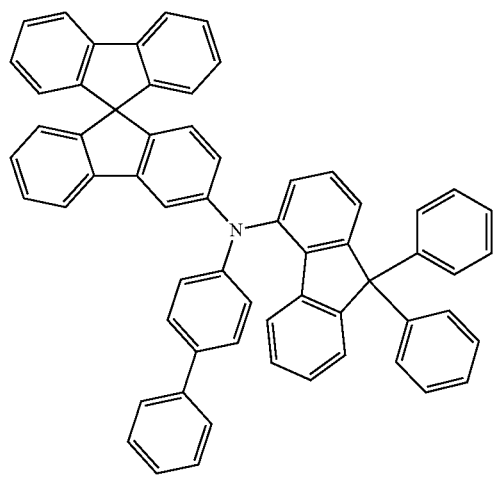
N-48
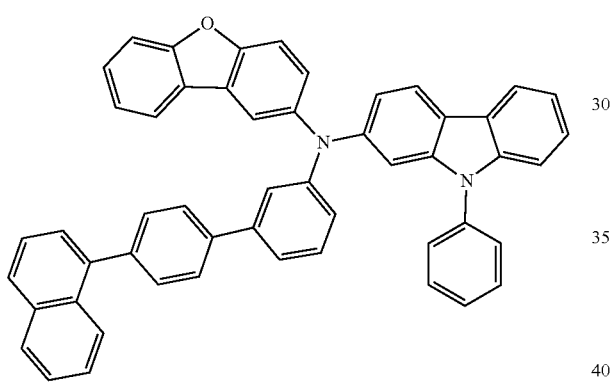
N-49
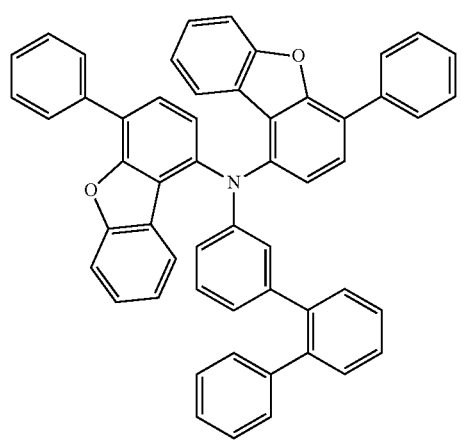
N-50
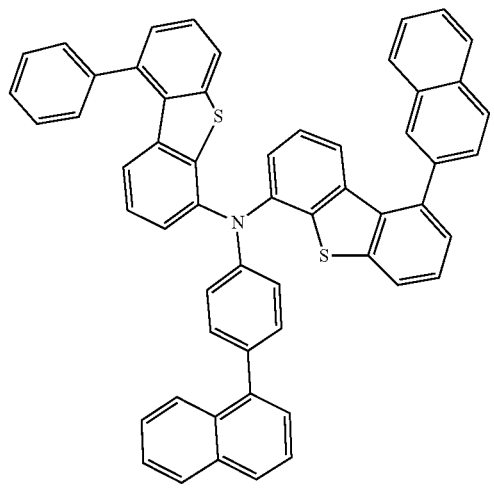
N-51
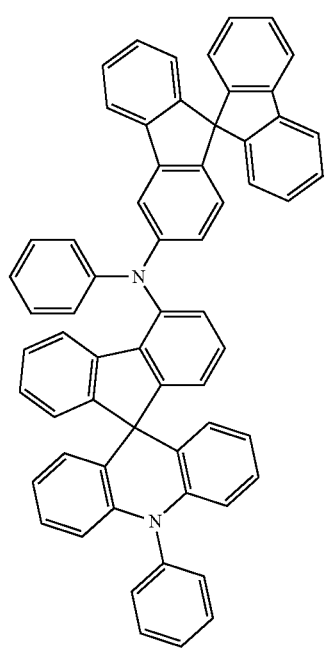

N-52
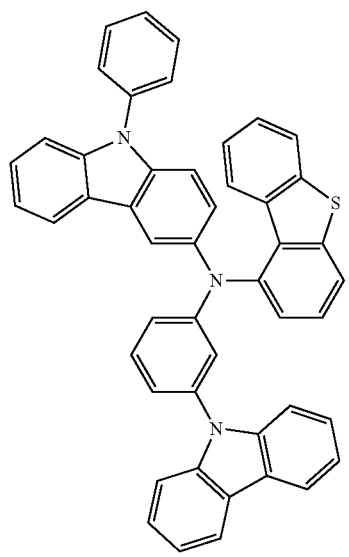
N-53
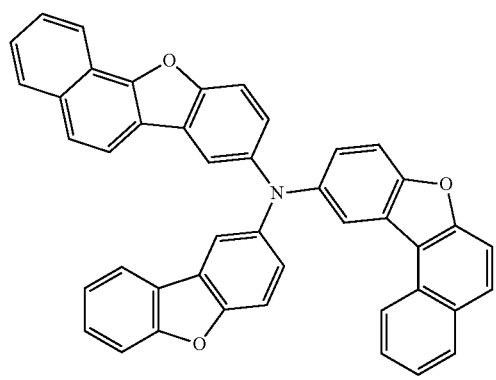
N-54
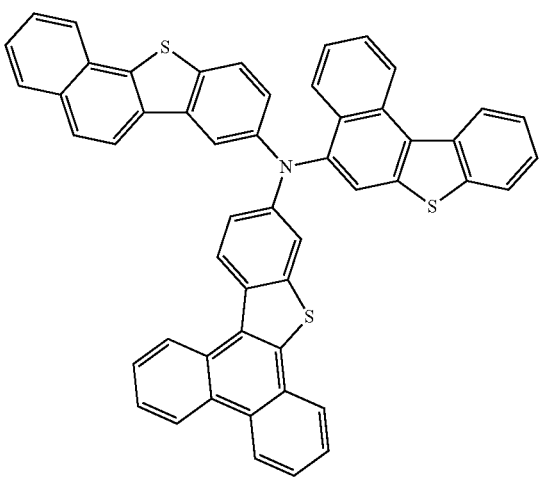
N-55
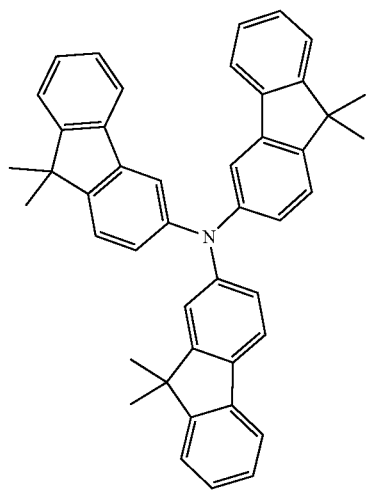
N-56
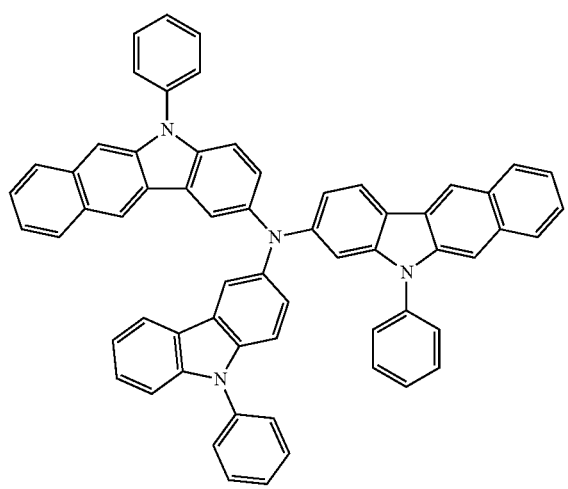
N-57
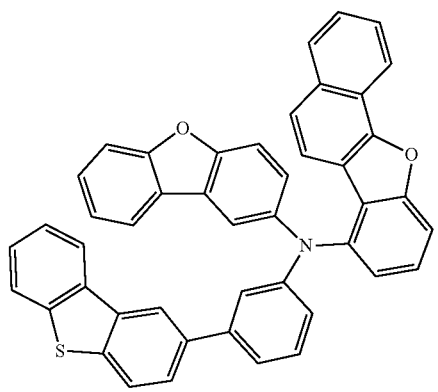

N-58
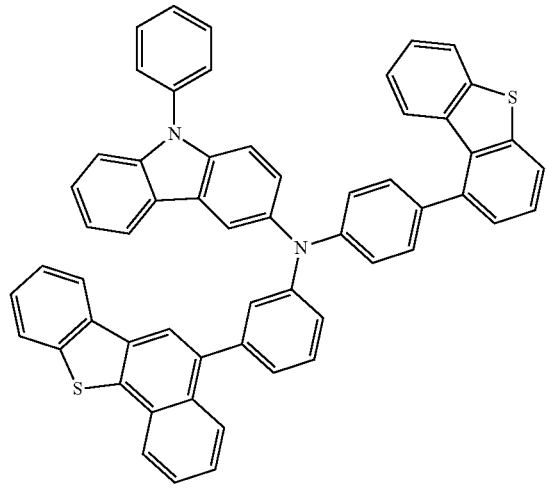
N-61
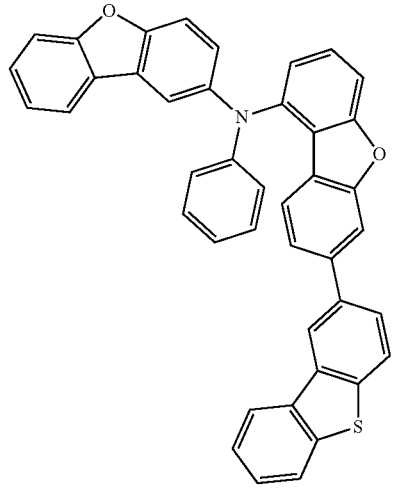
N-59
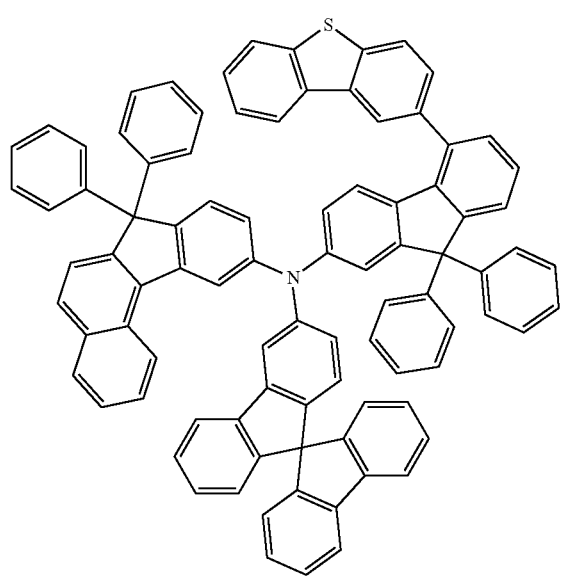
N-62
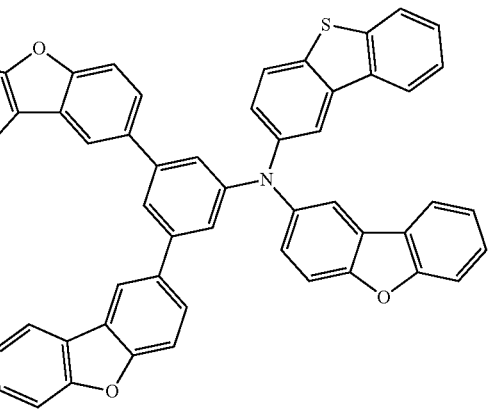
N-60
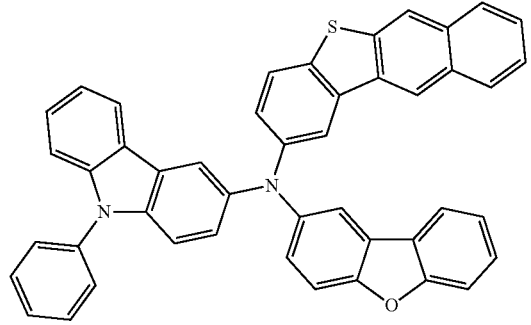
N-63
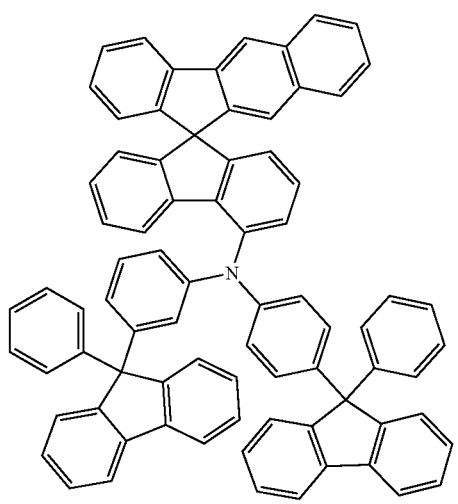

N-64
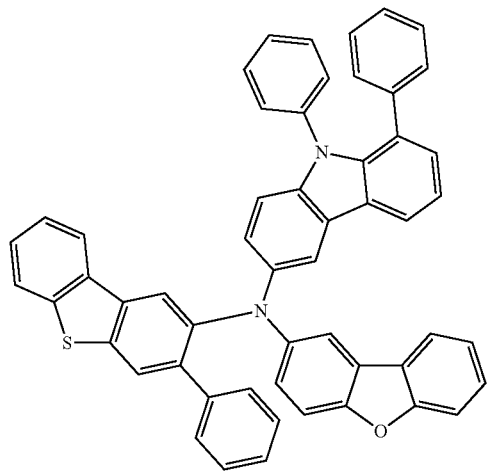
N-67
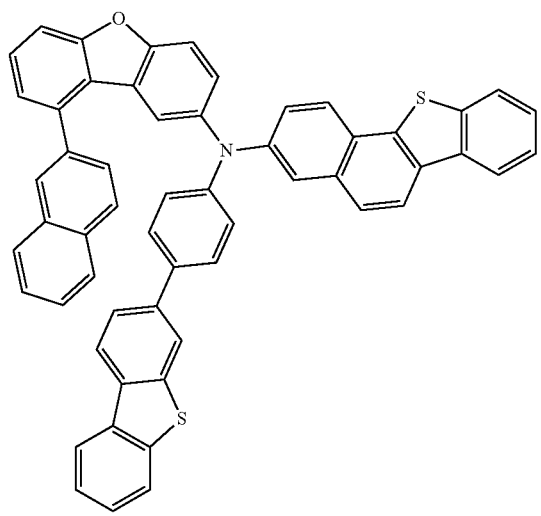
N-65
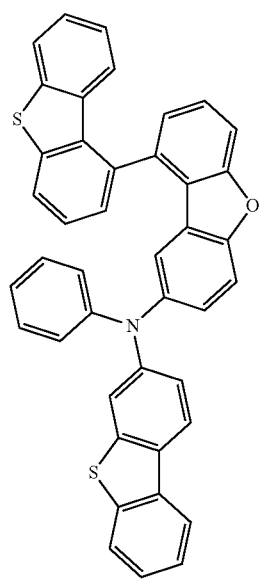
N-68
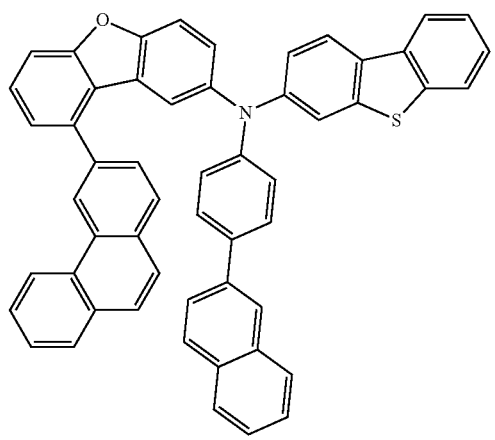
N-66
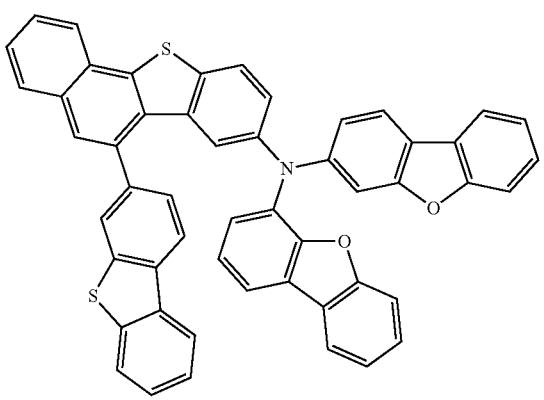
N-69
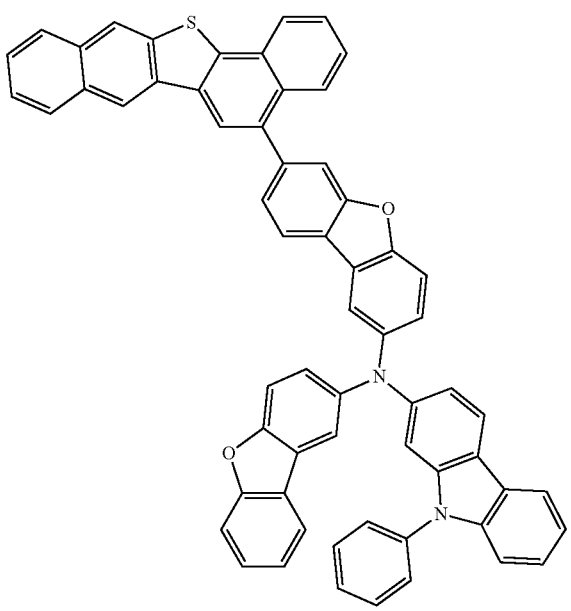

N-70
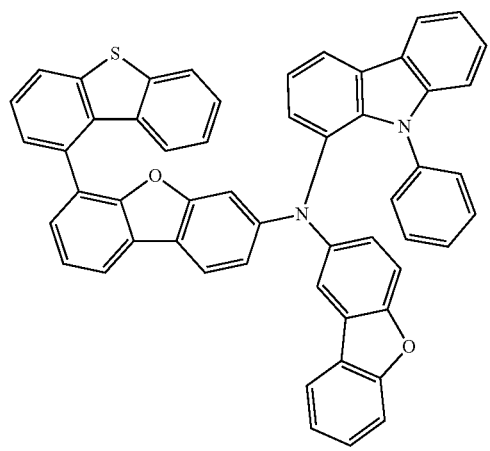
N-71
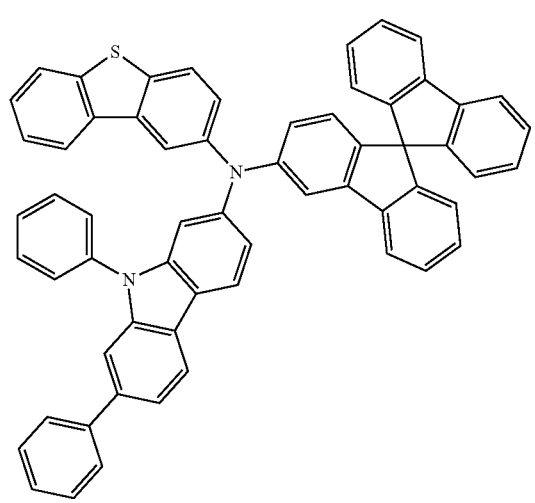
N-72
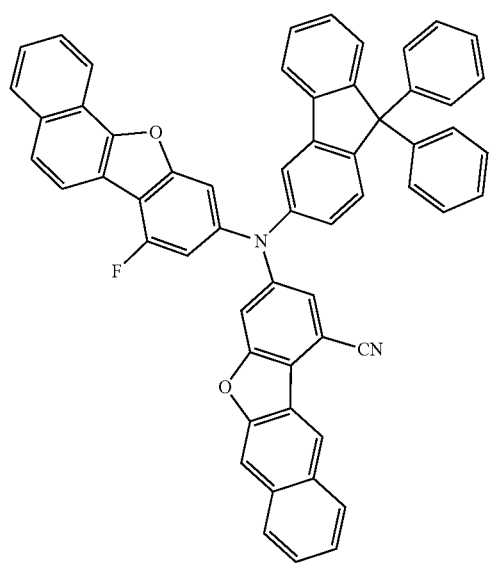
N-73
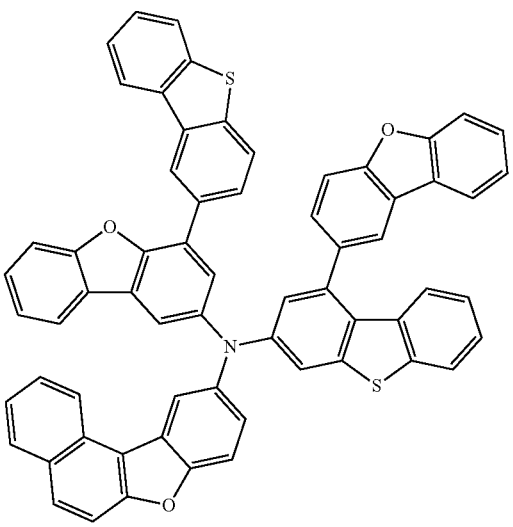
N-74
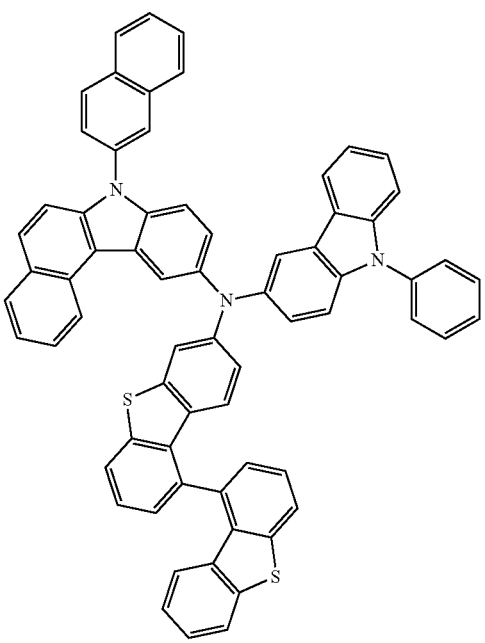

N-75
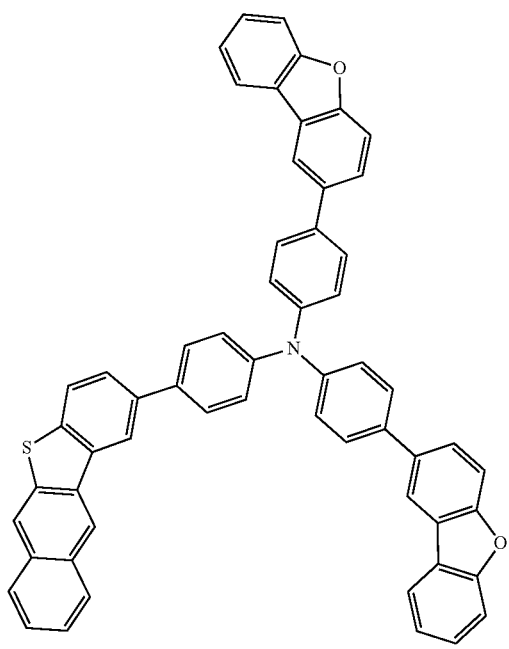
N-77
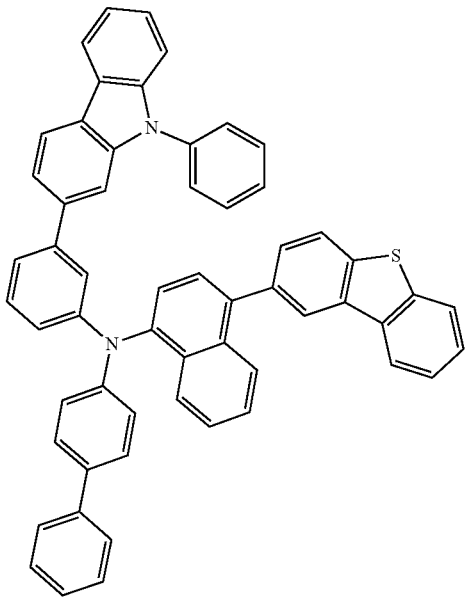
N-76
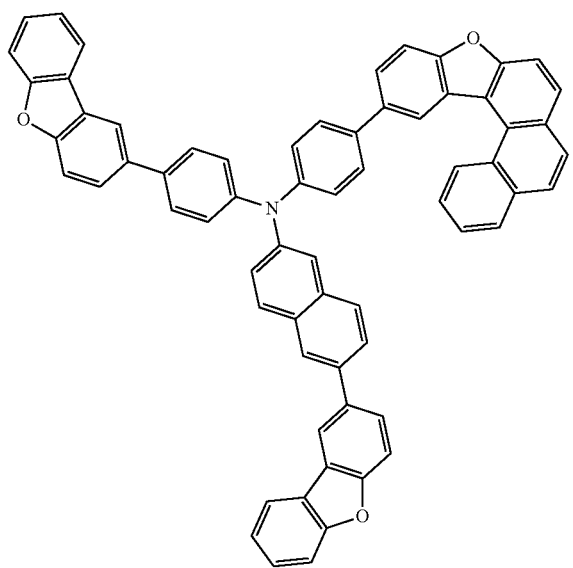
N-78
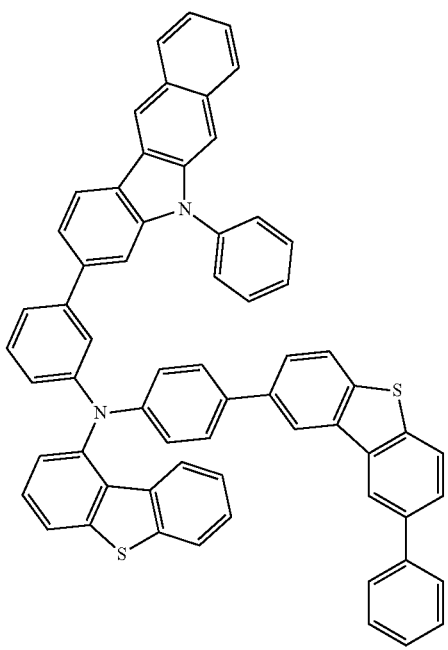

N-79
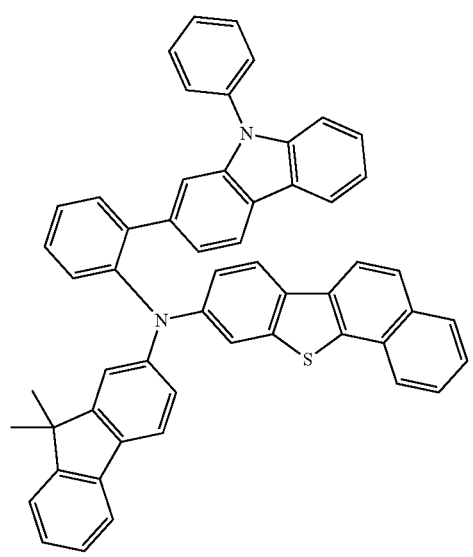
N-81
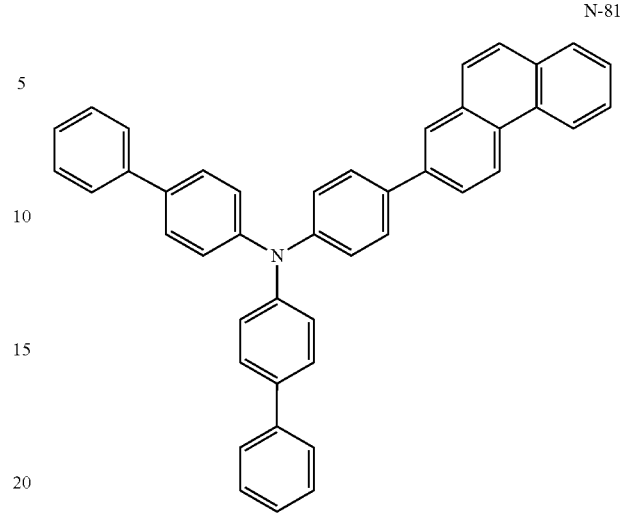
N-80
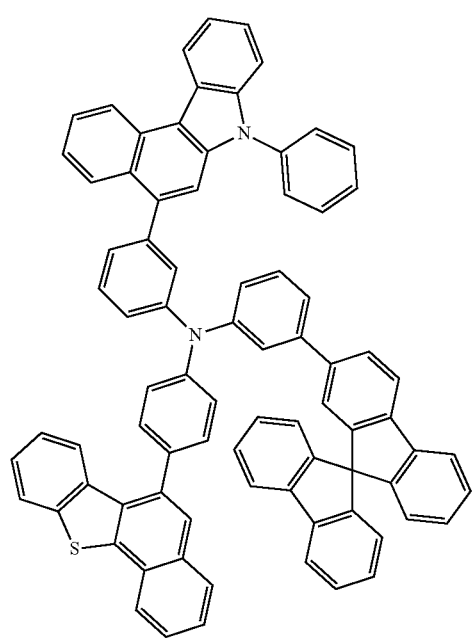
N-82
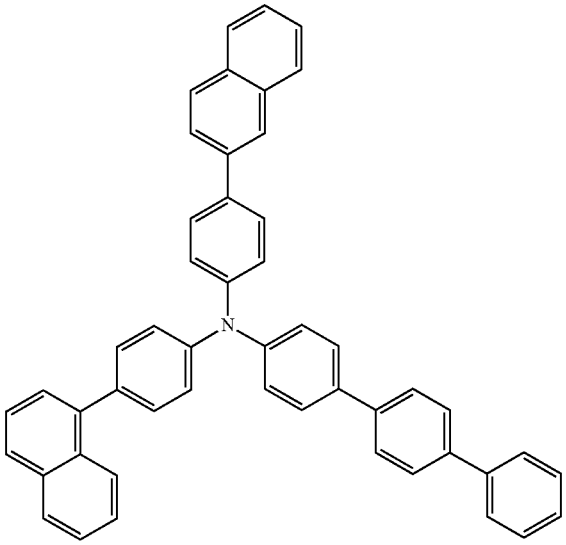

N-83
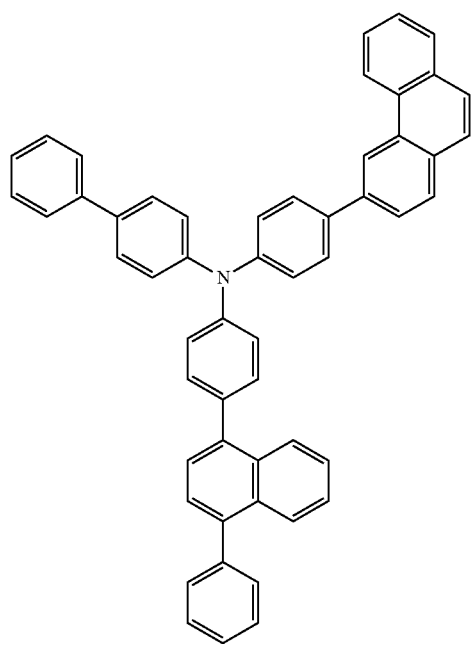
N-85
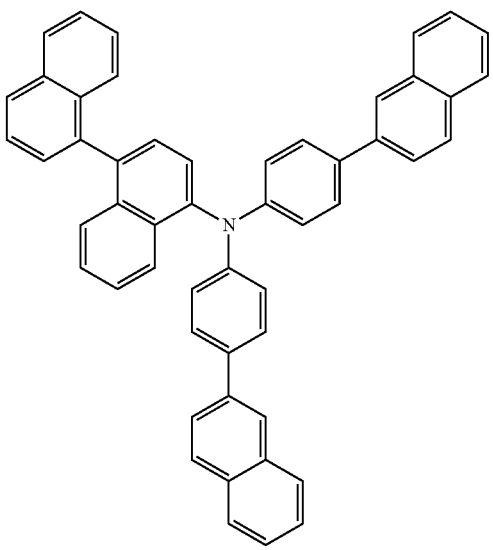
N-86
N-84
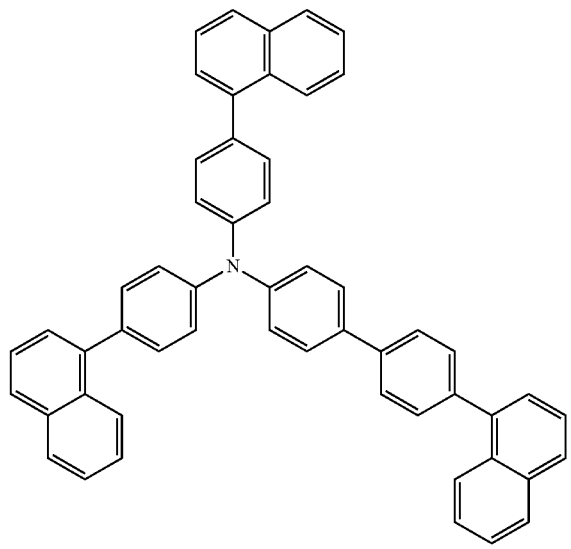
N-87
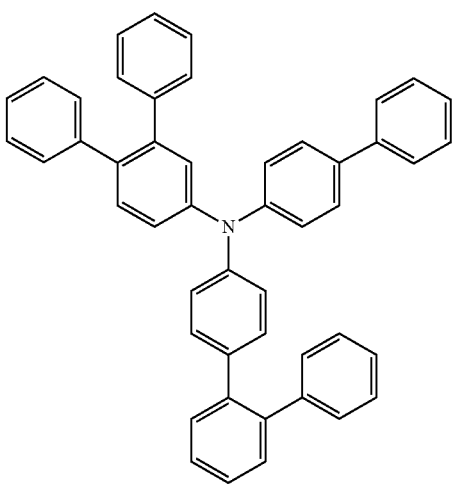

-continued
N-88
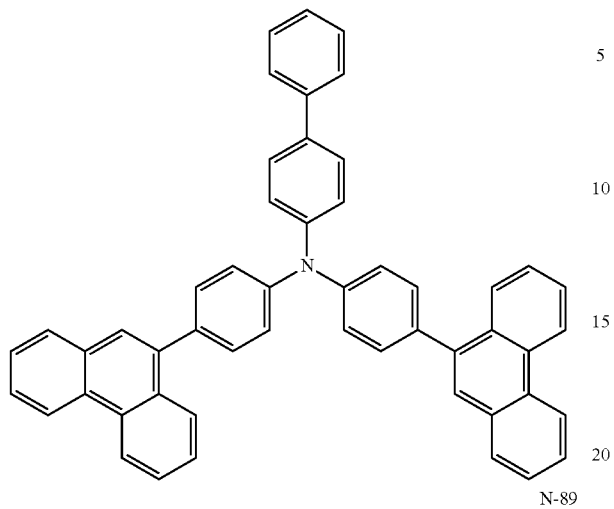
N-89
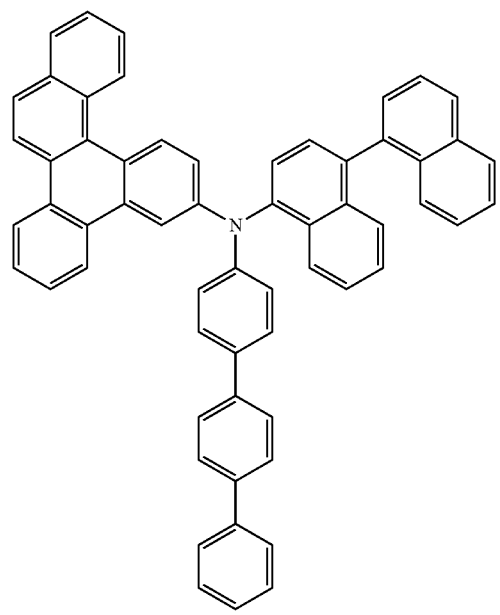
N-90
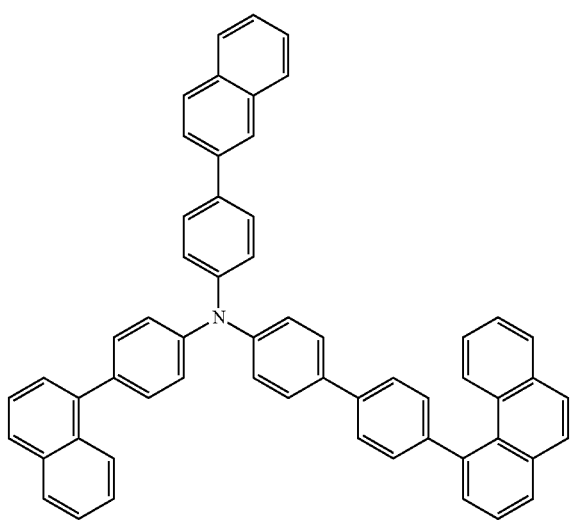
-continued
P-91
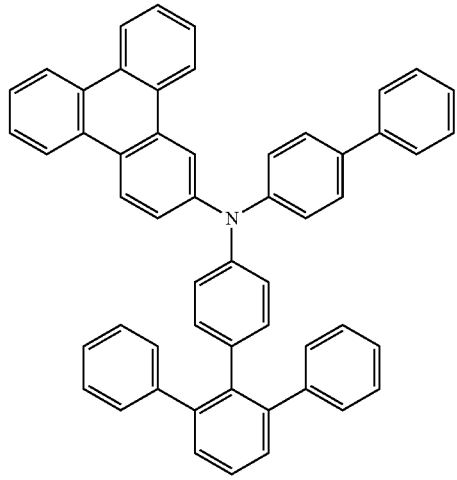
P-92
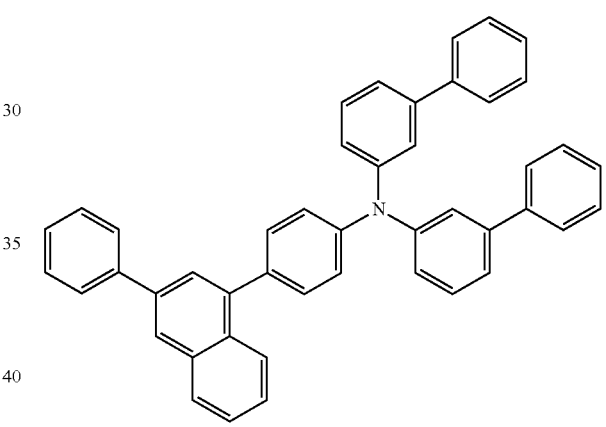
P-93
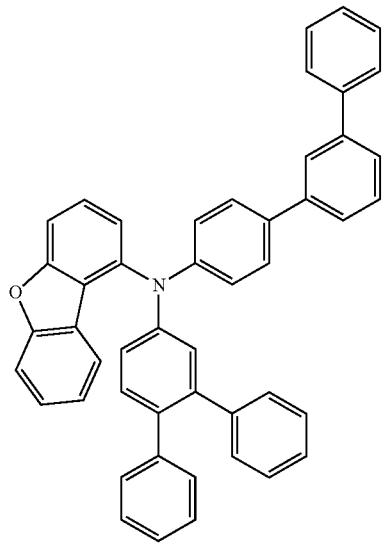

-continued
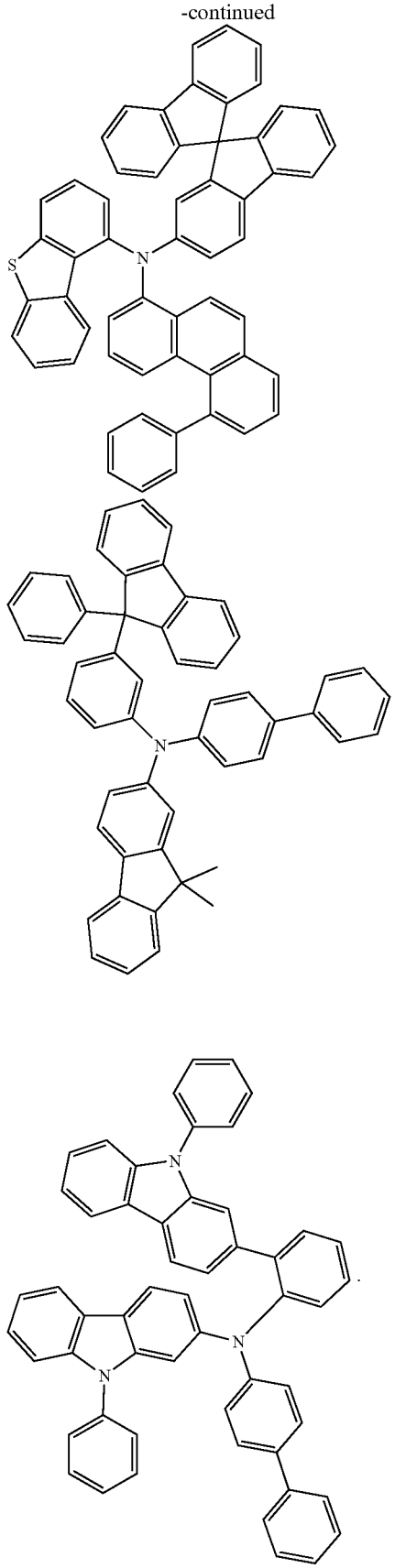
7. The organic electronic element of claim 5, wherein the compound represented by Formula 3 is any one of compounds S-1 to S-108:
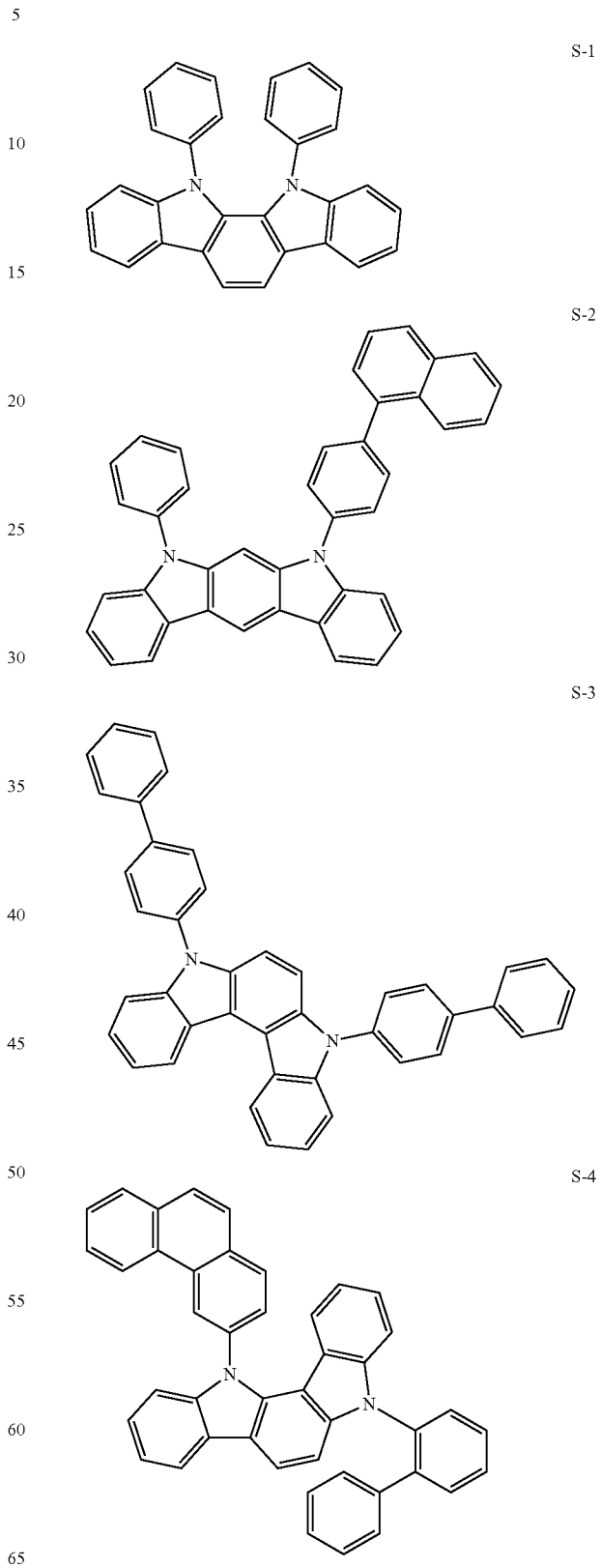

S-5
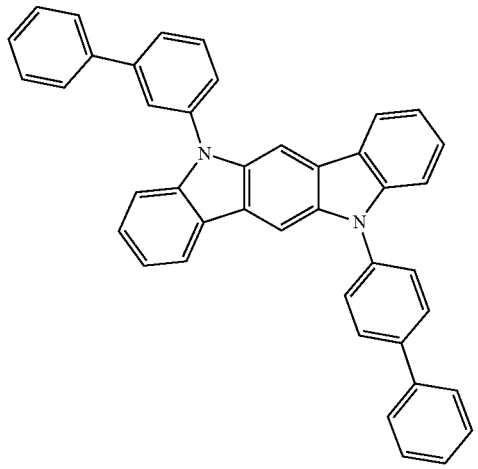
S-6
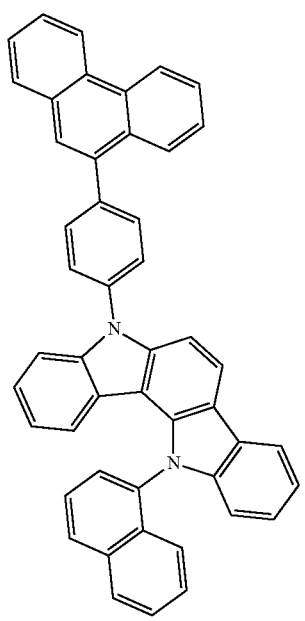
S-7
S-8
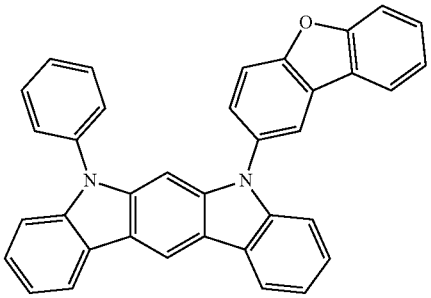
S-9
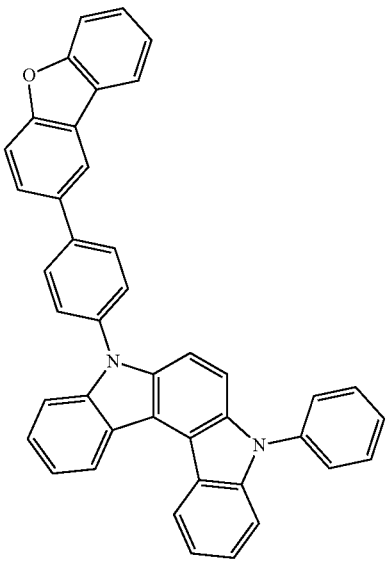
S-10
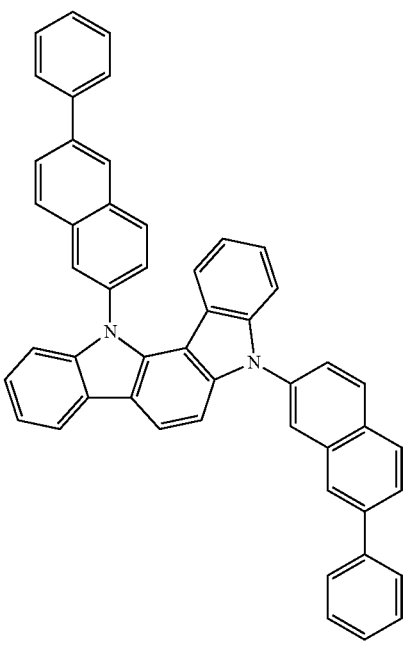

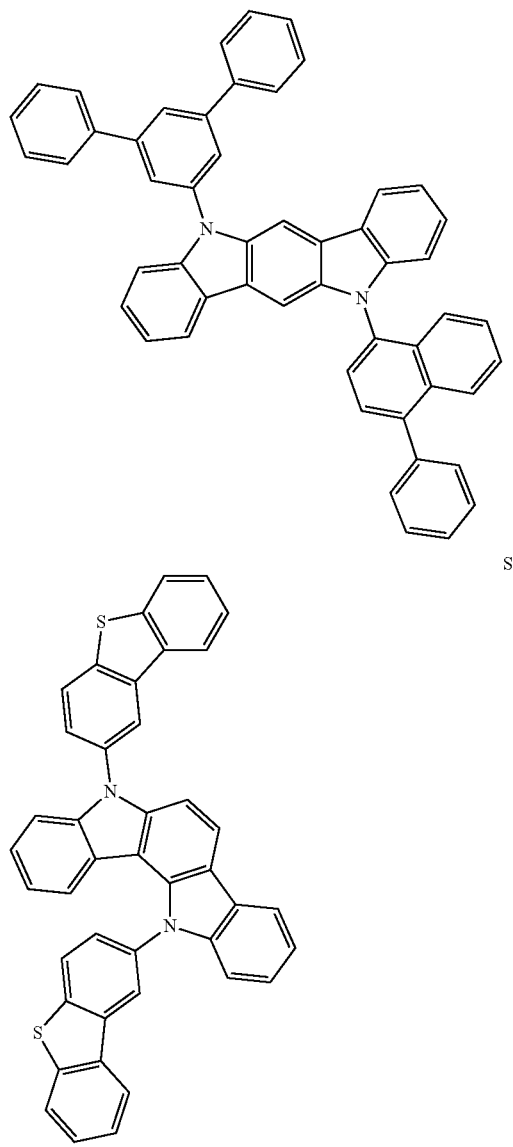
S-11
S-12
S-13
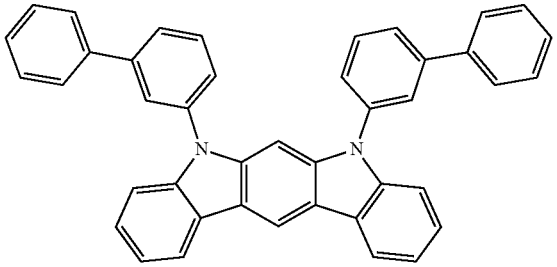
S-14
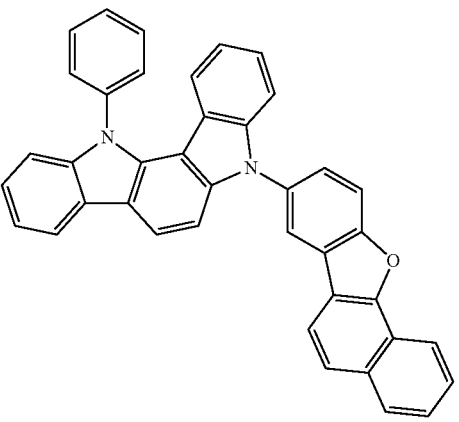
S-15
S-16
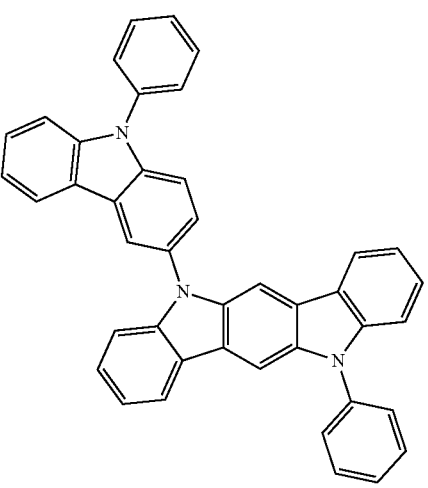
S-17

-continued
S-18
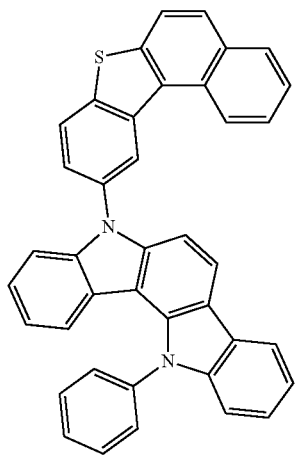
S-19
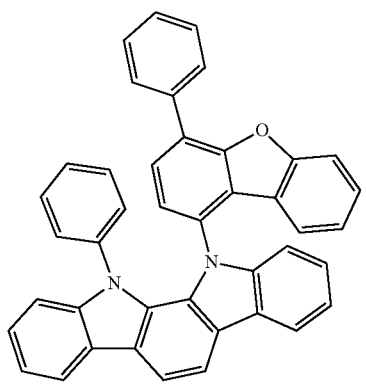
S-20
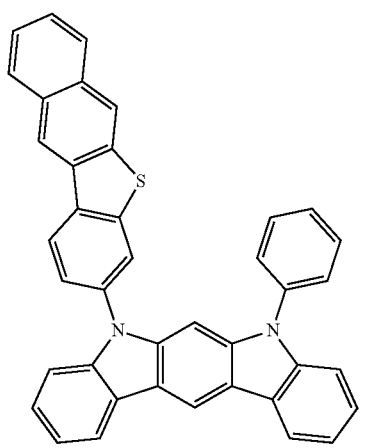
S-21
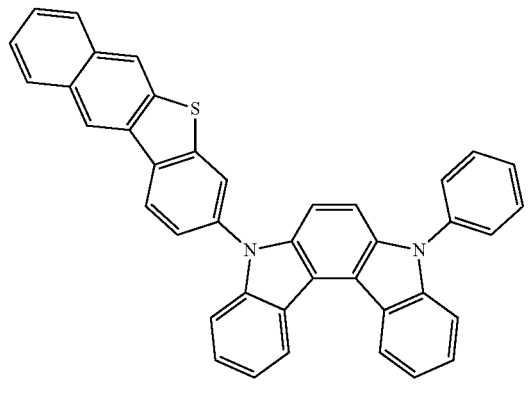
S-22
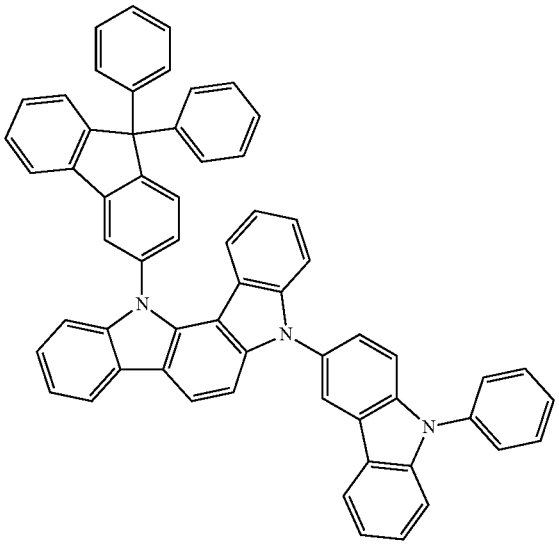
S-23
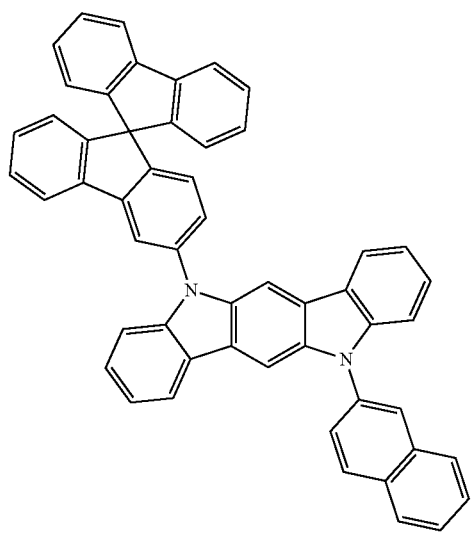

S-24
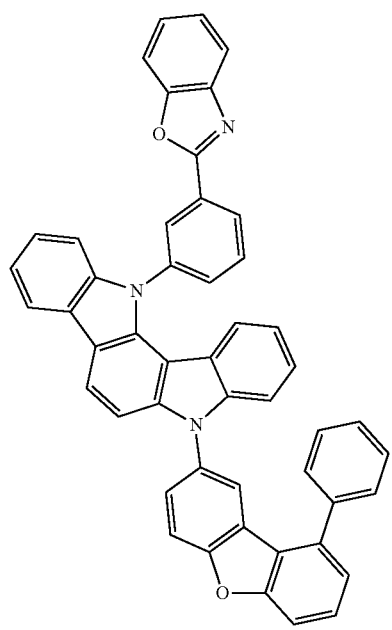
S-27
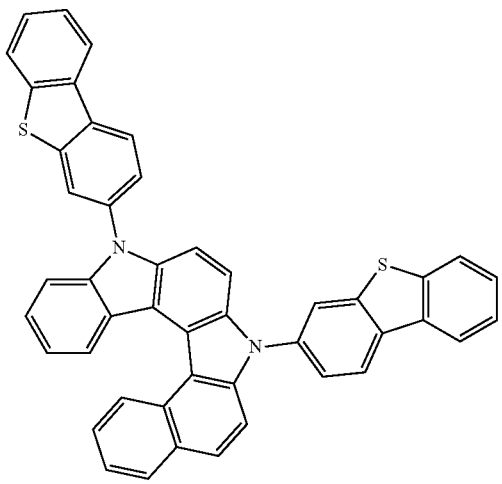
S-25
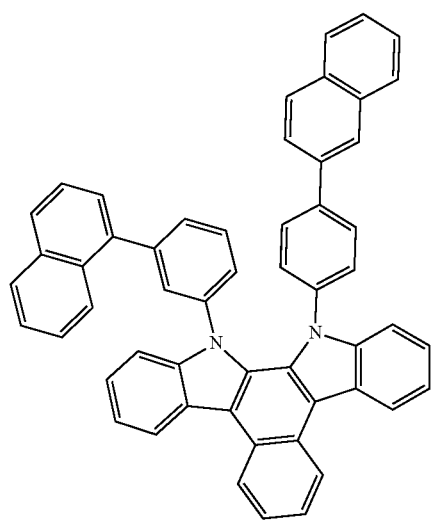
S-28
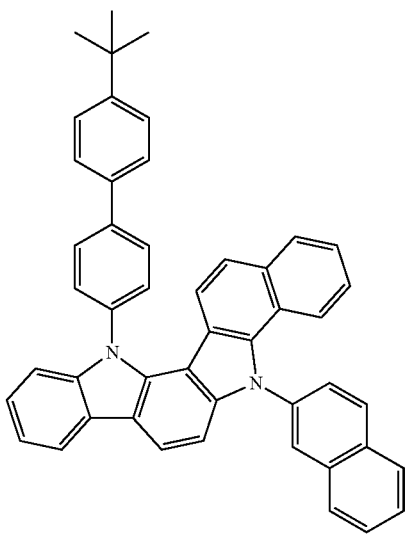
S-26
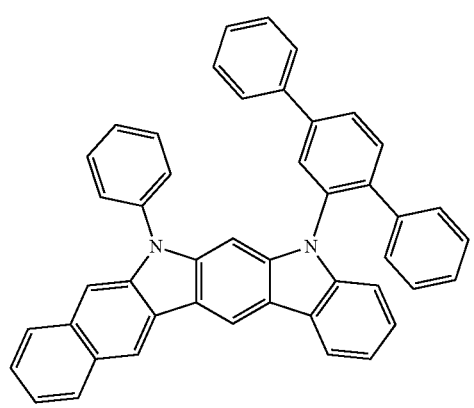
S-29
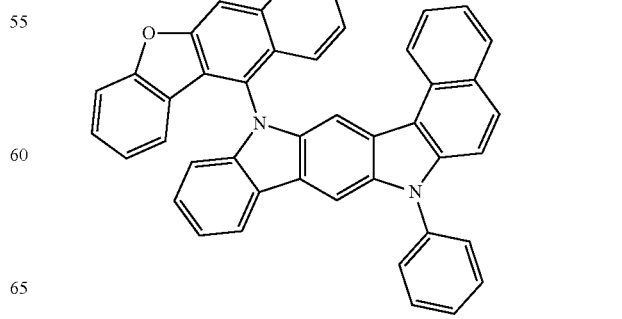

-continued
S-30
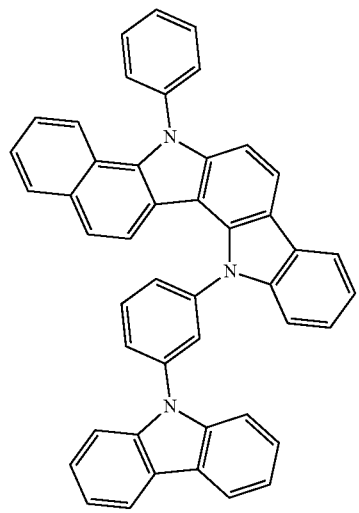
S-31
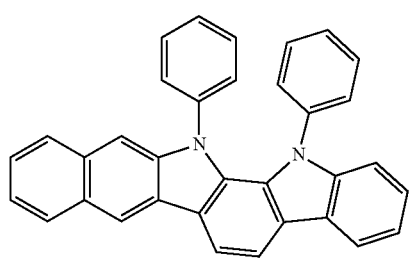
S-32
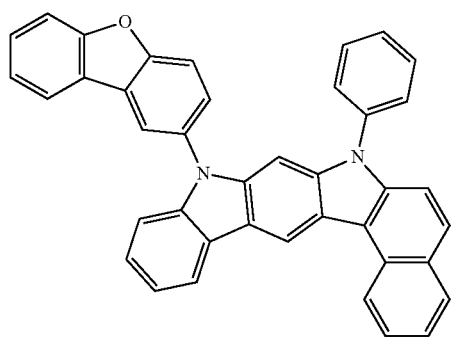
S-33
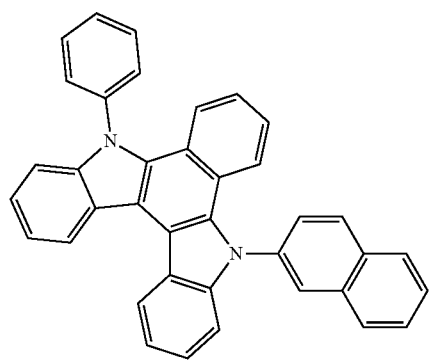
S-34
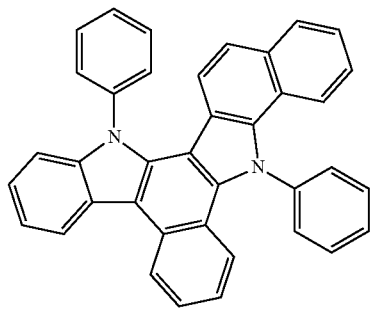
S-35
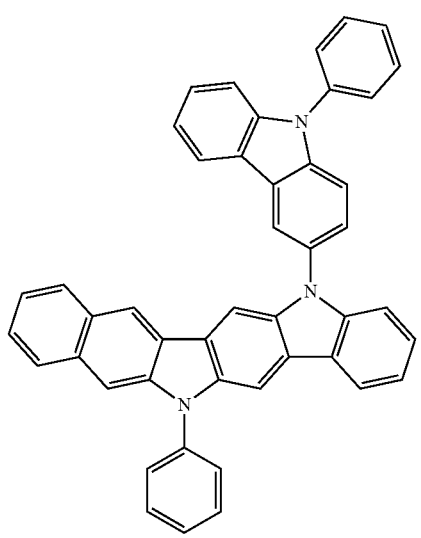
S-36
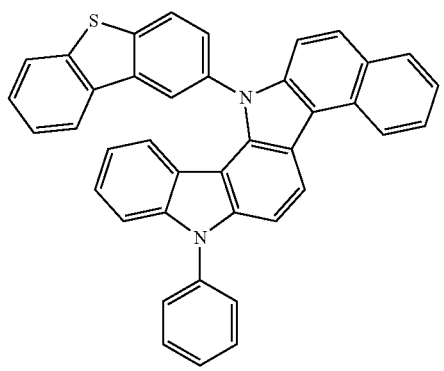
S-37
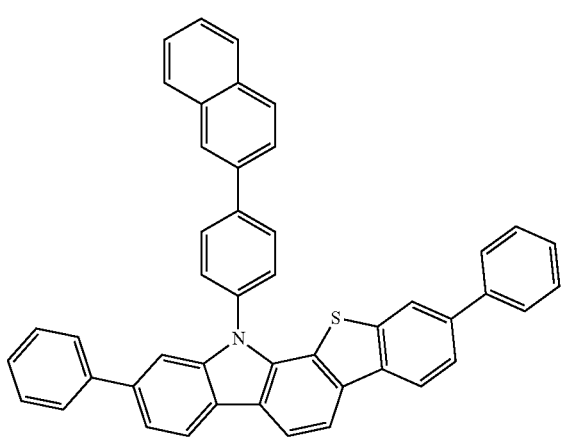

S-38 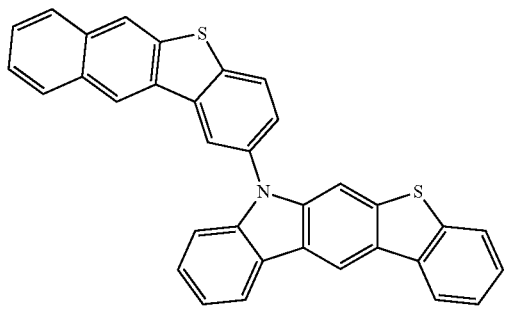
S-39 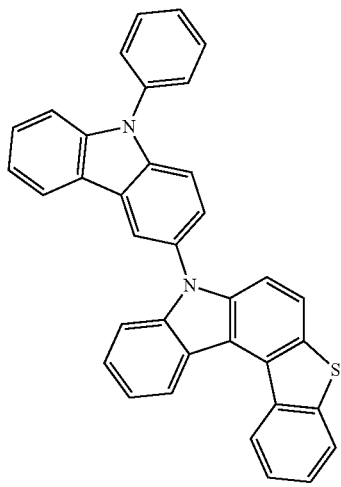
S-40 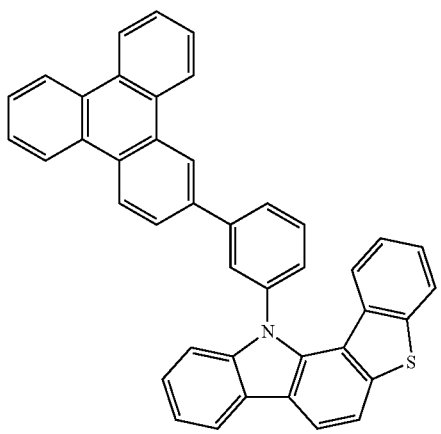
S-41 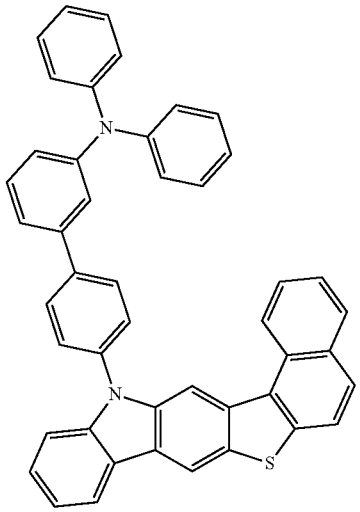
S-42 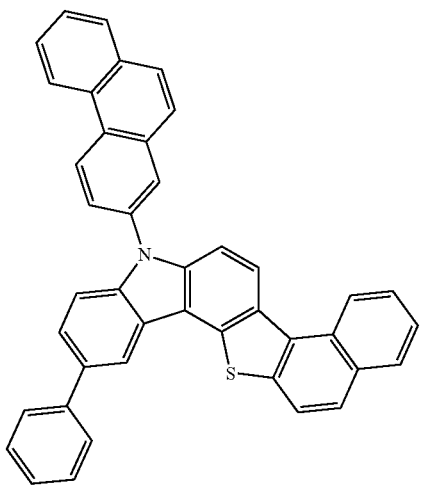
S-43 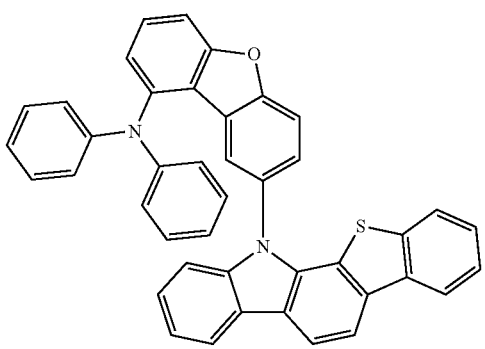

-continued
S-44
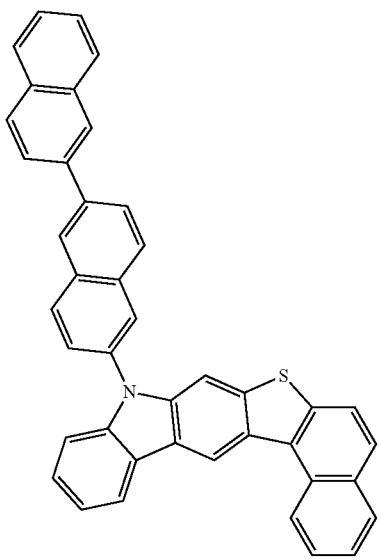
S-45
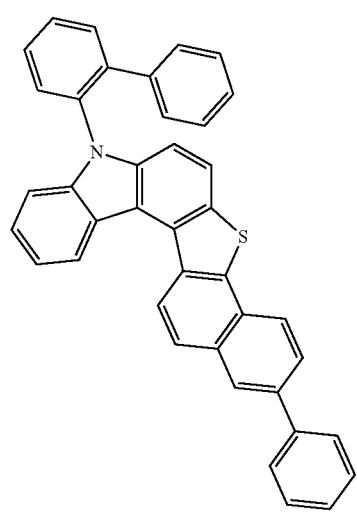
S-46
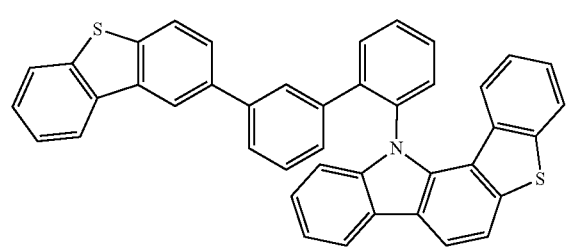
-continued
S-47
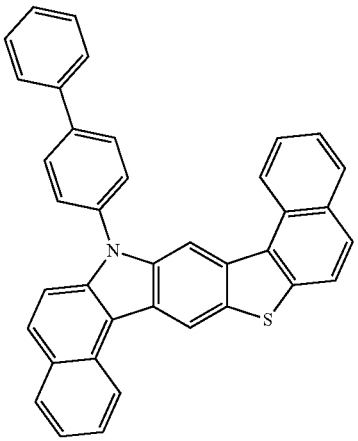
S-48
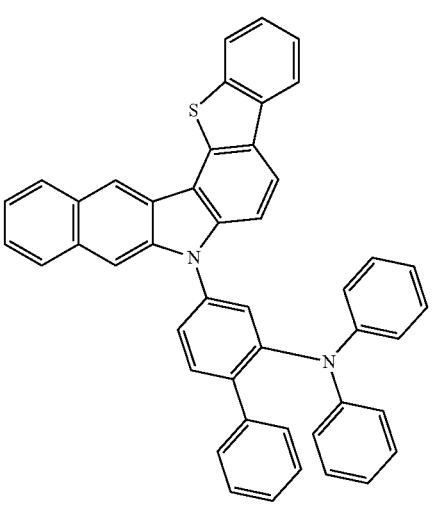
S-49
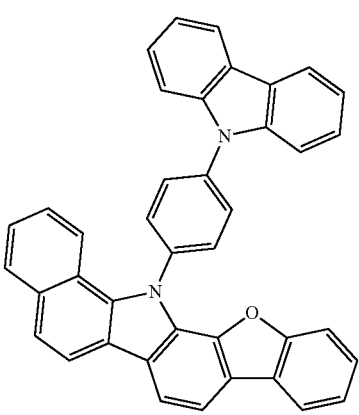

-continued
S-50
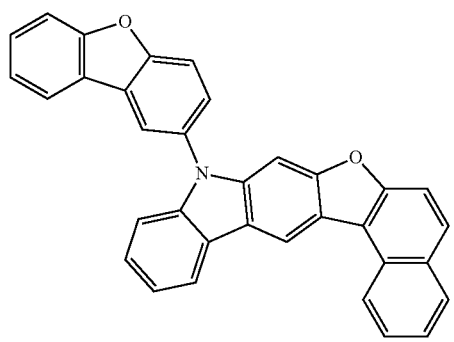
S-51
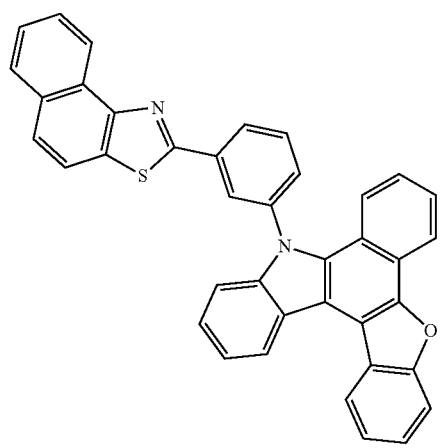
S-52
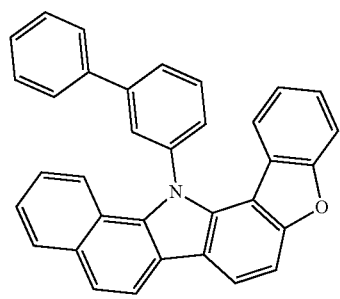
S-53
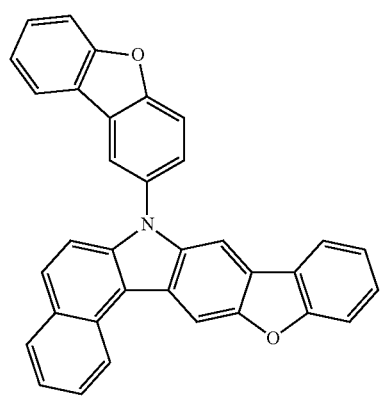
-continued
S-54
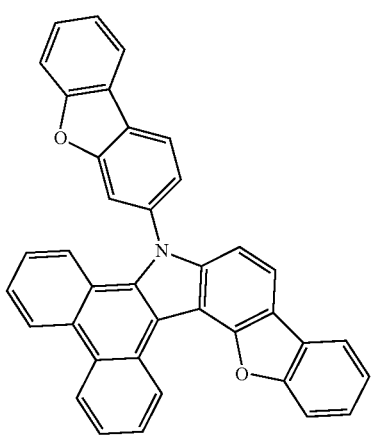
S-55
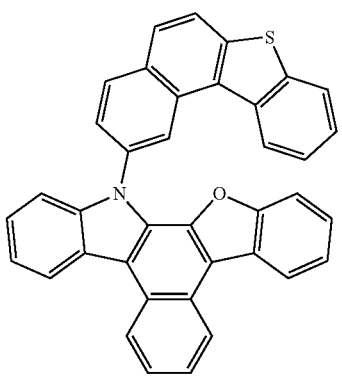
S-56
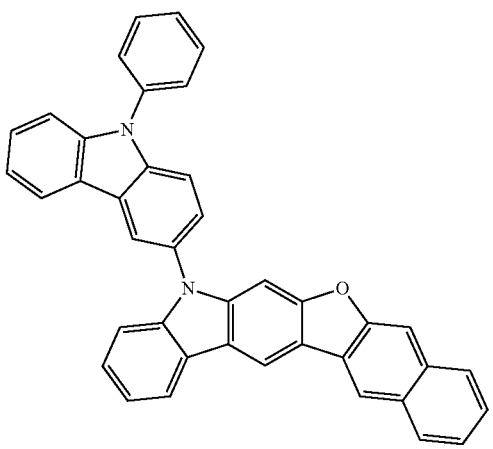
S-57
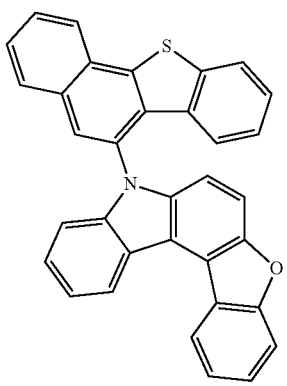

S-58
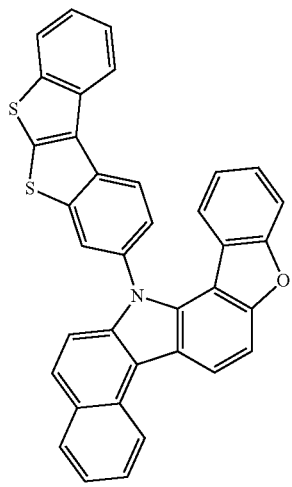
S-61
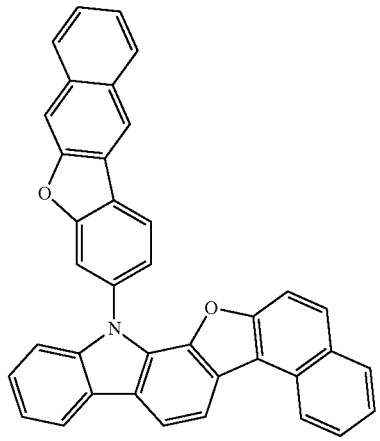
S-59
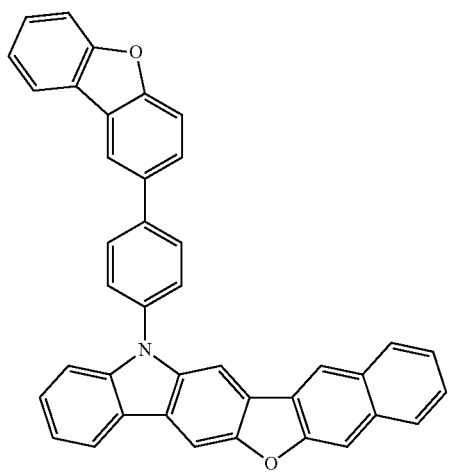
S-62
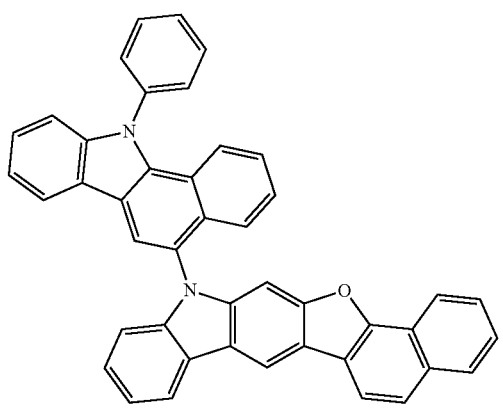
S-60
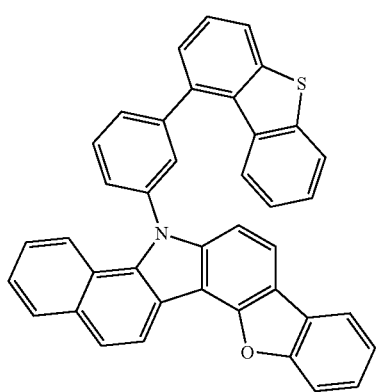
S-63
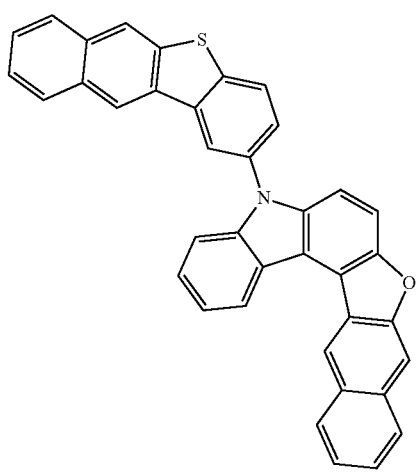

-continued
S-64
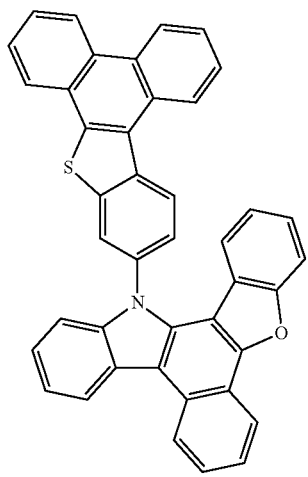
S-65
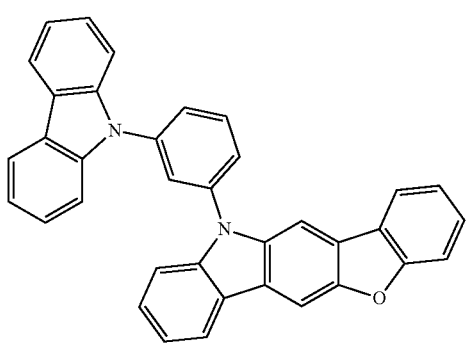
S-66
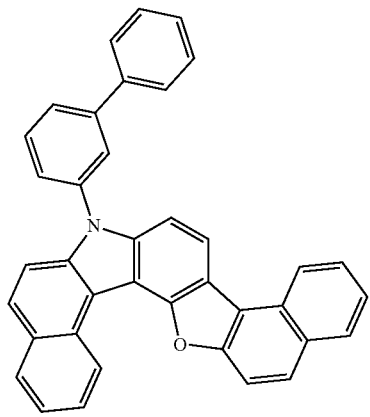
S-67
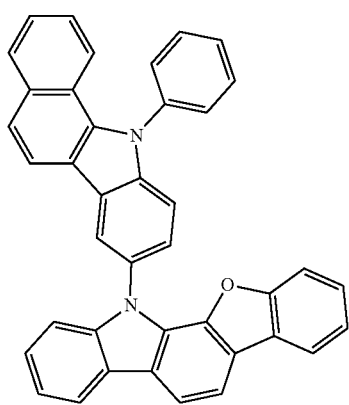
-continued
S-68
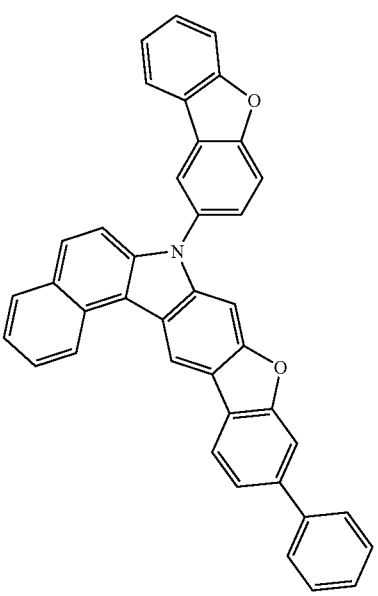
S-69
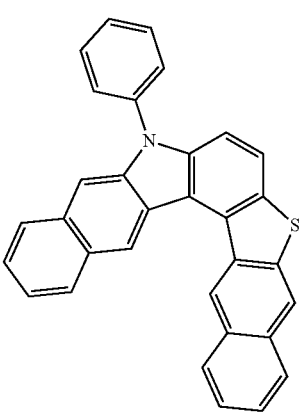
S-70
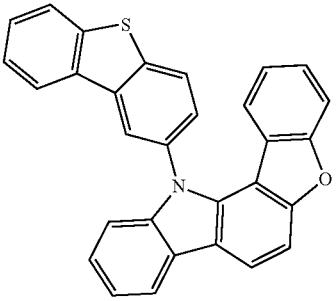

S-71
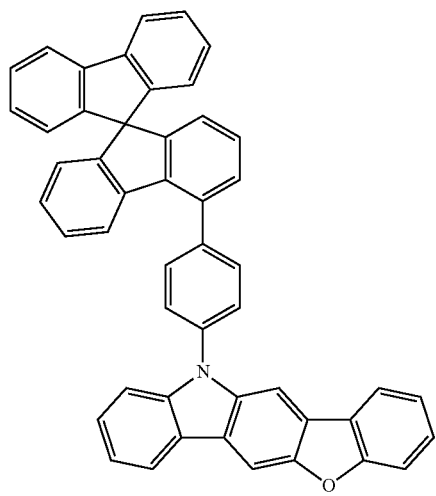
S-74
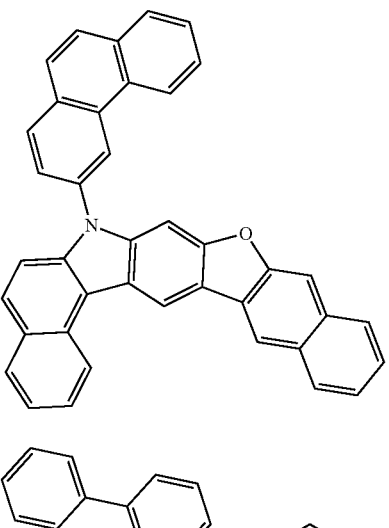
S-75
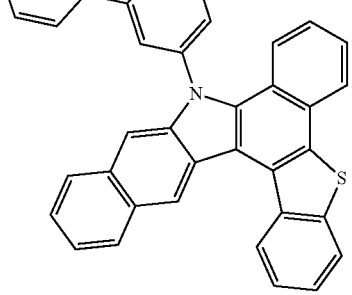
S-72
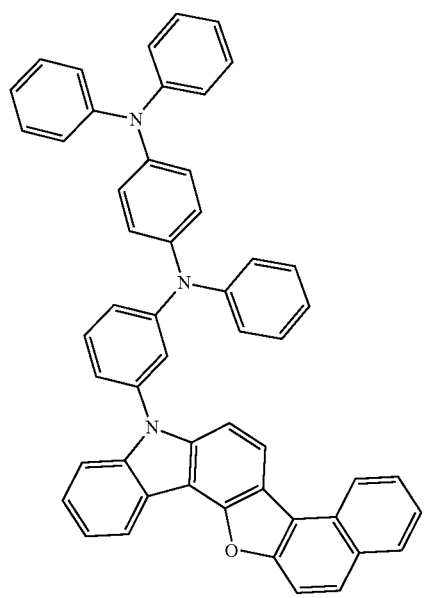
S-76
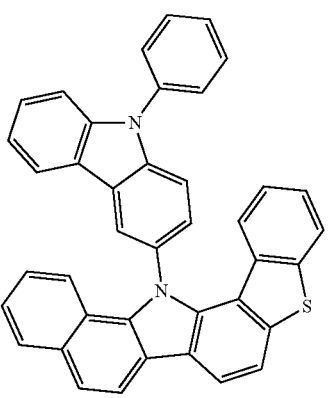
S-73
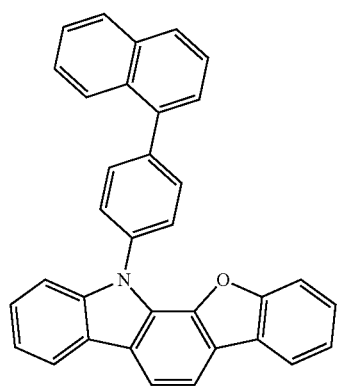
S-77
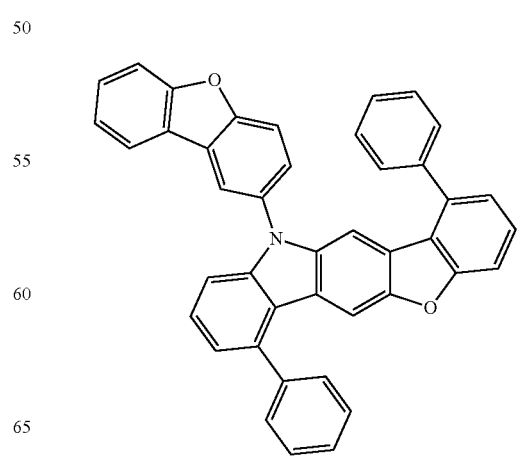

S-78
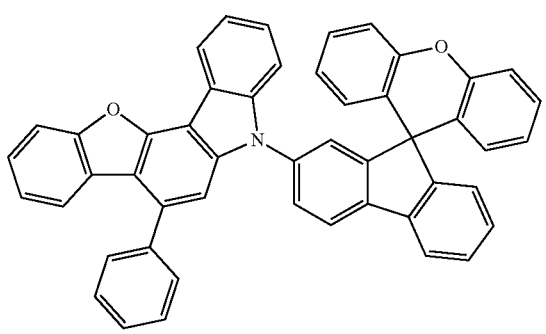
S-79
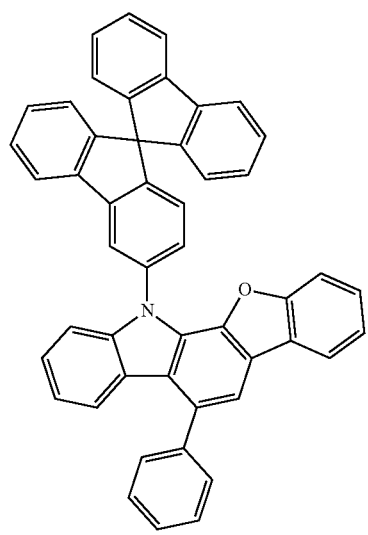
S-80
S-81
S-82
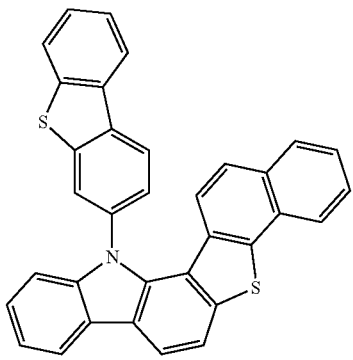
S-83
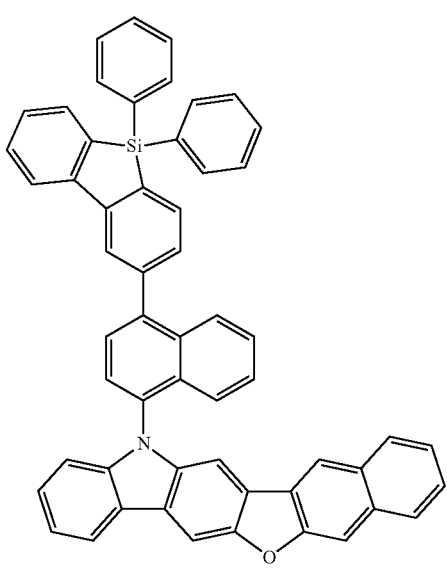
S-84
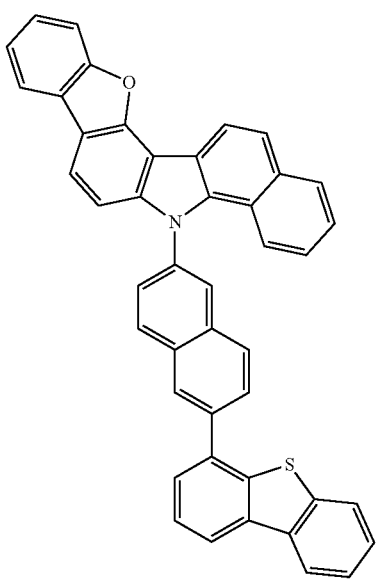

S-85
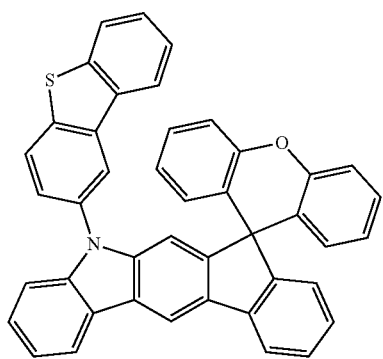
S-88
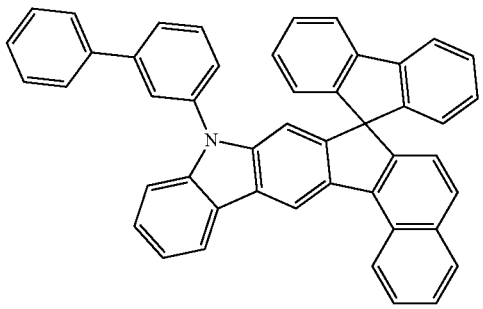
S-86
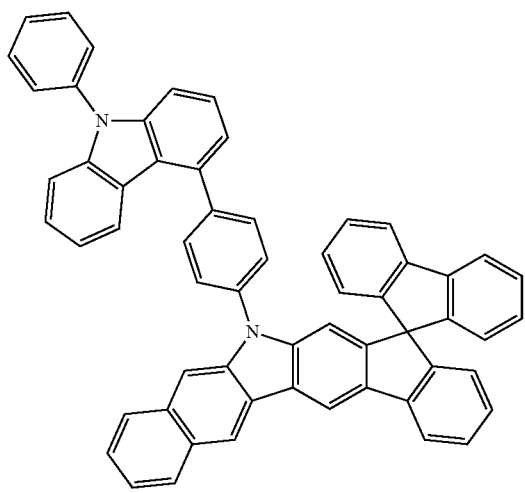
S-89
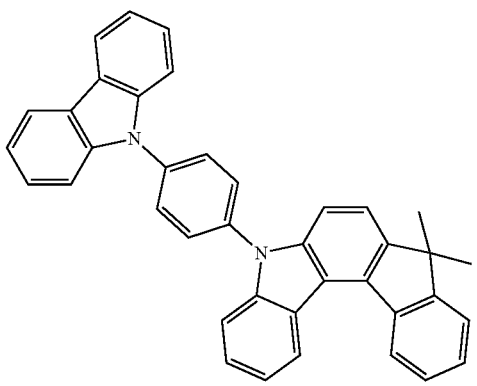
S-90
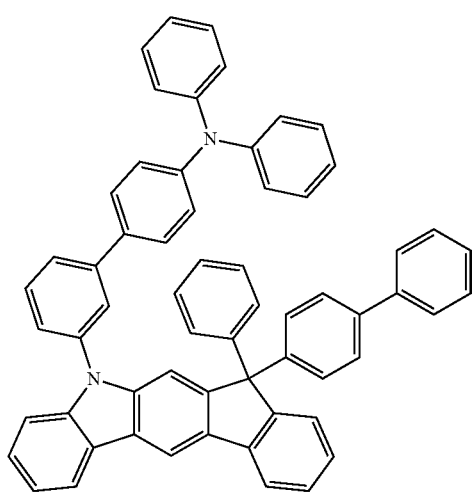
S-87
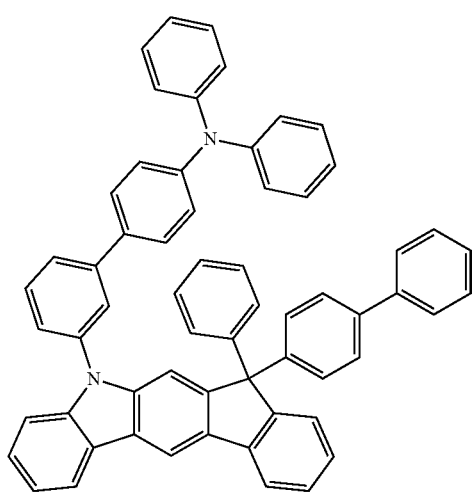
S-91
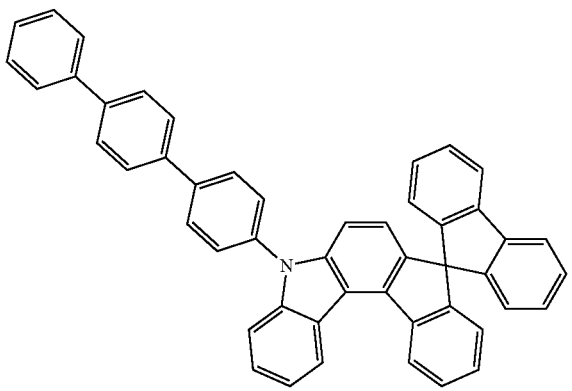

S-92
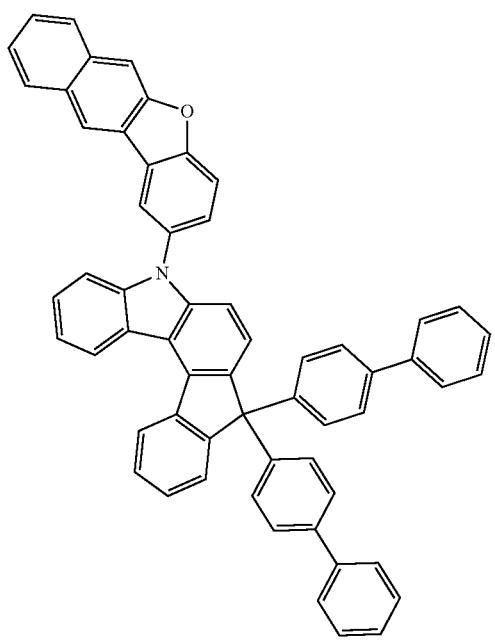
S-93
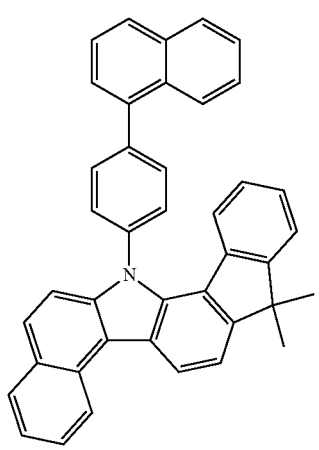
S-94
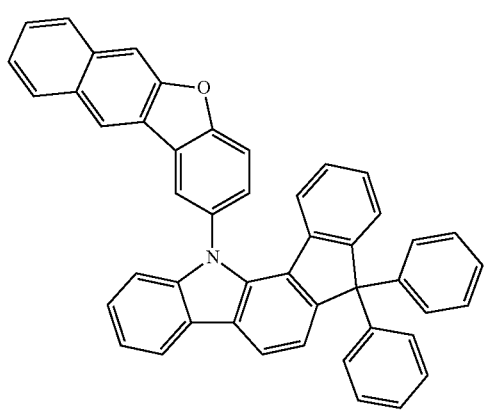
S-95
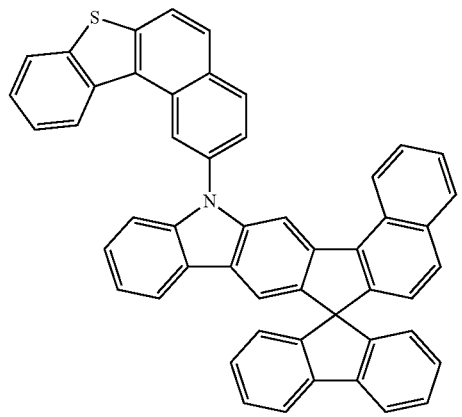
S-96
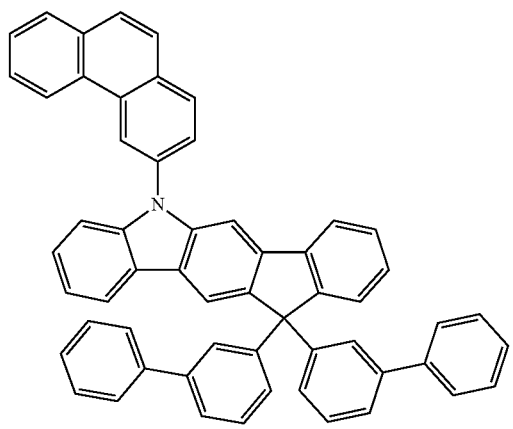
S-97
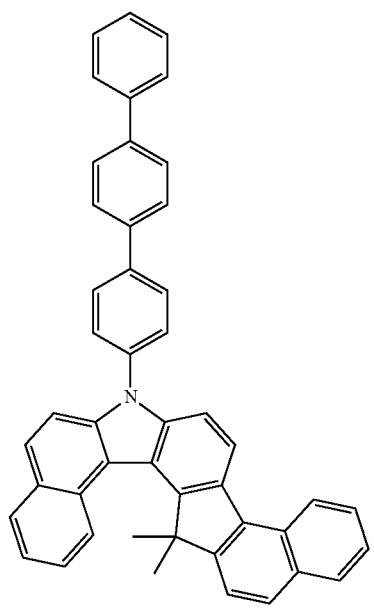

S098
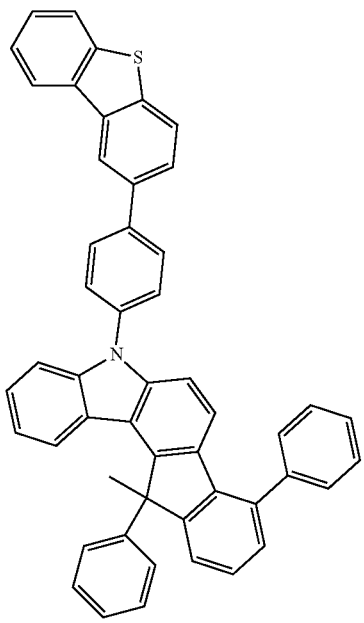
S-99
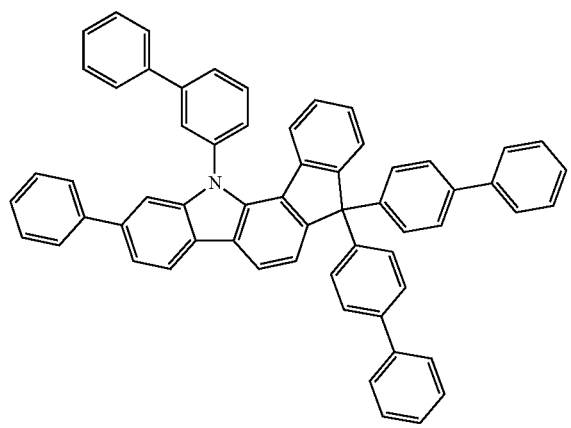
S-100
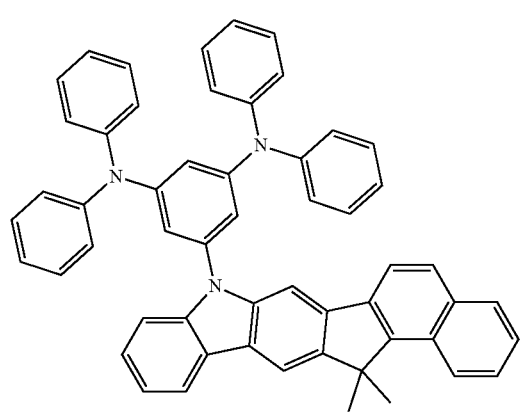
S-101
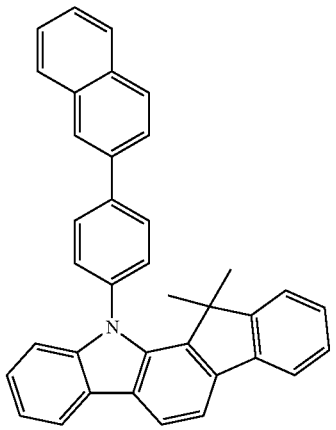
S-102
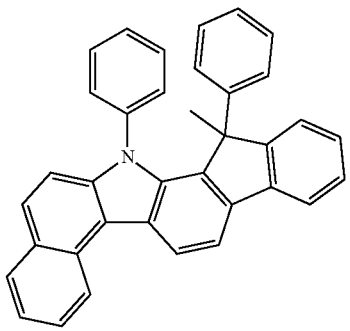
S-103
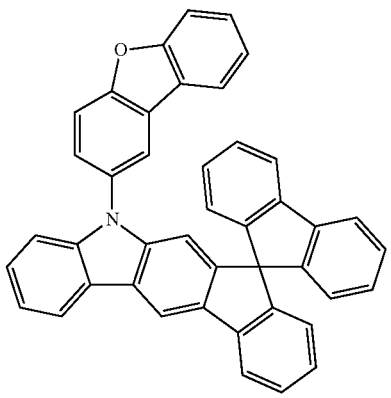
S-104
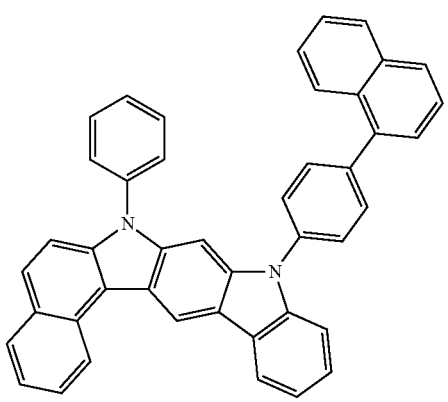

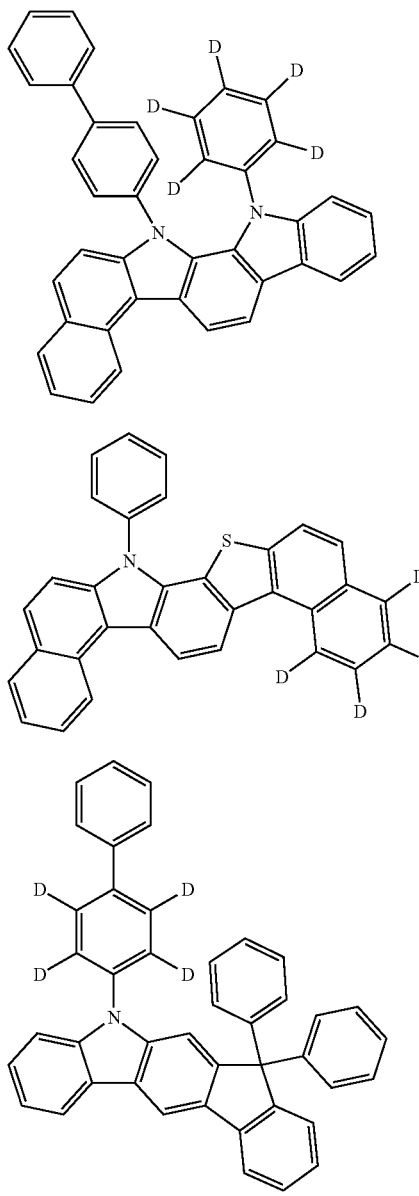

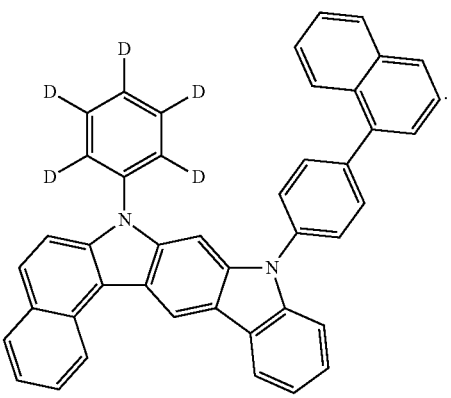

8. The organic electronic element of claim 5, wherein the organic electronic element further comprises a light efficiency enhancing layer formed on at least one surface of the first electrode and the second electrode, the surface being opposite to the organic material layer.

9. The organic electronic element of claim 5, wherein the organic material layer comprises 2 or more stacks including a hole transport layer, an emitting layer, and an electron transport layer sequentially formed on the first electrode.

10. The organic electronic element of claim 9, wherein the organic material layer further comprises a charge generation layer formed between the 2 or more stacks.

11. An electronic device comprising a display device comprising the organic electronic element of claim 5; and a control unit for driving the display device.

12. The electronic device according to claim 11, wherein the organic electronic element is at least one of an OLED, an organic solar cell, an organic photo conductor (OPC), organic transistor (organic TFT) and an element for monochromic or white illumination.

* * * * *

UNITED STATES PATENT AND TRADEMARK OFFICE
CERTIFICATE OF CORRECTION

PATENT NO. : 11,696,501 B2
APPLICATION NO. : 18/057570
DATED : July 4, 2023
INVENTOR(S) : Jin et al.

Page 1 of 8

It is certified that error appears in the above-identified patent and that said Letters Patent is hereby corrected as shown below:

In the Claims

Column 187, Claim 2, Line 41:
Delete "and $R^6$" and replace with -- and $R^8$ --

Column 188, Claim 4, P-3:

Please delete " 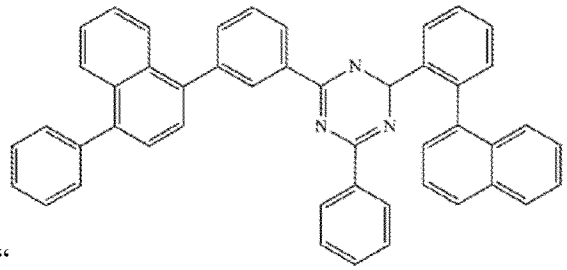 "

And replace with -- 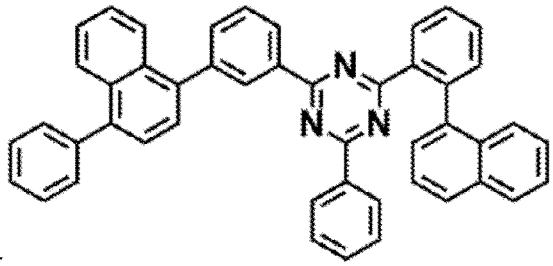 --

Signed and Sealed this
Twelfth Day of September, 2023

Katherine Kelly Vidal
*Director of the United States Patent and Trademark Office*

Column 194, Claim 4, P-26:
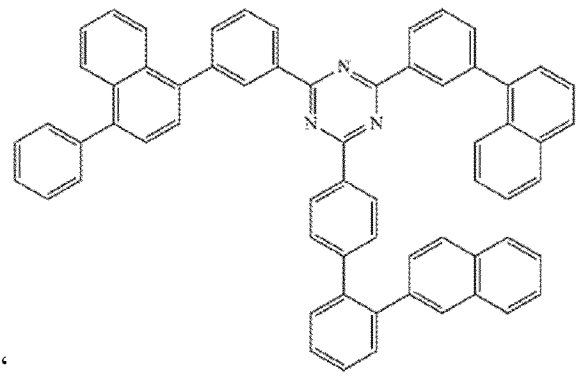
Please delete "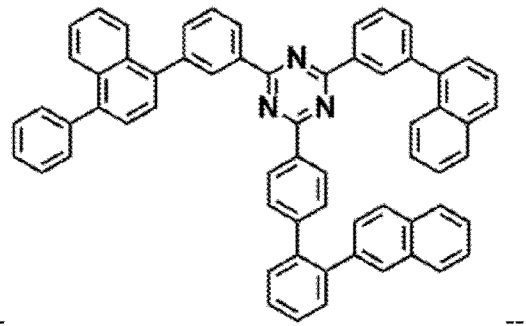"
And replace with --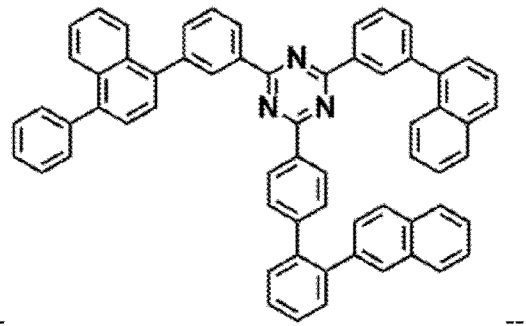--
Column 197, Claim 4, P-36:
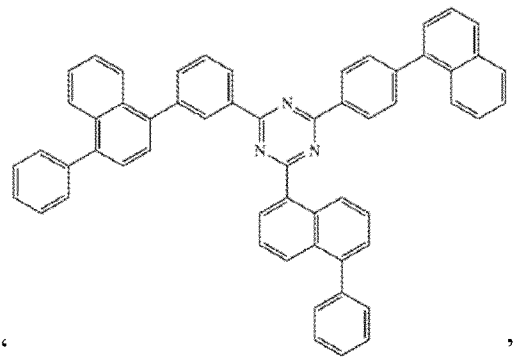
Please delete "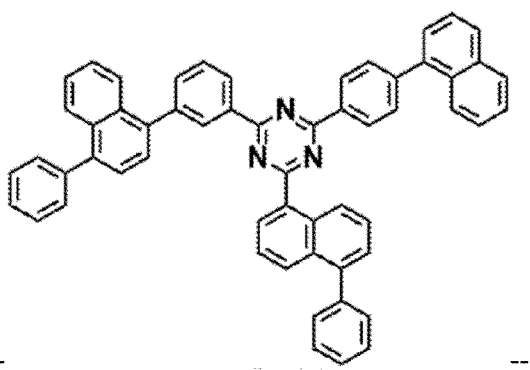"
And replace with --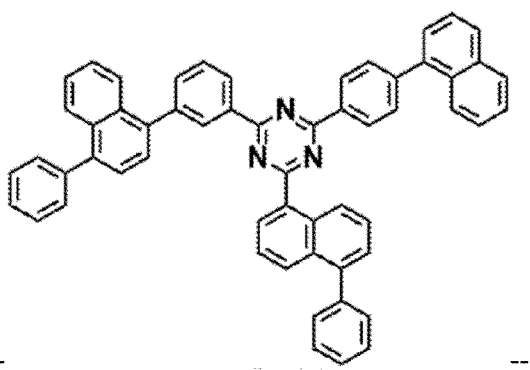--

Column 199, Claim 4, P-46:
Please delete " 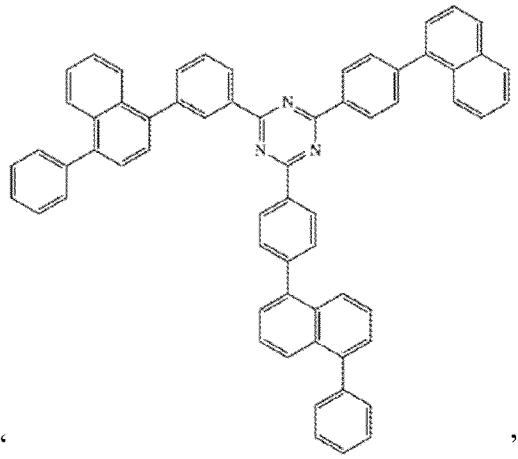 "
And replace with -- 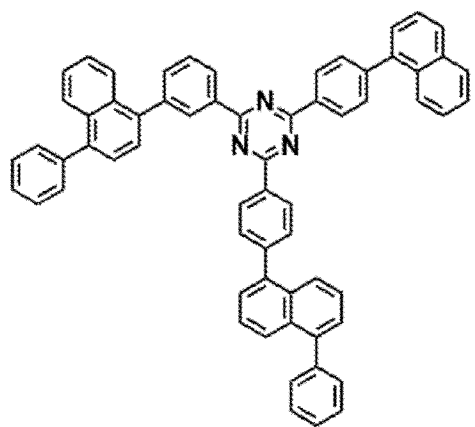 --
Column 202, Claim 4, P-55:
Please delete " 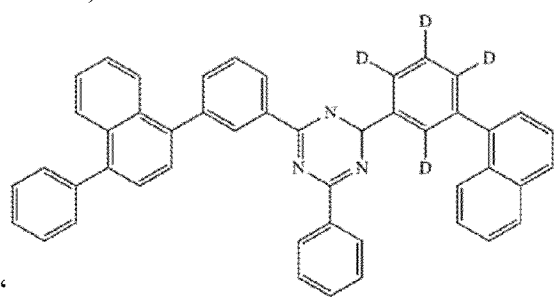 "
And replace with -- 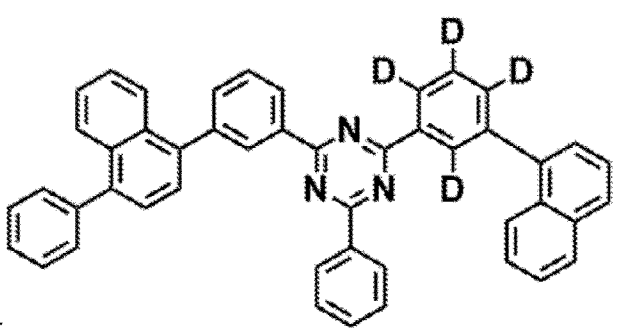 --

Column 213, Claim 5, Line 11:
Delete "L¹" and replace with -- L' --
Column 213, Claim 5, Line 29:
Delete "$C_1$-$C_{60}$" and replace with -- $C_1$-$C_{50}$ --
Column 213, Claim 5, Line 42:
Delete "$C_1$-$C_6$" and replace with -- $C_1$-$C_{60}$ --
Column 216, Claim 6, N-9:
Please delete " 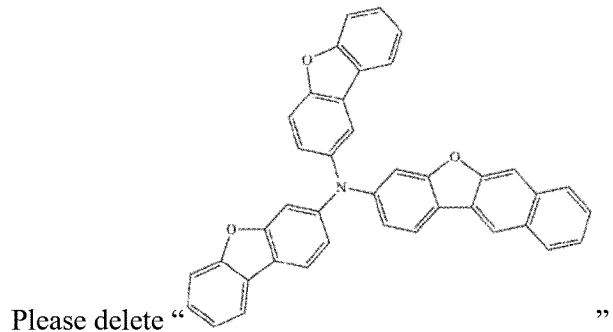 "
And replace with -- 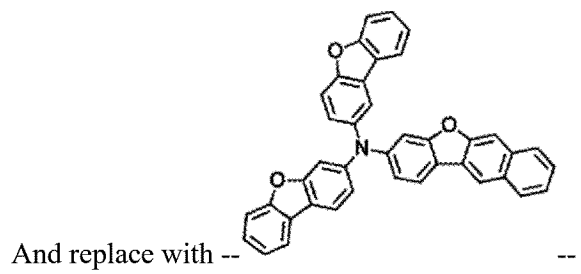 --
Column 219, Claim 6, N-18:
Please delete " 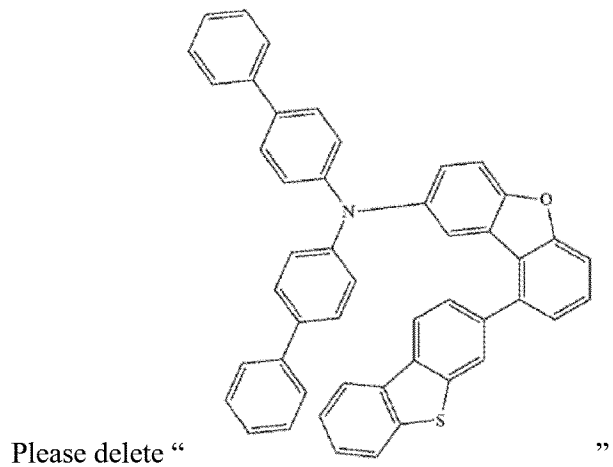 "

CERTIFICATE OF CORRECTION (continued)
U.S. Pat. No. 11,696,501 B2

And replace with -- 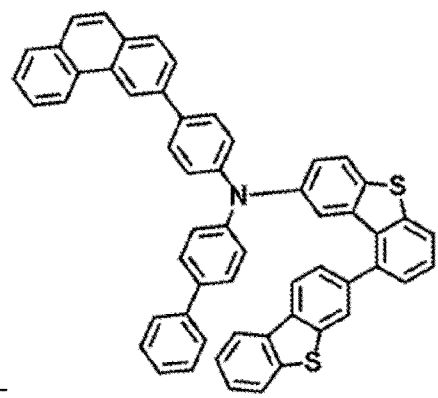 --

Column 245, Claim 6, N-90:

Please delete " 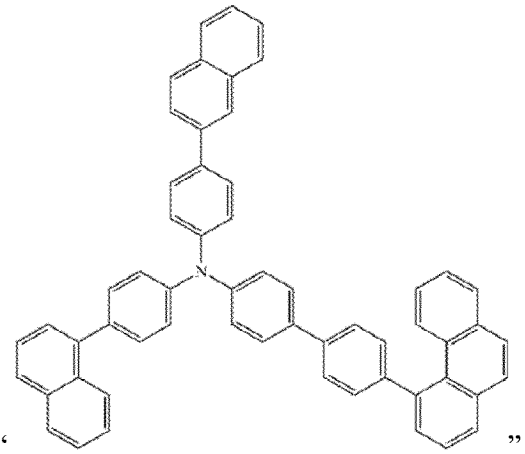 "

And replace with -- 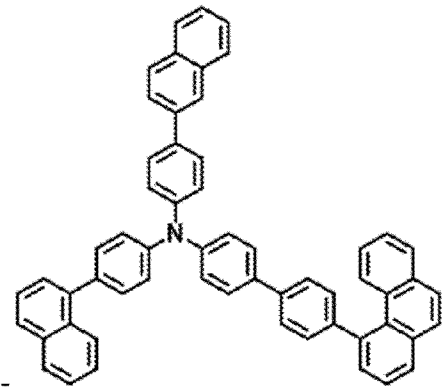 --

Column 247, Claim 6, N-94, N-95, N-96:

Please add N-94 to 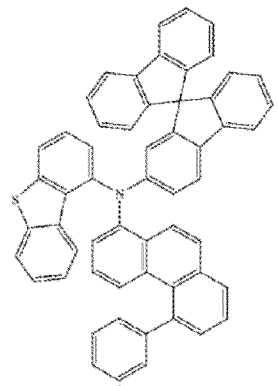 Please add N-95 to 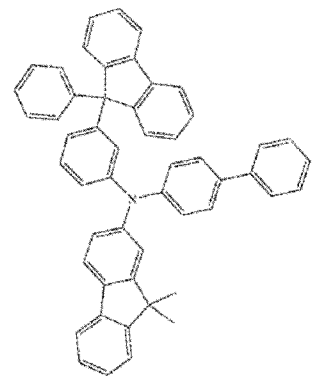
Please add N-96 to 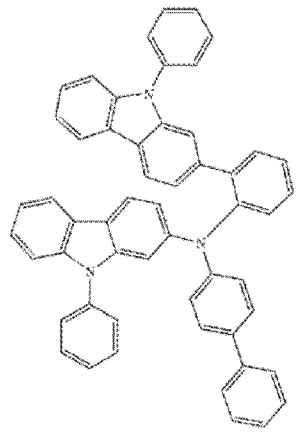
Column 250, Claim 7, S-10:
Please delete " 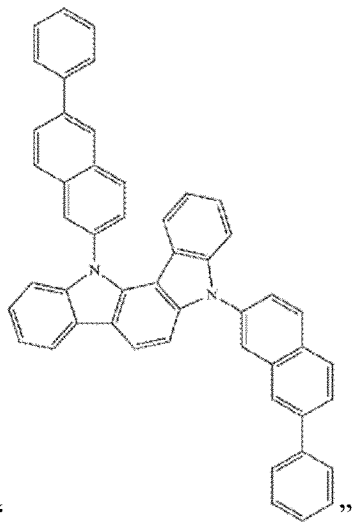 "

CERTIFICATE OF CORRECTION (continued)
U.S. Pat. No. 11,696,501 B2

And replace with -- 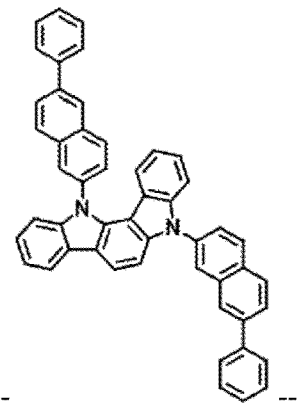 --

Column 255, Claim 7, S-25:

Please delete " 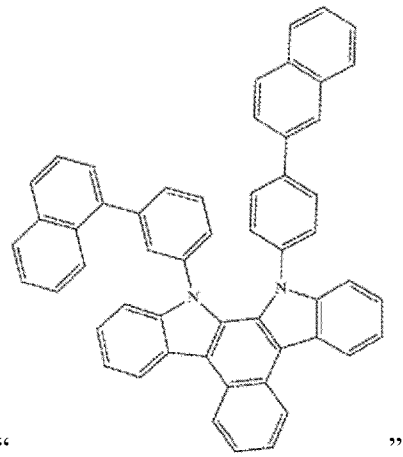 "

And replace with -- 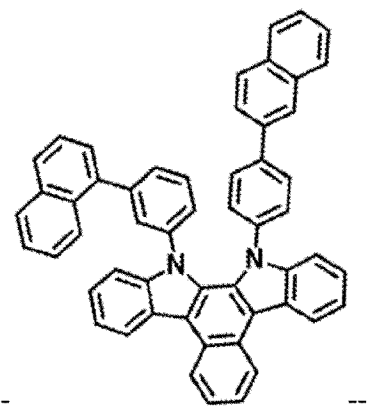 --

CERTIFICATE OF CORRECTION (continued)  Page 8 of 8
U.S. Pat. No. 11,696,501 B2

Column 257, Claim 7, S-33:

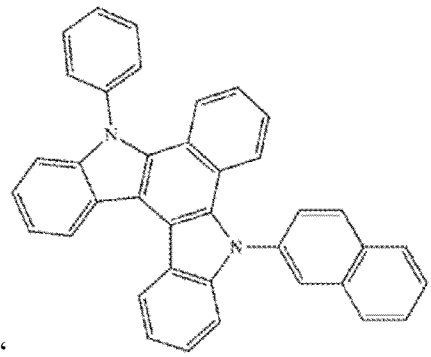

Please delete " "

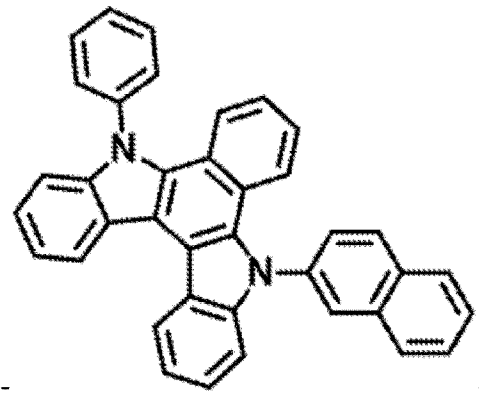

And replace with -- --

Column 270, Claim 7, S-75:

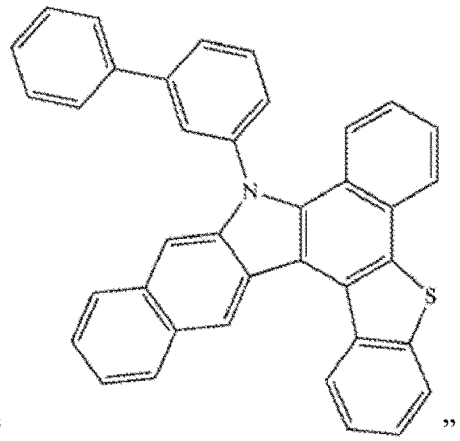

Please delete " "

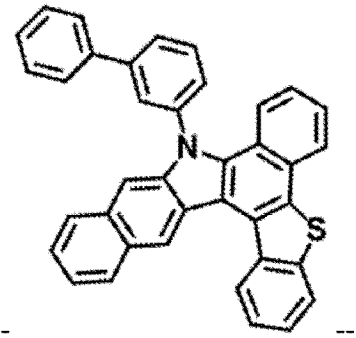

And replace with -- --